（12）United States Patent
Wortz et al.

(10) Patent No.: US 10,898,315 B2
(45) Date of Patent: Jan. 26, 2021

(54) PROSTHETIC CAPSULAR DEVICES, SYSTEMS, AND METHODS

(71) Applicant: Omega Ophthalmics LLC, Versailles, KY (US)

(72) Inventors: Gary N. Wortz, Nicholasville, KY (US); Rick William Ifland, Versailles, KY (US)

(73) Assignee: Omega Ophthalmics LLC, Versailles, KY (US)

( * ) Notice: Subject to any disclaimer, the term of this patent is extended or adjusted under 35 U.S.C. 154(b) by 0 days.

(21) Appl. No.: 16/128,233

(22) Filed: Sep. 11, 2018

(65) Prior Publication Data

US 2019/0076239 A1 Mar. 14, 2019

Related U.S. Application Data

(63) Continuation of application No. 15/789,555, filed on Oct. 20, 2017, now Pat. No. 10,111,746.

(60) Provisional application No. 62/500,932, filed on May 3, 2017, provisional application No. 62/461,675, filed on Feb. 21, 2017, provisional application No.
(Continued)

(51) Int. Cl.
*A61F 2/16* (2006.01)
*A61F 2/14* (2006.01)

(52) U.S. Cl.
CPC ............ *A61F 2/1613* (2013.01); *A61F 2/15* (2015.04); *A61F 2/1601* (2015.04); *A61F 2/1618* (2013.01); *A61F 2/1624* (2013.01); *A61F 2/1648* (2013.01); *A61F 2/1627* (2013.01); *A61F 2002/1681* (2013.01); *A61F 2002/16901* (2015.04)

(58) Field of Classification Search
CPC .. A61F 2/14; A61F 2/1618; A61F 2/15; A61F 2/1601; A61F 2/1648; A61F 2/1624; A61F 2/1613; A61F 2/1694; A61F 2002/16901; A61F 2002/16902; A61F 2/16

See application file for complete search history.

(56) References Cited

U.S. PATENT DOCUMENTS

| 4,073,014 A | 2/1978 | Poler |
| 4,373,218 A | 2/1983 | Schachar |

(Continued)

FOREIGN PATENT DOCUMENTS

| AU | 2013/212271 | 8/2015 |
| CA | 2 864 882 | 6/2015 |

(Continued)

OTHER PUBLICATIONS

"Tracking IOP With an IOL," Sep. 15, 2014.
(Continued)

*Primary Examiner* — William H Matthews
(74) *Attorney, Agent, or Firm* — Knobbe Martens Olson & Bear, LLP

(57) ABSTRACT

A prosthetic capsular device configured to be inserted in an eye after removal of a lens, in some embodiments, can comprise a housing structure comprising capable of containing an intraocular device and an equiconvex refractive surface. The housing structure can comprise an anterior portion comprising an anterior opening, a posterior portion comprising a posterior opening, and a continuous lateral portion between the anterior portion and the posterior portion.

19 Claims, 87 Drawing Sheets

Related U.S. Application Data

62/411,129, filed on Oct. 21, 2016, provisional application No. 62/421,929, filed on Nov. 14, 2016.

(56) References Cited

U.S. PATENT DOCUMENTS

| | | |
|---|---|---|
| 4,402,579 A | 10/1983 | Poler |
| 4,423,856 A | 1/1984 | Takahashi et al. |
| 4,435,856 A | 3/1984 | L'Esperance |
| 4,575,373 A | 3/1986 | Johnson |
| 4,585,456 A | 4/1986 | Blackmore |
| 4,629,461 A | 12/1986 | Clayman et al. |
| 4,685,921 A | 8/1987 | Peyman |
| 4,704,124 A | 11/1987 | Shearing |
| 4,731,078 A | 3/1988 | Stoy et al. |
| 4,816,031 A | 3/1989 | Pfoff |
| 4,833,890 A | 5/1989 | Kelman |
| 4,842,601 A | 6/1989 | Smith |
| 4,888,012 A | 12/1989 | Horn et al. |
| 4,888,016 A | 12/1989 | Langerman |
| 4,892,543 A | 1/1990 | Turley |
| 4,932,966 A | 6/1990 | Christie et al. |
| 5,147,395 A | 9/1992 | Willis |
| 5,171,266 A | 12/1992 | Wiley et al. |
| 5,180,390 A | 1/1993 | Drews |
| 5,203,788 A | 4/1993 | Wiley |
| 5,222,981 A | 6/1993 | Werblin |
| 5,275,623 A | 1/1994 | Sarfarazi |
| 5,326,347 A | 7/1994 | Cumming |
| 5,358,520 A | 10/1994 | Patel |
| 5,522,891 A | 6/1996 | Klaas |
| 5,562,731 A | 10/1996 | Cumming |
| 5,628,795 A | 5/1997 | Langerman |
| 5,628,798 A | 5/1997 | Eggleston et al. |
| 5,653,751 A | 8/1997 | Samiy et al. |
| 5,674,282 A | 10/1997 | Cumming |
| 5,676,669 A | 10/1997 | Colvard |
| 5,697,973 A | 12/1997 | Peyman et al. |
| 5,702,402 A | 12/1997 | Brady |
| 5,800,533 A | 9/1998 | Eggleston et al. |
| 5,964,802 A | 10/1999 | Anello et al. |
| 5,968,094 A | 10/1999 | Werblin et al. |
| 5,984,962 A | 11/1999 | Anello et al. |
| 6,015,435 A | 1/2000 | Valunin |
| 6,027,531 A | 2/2000 | Tassignon |
| 6,113,633 A | 9/2000 | Portney |
| 6,117,171 A | 9/2000 | Skottun |
| 6,136,026 A * | 10/2000 | Israel ................. A61F 2/16 623/6.11 |
| 6,143,244 A | 11/2000 | Xia et al. |
| 6,217,612 B1 | 4/2001 | Woods |
| 6,235,055 B1 | 5/2001 | Chu |
| 6,280,471 B1 | 8/2001 | Peyman et al. |
| 6,299,641 B1 | 10/2001 | Woods |
| 6,322,589 B1 | 11/2001 | Cumming |
| 6,413,276 B1 | 7/2002 | Werblin |
| 6,428,574 B1 | 8/2002 | Valunin |
| 6,443,985 B1 | 9/2002 | Woods |
| 6,450,642 B1 | 9/2002 | Jethmalani et al. |
| 6,454,801 B1 | 9/2002 | Portney |
| 6,464,725 B2 | 10/2002 | Skotton |
| 6,488,708 B2 | 12/2002 | Sarfarazi |
| 6,503,276 B2 | 1/2003 | Lang et al. |
| 6,506,212 B2 | 1/2003 | Zhou et al. |
| 6,524,340 B2 | 2/2003 | Israel |
| 6,533,813 B1 | 3/2003 | Lin et al. |
| 6,537,281 B1 | 3/2003 | Portney |
| 6,537,317 B1 | 3/2003 | Steinert |
| 6,576,012 B2 | 6/2003 | Lang |
| 6,596,026 B1 | 7/2003 | Gross |
| 6,645,246 B1 | 11/2003 | Weinschenk |
| 6,695,881 B2 | 2/2004 | Peng et al. |
| 6,721,043 B2 | 4/2004 | Platt et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,786,934 B2 | 9/2004 | Zadno-Azizi et al. |
| 6,797,004 B1 | 9/2004 | Brady et al. |
| 6,813,097 B2 | 11/2004 | Jethmalani et al. |
| 6,818,158 B2 | 11/2004 | Pham et al. |
| 6,824,266 B2 | 11/2004 | Jethmalani et al. |
| 6,827,738 B2 | 12/2004 | Willis et al. |
| 6,846,326 B2 | 1/2005 | Zadno-Azizi et al. |
| 6,851,804 B2 | 2/2005 | Jethmalani et al. |
| 6,858,040 B2 | 2/2005 | Nguyen et al. |
| 6,881,225 B2 | 4/2005 | Okada |
| 6,884,261 B2 | 4/2005 | Zadno-Azizi et al. |
| 6,884,263 B2 | 4/2005 | Valyunin et al. |
| 6,899,732 B2 | 5/2005 | Zadno-Azizi et al. |
| 6,905,641 B2 | 6/2005 | Platt et al. |
| 6,917,416 B2 | 7/2005 | Platt et al. |
| 6,921,416 B2 | 7/2005 | Khoury |
| 6,926,736 B2 | 8/2005 | Peng et al. |
| 6,960,230 B2 | 11/2005 | Haefliger |
| 6,960,231 B2 | 11/2005 | Tran |
| 6,972,033 B2 | 12/2005 | McNicholas |
| 6,986,900 B2 | 1/2006 | Yaacobi |
| 7,001,374 B2 | 2/2006 | Peyman |
| 7,001,427 B2 | 2/2006 | Aharoni et al. |
| 7,025,783 B2 | 4/2006 | Brady et al. |
| 7,029,497 B2 | 4/2006 | Zhang et al. |
| 7,041,134 B2 | 5/2006 | Nguyen et al. |
| 7,074,840 B2 | 7/2006 | Chang et al. |
| 7,087,080 B2 | 8/2006 | Zadno-Azizi et al. |
| 7,105,110 B2 | 9/2006 | Platt et al. |
| 7,118,596 B2 | 10/2006 | Zadno-Azizi et al. |
| 7,119,894 B2 | 10/2006 | Platt et al. |
| 7,122,053 B2 | 10/2006 | Esch |
| 7,125,422 B2 | 10/2006 | Woods |
| 7,134,755 B2 | 11/2006 | Jethmalani et al. |
| 7,144,423 B2 | 12/2006 | McDonald |
| 7,150,760 B2 | 12/2006 | Zhang |
| 7,198,640 B2 | 4/2007 | Nguyen |
| 7,210,783 B2 | 5/2007 | Jethmalani et al. |
| 7,223,288 B2 | 5/2007 | Zhang et al. |
| 7,226,478 B2 | 6/2007 | Ting et al. |
| 7,237,893 B2 | 7/2007 | Chang et al. |
| 7,241,009 B2 | 7/2007 | Kornfield et al. |
| 7,281,795 B2 | 10/2007 | Sandstedt et al. |
| 7,300,464 B2 | 11/2007 | Tran |
| 7,414,714 B2 | 8/2008 | Platt et al. |
| 7,452,362 B2 | 11/2008 | Zadno-Azizi et al. |
| 7,452,378 B2 | 11/2008 | Zadno-Azizi et al. |
| 7,462,193 B2 | 12/2008 | Nagamoto |
| 7,560,499 B2 | 7/2009 | Jethmalani et al. |
| 7,658,364 B2 | 2/2010 | Robinson et al. |
| 7,662,179 B2 | 2/2010 | Sarfarazi |
| 7,713,299 B2 | 5/2010 | Brady et al. |
| 7,744,603 B2 | 6/2010 | Zadno-Azizi et al. |
| 7,744,646 B2 | 6/2010 | Zadno-Azizi et al. |
| 7,771,471 B2 | 8/2010 | Dell |
| 7,780,729 B2 | 8/2010 | Nguyen et al. |
| 7,798,644 B2 | 9/2010 | Jethmalani et al. |
| 7,806,929 B2 | 10/2010 | Brown |
| 7,811,320 B2 | 10/2010 | Werblin et al. |
| 7,837,326 B2 | 11/2010 | Jethmalani et al. |
| 7,871,437 B2 | 1/2011 | Hermans et al. |
| 7,988,285 B2 | 8/2011 | Sandstedt et al. |
| 7,988,291 B2 | 8/2011 | Ianchulev |
| 8,025,823 B2 | 9/2011 | Pham et al. |
| 8,034,107 B2 | 10/2011 | Stenger |
| 8,048,155 B2 | 11/2011 | Shadduck |
| 8,052,752 B2 | 11/2011 | Woods et al. |
| 8,062,361 B2 | 11/2011 | Nguyen et al. |
| 8,088,161 B2 | 1/2012 | Aharoni et al. |
| 8,100,965 B2 | 1/2012 | Cumming |
| 8,128,693 B2 | 3/2012 | Tran et al. |
| 8,162,927 B2 | 4/2012 | Peyman et al. |
| 8,187,325 B2 | 5/2012 | Zadno-Azizi et al. |
| 8,197,539 B2 | 6/2012 | Nasiatka et al. |
| 8,246,679 B2 | 8/2012 | Nguyen et al. |
| 8,273,123 B2 | 9/2012 | Nun |
| 8,343,216 B2 | 1/2013 | Brady et al. |
| 8,361,353 B2 | 1/2013 | Brait et al. |
| 8,398,709 B2 | 3/2013 | Nun et al. |

(56) References Cited

U.S. PATENT DOCUMENTS

| | | |
|---|---|---|
| 8,486,142 B2 | 7/2013 | Bumbalough et al. |
| 8,505,822 B2 | 8/2013 | Wang et al. |
| 8,506,074 B2 | 8/2013 | Gerbaud |
| 8,545,556 B2 | 10/2013 | Woods et al. |
| 8,556,967 B2 | 10/2013 | Sarfarazi et al. |
| 8,574,295 B2 | 11/2013 | Roholt |
| 8,579,971 B2 | 11/2013 | Webb |
| 8,585,556 B2 | 11/2013 | Woods et al. |
| 8,585,758 B2 | 11/2013 | Woods |
| 8,608,799 B2 | 12/2013 | Blake et al. |
| 8,663,235 B2 | 3/2014 | Tassignon |
| 8,728,158 B2 | 5/2014 | Whitsett |
| 8,778,022 B2 | 7/2014 | Blum et al. |
| 8,821,166 B2 | 9/2014 | Akura et al. |
| 8,834,565 B2 | 9/2014 | Nun |
| 8,900,300 B1 | 12/2014 | Wortz |
| 8,915,588 B2 | 12/2014 | Blum et al. |
| 8,931,896 B2 | 1/2015 | Blum et al. |
| 9,005,282 B2 | 4/2015 | Chang et al. |
| 9,005,283 B2 | 4/2015 | Nguyen et al. |
| 9,039,760 B2 | 5/2015 | Brady et al. |
| 9,072,600 B2 | 7/2015 | Tran |
| 9,078,744 B2 | 7/2015 | Van Noy |
| 9,095,424 B2 | 8/2015 | Kahook et al. |
| 9,119,710 B2 | 9/2015 | Grubbs et al. |
| 9,124,796 B2 | 9/2015 | Blum et al. |
| 9,125,736 B2 | 9/2015 | Kahook et al. |
| 9,149,356 B2 | 10/2015 | Sarfarazi |
| 9,173,527 B2 | 11/2015 | Ulrich et al. |
| 9,186,243 B2 | 11/2015 | Van Noy |
| 9,198,752 B2 | 12/2015 | Woods |
| 9,289,287 B2 | 3/2016 | Kahook et al. |
| 9,339,375 B2 | 5/2016 | Lee et al. |
| 9,358,103 B1 | 6/2016 | Wortz et al. |
| 9,364,316 B1 | 6/2016 | Kahook et al. |
| 9,387,069 B2 | 7/2016 | Kahook et al. |
| 9,414,907 B2 | 8/2016 | Wortz et al. |
| 9,421,088 B1 | 8/2016 | Kahook et al. |
| 9,439,754 B2 | 9/2016 | Wortz |
| 9,504,558 B2 | 11/2016 | Wortz et al. |
| 9,517,127 B2 | 12/2016 | Wortz et al. |
| 9,522,059 B2 | 12/2016 | Wortz et al. |
| 9,522,060 B2 | 12/2016 | Wortz et al. |
| 9,554,890 B2 | 1/2017 | Wortz et al. |
| 9,597,176 B2 | 3/2017 | Wortz et al. |
| 9,629,712 B2 | 4/2017 | Stenger |
| 9,642,699 B2 | 5/2017 | Wortz et al. |
| 9,681,946 B2 | 6/2017 | Kahook et al. |
| 9,763,771 B1 | 9/2017 | Wortz et al. |
| 9,925,037 B2 | 3/2018 | Wortz et al. |
| 9,993,336 B2 | 6/2018 | Wortz et al. |
| 10,004,594 B2 | 6/2018 | Wortz et al. |
| 10,111,746 B2 | 10/2018 | Wortz et al. |
| 10,136,989 B2 | 11/2018 | Wortz et al. |
| 10,271,945 B2 | 4/2019 | Wortz et al. |
| 10,492,903 B1 | 12/2019 | Wortz |
| 2001/0047204 A1 | 11/2001 | Zhou et al. |
| 2001/0051825 A1 | 12/2001 | Peterson |
| 2002/0128710 A1 | 9/2002 | Eggleston |
| 2002/0143395 A1 | 10/2002 | Skottun |
| 2002/0173846 A1 | 11/2002 | Blake et al. |
| 2003/0004569 A1 | 1/2003 | Haefliger |
| 2003/0050695 A1 | 3/2003 | Lin et al. |
| 2003/0090624 A1 | 5/2003 | Jethmalani et al. |
| 2003/0149479 A1 | 8/2003 | Snyder et al. |
| 2003/0149480 A1 | 8/2003 | Shadduck |
| 2003/0151831 A1 | 8/2003 | Sandstedt et al. |
| 2003/0176521 A1 | 9/2003 | Jethmalani et al. |
| 2003/0187505 A1 | 10/2003 | Liao |
| 2004/0064182 A1 | 4/2004 | Kelman |
| 2004/0082993 A1 | 4/2004 | Woods |
| 2004/0082995 A1 | 4/2004 | Woods |
| 2004/0106993 A1 | 6/2004 | Portney |
| 2004/0117011 A1 | 6/2004 | Aharoni et al. |
| 2004/0148022 A1 | 7/2004 | Eggleston |
| 2004/0158322 A1 | 8/2004 | Shen et al. |
| 2004/0167622 A1 | 8/2004 | Sunlap et al. |
| 2004/0208910 A1 | 10/2004 | Ashton et al. |
| 2004/0254438 A1 | 12/2004 | Chuck et al. |
| 2005/0021138 A1 | 1/2005 | Woods |
| 2005/0085907 A1 | 4/2005 | Hanna |
| 2005/0099597 A1 | 5/2005 | Sandstedt et al. |
| 2005/0107875 A1 | 5/2005 | Cumming |
| 2005/0113911 A1 | 5/2005 | Peyman |
| 2005/0113913 A1 | 5/2005 | Duvert et al. |
| 2005/0137703 A1 | 6/2005 | Chen |
| 2005/0154457 A1 | 7/2005 | Aharoni et al. |
| 2005/0187623 A1 | 8/2005 | Tassignon |
| 2005/0222577 A1 | 10/2005 | Vaquero |
| 2005/0234285 A1 | 10/2005 | Khoury |
| 2005/0246018 A1 | 11/2005 | Grubbs et al. |
| 2006/0027939 A1 | 2/2006 | Brait et al. |
| 2006/0047339 A1 | 3/2006 | Brown |
| 2006/0064161 A1 | 3/2006 | Blake |
| 2006/0095128 A1 | 5/2006 | Blum et al. |
| 2006/0212116 A1 | 9/2006 | Woods |
| 2006/0253196 A1 | 11/2006 | Woods |
| 2006/0259139 A1 | 11/2006 | Zadno-Azizi et al. |
| 2006/0261502 A1 | 11/2006 | Platt et al. |
| 2007/0027538 A1 | 2/2007 | Aharoni et al. |
| 2007/0027541 A1 | 2/2007 | Aharoni et al. |
| 2007/0032868 A1 | 2/2007 | Woods |
| 2007/0083261 A1 | 4/2007 | Colvard |
| 2007/0093892 A1 | 4/2007 | MacKool |
| 2007/0100444 A1 | 5/2007 | Brady et al. |
| 2007/0118216 A1 | 5/2007 | Pynson |
| 2007/0123767 A1 | 5/2007 | Montegrande et al. |
| 2007/0123981 A1 | 5/2007 | Tassignon |
| 2007/0162118 A1 | 7/2007 | Rozakis et al. |
| 2007/0213816 A1 | 9/2007 | Sarfarazi |
| 2007/0244560 A1 | 10/2007 | Ossipov et al. |
| 2007/0260308 A1 | 11/2007 | Tran |
| 2008/0086206 A1 | 4/2008 | Nasiatka et al. |
| 2008/0097599 A1 | 4/2008 | Rozakis et al. |
| 2008/0221676 A1 | 9/2008 | Coleman et al. |
| 2008/0300680 A1 | 12/2008 | Joshua |
| 2009/0005864 A1 | 1/2009 | Eggleston |
| 2009/0182423 A1 | 7/2009 | Zheng |
| 2010/0022945 A1 | 1/2010 | Rodstrom |
| 2010/0030225 A1 | 2/2010 | Ianchulev |
| 2010/0204788 A1 | 8/2010 | Van Noy |
| 2010/0211171 A1 | 8/2010 | Sarfarazi |
| 2010/0228344 A1 | 9/2010 | Shadduck |
| 2010/0280609 A1 | 11/2010 | Simonov et al. |
| 2011/0015541 A1 | 1/2011 | Padrick et al. |
| 2011/0153014 A1 | 6/2011 | Zhang et al. |
| 2011/0181834 A1 | 7/2011 | Gerbaud |
| 2011/0224788 A1 | 9/2011 | Webb |
| 2011/0288638 A1 | 11/2011 | Smiley et al. |
| 2011/0040378 A1 | 12/2011 | Werblin |
| 2011/0295367 A1 | 12/2011 | Cuevas |
| 2011/0313521 A1 | 12/2011 | Angelopoulos |
| 2012/0078363 A1 | 3/2012 | Lu et al. |
| 2012/0078364 A1 | 3/2012 | Stenger |
| 2012/0179249 A1 | 7/2012 | Coleman |
| 2012/0226351 A1 | 9/2012 | Peyman |
| 2012/0238857 A1 | 9/2012 | Wong et al. |
| 2012/0253458 A1 | 10/2012 | Geraghty et al. |
| 2013/0072591 A1 | 3/2013 | Sandstedt et al. |
| 2013/0116781 A1 | 5/2013 | Nun |
| 2013/0184815 A1 | 7/2013 | Roholt |
| 2013/0190868 A1 | 7/2013 | Kahook et al. |
| 2013/0197637 A1 | 8/2013 | Brait et al. |
| 2013/0245754 A1 | 9/2013 | Blum et al. |
| 2013/0289153 A1 | 10/2013 | Sandstedt et al. |
| 2013/0304206 A1 | 11/2013 | Pallikaris et al. |
| 2013/0310931 A1 | 11/2013 | Kahook et al. |
| 2013/0317458 A1 | 11/2013 | Kopczynski et al. |
| 2014/0052246 A1 | 2/2014 | Kahook et al. |
| 2014/0067059 A1 | 3/2014 | Webb |
| 2014/0172089 A1 | 6/2014 | Lee et al. |
| 2014/0228949 A1 | 8/2014 | Argento et al. |
| 2014/0343379 A1 | 11/2014 | Pugh |
| 2014/0371852 A1 | 12/2014 | Aharoni et al. |

(56) References Cited

U.S. PATENT DOCUMENTS

| | | |
|---|---|---|
| 2014/0379079 A1 | 12/2014 | Ben Nun |
| 2015/0061990 A1 | 3/2015 | Toner et al. |
| 2015/0088253 A1 | 3/2015 | Doll et al. |
| 2015/0100046 A1 | 4/2015 | Ambati et al. |
| 2015/0127102 A1 | 5/2015 | Wortz |
| 2015/0142106 A1 | 5/2015 | Wortz |
| 2015/0157452 A1 | 6/2015 | Maliarov et al. |
| 2015/0182330 A1 | 7/2015 | Grant |
| 2015/0230981 A1 | 8/2015 | Kahook et al. |
| 2015/0238309 A1 | 8/2015 | Jansen et al. |
| 2015/0272727 A1 | 10/2015 | Humayun et al. |
| 2015/0289970 A1 | 10/2015 | Akura |
| 2015/0335420 A1 | 11/2015 | Blum et al. |
| 2015/0366656 A1 | 12/2015 | Wortz et al. |
| 2015/0366659 A1 | 12/2015 | Wortz et al. |
| 2015/0366660 A1 | 12/2015 | Martinez et al. |
| 2016/0000558 A1 | 1/2016 | Honigsbaum |
| 2016/0008126 A1 | 1/2016 | Salahieh et al. |
| 2016/0030161 A1 | 2/2016 | Brady et al. |
| 2016/0030163 A1 | 2/2016 | Akahoshi |
| 2016/0058552 A1 | 3/2016 | Argal et al. |
| 2016/0058553 A1 | 3/2016 | Salahieh et al. |
| 2016/0074154 A1 | 3/2016 | Woods |
| 2016/0113760 A1 | 4/2016 | Conrad |
| 2016/0113761 A1 | 4/2016 | Nishi et al. |
| 2016/0235524 A1 | 8/2016 | Wortz et al. |
| 2016/0278912 A1 | 9/2016 | Kahook et al. |
| 2016/0310263 A1 | 10/2016 | Akura |
| 2016/0317287 A1 | 11/2016 | Silverstrini et al. |
| 2016/0324629 A1 | 11/2016 | Sandstedt et al. |
| 2016/0331519 A1 | 11/2016 | Kahook et al. |
| 2016/0338825 A1 | 11/2016 | Wortz et al. |
| 2016/0339657 A1 | 11/2016 | Grubbs et al. |
| 2017/0000602 A1 | 1/2017 | Sohn et al. |
| 2017/0020658 A1 | 1/2017 | Grubbs et al. |
| 2017/0042667 A1 | 2/2017 | Collins et al. |
| 2017/0049560 A1 | 2/2017 | Cherne |
| 2017/0119521 A1 | 5/2017 | Kahook et al. |
| 2017/0172732 A1 | 6/2017 | Lu et al. |
| 2017/0319332 A1 | 11/2017 | Kahook et al. |
| 2017/0348094 A1 | 12/2017 | Sohn |
| 2017/0348095 A1 | 12/2017 | Wortz et al. |
| 2018/0055625 A1 | 3/2018 | Wortz et al. |
| 2018/0271642 A1 | 9/2018 | Wortz et al. |
| 2019/0015197 A1 | 1/2019 | Wortz et al. |
| 2019/0083235 A1 | 3/2019 | Wortz |
| 2019/0307552 A1 | 10/2019 | Wortz et al. |
| 2019/0343621 A1 | 11/2019 | Wortz et al. |

FOREIGN PATENT DOCUMENTS

| | | |
|---|---|---|
| EP | 0 337 390 | 2/1993 |
| EP | 0 294 039 | 7/1993 |
| EP | 0 528 325 | 12/1996 |
| EP | 916320 | 5/1999 |
| EP | 0 732 090 | 6/2002 |
| EP | 1 653 886 | 5/2006 |
| EP | 1 499 264 | 8/2006 |
| EP | 1 100 411 | 11/2006 |
| EP | 1 694 253 | 8/2007 |
| EP | 1 852 090 | 11/2007 |
| EP | 1 562 521 | 12/2009 |
| EP | 1 475 055 | 4/2010 |
| EP | 1 933 768 | 10/2010 |
| EP | 2 315 559 | 5/2011 |
| EP | 1 438 930 | 9/2011 |
| EP | 2 412 337 | 2/2012 |
| EP | 1 296 616 | 5/2012 |
| EP | 1 906 881 | 8/2012 |
| EP | 2 512 374 | 10/2012 |
| EP | 2 851 038 | 3/2015 |
| EP | 2 620 130 | 7/2016 |
| EP | 2 816 972 | 3/2017 |
| EP | 3 181 095 | 6/2017 |
| EP | 3 157 466 | 12/2017 |
| FR | 2 799 637 | 4/2001 |
| FR | 2 804 860 | 8/2001 |
| FR | 2 966 340 | 4/2012 |
| JP | S63-89154 | 4/1988 |
| JP | 02-011134 | 1/1990 |
| JP | H08-317943 | 12/1996 |
| JP | H09-173363 | 7/1997 |
| JP | 2004-523316 | 6/2005 |
| JP | 2005-143886 | 6/2005 |
| JP | 2013-544116 | 12/2013 |
| JP | 5785678 | 9/2015 |
| JP | 2017-519221 | 7/2017 |
| WO | WO 1998/017205 | 4/1998 |
| WO | WO 1999/024541 | 5/1999 |
| WO | WO 1999/062433 | 12/1999 |
| WO | WO 01/64136 | 9/2001 |
| WO | WO 2002/026121 | 4/2002 |
| WO | WO 2002/071983 | 9/2002 |
| WO | WO 2003/058296 | 7/2003 |
| WO | WO 2005/016191 | 2/2005 |
| WO | WO 2005/094727 | 10/2005 |
| WO | WO 2005/107649 | 11/2005 |
| WO | WO 2006/002201 | 1/2006 |
| WO | WO 2006/050171 | 5/2006 |
| WO | WO 2006/124016 | 11/2006 |
| WO | WO 2006/135572 | 12/2006 |
| WO | WO 2007/030799 | 3/2007 |
| WO | WO 2006/015315 | 4/2007 |
| WO | WO 07/121296 | 10/2007 |
| WO | WO 2010/002215 | 4/2010 |
| WO | WO 2011/163080 | 12/2011 |
| WO | WO 12/067994 | 5/2012 |
| WO | WO 12/161749 | 11/2012 |
| WO | WO 2013/039707 | 3/2013 |
| WO | WO 2013/112589 | 8/2013 |
| WO | WO 2013/126380 | 8/2013 |
| WO | WO 2014/167425 | 10/2014 |
| WO | WO 2014/197170 | 12/2014 |
| WO | WO 2014/201956 | 12/2014 |
| WO | WO 2015/044235 | 4/2015 |
| WO | WO 2015/066532 | 5/2015 |
| WO | WO 2015/126604 | 8/2015 |
| WO | WO 2015/195825 | 12/2015 |
| WO | WO 2015/198236 | 12/2015 |
| WO | WO 2015/200056 | 12/2015 |
| WO | WO 2016/122805 | 8/2016 |
| WO | WO 2016/187497 | 11/2016 |
| WO | WO 2017/030582 | 2/2017 |
| WO | WO 2017/079449 | 5/2017 |
| WO | WO 2017/192855 | 11/2017 |

OTHER PUBLICATIONS

Becker, K.A., Et al.; accuracy of lens power calculation and centration of an aspheric intraocular lens, Ophthalmologe, Oct. 2006, pp. 873-876, vol. 103, Issue 10, Springer. France.

English Machine Translation of European Patent No. EP 2412337.

International Preliminary Report on Patentability, dated Aug. 26, 2014, in PCT App. No. PCT/US2013/026820.

International Preliminary Report on Patentability, dated Dec. 20, 2016, in PCT App. No. PCT/US2015/036263.

International Search Report and Written Opinion issued in PCT App. No. PCT/US2015/036263, dated Oct. 7, 2015.

International Search Report and Written Opinion issued in PCT Application No. PCT/US2015/065887, dated Apr. 6, 2016.

International Search report and Written Opinoin dated May 31, 2013 for Application No. PCT/US2013/026820.

Kleiman, L.Z., et al.; Post-operative Results with Implantation of the Acrysof SA-60 Intraocular lens into the Ciliary Sulcus, Arvo Annual meeting Abstract Search and Program Planner, May 2002; pp. Abstract No. 380; vol. 2002., Annual Meeting of the Association for Research in Vision and Ophthalmology, Ft. Lauderdale, Florida, USA.

Kleinmann, "Open-Capsule Device for PCO Prevention", Oct. 17, 2013.

Koeppl, C. et al.; Change in IOL position and capsular bag size with an angulated intraocular lens early after cataract surgery, Journal of

(56) References Cited

OTHER PUBLICATIONS

Cataract and Refractive Surgery, Feb. 2005, pp. 348-353, vol. 31, issue 2., Elsevier Science, Inc. New York City, NY, USA.
Krader, "Small-aperture optic IOL broadens range of vision", Dec. 1, 2014.
Lim, Mcc, Et al.; Surgical management of late dislocated lens capsular bag with intraocular lens and endocapsular tension ring, Journal of Cataract and Refractive Surgery, Mar. 2006, pp. 533-535, vol. 32, Issue 3, Elsevier Science, Inc., New York City, NY, USA.
Notice of Allowance issued in Japanese Patent Application No. 2014-558790, dated Jun. 25, 2015, in 3 pages.
Notice of Allowance issued in U.S. Appl. No. 14/968,427, dated Apr. 26, 2016.
Office Action issued in European Application No. 13710641.5, dated Oct. 1, 2015, in 5 pages.
Office Action issued in Japanese Patent Application No. 2014-558790, dated Feb. 3, 2015, in 9 pages.
Office Action issued in Japanese Patent Application No. 2015-146248, dated Nov. 28, 2016, in 13 pages.
Postive Phase I/II Interim Data of Bimatoprost Sustained-Release Implant for IOP Therapy in Glaucoma, Nov. 16, 2015, http://www.allergan.com/NEWS/News/Thomson-Reuters/Positive-Phase-I-II-Interim-Data-of-Bimatoprost-Su.
Restriction Requirement issued in U.S. Appl. No. 14/968,427, dated Mar. 24, 2016.
Wirtitsch, M.g., Et al.; Effect of haptic design on change in axial lens posiiton after cataract surgery, Journal of Cataract and Refractive Surgery, Jan. 2004, pp. 45-51, vol. 30, issue 1. 19th Congress of the European-Society-of-Cataract-and-Refractive-Surgeons, Elsevier Science, inc., New York City, NY, USA.
International Search Report and Written Opinion dated Feb. 8, 2018 in application No. PCT/US2017/057666.

\* cited by examiner

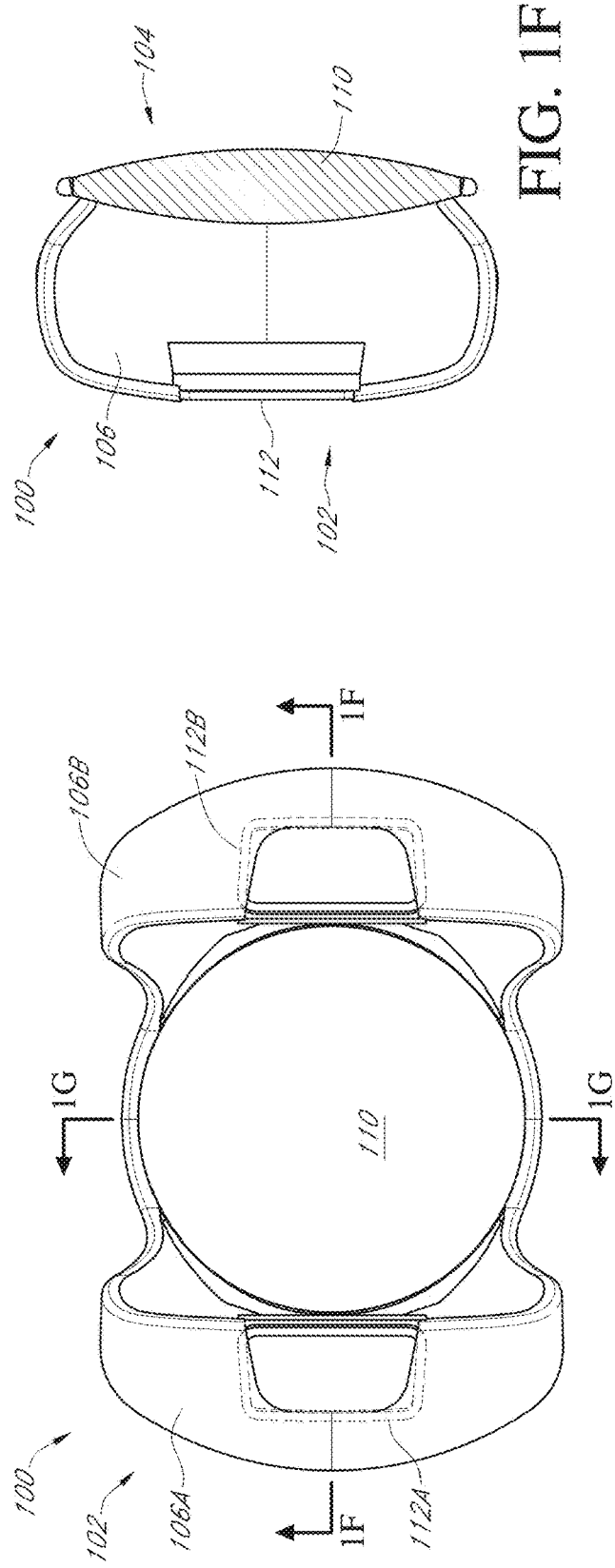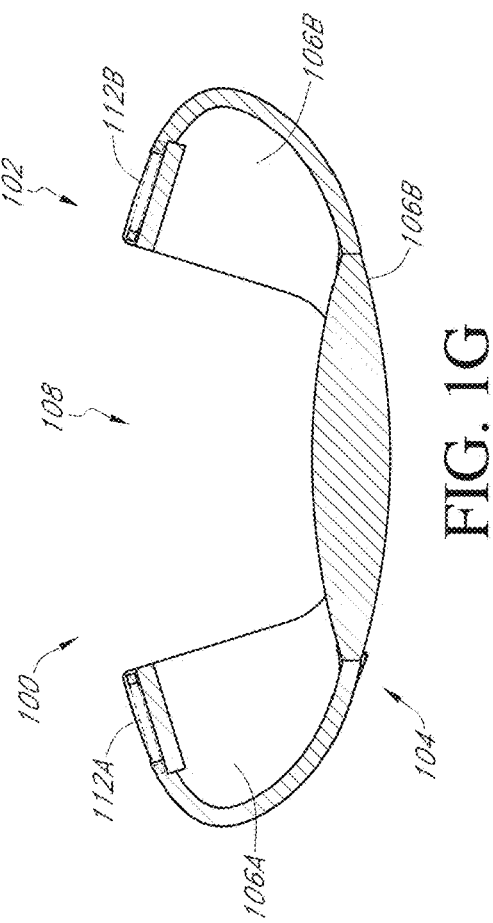

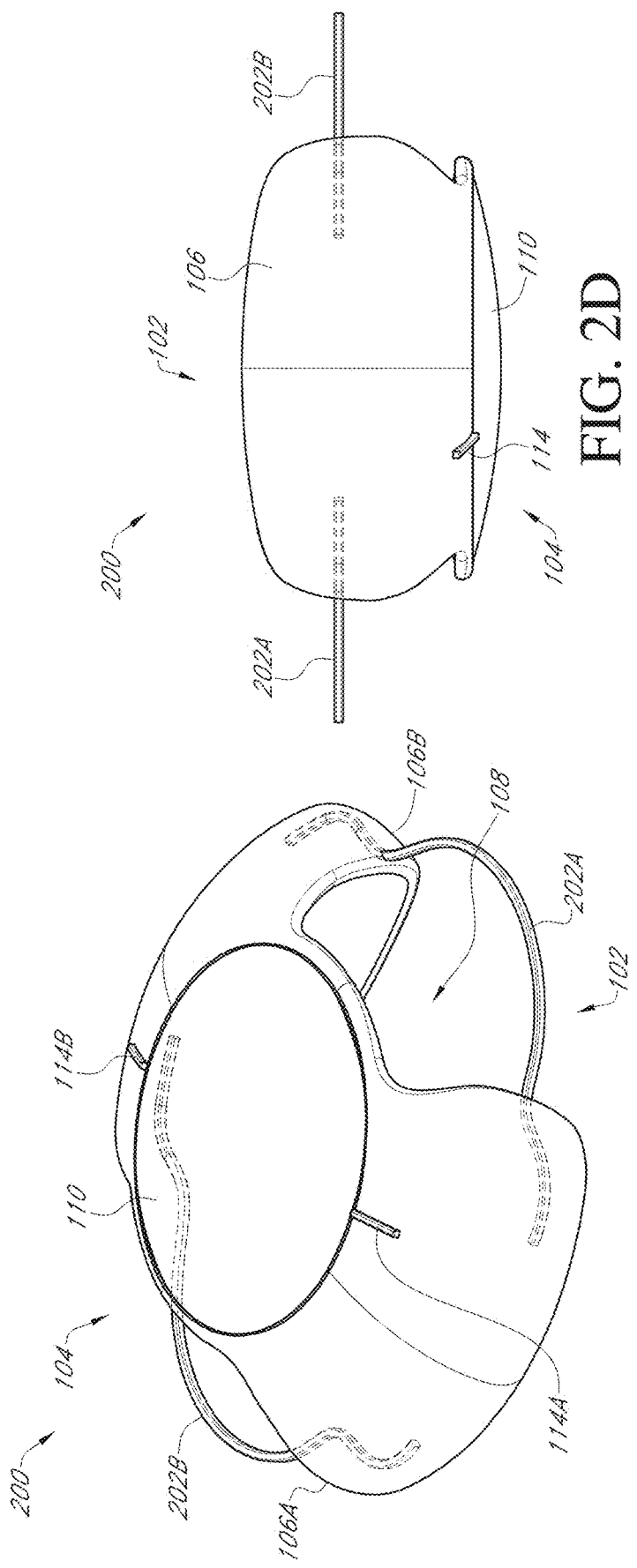

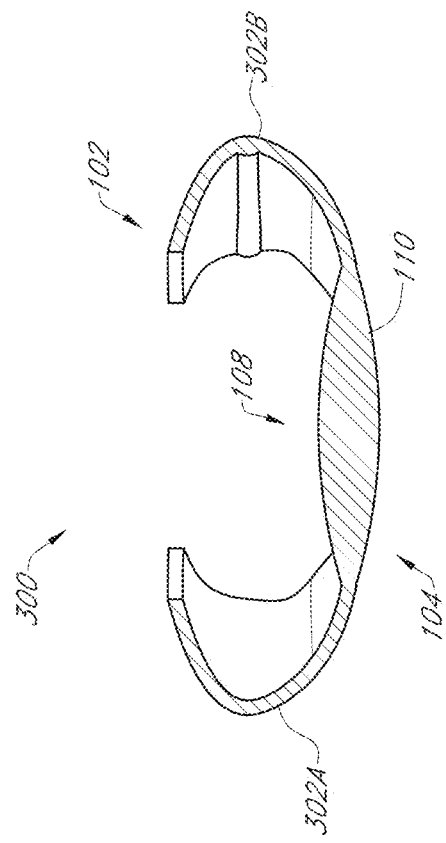
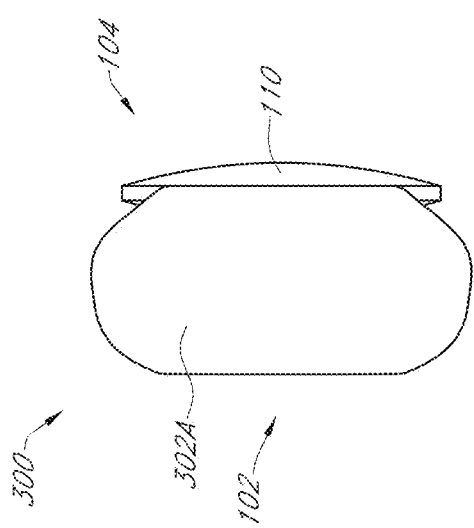
FIG. 3D
FIG. 3C

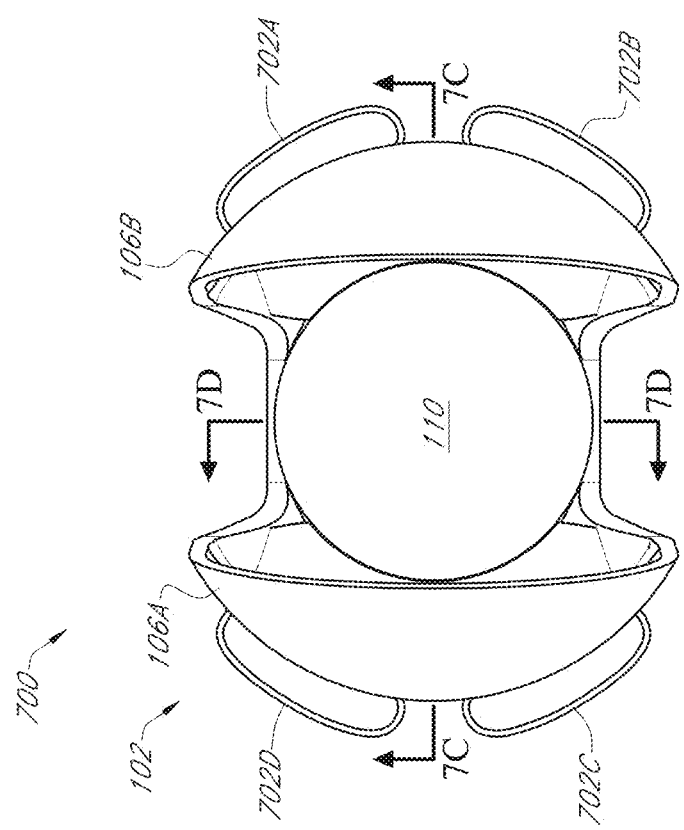
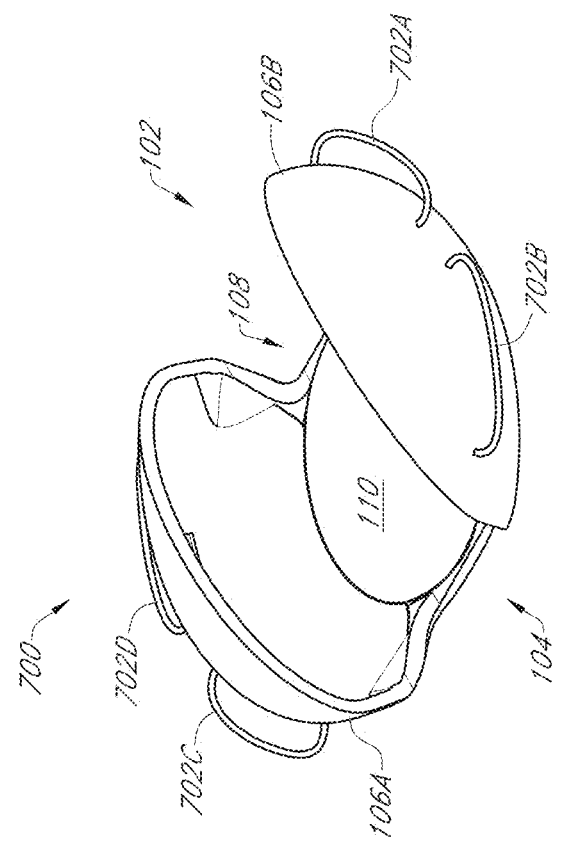
FIG. 7B
FIG. 7A

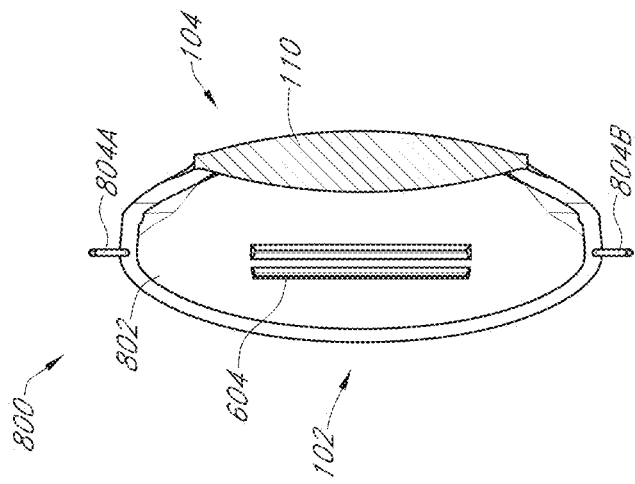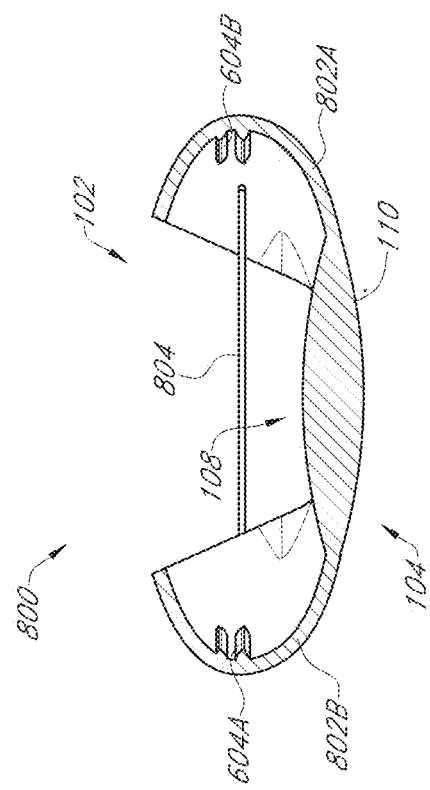
FIG. 8D
FIG. 8C

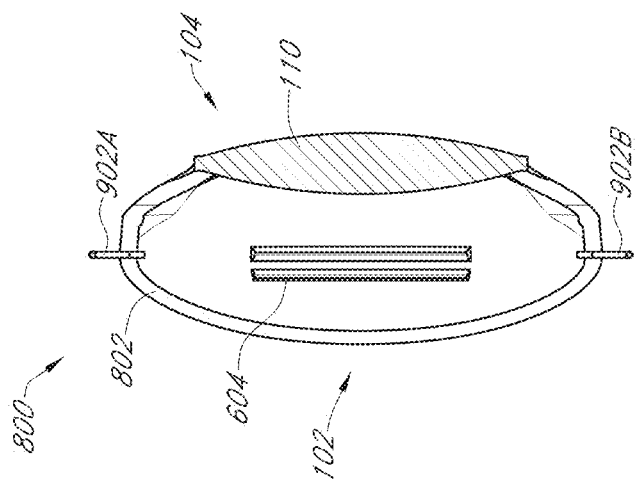
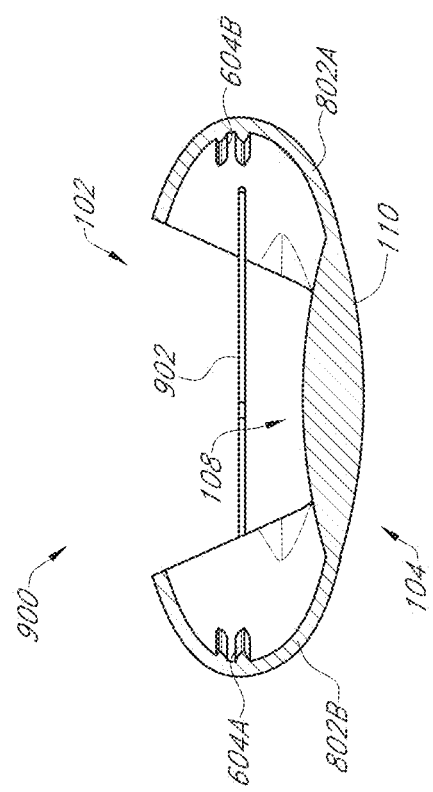
FIG. 9D
FIG. 9C

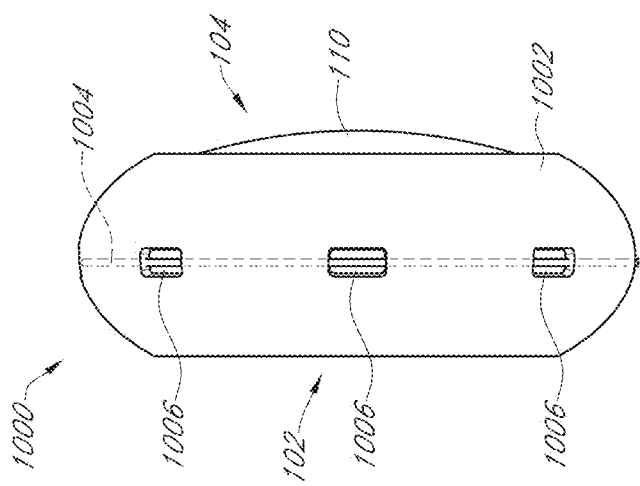
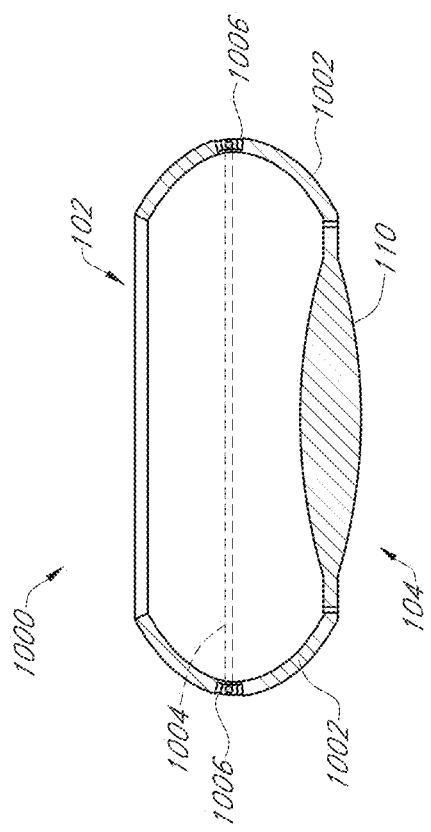
FIG. 10D
FIG. 10C

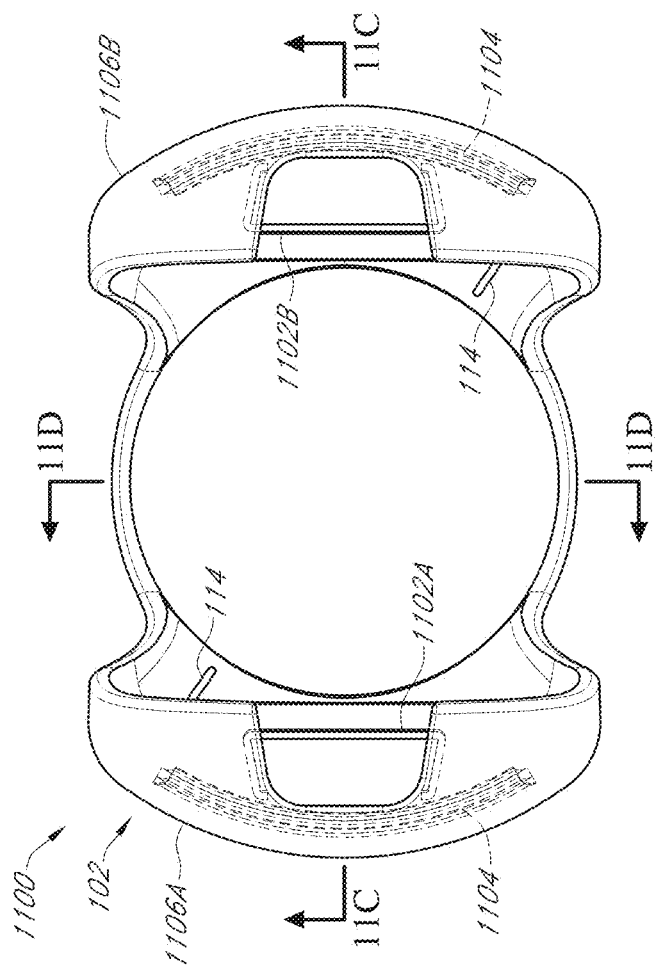
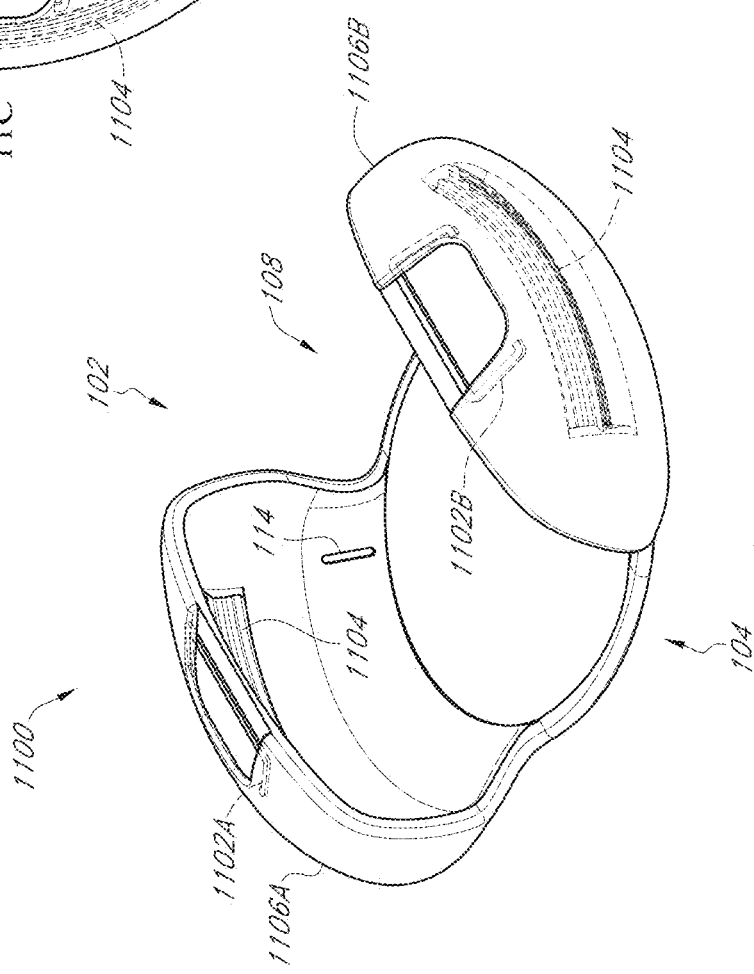
FIG. 11B
FIG. 11A

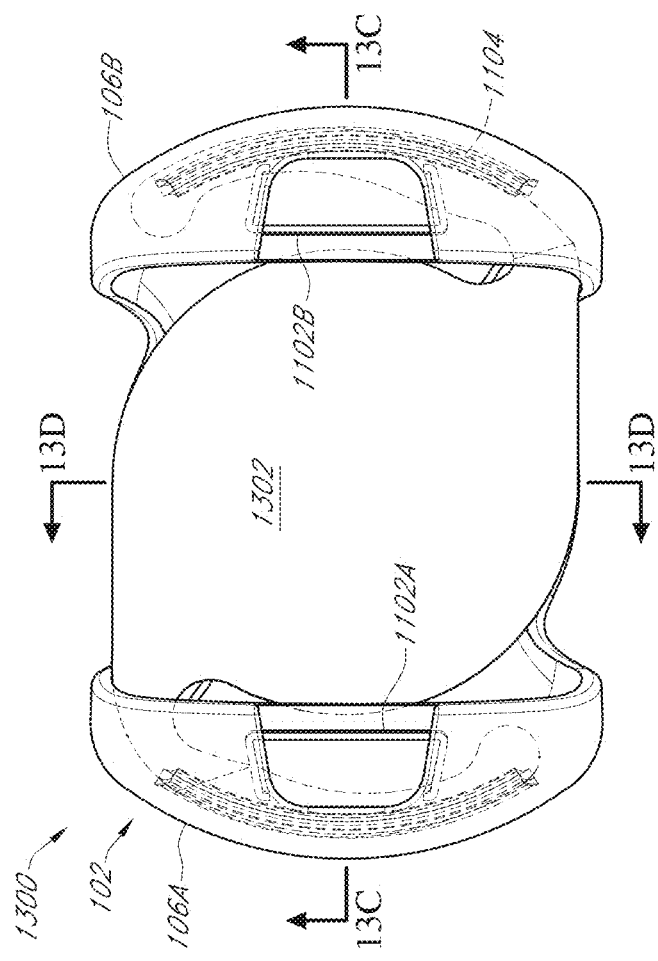
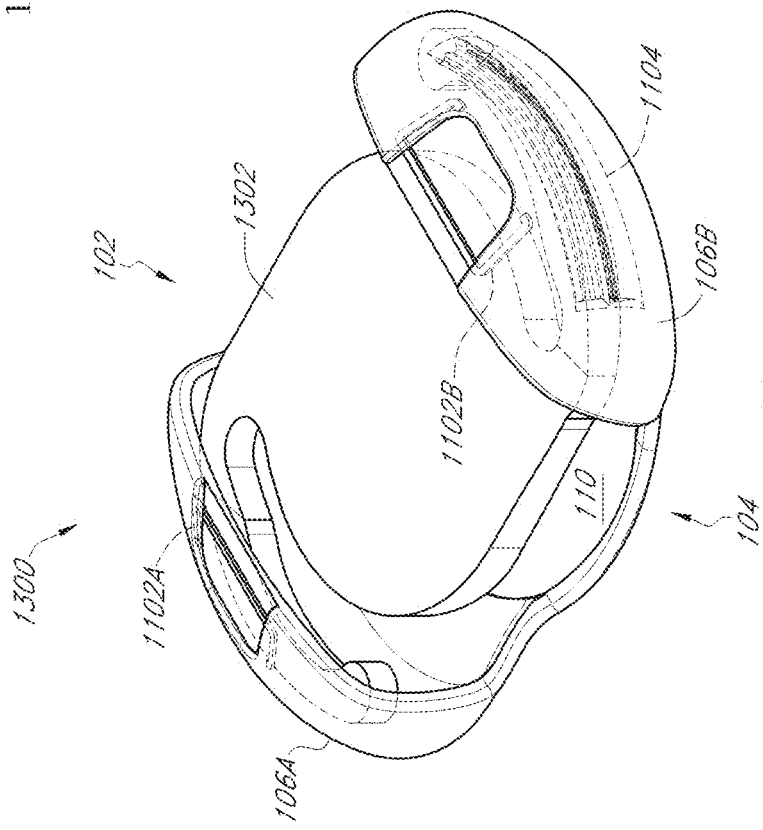
FIG. 13B
FIG. 13A

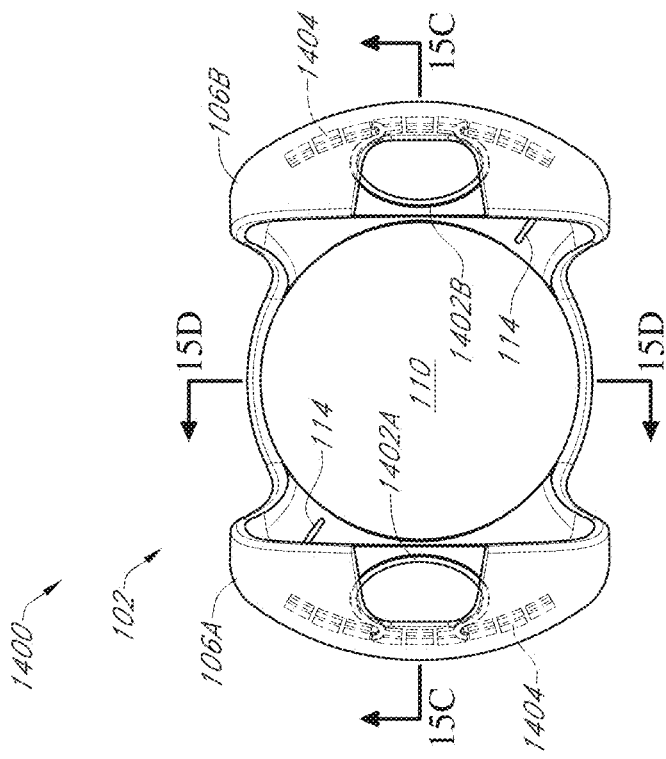
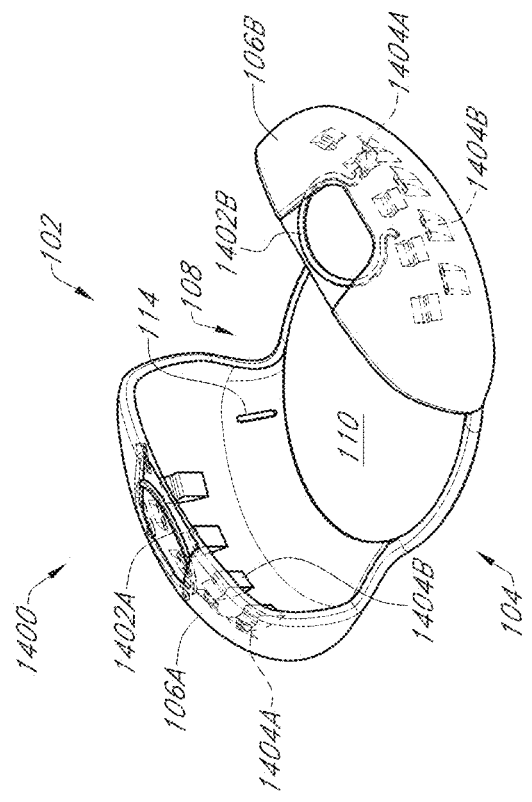
FIG. 15B
FIG. 15A

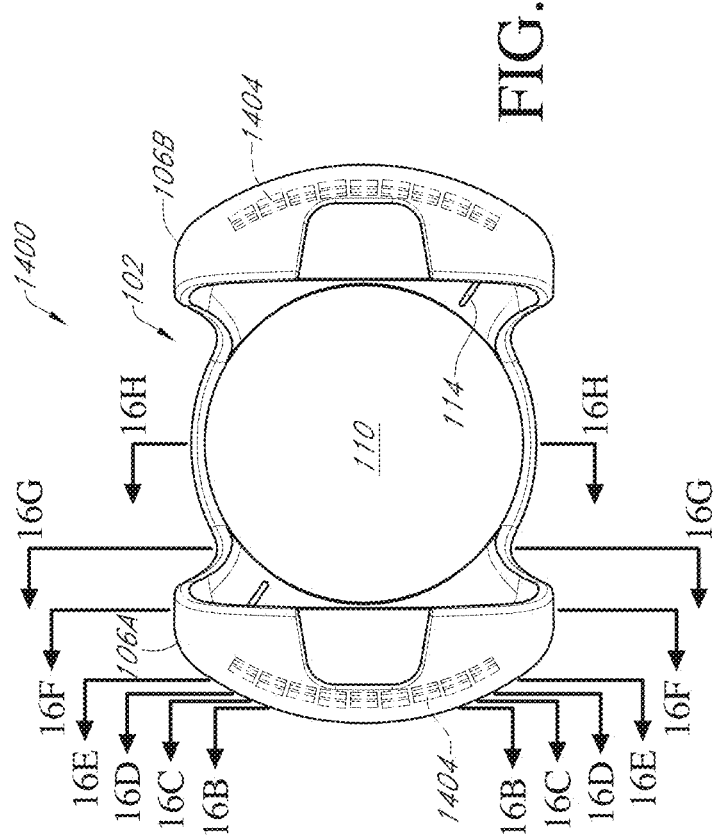
FIG. 16A
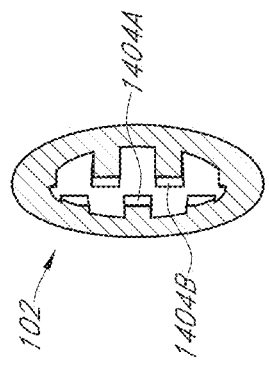
FIG. 16D
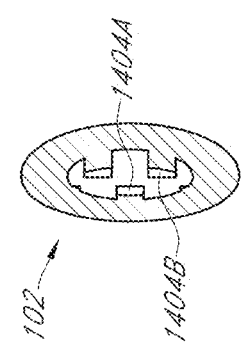
FIG. 16C
FIG. 16B

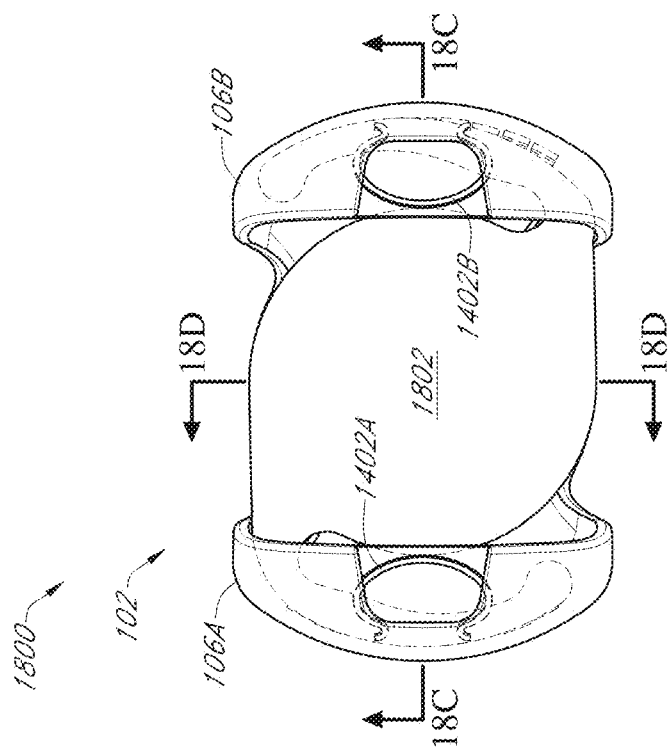
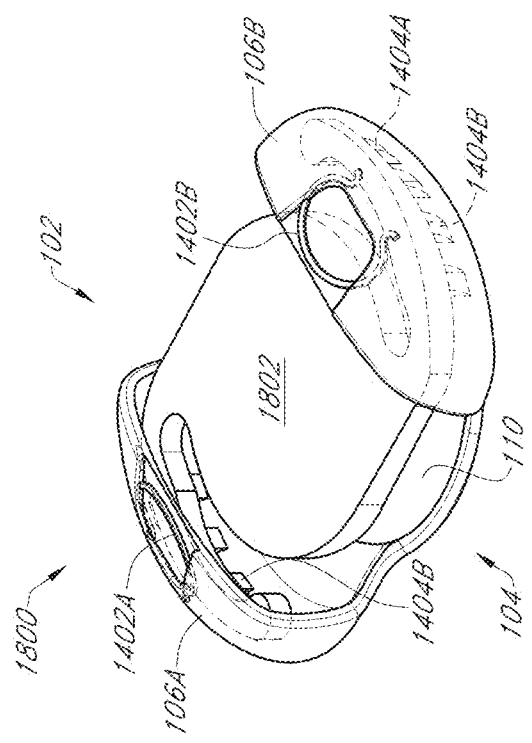
FIG. 18B
FIG. 18A

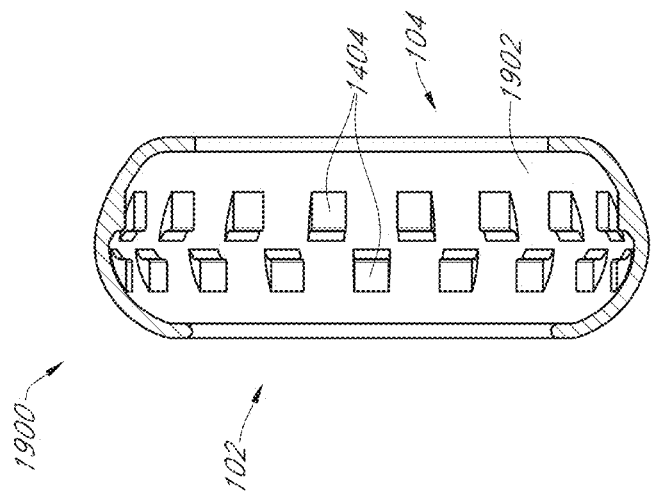
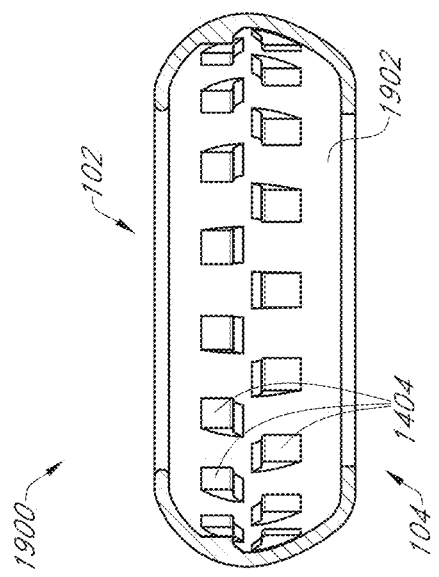
FIG. 19D
FIG. 19C

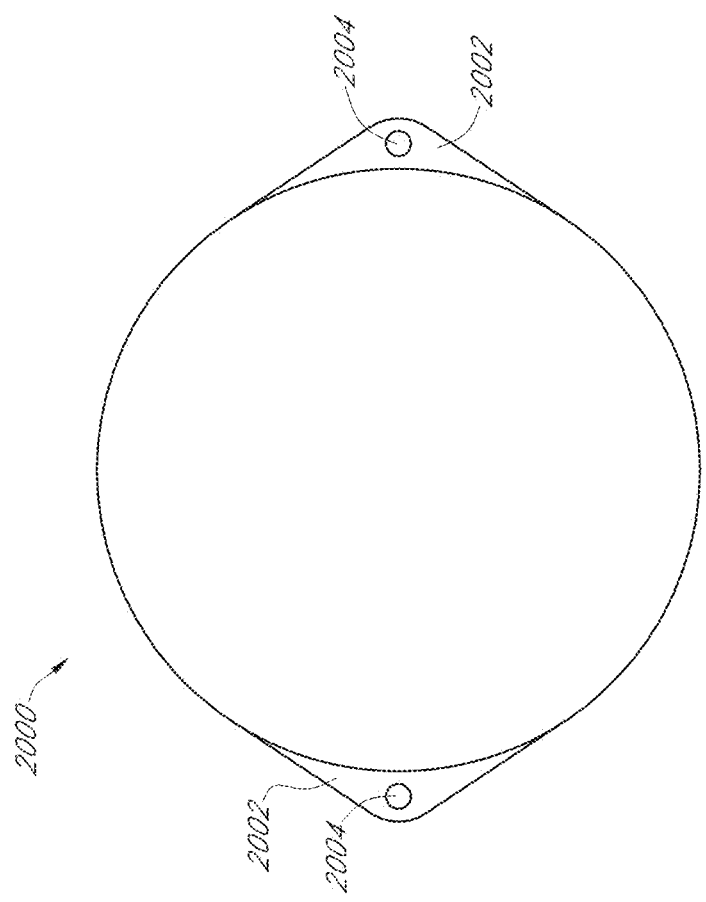
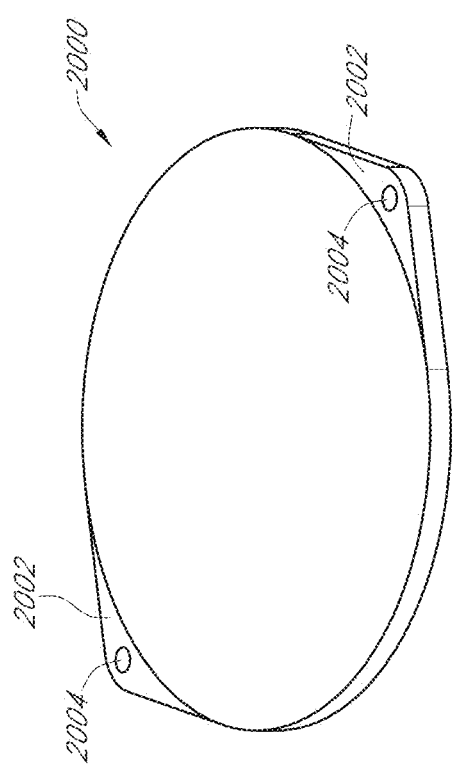
FIG. 20B
FIG. 20A

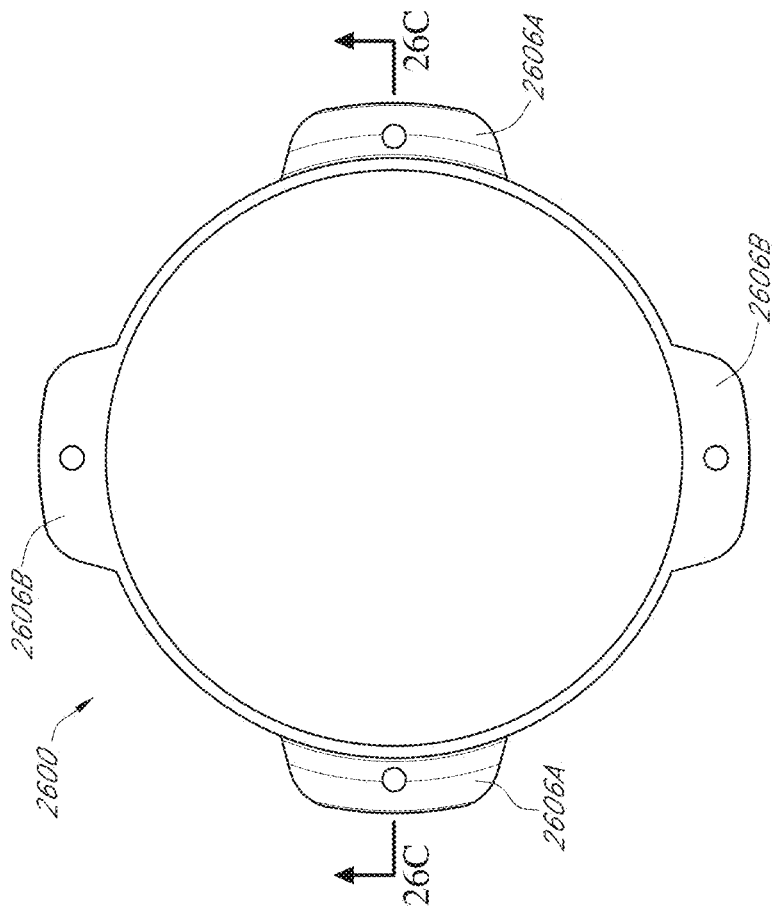
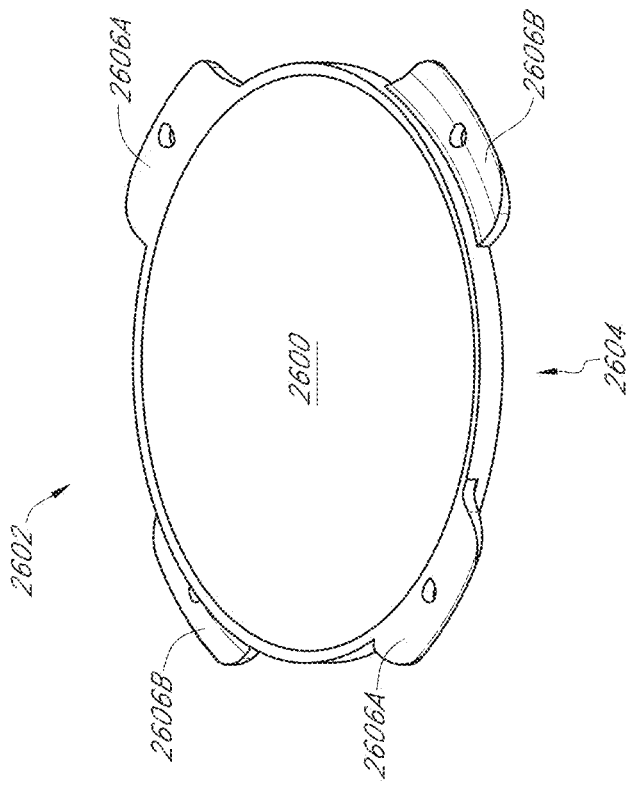
FIG. 26B
FIG. 26A

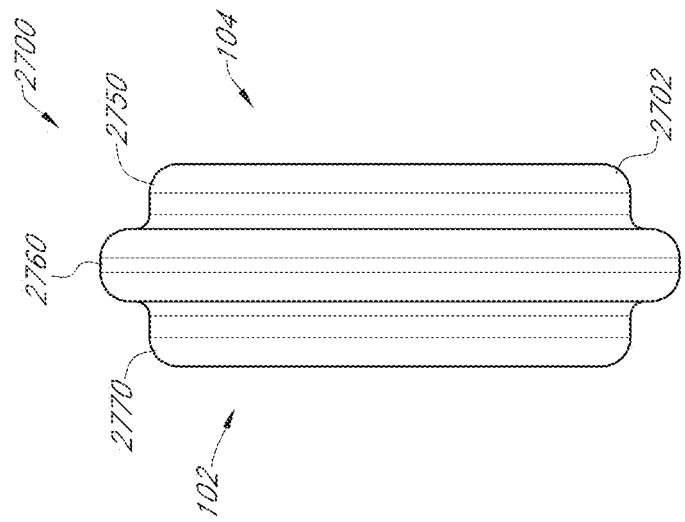
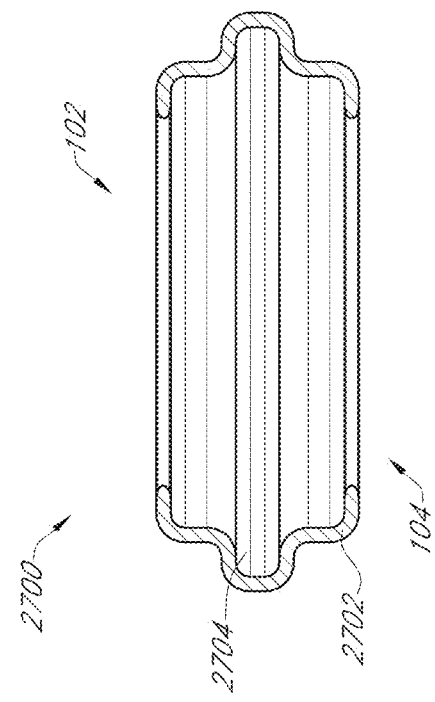
FIG. 27D
FIG. 27C

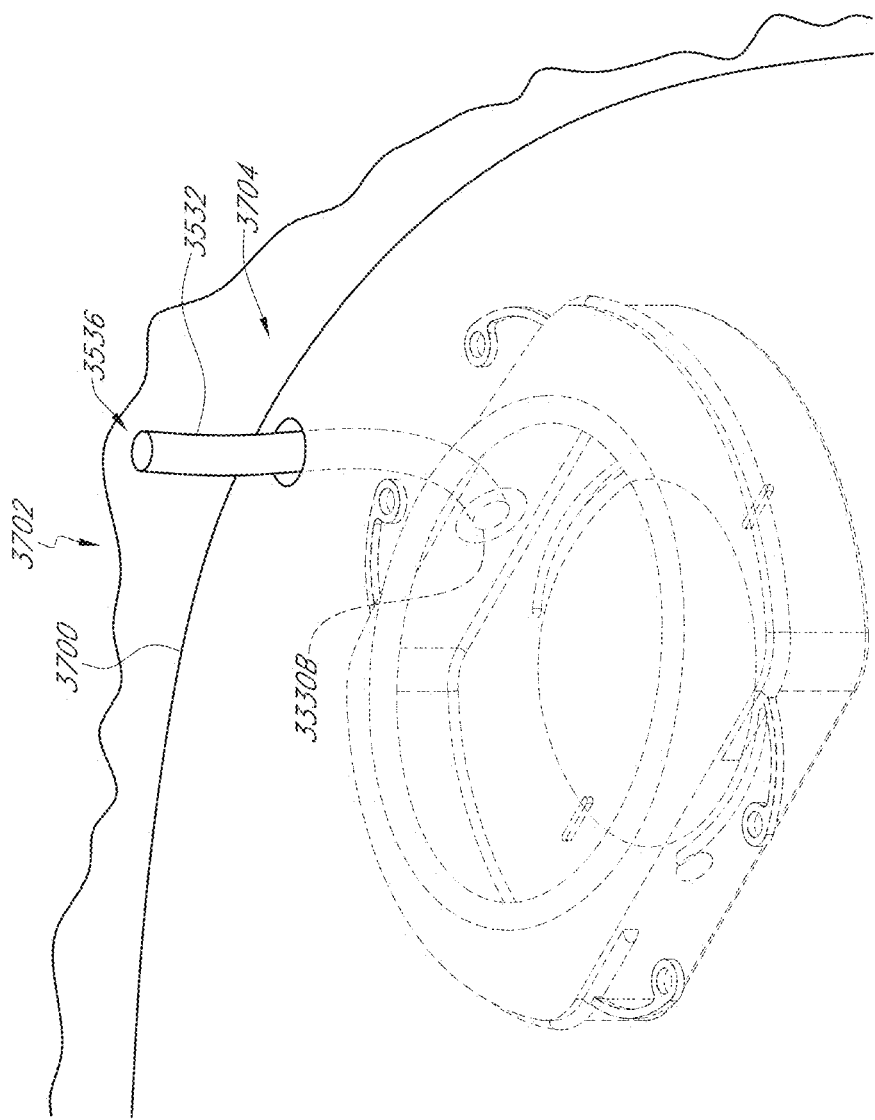

PROSTHETIC CAPSULAR DEVICES, SYSTEMS, AND METHODS

CROSS-REFERENCE TO RELATED APPLICATIONS

The present application is a continuation of U.S. patent application Ser. No. 15/789,555, filed Oct. 20, 2017, which claims the benefit under 35 U.S.C. § 119(c) of U.S. Provisional Patent Application No. 62/411,129, filed Oct. 21, 2016, U.S. Provisional Patent Application No. 62/421,929, filed Nov. 14, 2016, U.S. Provisional Patent Application No. 62/461,675, filed Feb. 21, 2017, and U.S. Provisional Patent Application No. 62/500,932, filed May 3, 2017, each of which is incorporated herein by reference in its entirety under 37 C.F.R. § 1.57. Any and all applications for which a foreign or domestic priority claim is identified in the Application Data Sheet as filed with the present application are hereby incorporated by reference under 37 C.F.R. § 1.57.

BACKGROUND

Field

The present application relates to prosthetic capsular devices, systems, and methods for insertion into the eye.

Description

Cataract surgery is one of the most successfully and most frequently performed surgical procedures in the United States. Each year, millions of people achieve a dramatic improvement in their visual function thanks to this procedure. With the increasing proportion of the U.S. population reaching their retirement years, there is expected to be an almost doubling of the demand for cataract surgery over the next twenty years from 3.3 million to over 6 million annually. In response to the increased demand, more ophthalmologists may be trained and certified to perform cataract surgery, and each trained and certified ophthalmologist may perform more cataract surgeries each year.

SUMMARY

Various embodiments described herein relate to prosthetic capsular devices, systems, and methods for insertion into the eye. In some embodiments, a prosthetic capsular device that is configured to be inserted in an eye after removal of a lens comprises a housing structure capable of containing an intraocular device. In certain embodiments, the housing structure comprises an anterior portion, wherein the anterior portion comprises an anterior opening, wherein the anterior opening is capable of allowing at least one of insertion, removal, or replacement of the intraocular device, and wherein the anterior opening is further configured to be coupled to a refractive surface to cover the anterior opening; a posterior portion, wherein the posterior portion comprises a posterior opening wherein the posterior opening is capable of allowing at least one of insertion, removal, or replacement of the intraocular device, and wherein the posterior opening is further configured to be coupled to a refractive surface to cover the posterior opening; and a continuous lateral portion interposed between the anterior portion and the posterior portion, wherein the continuous lateral portion protrudes radially beyond the anterior portion and the posterior portion, wherein the continuous lateral portion fully encloses a lateral side of the housing structure, wherein an internal cavity of the continuous lateral portion forms a groove for containing the intraocular device, wherein the housing structure is symmetrical over a plane at a midpoint of the continuous lateral portion between the anterior portion and the posterior portion.

In certain embodiments, the prosthetic capsular device can be capable of holding a refractive surface and at least one additional intraocular device. In certain embodiments, the groove is configured to contain haptics of the intraocular device or a capsular tension ring potentially attached to another intraocular device. In certain embodiments, the intraocular device is at least one of an intraocular lens, intraocular pressure sensor, electronic intraocular pressure sensor, photovoltaic cells, solar cells, battery, computer, antennae, sensor, fixation device, capsular tension ring, electronic device, electronic accommodating intraocular lens, liquid crystal display optic, input/output device, or one or more components thereof. In certain embodiments, the prosthetic capsular device comprises at least one of silicone, hydrogel, collamer, acrylic, or an acrylic derivative. In certain embodiments, the prosthetic capsular device is self-expandable upon insertion in the natural capsular bag. In certain embodiments, the prosthetic capsular device is deformable for insertion in the natural capsular bag.

In certain embodiments, the continuous lateral portion comprises a straight-walled portion, a first curved portion, and a second curved portion. In certain embodiments, the straight-walled portion is substantially perpendicular to the anterior opening and the posterior opening. In certain embodiments, the first curved portion extends from the anterior portion, and wherein the second curved portion extends from the posterior portion. In certain embodiments, the intraocular device comprises at least one of a Galilean telescope or microscope. In certain embodiments, the intraocular device comprises an electronic accommodating intraocular lens.

In certain embodiments, the prosthetic capsular device further comprises an equiconvex refractive surface, wherein the refractive surface comprises a plurality of tabs for affixing the refractive surface to at least one of the circular anterior opening or the circular posterior opening, and wherein the plurality of tabs protrudes from the refractive surface in alternating posterior and anterior directions. In certain embodiments, the tabs are configured to be affixed to the interior of the device and the exterior of the device in alternating order. In certain embodiments, each of the plurality of tabs comprises an eyelet opening for affixing the tab to the device or to hold suture for scleral fixation. In certain embodiments, the refractive surface is capable of being inserted separately from the housing structure into the natural capsular bag without being attached to the housing structure.

In certain embodiments, the refractive surface comprises a refractive power between −35D and +35D. In certain embodiments, the refractive surface is affixed to at least one of the circular anterior opening or the circular posterior opening using a friction fit. In certain embodiments, the refractive surface is affixed to at least one of the circular anterior opening or the circular posterior opening using sutures. In certain embodiments, the refractive surface is usable as a reference point for selection of an intraocular lens for placement in the internal cavity of the continuous lateral portion. In certain embodiments, the refractive surface comprises a refractive power less than −35D. In certain embodiments, the refractive surface comprises a refractive power greater than +35D.

The methods summarized above and set forth in further detail below may describe certain actions taken by a practitioner; however, it should be understood that these steps can also include the instruction of those actions by another party. Thus, actions such as "inserting an intraocular lens into a prosthetic capsular device" include "instructing the insertion of an intraocular lens into a prosthetic capsular device."

BRIEF DESCRIPTION OF THE DRAWINGS

A better understanding of the devices and methods described herein will be appreciated upon reference to the following description in conjunction with the accompanying drawings, wherein:

FIG. 1E is an anterior plan view of the example prosthetic capsular device of FIG. 1A;

FIG. 1F is a cross-sectional view of the example prosthetic capsular device of FIG. 1A along the line 1F-1F of FIG. 1E;

FIG. 1G is a cross-sectional view of the example prosthetic capsular device of FIG. 1A along the line 1G-1G of FIG. 1E;

FIG. 2C is a posterior side perspective view of the example prosthetic capsular device of FIG. 2A;

FIG. 2D is a side plan view of the example prosthetic capsular device of FIG. 2A;

FIG. 3C is a side plan view of the example prosthetic capsular device of FIG. 3A;

FIG. 3D is a cross-sectional view of the example prosthetic capsular device of FIG. 3A along the line 3D-3D of FIG. 3B;

FIG. 7A is an anterior side perspective view of another example prosthetic capsular device;

FIG. 7B is an anterior plan view of the example prosthetic capsular device of FIG. 7A;

FIG. 8C is a cross-sectional view of the example prosthetic capsular device of FIG. 8A along the line 8C-8C of FIG. 8B;

FIG. 8D is a cross-sectional view of the example prosthetic capsular device of FIG. 8A along the line 8D-8D of FIG. 8B;

FIG. 9C is a cross-sectional view of the example prosthetic capsular device of FIG. 9A along the line 9C-9C of FIG. 9B;

FIG. 9D is a cross-sectional view of the example prosthetic capsular device of FIG. 9A along the line 9D-9D of FIG. 9B;

FIG. 10C is a cross-sectional view of the example prosthetic capsular device of FIG. 10A along the line 10C-10C of FIG. 10B;

FIG. 10D is a side plan view of the example prosthetic capsular device of FIG. 10A;

FIG. 11A is an anterior side perspective view of another example prosthetic capsular device;

FIG. 11B is an anterior plan view of the example prosthetic capsular device of FIG. 11A;

FIG. 13A is an anterior side perspective view of the example prosthetic capsular device of FIG. 11A with a secondary device inserted therein;

FIG. 13B is an anterior plan view of the example prosthetic capsular device of FIG. 11A with a secondary device inserted therein;

FIG. 15A is another anterior side perspective view of the example prosthetic capsular device of FIG. 14A;

FIG. 15B is another anterior plan view of the example prosthetic capsular device of FIG. 14A;

FIG. 16A is another anterior plan view of the example prosthetic capsular device of FIG. 14A;

FIG. 16B is a cross-sectional view of the example prosthetic capsular device of FIG. 14A along the line 16B-16B of FIG. 16A;

FIG. 16C is a cross-sectional view of the example prosthetic capsular device of FIG. 14A along the line 16C-16C of FIG. 16A;

FIG. 16D is a cross-sectional view of the example prosthetic capsular device of FIG. 14A along the line 16D-16D of FIG. 16A;

FIG. 18A is an anterior side perspective view of the example prosthetic capsular device of FIG. 14A with a secondary device inserted therein;

FIG. 18B is an anterior plan view of the example prosthetic capsular device of FIG. 14A with a secondary device inserted therein;

FIG. 19C is a cross-sectional view of the example prosthetic capsular device of FIG. 19A along the line 19C-19C of FIG. 19B;

FIG. 19D is a cross-sectional view of the example prosthetic capsular device of FIG. 19A along the line 19D-19D of FIG. 19B;

FIG. 20A is an anterior side perspective view of an example optic configured to be used in conjunction with a prosthetic capsular device;

FIG. 20B is an anterior plan view of the example optic of FIG. 20A;

FIG. 25A is an anterior side perspective view of another example prosthetic capsular device;

FIG. 25B is an anterior plan view of the example prosthetic capsular device of FIG. 25A;

FIG. 25C is a cross-sectional view of the example prosthetic capsular device of FIG. 25A along the line 25C-25C of FIG. 25B;

FIG. 25D is a cross-sectional view of the example prosthetic capsular device of FIG. 25A along the line 25D-25D of FIG. 25B;

FIG. 26A is an anterior side perspective view of another example refractive surface or intraocular lens that can be configured to be used in conjunction with a prosthetic capsular device;

FIG. 26B is an anterior plan view of the example refractive surface or intraocular lens of FIG. 26A;

FIG. 26C is a cross-sectional view of the example refractive surface or intraocular lens of FIG. 26A along the line 26C-26C of FIG. 26B;

FIG. 26D is a side plan view of the example refractive surface or intraocular lens of FIG. 26A;

FIG. 27A is an anterior side perspective view of another example prosthetic capsular device;

FIG. 27B is an anterior plan view of the example prosthetic capsular device of FIG. 25A;

FIG. 27C is a cross-sectional view of the example prosthetic capsular device of FIG. 27A along the line 27C-27C of FIG. 27B;

FIG. 27D is a side plan view of the example prosthetic capsular device of FIG. 27A;

Figure 28B:
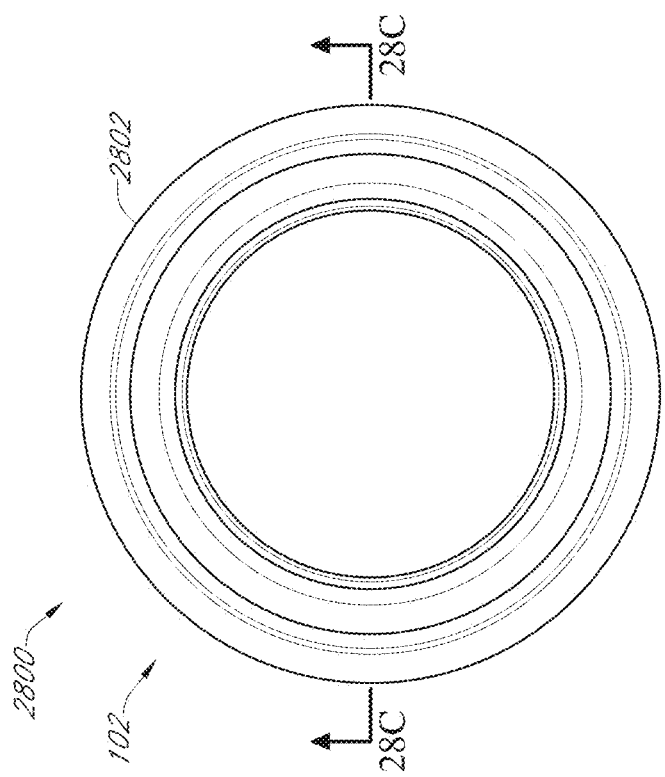
Figure 28A:
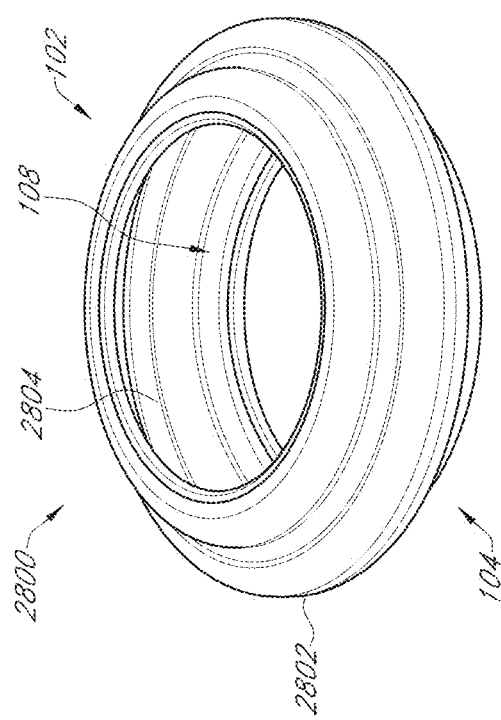
Figure 28D:
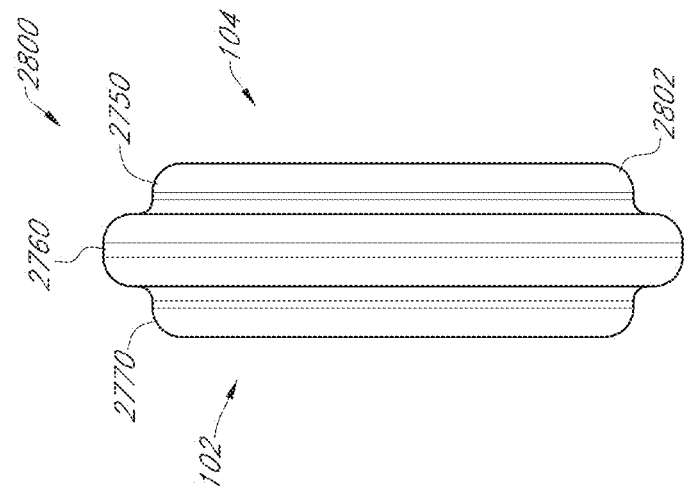
Figure 28C:
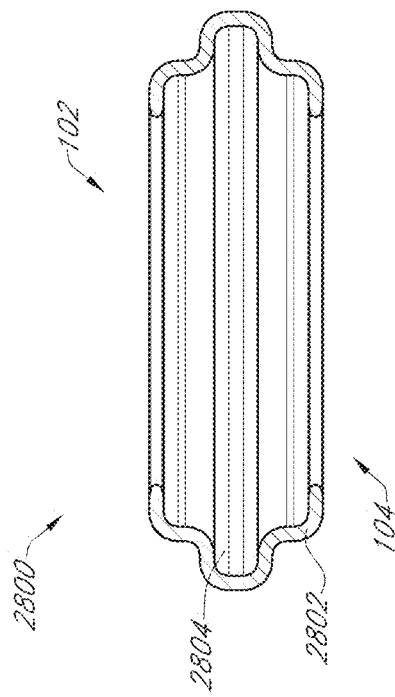
Figure 29B:
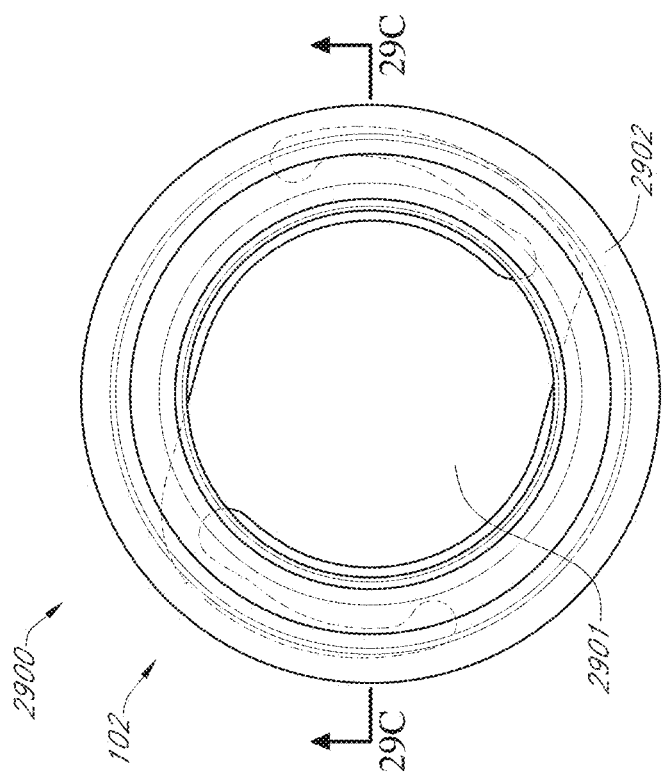
Figure 29A:
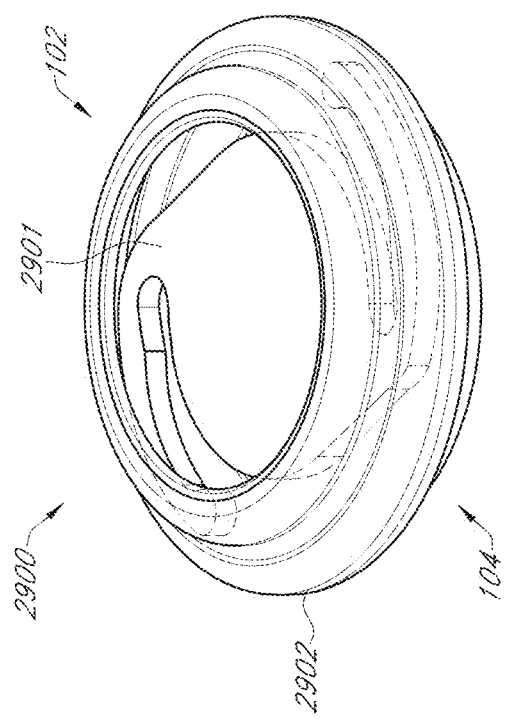
Figure 29D:
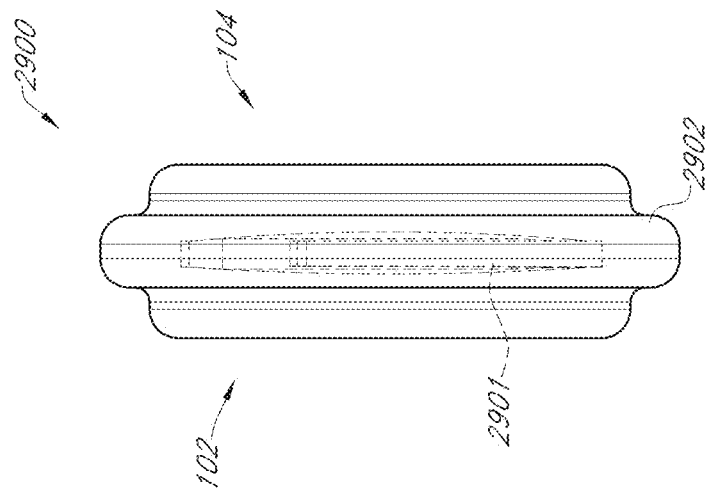
Figure 29C:
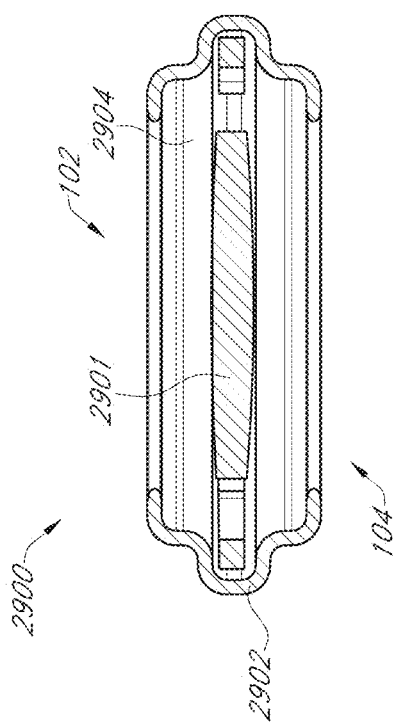
Figure 30B:
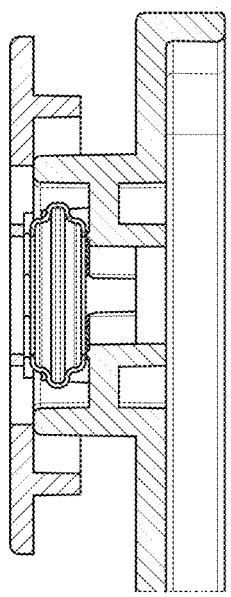
Figure 30A:
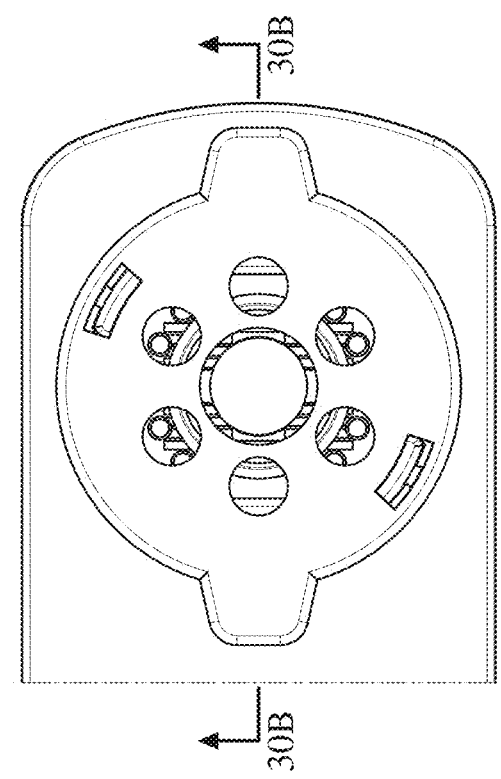
Figure 31B:
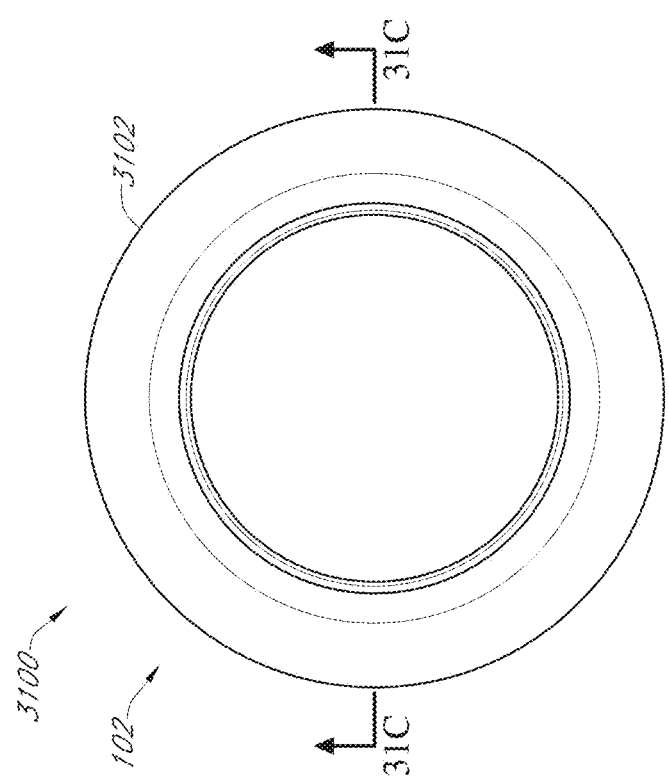
Figure 31A:
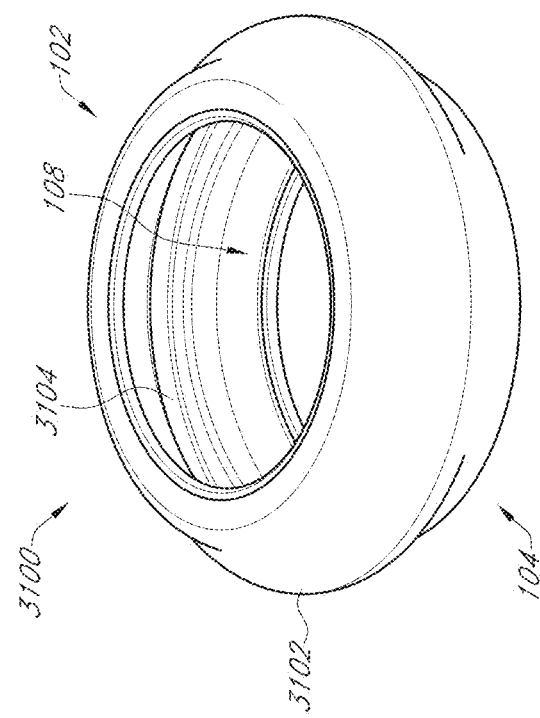
Figure 31D:
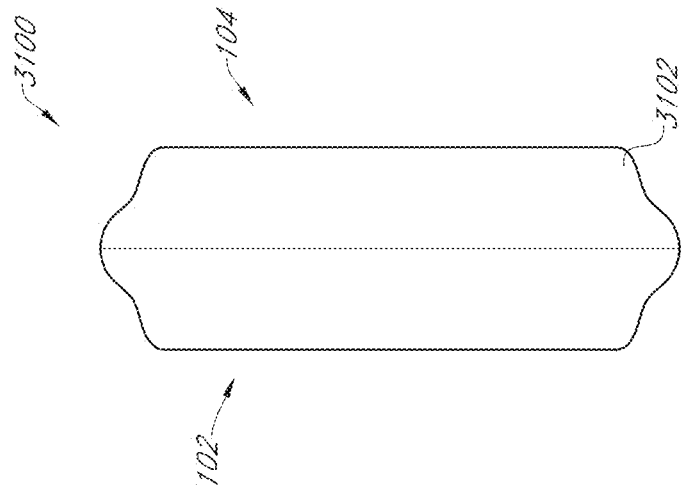
Figure 31C:
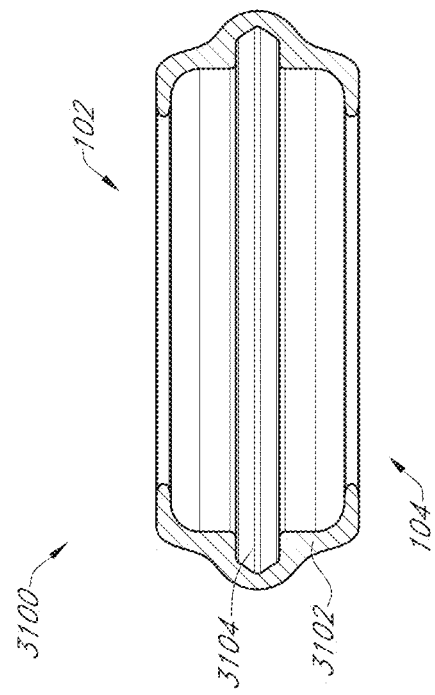
Figure 32B:
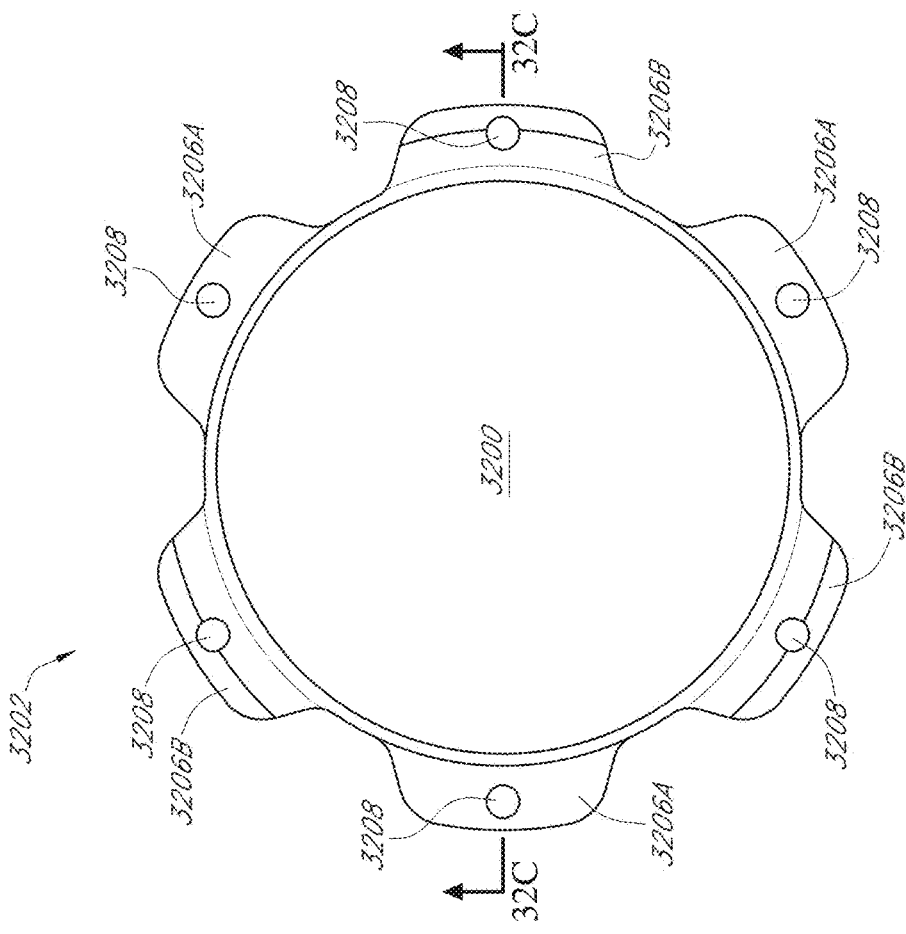
Figure 32A:
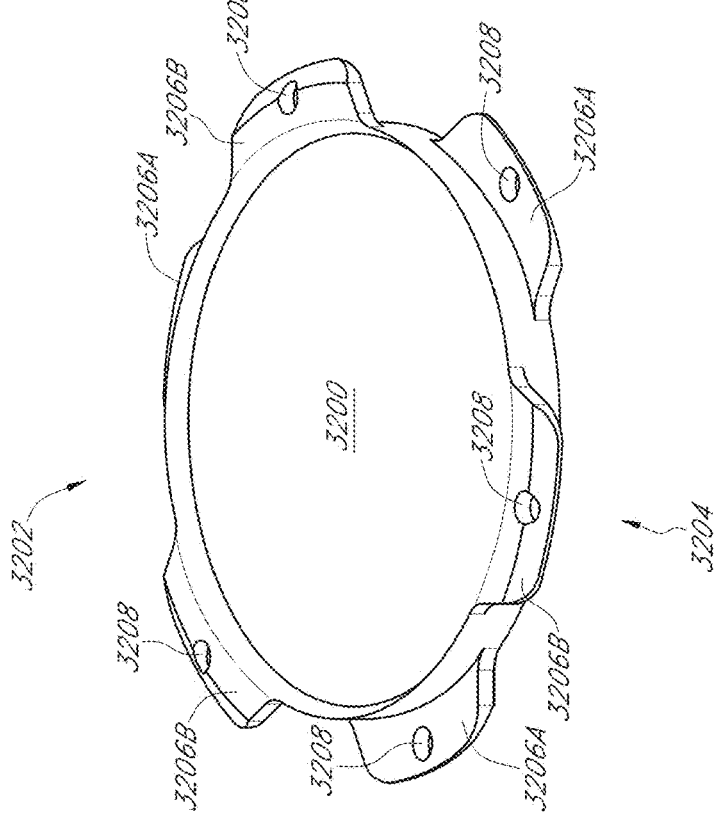
Figure 32D:
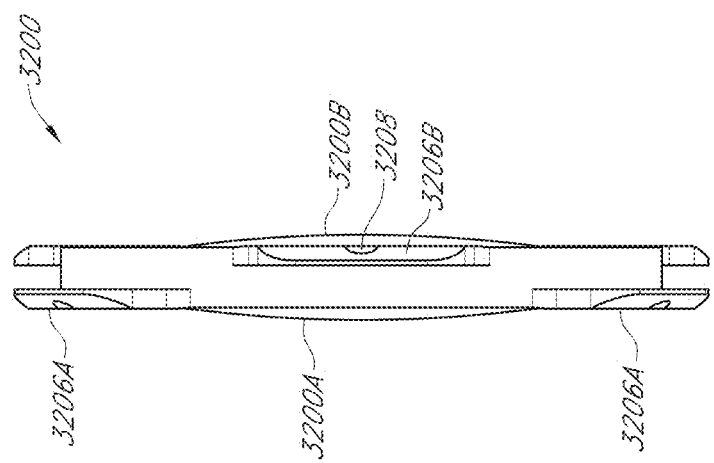
Figure 32C:
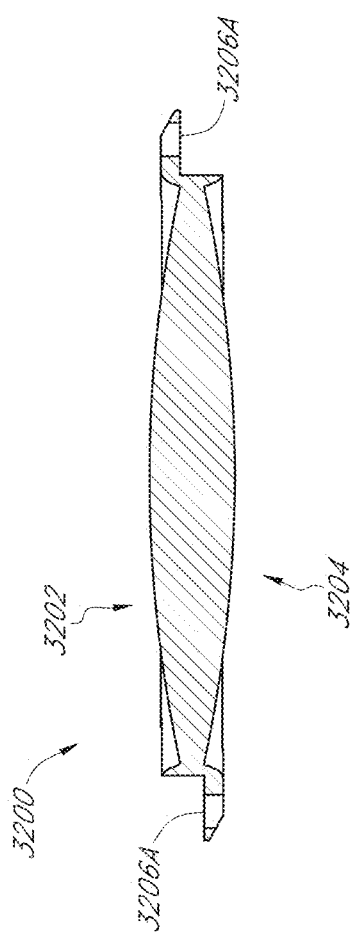
Figure 33A:
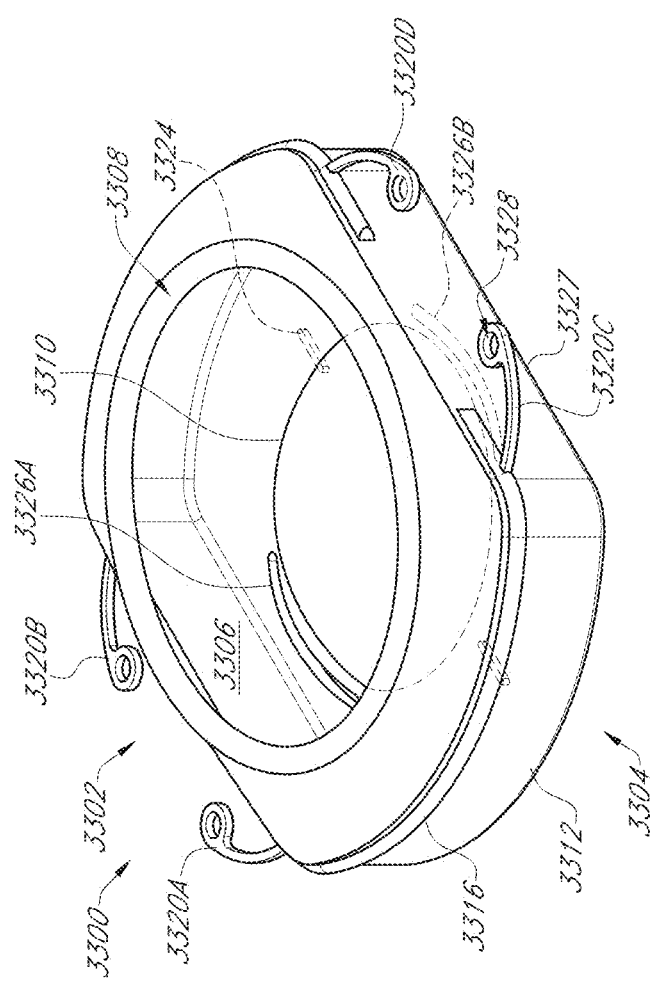
Figure 33C:
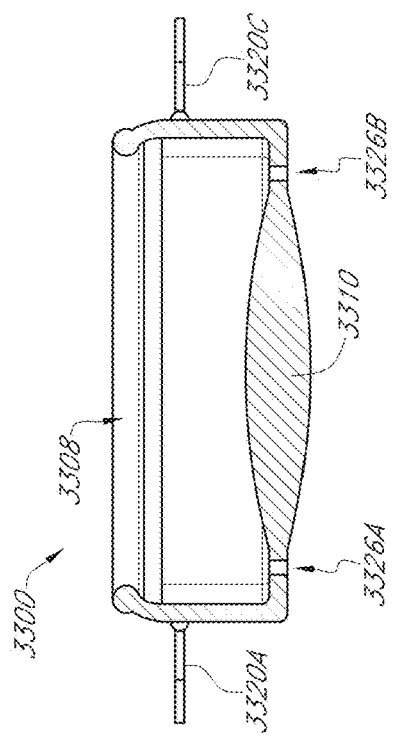
Figure 33B:
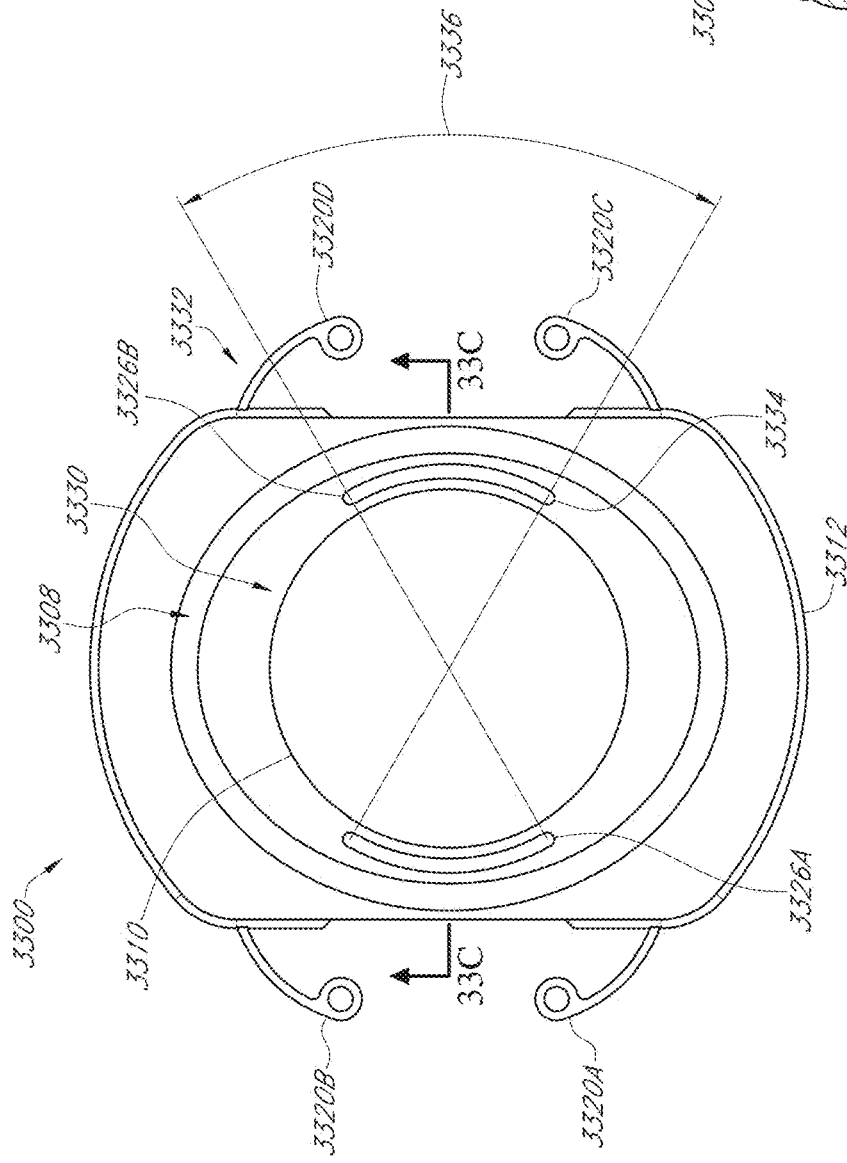
Figure 34:
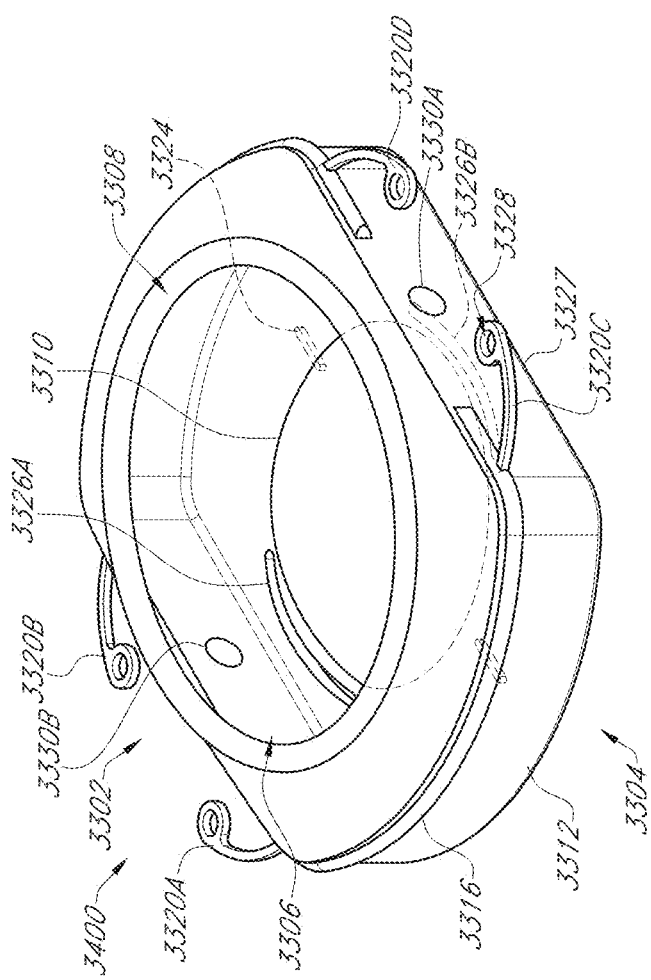
Figure 35B:
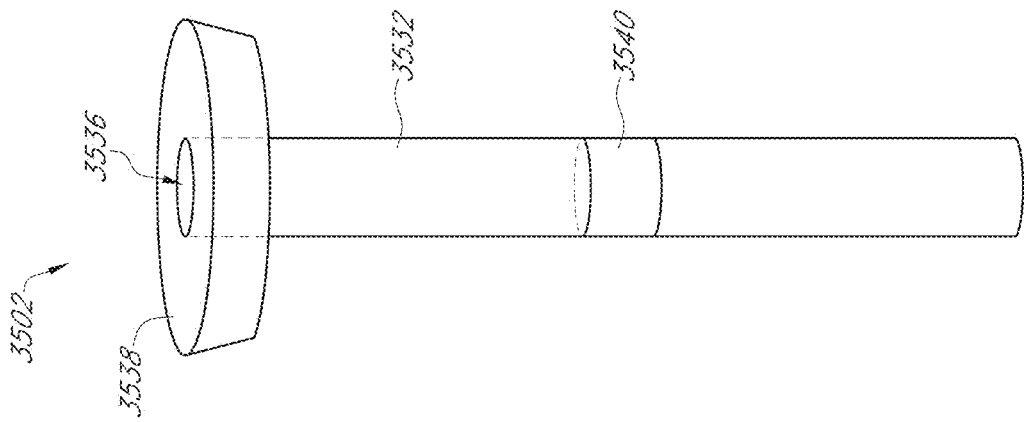
Figure 35A:
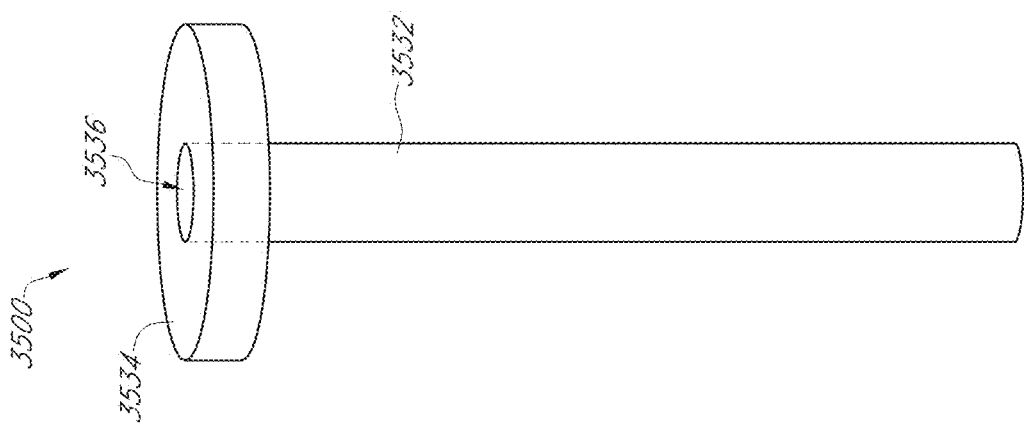
Figure 35E:
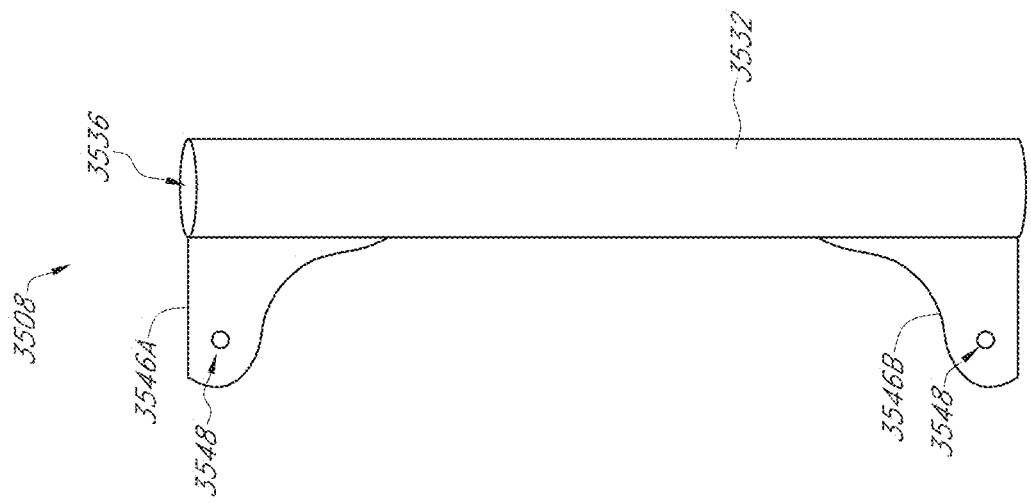
Figure 35D:
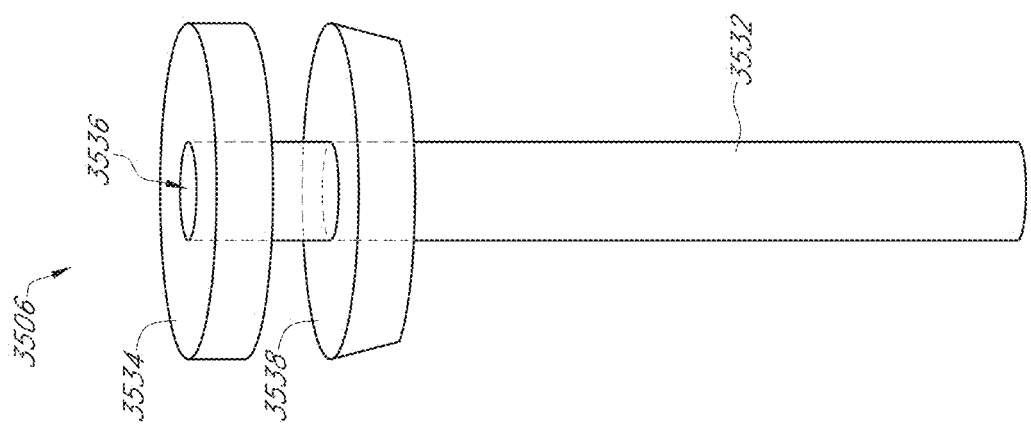
Figure 35C:
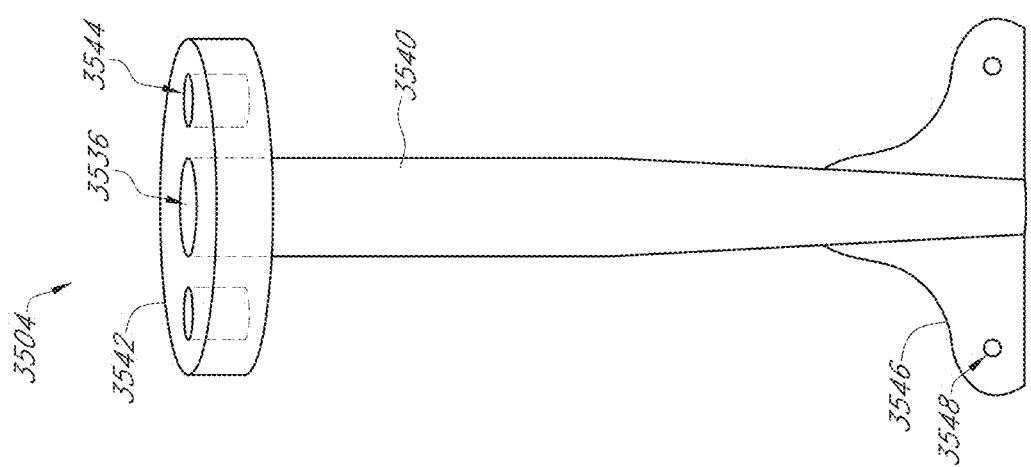
Figure 36:
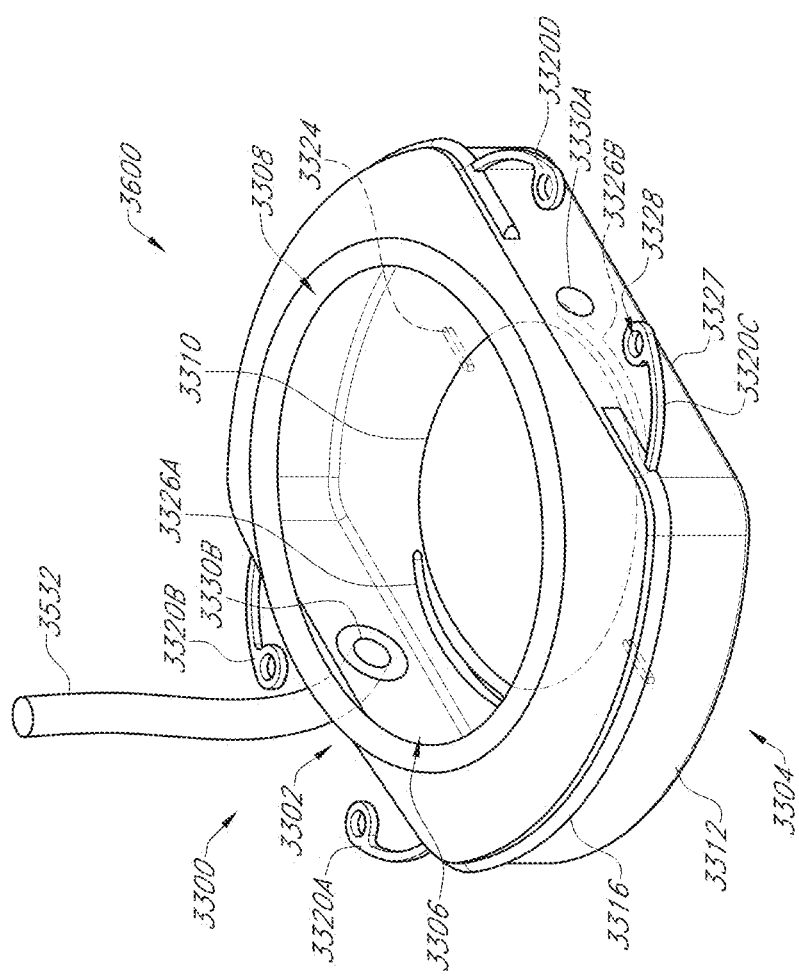
Figure 38A:
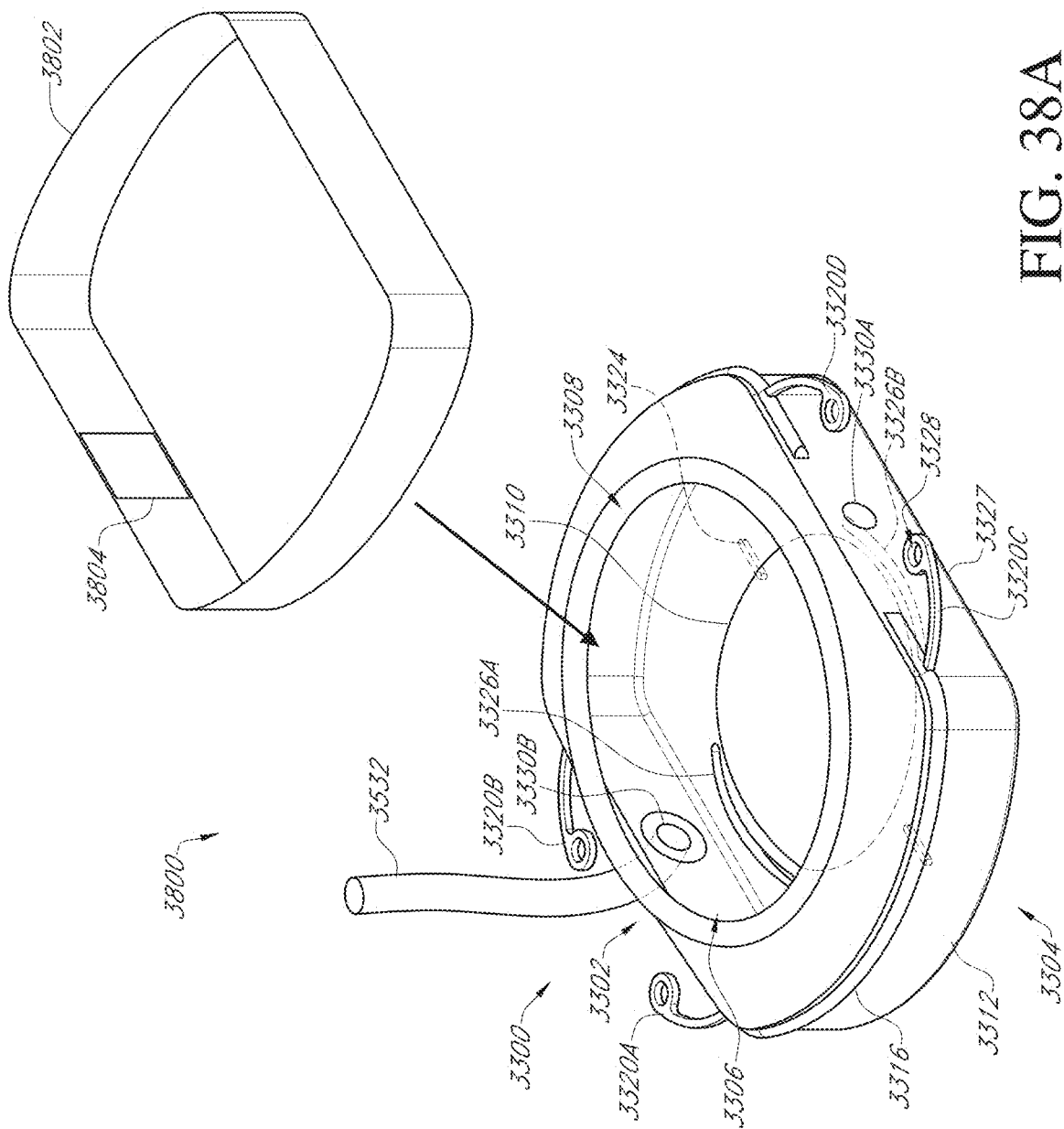
Figure 38B:
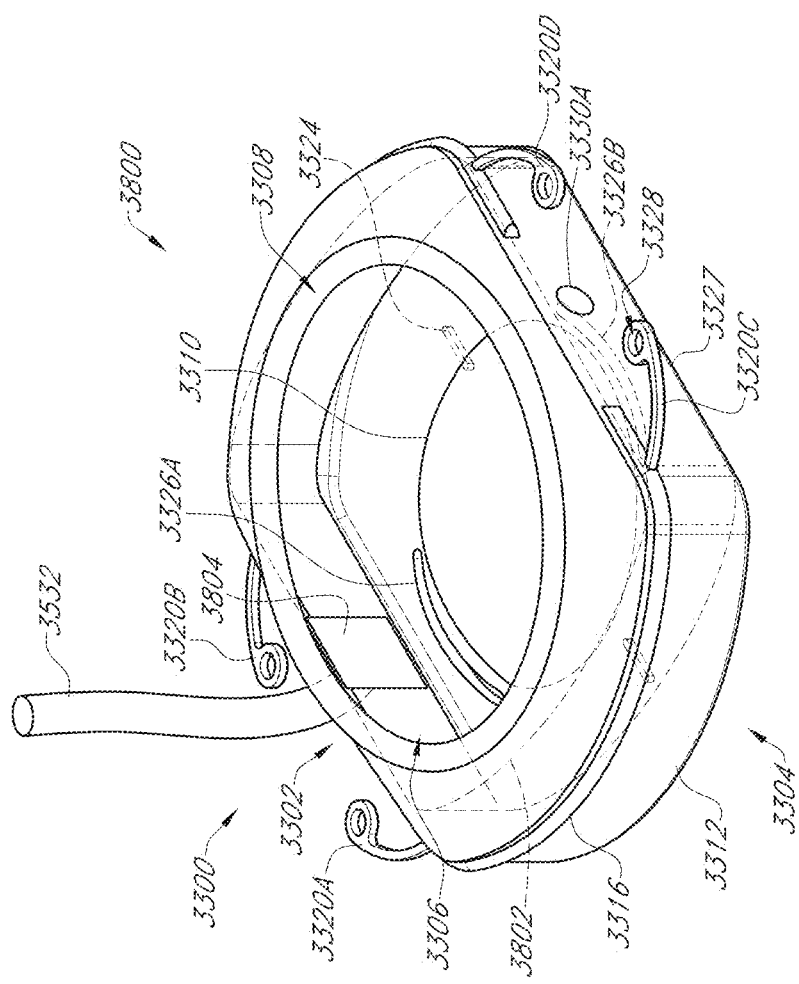
Figure 39:
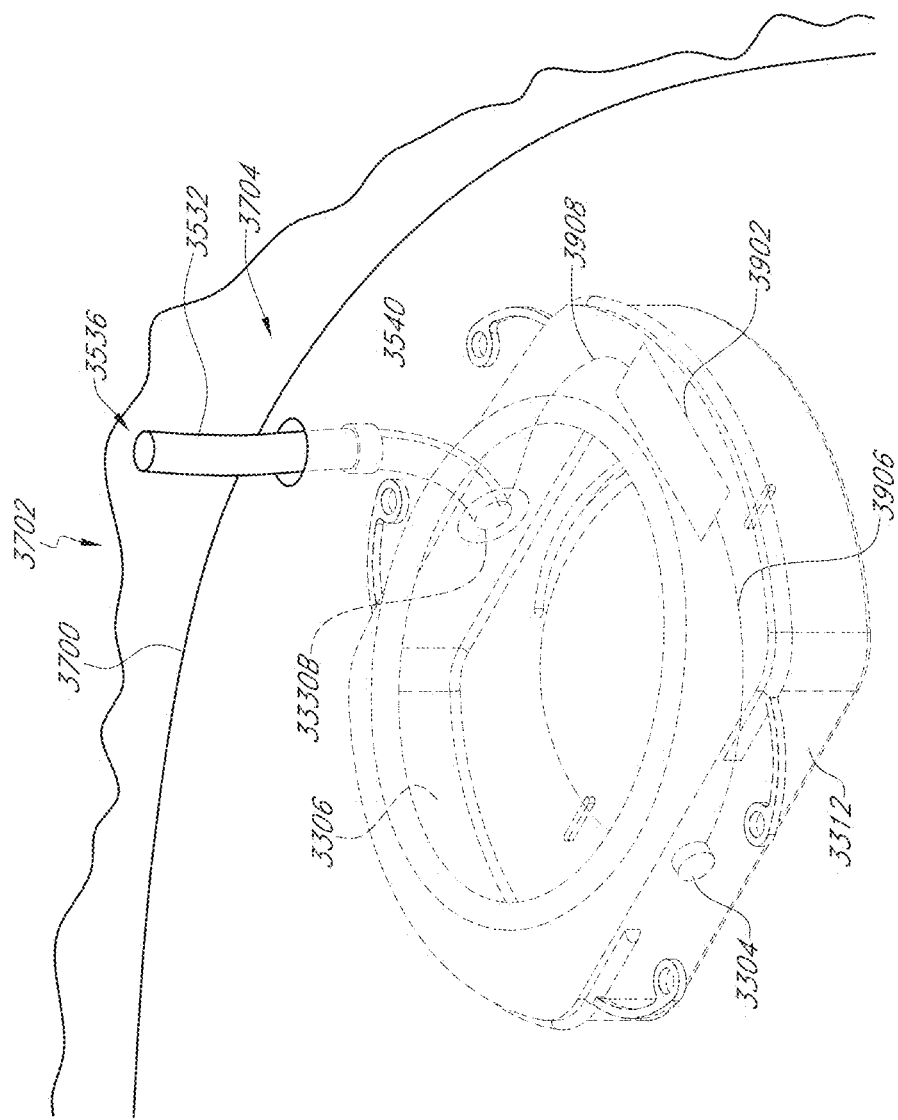
Figure 40:
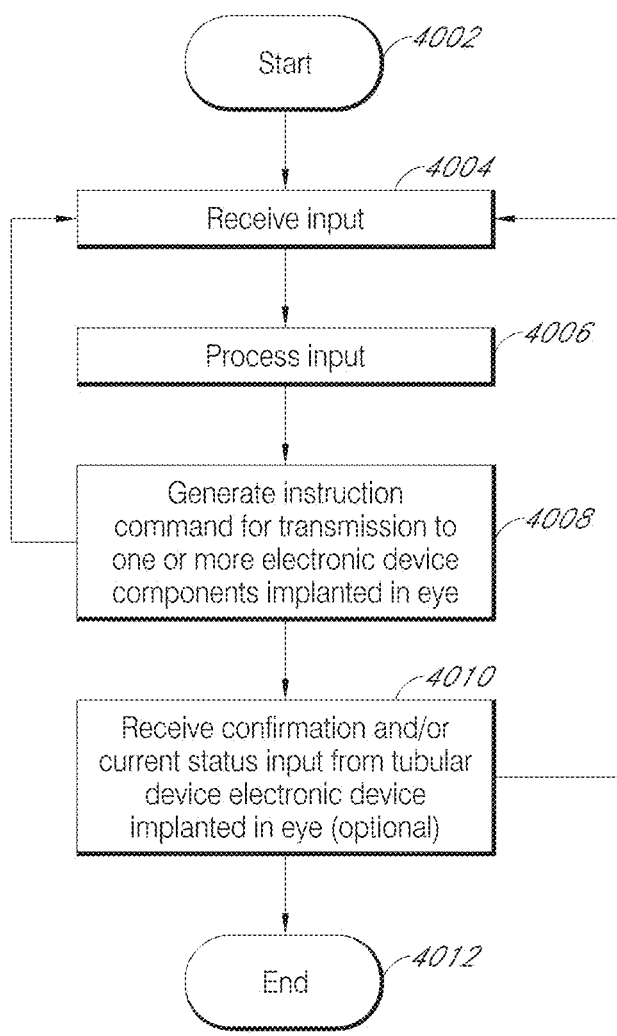
Figure 41:
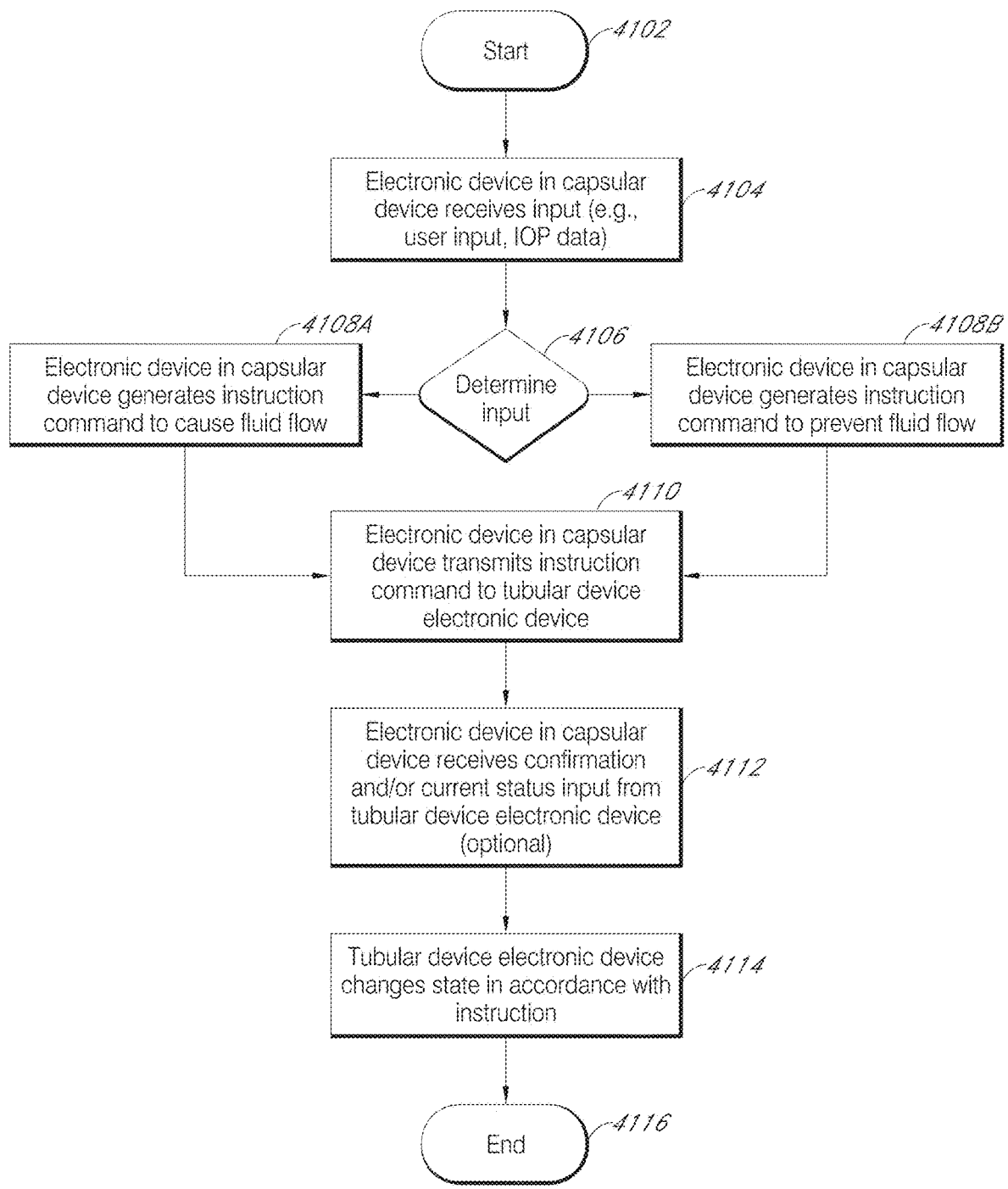
Figure 42:
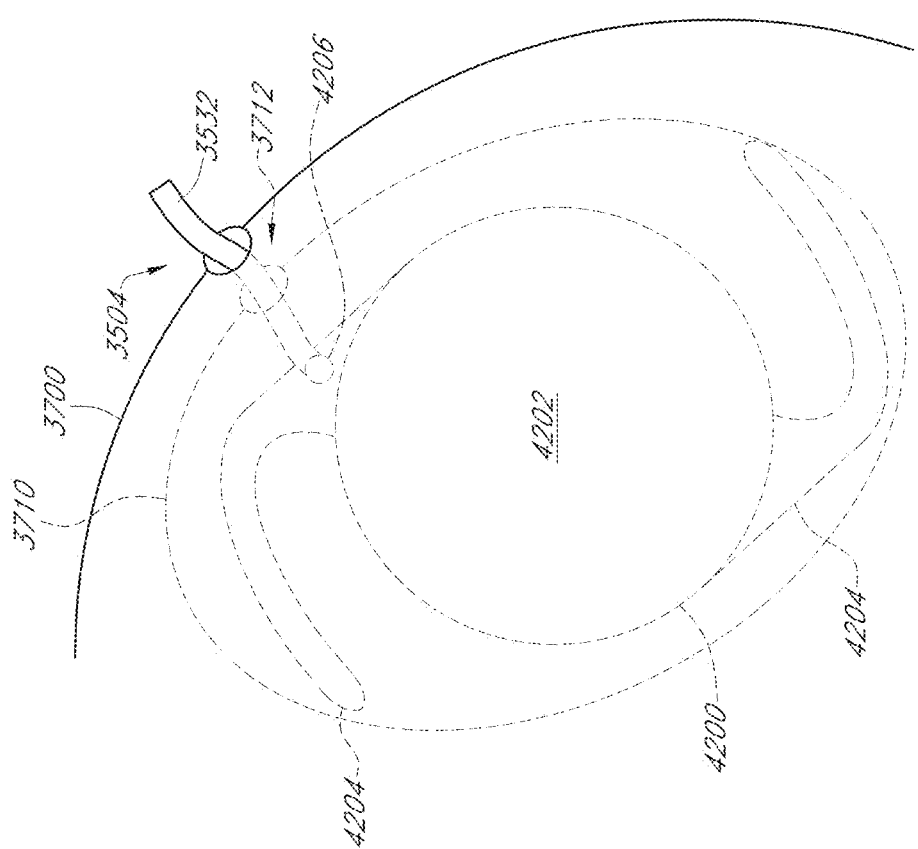
Figure 43:
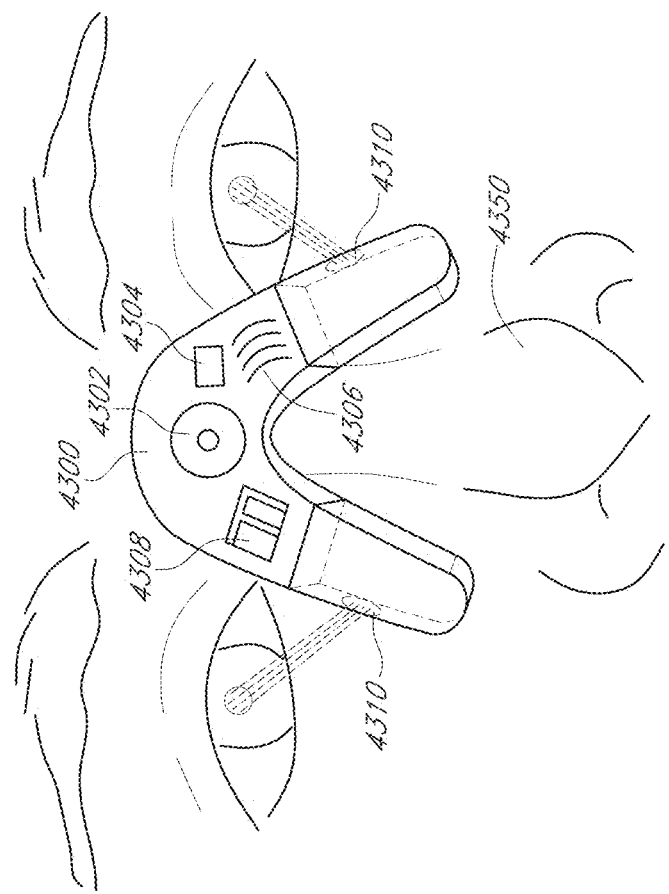
Figure 44:
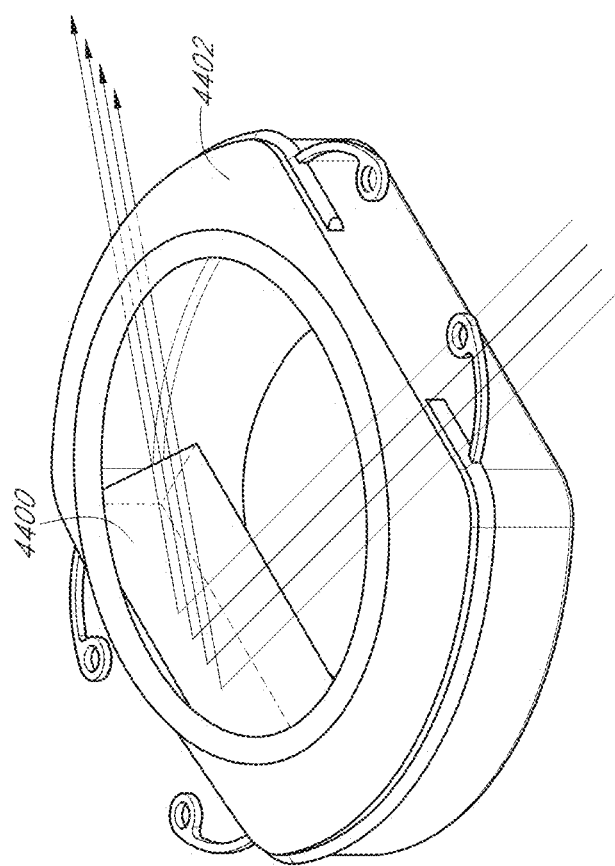
Figure 45:
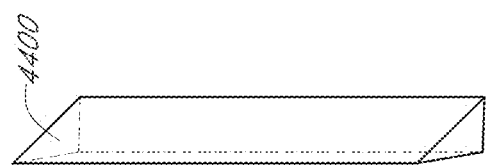
Figure 46:
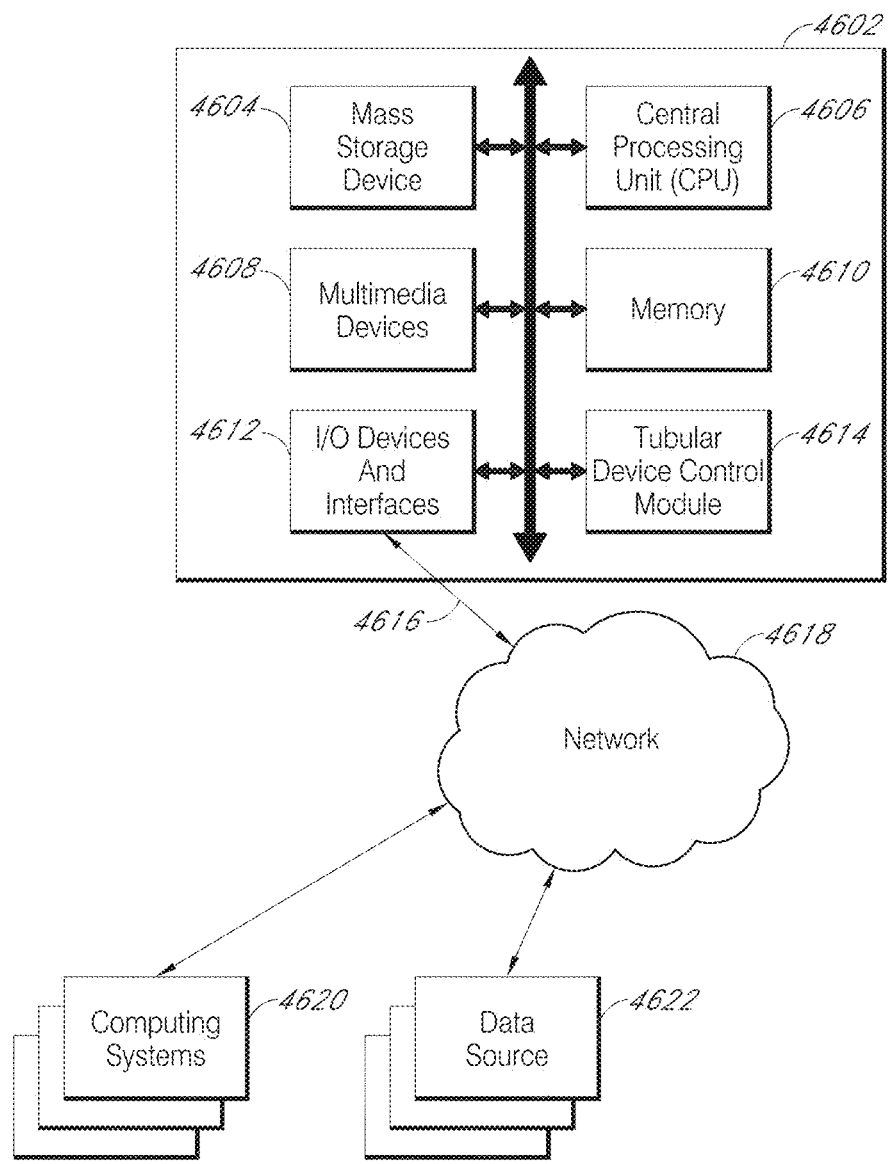
Figure 47:
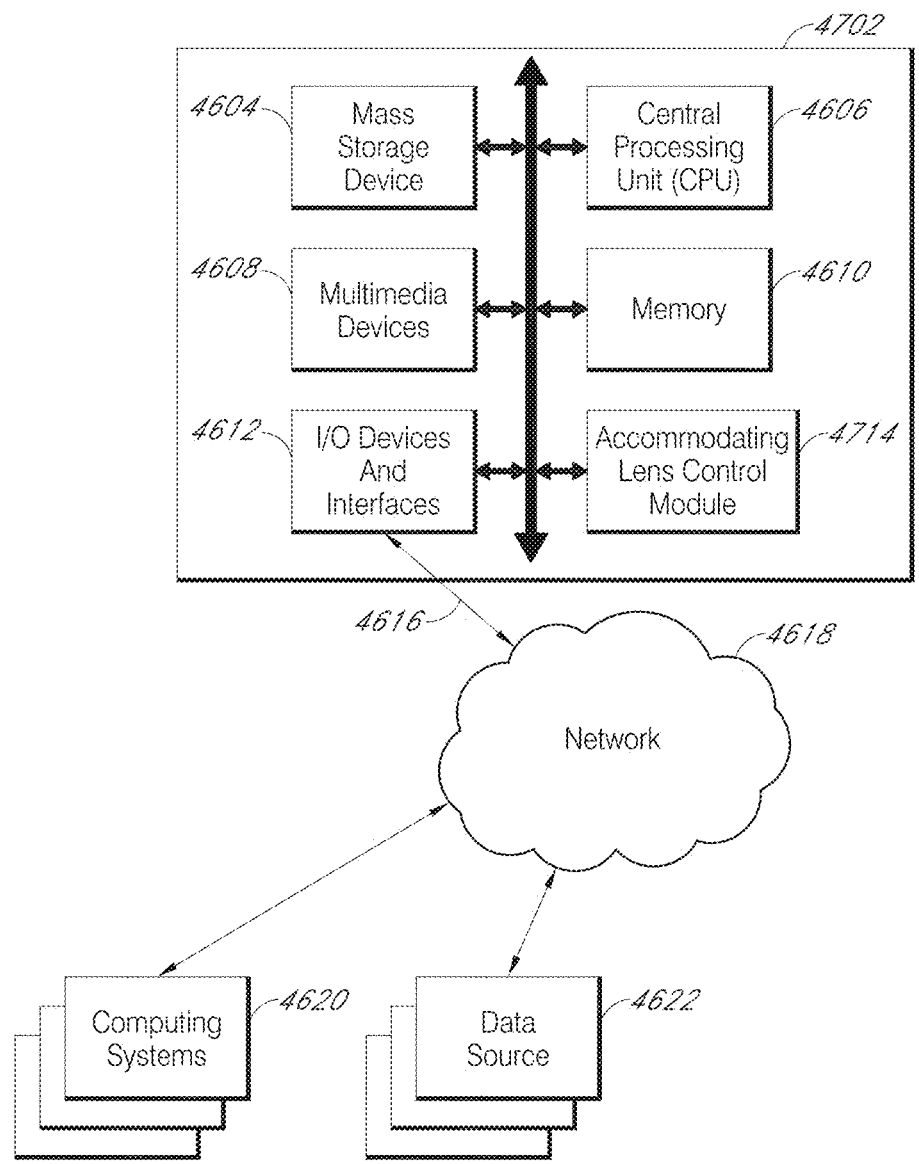
Figure 48:
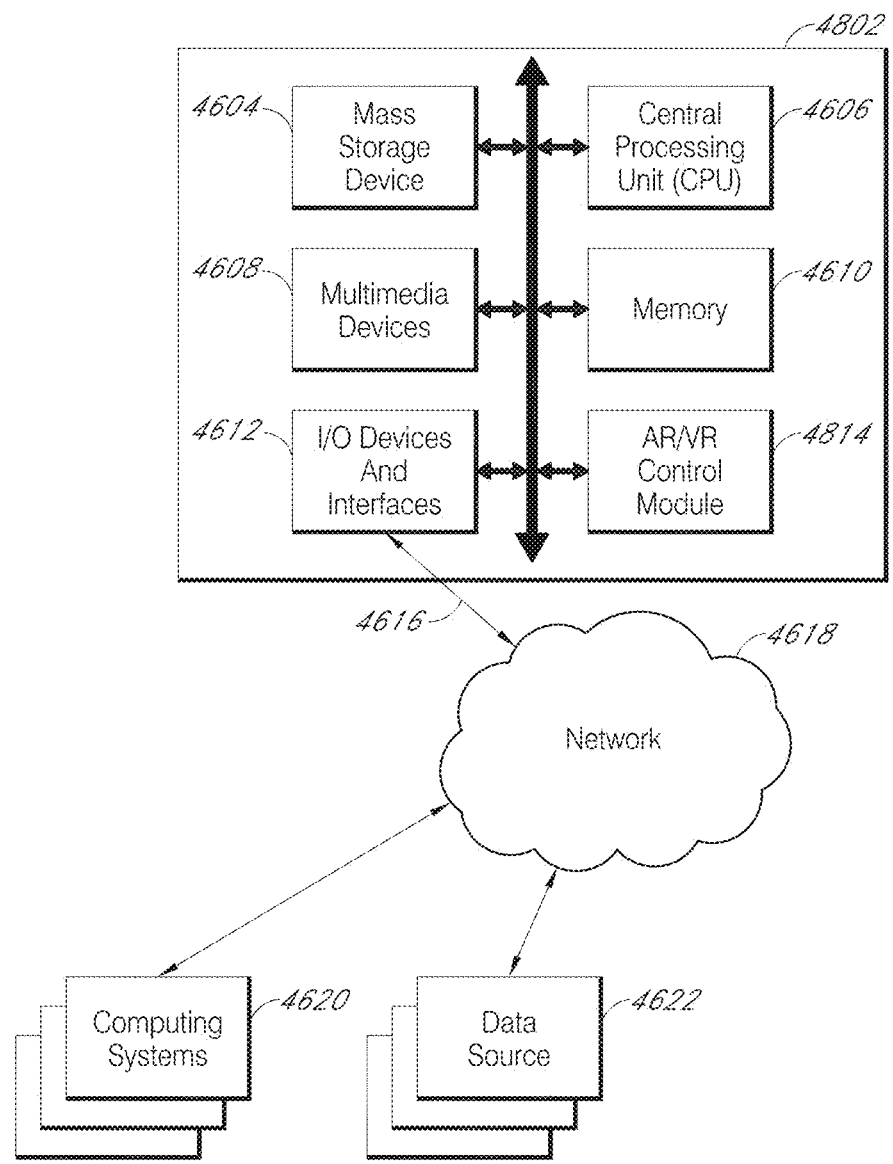

FIG. 28A is an anterior side perspective view of another example prosthetic capsular device;

FIG. 28B is an anterior plan view of the example prosthetic capsular device of FIG. 28A;

FIG. 28C is a cross-sectional view of the example prosthetic capsular device of FIG. 28A along the line 28C-28C of FIG. 28B;

FIG. 28D is a side plan view of the example prosthetic capsular device of FIG. 28A;

FIG. 29A is an anterior side perspective view of another example prosthetic capsular device;

FIG. 29B is an anterior plan view of the example prosthetic capsular device of FIG. 29A;

FIG. 29C is a cross-sectional view of the example prosthetic capsular device of FIG. 29A along the line 29C-29C of FIG. 29B;

FIG. 29D is a side plan view of the example prosthetic capsular device of FIG. 29A;

FIG. 30A is an anterior plan view of another example prosthetic capsular device;

FIG. 30B is a cross-sectional view of the example prosthetic capsular device of FIG. 30A along the line 30B-30B of FIG. 30A;

FIG. 31A is an anterior side perspective view of another example prosthetic capsular device;

FIG. 31B is an anterior plan view of the example prosthetic capsular device of FIG. 31A;

FIG. 31C is a cross-sectional view of the example prosthetic capsular device of FIG. 31A along the line 31C-31C of FIG. 31B;

FIG. 31D is a side plan view of the example prosthetic capsular device of FIG. 31A;

FIG. 32A is an anterior side perspective view of another example refractive surface or intraocular lens that can be configured to be used in conjunction with a prosthetic capsular device;

FIG. 32B is an anterior plan view of the example refractive surface or intraocular lens of FIG. 32A;

FIG. 32C is a cross-sectional view of the example refractive surface or intraocular lens of FIG. 32A along the line 32C-32C of FIG. 32B;

FIG. 32D is a side plan view of the example refractive surface or intraocular lens of FIG. 32A;

FIG. 33A is an anterior side perspective view of an example prosthetic capsular device;

FIG. 33B is an anterior plan view of the example prosthetic capsular device of FIG. 33A;

FIG. 33C is a cross-sectional view of the example prosthetic capsular device of FIG. 33A along the line 33C-33C of FIG. 33B;

FIG. 34 is an anterior side perspective view of another example prosthetic capsular device;

FIG. 35A is a side perspective view of an example tubular device;

FIG. 35B is a side perspective view of another example tubular device;

FIG. 35C is a side perspective view of another example tubular device;

FIG. 35D is a side perspective view of another example tubular device;

FIG. 35E is a side perspective view of another example tubular device;

FIG. 36 is an anterior side perspective view of an example prosthetic capsular system comprising an example prosthetic capsular device and an example tubular device;

FIG. 37 is an anterior side perspective view of the example prosthetic capsular system of FIG. 36 in an eye;

FIG. 38A is an anterior side perspective partially-exploded view of an example prosthetic capsular system comprising an example prosthetic capsular device, an example tubular device, and an example containment structure;

FIG. 38B is an anterior side perspective view of the example prosthetic capsular system of FIG. 38A;

FIG. 39 is an anterior side perspective view of another example prosthetic capsular system in an eye;

FIG. 40 is a block diagram depicting an example control process for a prosthetic capsular system comprising a tubular device;

FIG. 41 is a block diagram depicting another example control process for a prosthetic capsular system comprising a tubular device; and FIG. 42 is an anterior side perspective view of another example prosthetic capsular system comprising a tubular device in an eye;

FIG. 43 is a perspective view of an example AR/VR projection device or system configured to be placed over a nose bridge of a user;

FIG. 44 is a perspective view of an example prosthetic capsular device comprising a prism or prism bar;

FIG. 45 is a perspective view of an example prism or prism bar configured to be used in conjunction with a prosthetic capsular device and/or AR/VR projection device or system;

FIG. 46 is a block diagram depicting an example of a computer hardware system configured to run software for implementing one or more embodiments of a prosthetic capsular device system;

FIG. 47 is a block diagram depicting another example of a computer hardware system configured to run software for implementing one or more embodiments of a prosthetic capsular device system; and FIG. 48 is a block diagram depicting another example of a computer hardware system configured to run software for implementing one or more embodiments of a prosthetic capsular device system.

DETAILED DESCRIPTION

In addition to the increase in demand for cataract surgery, technological advances have increased patient expectations for the surgery. The procedure takes a short amount of time to perform, and patients expect quick recovery of visual function. Patients are also asking their ophthalmologist to give them the restoration of more youthful vision without glasses through the use multifocal intraocular lenses, presbyopia correcting lenses, toric lenses, and monovision, to name a few. Despite accurate preoperative measurements and excellent surgical technique, the desired refractive outcome requires a dose of good fortune as there are numerous uncontrolled variables involved. As many as 20-50% of post-operative cataract patients may benefit from glasses or follow-up refractive surgical enhancements to achieve their desired refractive endpoint. One of the main reasons for this high amount of refractive unpredictability is believed to be the final resting position of the lens implant in the eye, mathematically expressed as the effective lens position (ELP), which can be quite variable and unpredictable in the current state of cataract surgery. Recently, hundreds of millions of dollars have been invested into developing highly sophisticated femtosecond laser systems that are able to more precisely control the size and shape of the capsulotomy and corneal incisions with the stated goal of lessening the variability of the ELP and thus aiding in better refractive outcomes. Unfortunately, the increased precision of the femtosecond laser systems has not been able to account for the major problem plaguing the variability of the ELP, which is the volumetric difference between the cataract, natural capsular bag, and intraocular lens implant (IOL).

Devices and methods that help provide the desired refractive endpoint in cataract surgery are described in U.S. Pat. Nos. 8,900,300, 9,414,907, and 9,358,103, each of which is hereby incorporated by reference in its entirety. All patents, patent applications, and other documents referred to in this application are incorporated by reference herein in their entirety.

Figure 1B:
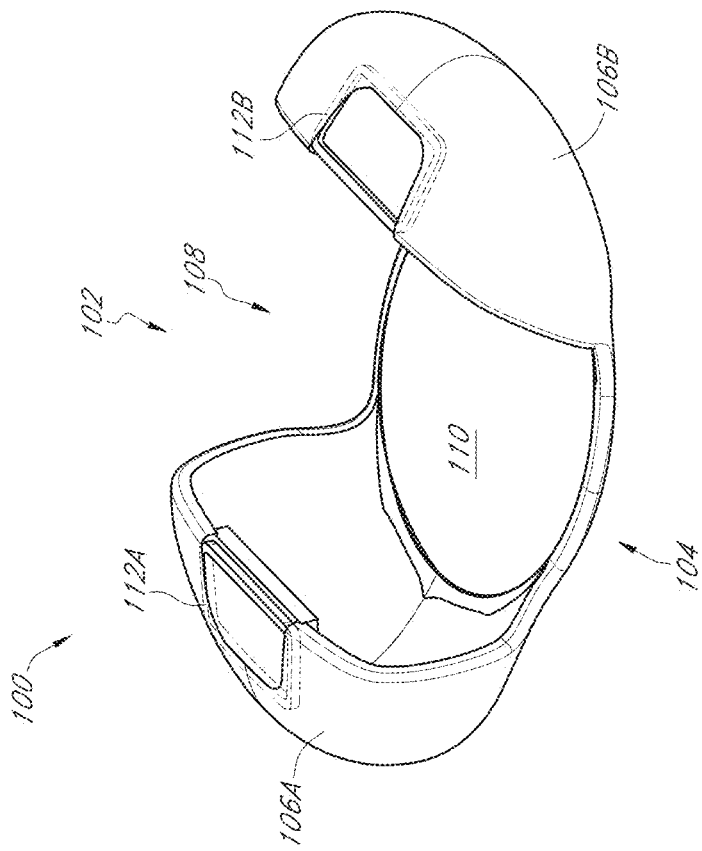
FIG. 1B is another anterior side perspective view of the example prosthetic capsular device of FIG. 1A.
Figure 1A:
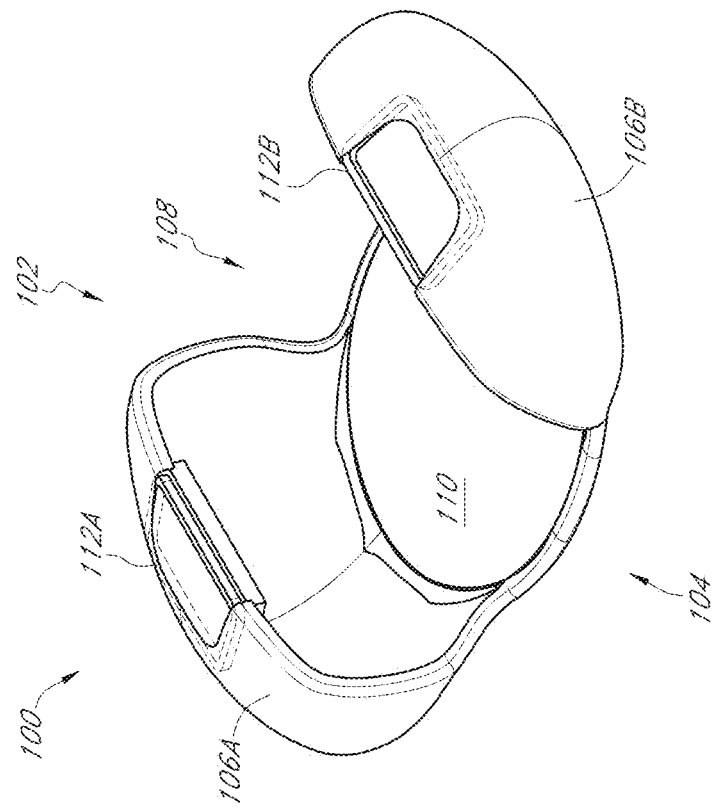
FIG. 1A is an anterior side perspective view of an example prosthetic capsular device.

FIG. 1A illustrates an anterior side perspective view of an example of a prosthetic capsular device 100. FIG. 1B illustrates another anterior side perspective view of the example prosthetic capsular device 100 for FIG. 1A.

In some embodiments, the device 100 includes features described with respect to the devices described in U.S. Pat. No. 9,358,103, which is hereby incorporated by reference in its entirety, or modifications thereof. For example, the device 100 can comprise an anterior side 102, a posterior side 104, and one or more sidewalls 106 extending between the anterior side 102 and the posterior side 104; a cavity or opening 108 defined by the anterior side 102, posterior side 104, and the one or more sidewalls 106, and the posterior side 104 optionally comprises a refractive surface 110. As such, the device 100 can be configured to comprise both a refractive surface 110 and a secondary or additional intraocular lens, electronic device, or other intraocular device held within the cavity 108.

At least a portion of the posterior side 104 can comprise a refractive surface, which may, for example, allow a pseudophakic refraction to be performed intraoperatively with a known lens already inside the eye. The refractive surface 110 can comprise a refractive power of about +1 diopter. In other embodiments, the refractive surface 110 may comprise any and all lens powers and designs that are currently known in the art of intraocular lenses, including, but not limited to: spherical, aspheric, wavefront, convex, concave, multifocal (diffractive, refractive, zonal), toric, accommodative, ultraviolet (UV) filtering, diffractive chromatic aberration reducing lenses, light adjustable lenses (ultraviolet light adjustable, femtosecond phase wrapping), and optical powers ranging from any positive diopter value (e.g., including +35 D and above) to any negative diopter value (e.g., including −35 D and below).

The refractive surface 110 may advantageously reduce the refractive power of an IOL to be placed in the device 100. For example, if the device did not include a refractive surface 110 (e.g., comprised a simple or modified ring), then one or more IOL devices would need to provide all of the refractive power, which could increase the volume of the IOL, leading to a larger incision and associated complications. A device 100 comprising a refractive surface 110 implanted in the eye can advantageously allow for a second refractive device or IOL to be coupled with (e.g., placed within, next to, and/or on top of) the refractive surface 110. The posterior refractive surface 110 can allow the ELP of the eye to be determined along with any residual refractive error. If any further refractive error is discovered, a second refractive device or IOL can be added to the refractive surface 110 (e.g., immediately), which can neutralize the deficit and help ensure that the desired outcome is achieved. The posterior refractive surface 110 can be accurately placed and anchored and/or can inhibit or prevent shifting of lateral and/or posterior-anterior position, rotation, tilt, etc. of the posterior refractive surface 110 that could lead to degradation of vision.

Further, in certain embodiments, the device 100 includes one or more additional features. For example, the device 100 can comprise a generally lenticular or lens-like shape as opposed to a box-like design. In other words, the generally shape of the device 100 can be more like the shape of a natural lens. Risks of negative and/or positive dysphotopsia can be reduced due to the generally lenticular shape of the device 100. Negative dysphotopsia is a common problem in cataract surgery, generally described by patients as a temporal dark crescent in their vision and is believed to occur either due to the optical phenomenon known as total internal reflection or by obstruction of light. This can occur either at the junction of the optic edge and the empty collapsed surrounding capsule forming a relatively planar surface, or due to the capsule overlapping a portion of the optic, most commonly the nasal aspect. In embodiments in which the implantable device 100 comprises an overall lens-like configuration, the capsule can be held open, preventing a relatively planar surface from being formed by fusion of the posterior and anterior capsule. More specifically, when light hits a curvilinear slice of the device 100, which can be made from silicone for example, it may travel through the curvilinear slice instead of bouncing off and causing a negative shadow as it generally would for flat surfaces. This may be especially true in the horizontal meridian across the 180-degree plane. As such, in some embodiments, the device 100 does not comprise any flat edges or surfaces. In other words, every surface of the device 100 can be curvilinear. Flat optical surfaces can promote total internal reflection, and are not found in the natural human lens or lens capsule in the native state. One goal of some of the embodiments described herein is to reduce negative dysphotopsias by not having any flat optical surfaces.

In certain embodiments, one or more sidewalls 106 of the device 100 can extend from only a portion of the posterior 104 and/or anterior sides 102 instead of extending from the whole circumference of the posterior 104 and/or anterior sides 102. The outer periphery of a sidewall 106 can comprise an arc of a circle. For example, in the illustrated embodiment, the device 100 comprises two sidewalls 106A, 106B each of which extend from only a portion of the circumference of the posterior side 104 and/or refractive surface 110. In other words, certain portions of the anterior side 102 and posterior side 104 are not connected by a sidewall.

There can be a number of advantages for having only a portion of the sidewall present instead of having a sidewall encompass the whole circumference of the device 100. For example, by not having a sidewall at some portions, the area behind the refractive surface 110 can be more accessible. This can be important during surgical implantation of the device 100 to facilitate removal of viscoelastic material from behind the lens or refractive surface 110 immediately or shortly after the device 100 is implanted. In devices in which a sidewall encompasses the whole device 100, it can be difficult to maneuver between that space of the natural capsule and the sidewall capsular bag to get behind the lens or refractive surface 110 to vacuum out the viscoelastic material. Without having a sidewall present at least along some portions of the posterior side 104, it can be substantially easier to reach the area behind the lens or refractive surface 110 for removal of viscoelastic material and substantially reduce risks of posterior capsular distension syndrome due to remaining viscoelastic material.

In addition, by not having a sidewall present at least along some portions of the posterior side 104, the overall bulk of the device 100 can be reduced. As such, the device 100 can be compressed to fit into a smaller injector and incision in the eye compared to a device with sidewalls surrounding the whole device. In other words, the device 100 can be folded, rolled, or otherwise compressed over the longitudinal axis of the device, or line 1G-1G of FIG. 1E, such that line 1-F-1F of the device 100 is compressed to allow the device 100 to be inserted into a small injector and/or incision in the eye for implantation. For example, in some embodiments, the device 100 can be inserted into the eye through an incision of about 2.2 mm. In other embodiments, the device 100 can be inserted into the eye through an incision of about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, about 3.5 mm, and/or within a range defined by two of the aforementioned values.

Also, the reduced size of the device 100 can allow for use of a larger optic or lens, for example for use on the anterior side 104 and/or for placement within the cavity 108. More specifically, a larger lens or refractive surface 110 can be used with the device 100 due to the reduced bulk of the device 100 itself by removal of some of the sidewalls. Use of a larger lens or refractive surface 110 can be advantageous to reduce halos and/or glare post-surgery. For example, when the pupil dilates more than 5 mm, such as at night, light that reaches the outer portions of the refractive surface 110 may not be focused. A larger lens or refractive surface 110 can be generally better to address such issues, specifically to prevent nighttime symptoms when the pupil dilates to 6 or 7 mm for example.

In some embodiments, substantially the whole device 100, other than the lens or refractive surface 110 and/or one or more haptics 112, can comprise silicone and/or a soft silicone polymer. In addition, in certain embodiments, substantially the whole device 100, other than the lens or refractive surface 110 and/or one or more haptics 112, can comprise a flexible and/or elastic material. As such, the device 100 can be foldable or collapsible for implantation into the eye through a small incision. Once inserted into the eye, the device 100 can naturally unfold and self-expand into its expanded configuration as illustrated in FIG. 1A within the natural capsular bag. In certain embodiments, the device 100 without having sidewalls encompassing the whole device 100 is collapsible to a point where the size of the optic or refractive surface 110 is the rate limiting factor for the incision size for surgical implantation of the device 100.

The device 100 can comprise one or more capsular areas. The one or more capsular areas can be adapted to receive and/or hold a lens or a secondary lens in addition to a refractive surface 110 on the posterior side. By inserting a secondary lens, IOL, or other optical device into the device 100, a Galilean and/or reverse Galilean telescope can be provided. For example, a portion of the posterior side 104, a portion of the anterior side 102, and a portion of the side wall 106A, 106B can define a capsular area. In the embodiment shown in FIGS. 1A-1G, the device 100 comprises two capsular areas. The first capsular area is defined by a portion of the posterior side 104, a portion of the anterior side 102, and a portion of the side wall 106A. Similarly, a second capsular area is defined by another portion of the posterior side 104, another portion of the anterior side 102, and another portion of the side wall 106B. In other embodiments, the device 100 can comprise one, three, four, five, six, seven, eight, nine, or ten separate capsular areas.

Similarly, the device 100 can comprise one, two, three, four, five, six, seven, eight, nine, or ten sidewalls 106, each of which extend from only a portion of the circumference of the posterior side 104 and/or refractive surface 110. In some embodiments, one or more sidewalls 106 of the device 100 can extend from about 120° of the circumference of the posterior side 104 and/or refractive surface 110. In other embodiments, one or more sidewalls 106 of the device 100 can extend from about 15°, about 30°, about 45°, about 60°, about 75°, about 90°, about 105°, about 135°, about 150°, about 165°, about 180°, about 195°, about 210°, about 225°, about 240°, about 255°, about 270°, about 285°, about 300°, about 315°, about 330°, about 345°, and/or about 360° of the circumference of the posterior side 104 and/or refractive surface 110. In certain embodiments, one or more sidewalls 106 of the device 100 can extend from a portion of the circumference of the posterior side 104 and/or refractive surface within a circumferential range defined by two of the aforementioned values.

In some embodiments, the one or more sidewalls 106 can comprise a concave shape. For example, an interior surface of the one or more sidewalls 106 and/or interior surface of the refractive surface 110 or posterior side 104 can form a cavity 108. The cavity can be configured to hold an IOL, for example.

In some embodiments, the device 100 comprises one or more haptics 112. The one or more haptics 112 can be made of a rigid or semi-rigid material, such as polyimide, PMMA, polypropylene, and nylon. The one or more haptics 112 can also or alternatively be made of a biocompatible material, such as silicone, silicone polymers, SIBS (poly(styrene-block-isobutylene-block-styrene)), acrylic, acrylic polymers, polypropylene, polycarbonate, and Gore-Tex. One or more haptics 112 of the device 100 can provide a place for surrounding epithelial cells to grow and latch on to provide support for the device 100 within the natural capsular bag.

In the illustrated embodiment, the device 100 comprises two haptics 112, made of polyimide for example. In other embodiments, the device 100 can comprise one, three, four, five, six, seven, eight, nine, or ten haptics 112. Further, in the illustrated embodiment, the one or more haptics 112 comprise the general shape of an outer periphery of a rectangular or substantially rectangular shape, which can be attached to the anterior side of a sidewall extension. As shown, the one or more haptics 112 can be positioned close to and/or generally parallel to the posterior side 102 of the device 100 and do not extend radially outward of the device 100. This can present advantages during surgical implantation as radially extending haptics can potentially get hung up on the iris and/or anterior portion of the natural capsular bag, which can present complications during surgical implantation. In other embodiments, one or more haptics 112 can comprise a different shape while being positioned close to and/or generally parallel to the posterior side 102 and/or anterior side 104 of the device 100, such as circular, elliptical, round, square, triangular, or the like.

In some embodiments, a portion of a haptic 112 can be over-molded into the device 100 for maintaining the position of the haptic 112 and not exposing that portion of the haptic 112. Another portion of the haptic 112 can be exposed to the underside of the anterior natural capsular bag. For example, a peripheral portion of the haptic can be over-molded while the central portion is exposed. The portion of the device 100, for example made of silicone, underneath the central portion of the haptic 112 can be indented or recessed in some embodiments. As such, fibrotic bands can be formed over time to act as an anchor point and hold the whole device 100 in place, for example if a Yag capsulotomy is to be performed. More specifically, epithelial cells coating the anterior and/or posterior natural capsular bag can replicate and grow into the recessed area of the silicone device 100 underneath the haptic 112 and grow around the haptic 112.

In certain embodiments, one or more haptics 112 of the device 100 can comprise a "monkey bar" type configuration. More specifically, a portion of the device 100, for example a portion of a sidewall, can be recessed and/or indented. A haptic can extend across the recessed or indented portion. For example, one end of the haptic can be over-molded by silicone or other material of the device 100 at one end of the recessed or indented portion and the other end of the haptic can be over-molded by silicone or other material of the device 100 at the other end of the recessed or indented portion. As such, a haptic, for example made of polyimide, can be formed without radially extending out of the exterior surface of the device 100 while having void space all around the haptic. This can provide strands of exposed haptic or polyimide in some embodiments, while the haptic is stabilized as part of the overall device. Epithelial cells can grow around the haptic and latch on to provide lateral support along the monkey bar-type portion. One or more such haptics can be provided on each side of the device 100 in a symmetric manner.

In some embodiments, the device 100 comprises a single-molded design. In other words, the whole device 100, or substantially the whole device 100 other than the lens or refractive surface 110 and/or one or more haptics 112, can be molded from a single piece of material. For example, in some embodiments, substantially the whole device 100 can be molded of silicone using a silicone compression mold. In certain embodiments, one or more haptics 112, made of polyimide for example, are placed in the mold before silicone or other material of the device 100 is poured into the mold and compressed. In other embodiments, the device 100 or any portion thereof can be manufactured by 3D laser cutting, two photon lithography, additive manufacturing, 3D printing, compression molding, and/or any combination of the aforementioned manufacturing processes or others.

Figure 1D:
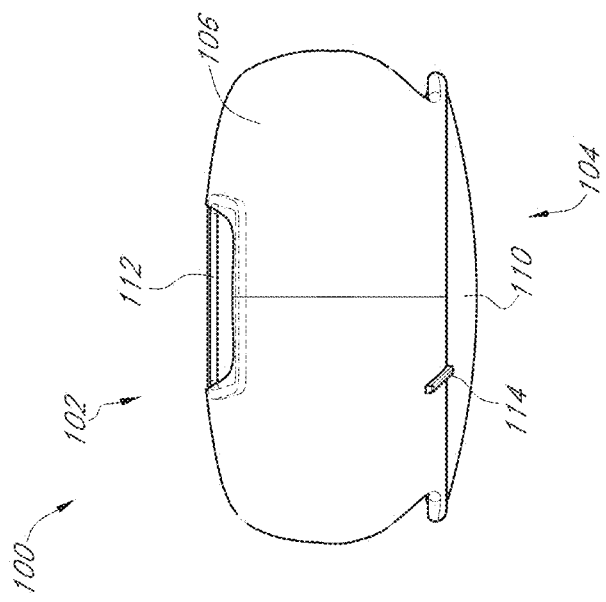
FIG. 1D is a side plan view of the example prosthetic capsular device of FIG. 1A.
Figure 1C:
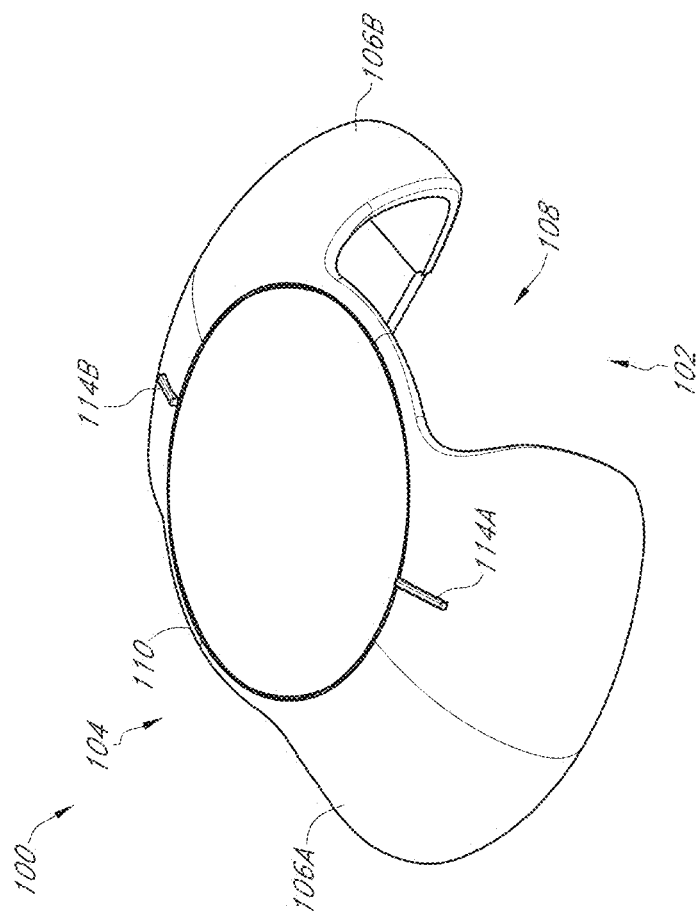
FIG. 1C is a posterior side perspective view of the example prosthetic capsular device of FIG. 1A.

FIG. 1C illustrates a posterior side perspective view of the example prosthetic capsular device of FIG. 1A. FIG. 1D illustrates a side plan view of the example prosthetic capsular device of FIG. 1A.

The device 100 optionally comprises one or more posterior fins 114. The device 100 shown includes two posterior fins 114A, 114B. The posterior fins 114 can be aligned along a diameter of the refractive surface 110. In some implementations, a plurality of posterior fins 114 (e.g., 2, 3, 4, 5, 6, or more fins 124) may be circumferentially offset (e.g., by about 180°, by about 120°, by about 90°, by about 72°, by about 60°, and the like). In some implementations, at least some or all of a plurality of posterior fins 114 (e.g., 2, 3, 4, 5, 6, or more fins 114) may be unaligned.

In the illustrated embodiment, a line between the two posterior fins 114 forms an angle with a major axis of the device 100. For example, the angle between a line connecting the posterior fins 114 and a major axis of the device 100 can be about 10°, about 20°, about 30°, about 40°, about 50°, about 60°, about 70°, about 80°, about 90°, about 100°, about 110°, about 120°, about 130°, about 140°, about 150°, about 160°, about 170°, about 180°, and/or within a range between two of the aforementioned values. In certain embodiments, the posterior fins 114 are aligned along a major axis of the device 100. In other implementations, the posterior fins 114 may be aligned along a minor axis of the device 100.

The posterior fin 114 may comprise the same material as the device 100 or a different material than the device 100. The posterior fin 114 may help to space a posterior surface of a natural capsular bag from the posterior end 104 of the device 100 radially outward of the refractive surface 110. Spacing the posterior surface of the natural capsular bag from the posterior end 104 of the device 100 radially outward of the refractive surface 110 may allow fluid to flow radially outward of the refractive surface 110, which may help to reduce opacification. Spacing the posterior surface of the natural capsular bag from the posterior end 104 of the device 100 radially outward of the refractive surface 110 may reduce the chance of retaining viscoelastic that has some residual trapped fibrin or inflammatory precipitate contained within it. In some embodiments, the posterior fin 114 may extend anterior from the posterior of the device 100 into the cavity of the device 100. In some embodiments, the posterior fin comprises a roughened or opacified interior and/or exterior surface of the device 100 (e.g., having the same thickness and material as the posterior wall radially outward of the refractive surface 110 but treated to provide an alignment mark).

The device 100 can be strategically aligned in an eye with use of the fins 114. For example, if an eye has astigmatism, a device 100 in which the refractive surface 110 comprises a toric lens can be used to at least partially correct the astigmatism if the device 100 is properly oriented (e.g., with the steep axis of a cornea). In some implementations, at least one of the fins 114 can be different (e.g., different shape, dimensions, etc.) to indicate a top or bottom of the device 100. In devices allowing any rotational orientation of an IOL inserted therein, a toric IOL can be rotated. Aligning the device 100 for alignment of a toric refractive surface 110 and/or a toric IOL contained in the device 100 can advantageously provide the advantages of limited IOL rotation, reduced volume, and astigmatism correction. For example, the optic haptic junction of a secondary IOL can be aligned or otherwise correlated with one or more fins 114 and allow a surgeon to align the device 100 in an optimal position for a secondary toric IOL to be placed. In some embodiments, the one or more fins 114 extending radially posterior or outward of the posterior of the device 100 can still be visualized from the interior of the refractive surface 110 to facilitate alignment of a secondary IOL or device, for example due to the transparent and/or semi-transparent nature of the posterior of the device 100. In other embodiments, the one or more fins 114 extend radially anterior or inward of the posterior of the device 100 such that it the fins 114 are viewable for facilitating alignment of a secondary IOL or device.

FIG. 1E illustrates an anterior plan view of the example prosthetic capsular device of FIG. 1A. FIG. 1F illustrates a cross-sectional view of the example prosthetic capsular device of FIG. 1A along the line 1F-1F of FIG. 1E. FIG. 1G illustrates a cross-sectional view of the example prosthetic capsular device of FIG. 1A along the line 1G-1G of FIG. 1E.

In the illustrated embodiment, the device 100 comprises a refractive surface 110 with a diameter of about 5.5 mm. In other embodiments, the device 100 can comprise a refractive surface 110 with a diameter of about 5.0 mm. The refractive surface 110 110 may have a diameter between about 4 mm and about 9 mm (e.g., about 4 mm, about 5 mm, about 6 mm, about 7 mm, about 8 mm, about 9 mm, ranges between such values, etc.).

In such embodiments, the device 100 can be configured to be inserted through a small incision of about 2.2 mm or about 2.4 mm. In certain embodiments, the device 100 can be inserted through an incision between about 1.5 mm and about 3 mm (e.g., about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, ranges between such values, etc.).

Further, in the illustrated embodiment, a length of a major axis of the device 100 or a length measured from the outermost end of one sidewall 106A to the outermost end of another sidewall 106B along a major axis of the device 100 can be about 10.00 mm. In other embodiments, the length of the major axis of the device 100 can be about 5.00 mm, about 6.00 mm, about 7.00 mm, about 8.00 mm, about 9.00 mm, about 10.00 mm, about 11.00 mm, about 12.00 mm, about 13.00 mm, about 14.00 mm, about 15.00 mm, and/or within a range defined by two of the aforementioned values.

Furthermore, in the illustrated embodiment, a length of a minor axis of the device 100 or a length measured from one end of a sidewall 106 to the other end of the same sidewall 106 along a minor axis of the device 100 can be about 6.57 mm. In other embodiments, the length of a minor axis of the device 100 can be about 4.0 mm, about 4.5 mm, about 5.0 mm, about 5.5 mm, about 6.0 mm, about 6.5 mm, about 7.0 mm, about 7.5 mm, about 8.0 mm, about 8.5 mm, about 9.0 mm, and/or within a range defined by two of the aforementioned values.

As illustrated in FIG. 1G, in some embodiments, a thickness of a haptic 112, made from polyimide for example, can be about 0.13 mm. In other embodiments, the thickness of the haptic 112 can be about 0.05 mm, about 0.06 mm, about 0.07 mm, about 0.08 mm, about 0.09 mm, about 0.10 mm, about 0.11 mm, about 0.12 mm, about 0.13 mm, about 0.14 mm, about 0.15 mm, about 0.16 mm, about 0.17 mm, about 0.18 mm, about 0.19 mm, about 0.20 mm, and/or within a range defined by two of the aforementioned values.

In certain embodiments, a length of the haptic 112 across the cross section formed by line 1G-1G or along a major axis of the device 100 can be about 1.4 mm. In other embodiments, a length of the haptic as seen in a cross section along a major axis of the device 100 can be about 0.05 mm, about 0.06 mm, about 0.07 mm, about 0.08 mm, about 0.09 mm, about 0.10 mm, about 0.11 mm, about 0.12 mm, about 0.13 mm, about 0.14 mm, about 0.15 mm, about 0.16 mm, about 0.17 mm, about 0.18 mm, about 0.19 mm, about 0.20 mm, and/or within a range defined by two of the aforementioned values.

In some embodiments, the thickness of silicone or other material of the device 100 can be about 0.2 mm. In certain embodiments, the thickness of silicone or other material of the device 100 can be about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, and/or within a range defined by two of the aforementioned values.

In some embodiments, the thickness of the silicone or other material of the device 100 varies depending on the portion of the device 100. In other words, some portions of the device 100 can be made of thinner materials while other portions of the device 100 can be made of thicker materials. For example, certain portions of the device that provide support to the anterior portion of the device 100 may be made with thicker materials for added support.

In some embodiments, a thickness of silicone or other material of the device 100 molded over the haptic 112 can be about 0.01 mm, about 0.02 mm, about 0.03 mm, about 0.04 mm, about 0.05 mm, about 0.06 mm, about 0.07 mm, about 0.08 mm, about 0.09 mm, about 0.10 mm, and/or within a range defined by two of the aforementioned values.

In certain embodiments, the width of an opening of the cavity formed by each end of the two sidewalls 106 can be about 5.82 mm. In some embodiments, the width of the opening of the cavity formed by each end of the two sidewalls can be about 4.0 mm, about 4.2 mm, about 4.4 mm, about 4.6 mm, about 4.8 mm, about 5.0 mm, about 5.2 mm, about 5.4 mm, about 5.6 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, and/or within a range defined by two of the aforementioned values.

Also, the height of the cavity as measured from a midpoint of the posterior refractive surface 110 to the top of the sidewall 106 opening can be about 3.21 mm in some embodiments. In certain embodiments, the height of the cavity as measured from a midpoint of the posterior refractive surface 110 to the top of the sidewall 106 opening can be about 2.0 mm, 2.2 mm, 2.4 mm, 2.6 mm, 2.8 mm, 3.0 mm, 3.2 mm, 3.4 mm, 3.6 mm, 3.8 mm, 4.0 mm, 4.2 mm, 4.4 mm, 4.6 mm, 4.8 mm, 5.0 mm, and/or within a range defined by two of the aforementioned values.

Figure 2B:
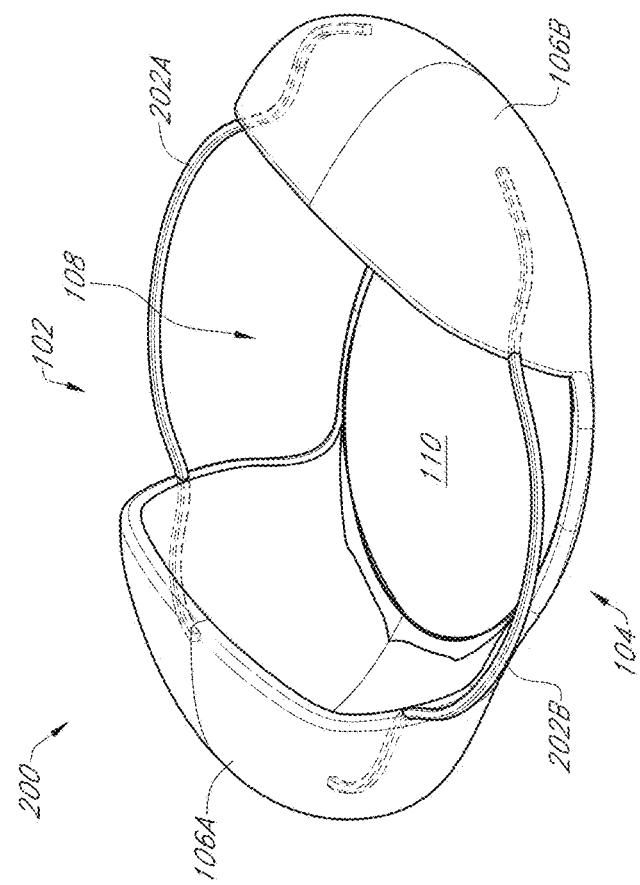
FIG. 2B is another anterior side perspective view of the example prosthetic capsular device of FIG. 2A.
Figure 2A:
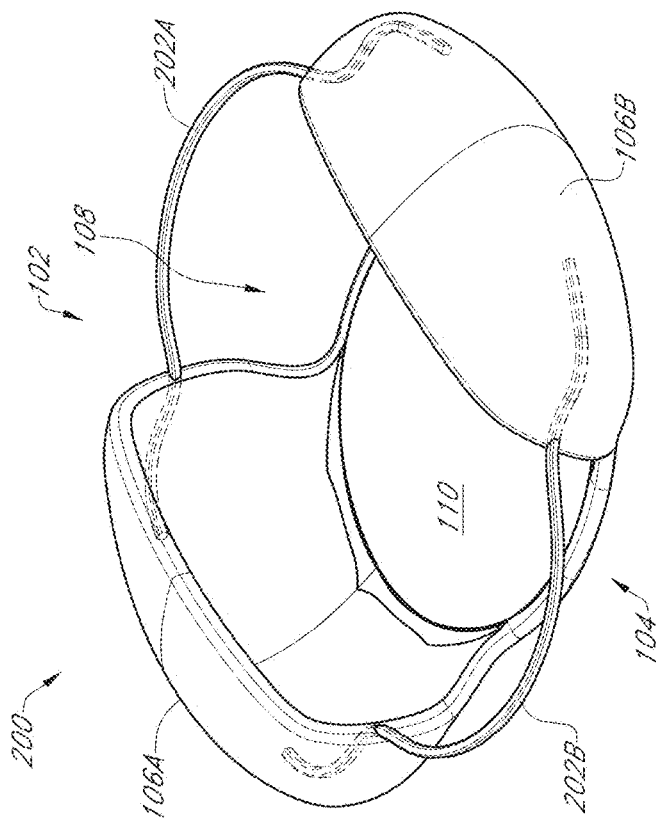
FIG. 2A is an anterior side perspective view of another example prosthetic capsular device.

FIG. 2A illustrates an anterior side perspective view of another example prosthetic capsular device. FIG. 2B illustrates another anterior side perspective view of the example prosthetic capsular device of FIG. 2A. The prosthetic capsular device of FIG. 2A incudes some or all of the features of the prosthetic capsular device of FIG. 1A, and like reference numerals include like features. In particular, in some embodiments, the prosthetic capsular device of FIG. 2A can be similar to the prosthetic capsular device of FIG. 1A, except for the configuration of the haptics 202. All other features of the device 200 or haptics 202, such as material, flexibility, function, or the like, can be similar to such features of the device 100 or haptics 112 described above in relation to FIGS. 1A-1G.

In some embodiments, the device 200 does not comprise haptics with a license plate or rectangular configuration as in FIGS. 1A-1G. Rather, the device 200 can comprise one or more haptics that connect the sidewalls 106 and expand radially to form a generally circular shape. For example, in the illustrated embodiment, one end of a haptic 202A can be anchored or over-molded on one sidewall 106A and the other end of the same haptic 202A can be anchored or over-molded on another sidewall 106B. Similarly, one end of a second haptic 202B can be anchored or over-molded on one sidewall 106A and the other end of the same haptic 202B can be anchored or over-molded on another sidewall 106B. The haptic 202 can form a radially outward shape or a substantially outwardly circular shape or loop. The haptic 202 202 can extend radially outward from a cavity between two or more sidewalls 106A, 106B. Such configuration of the haptic 202 can provide for stability of the device 200 within the natural capsular bag.

Figure 2F:
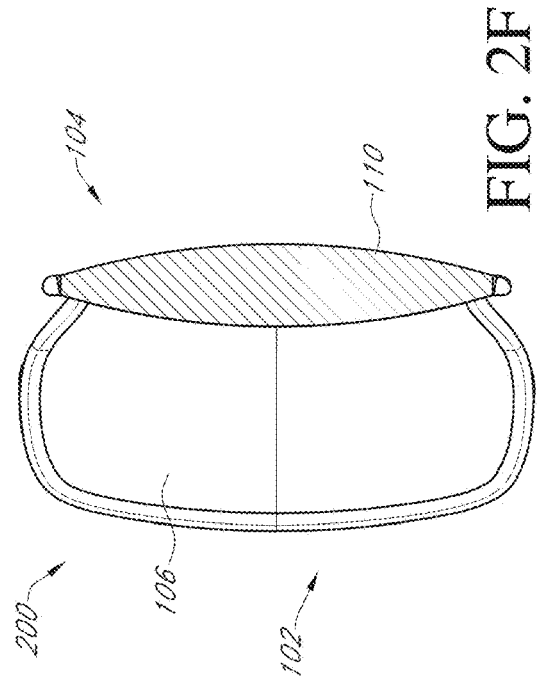
FIG. 2F is a cross-sectional view of the example prosthetic capsular device of FIG. 2A along the line 2F-2F of FIG. 2E.
Figure 2G:
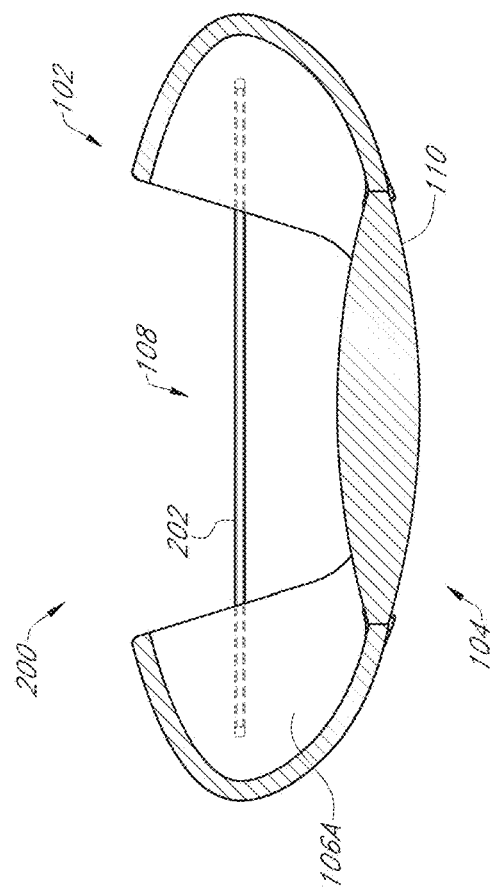
FIG. 2G is a cross-sectional view of the example prosthetic capsular device of FIG. 2A along the line 2G-2G of FIG. 2E.
Figure 2E:
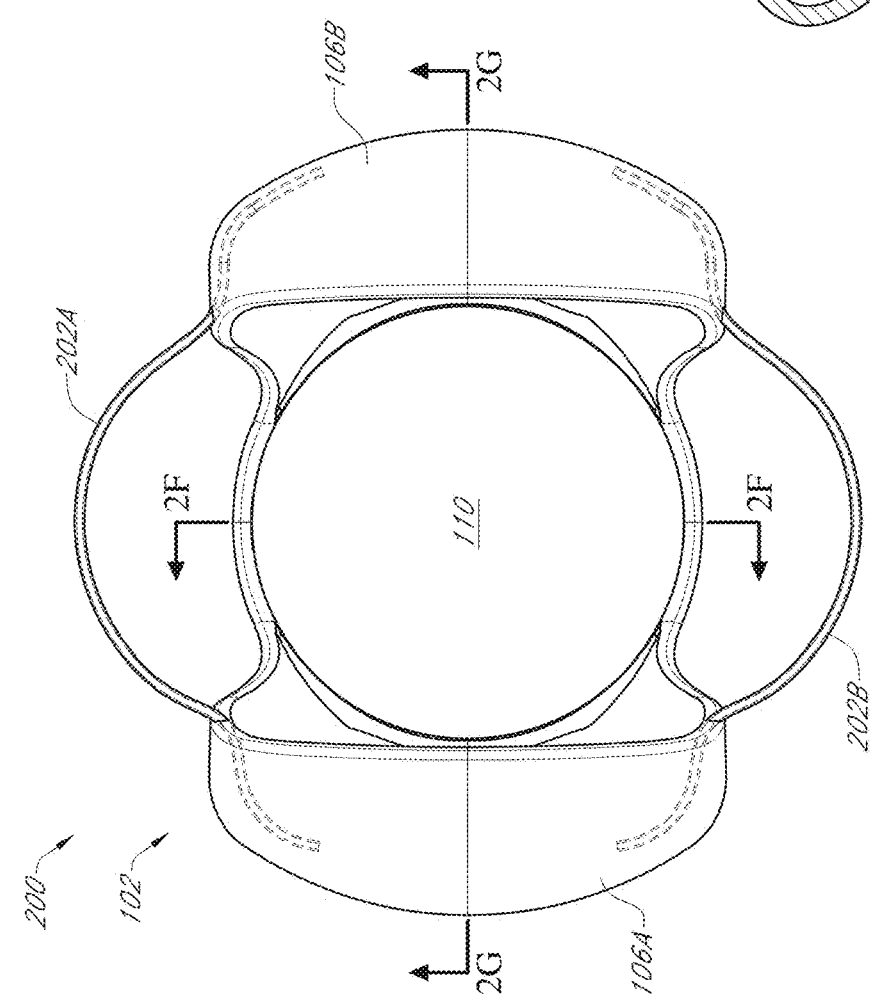
FIG. 2E is an anterior plan view of the example prosthetic capsular device of FIG. 2A.

FIG. 2C illustrates a posterior side perspective view of the example prosthetic capsular device of FIG. 2A. FIG. 2D illustrates a side plan view of the example prosthetic capsular device of FIG. 2A. FIG. 2E illustrates an anterior plan view of the example prosthetic capsular device of FIG. 2A. FIG. 2F illustrates a cross-sectional view of the example prosthetic capsular device of FIG. 2A along the line 2F-2F of FIG. 2E. FIG. 2G illustrates a cross-sectional view of the example prosthetic capsular device of FIG. 2A along the line 2G-2G of FIG. 2E.

As shown in FIG. 2E, in some embodiments, an outer or under certain circumstances maximum diameter of the device 200, for example accounting for extension of the haptics 202, may be about 10 mm. In certain embodiments, the outer or maximum diameter of the device 200 can be about 7 mm, about 8 mm, about 9 mm, about 10 mm, about 11 mm, about 12 mm, about 13 mm, and/or within a range defined by two of the aforementioned values.

As shown in FIG. 2F, in some embodiments, an outer or under certain circumstances maximum thickness of the device 200, for example accounting for the thickness of the refractive surface 110, may be about 3.65 mm. In certain embodiments, the outer or maximum thickness of the device 200 can be about 3.0 mm, about 3.1 mm, about 3.2 mm, about 3.3 mm, about 3.4 mm, about 3.5 mm, about 3.6 mm, about 3.7 mm, about 3.8 mm, about 3.9 mm, about 4.0 mm, about 4.1 mm, and/or within a range defined by two of the aforementioned values.

Figure 3B:
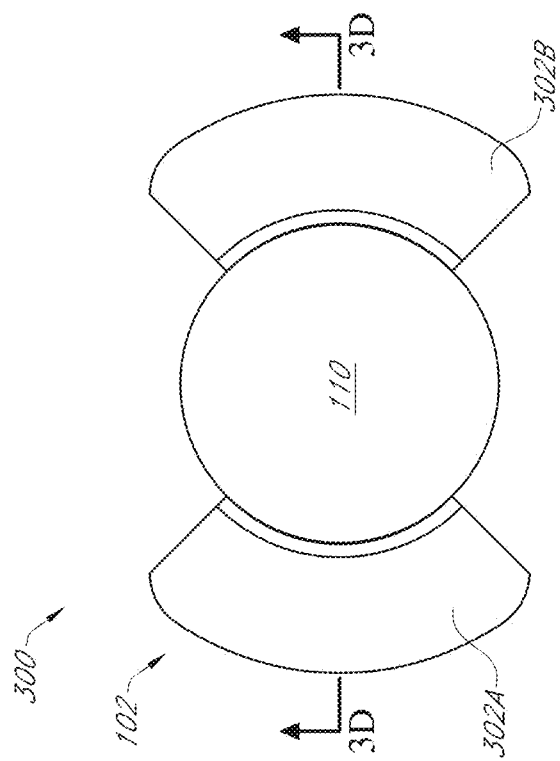
FIG. 3B is an anterior plan view of the example prosthetic capsular device of FIG. 3A.
Figure 3A:
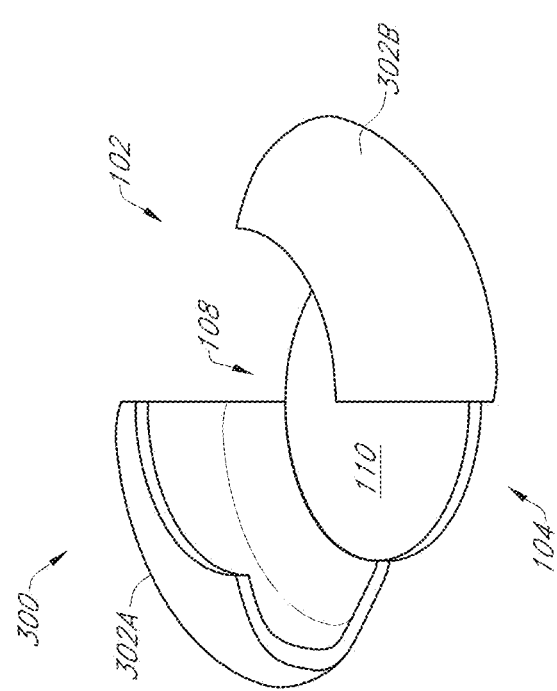
FIG. 3A is an anterior side perspective view of another example prosthetic capsular device.

FIG. 3A illustrates an anterior side perspective view of another example prosthetic capsular device. FIG. 3B illustrates an anterior plan view of the example prosthetic capsular device of FIG. 3A. FIG. 3C illustrates a side plan view of the example prosthetic capsular device of FIG. 3A. FIG. 3D illustrates a cross-sectional view of the example prosthetic capsular device of FIG. 3A along the line 3D-3D of FIG. 3B.

The prosthetic capsular device of FIG. 3A includes some or all of the features of the prosthetic capsular devices of FIGS. 1A and/or 2A, and like reference numerals include like features. In particular, in some embodiments, the prosthetic capsular device of FIG. 3A can be similar to the prosthetic capsular devices of FIGS. 1A and/or 2A, except for the haptics 112, 202 and sidewalls 302.

More specifically, in the illustrated embodiment, the device 300 does not comprise any haptics, such as haptics 112, 202 described above in relation to FIGS. 1A and 2A. In other embodiments, the device 300 can comprise one or more haptics 112, 202 described above in relation to FIGS. 1A and 2A.

Further, in certain embodiments, one or more sidewalls 302 of the device 300 can extend from only about 90° of the circumference of the posterior side 104 and/or refractive surface 110. In other words, a single capsular area defined by a portion of the anterior side 102, a portion of the posterior side 104, and a sidewall 302A, 302B, can cover about 90° of the circumference of the device 300.

The sidewalls 302 can include any and all other features of sidewalls 106 described above in relation to FIGS. 1A-1G. In some embodiments, all of the sidewalls 302A, 302B each extend from a substantially equal portion of the circumference of the posterior side 104 and/or refractive surface 110, for example each at about 90°. In other embodiments, some of the sidewalls 302 can extend from different amounts of portions of the circumference of the posterior side 104 and/or refractive surface 110. For example, one of a plurality of sidewalls 302 can extend from about 45° while another of the plurality of sidewalls 302 extends from about 90° of the circumference of the posterior side 104 and/or refractive surface 110.

In some embodiments, a single device 300 can be configured to be implanted into the eye with or without a second lens being placed inside the cavity 108. In certain embodiments, two devices 300 are configured to be coupled together prior to and/or during surgical implantation. More specifically, a first device 300 can be coupled with a second device 300 that is placed upside down to form a lens assembly with itself. In certain patients, this combination of lenses may move relative to one another creating a variable effective power of the lens system, enhancing the range of vision provided. A lens may be placed inside the empty cavity formed by the two devices 300.

Figure 4B:
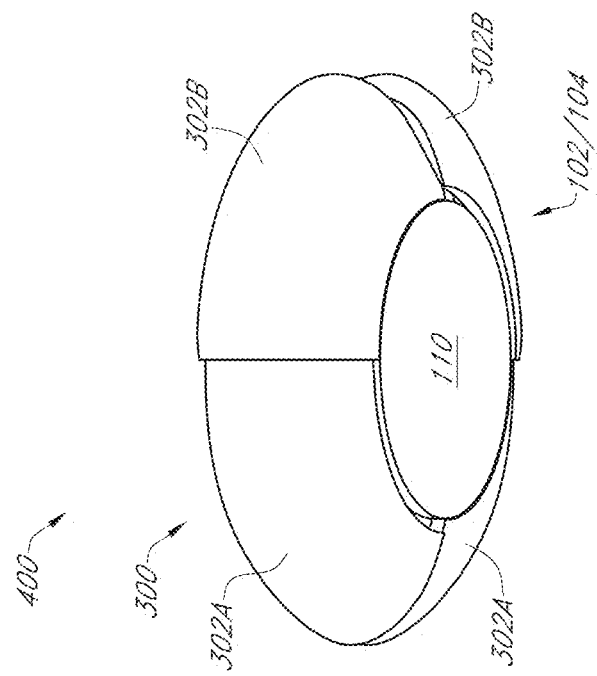
FIG. 4B is a posterior side perspective view of two (2) example prosthetic capsular devices of FIG. 3A coupled together.
Figure 4A:
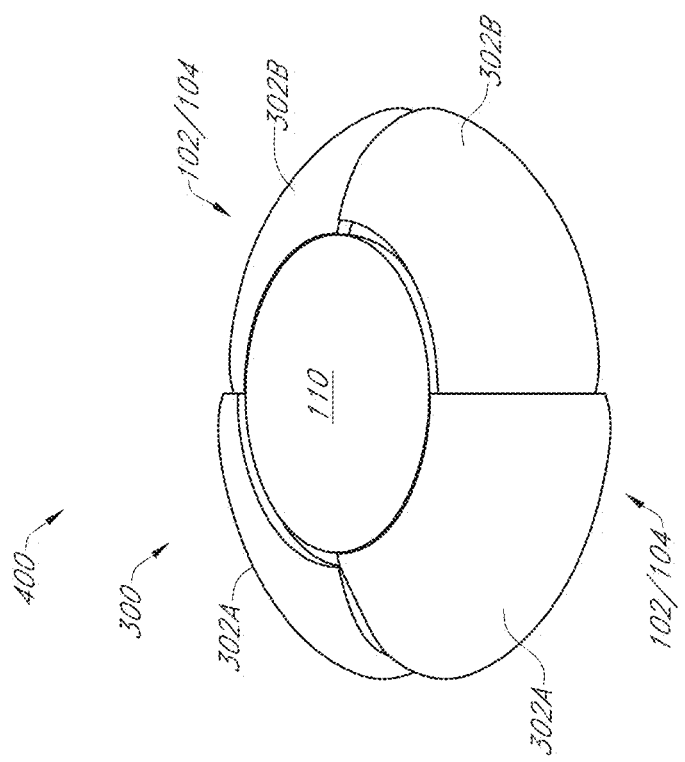
FIG. 4A is an anterior side perspective view of two (2) example prosthetic capsular devices of FIG. 3A coupled together.
Figure 4D:
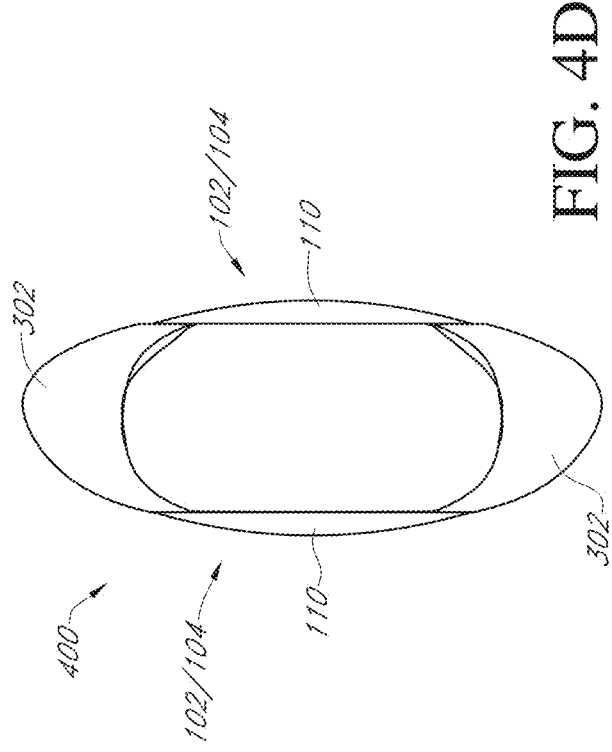
FIG. 4D is a side plan view of two (2) example prosthetic capsular devices of FIG. 3A coupled together.
Figure 4E:
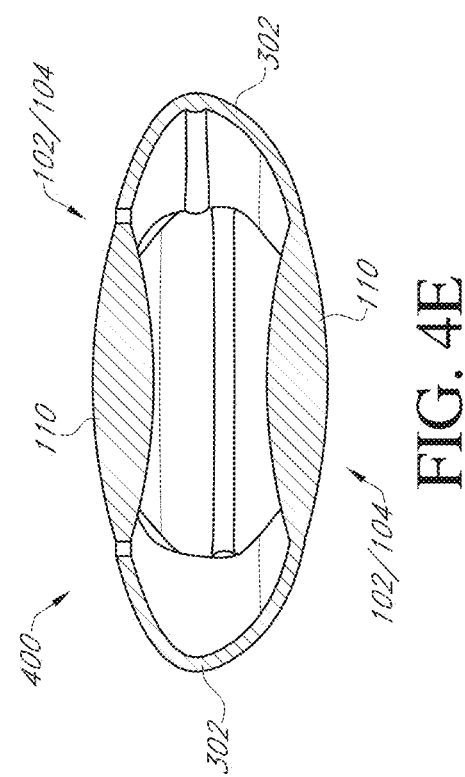
FIG. 4E is a cross-sectional view along the line 4E-4E of FIG. 4C of two (2) example prosthetic capsular devices of FIG. 3A coupled together.
Figure 4C:
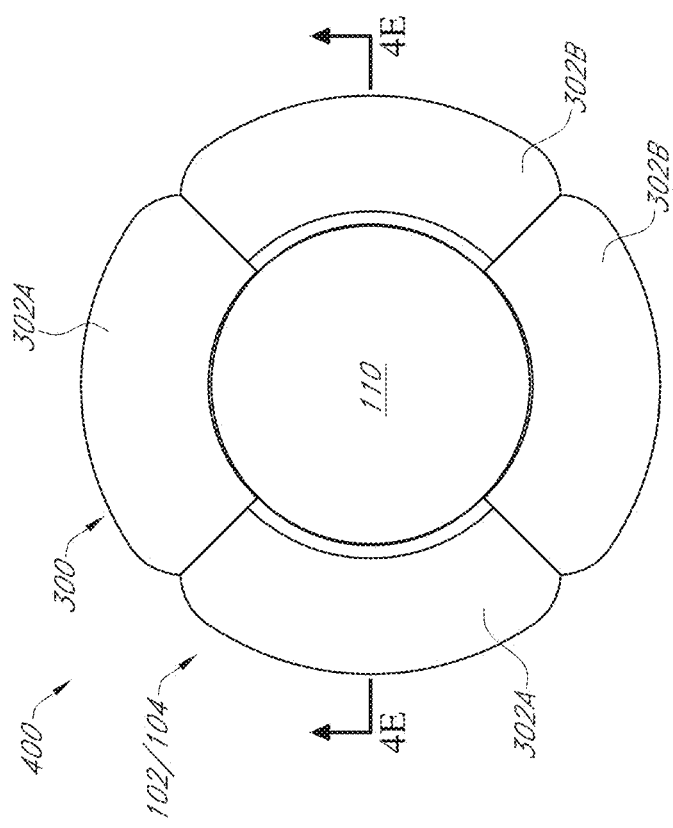
FIG. 4C is an anterior plan view of two (2) example prosthetic capsular devices of FIG. 3A coupled together.

FIG. 4A illustrates an anterior side perspective view of two (2) example prosthetic capsular devices of FIG. 3A coupled together. FIG. 4B illustrates a posterior side perspective view of two (2) example prosthetic capsular devices of FIG. 3A coupled together. FIG. 4C illustrates an anterior plan view of two (2) example prosthetic capsular devices of FIG. 3A coupled together. FIG. 4D illustrates a side plan view of two (2) example prosthetic capsular devices of FIG. 3A coupled together. FIG. 4E illustrates a cross-sectional view along the line 4E-4E of FIG. 4C of two (2) example prosthetic capsular devices of FIG. 3A coupled together.

In some embodiments, one device 300 can be coupled with another device 300 to form a closed cavity 108 inside an assembly 400 the two devices 300. To do so, one device 300 can coupled with another device 300 that is placed upside down. In certain embodiments, each device 300 can comprise two sidewalls that each extend from roughly 90° of the circumference of the posterior side 104 and/or refractive surface 110. As such, when coupled together, sidewalls of the two devices 300 can, in combination, form a sidewall that substantially covers all 360°.

In certain embodiments, a gap may be present between the end of a sidewall 302 of one device 300 and the refractive surface 110 of a second device 300. Instead of forming a complete seal, a gap between the two devices 300 when coupled together to form an assembly 400 can be advantageous to allow for fluid to pass to and from the cavity.

In some embodiments, this gap between the two devices 300 when coupled to form an assembly 400 (or more specifically, the gap between an end of a sidewall 302 of a first device 300 and the refractive surface 110 of a second device 300 when the first device 300 and second device 300 are coupled together) can be about 0.25 mm. In certain embodiments, this gap can be about 0.05 mm, about 0.10 mm, about 0.15 mm, about 0.20 mm, about 0.25 mm, about 0.30 mm, about 0.35 mm, about 0.40 mm, about 0.45 mm, about 0.50 mm, and/or within a range defined by two of the aforementioned values. The precise thickness of the gap can depend on the shape and/or volume of the natural capsular bag in some embodiments.

In certain embodiments, one device 300 is implanted into the eye first, followed by optional implantation and positioning of a refractive lens inside the cavity 108, and then the second device 300 is implanted into the eye to form a closure of the assembly 400. In some embodiments, the two devices 300 are coupled together first before implantation into the eye.

Figure 5B:
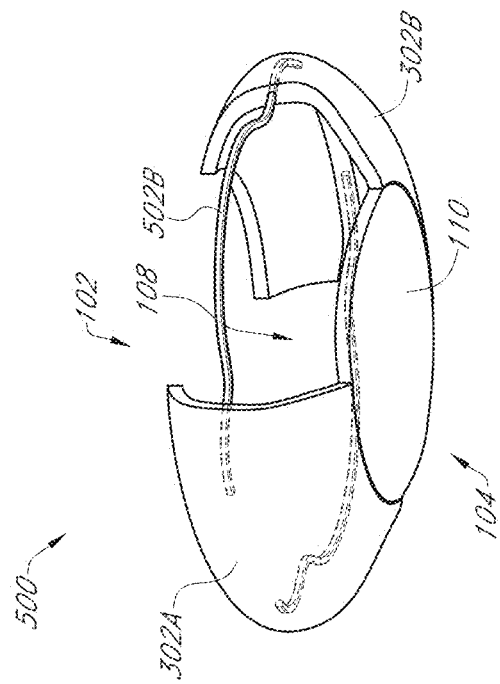
FIG. 5B is a posterior side perspective view of the example prosthetic capsular device of FIG. 5A.
Figure 5A:
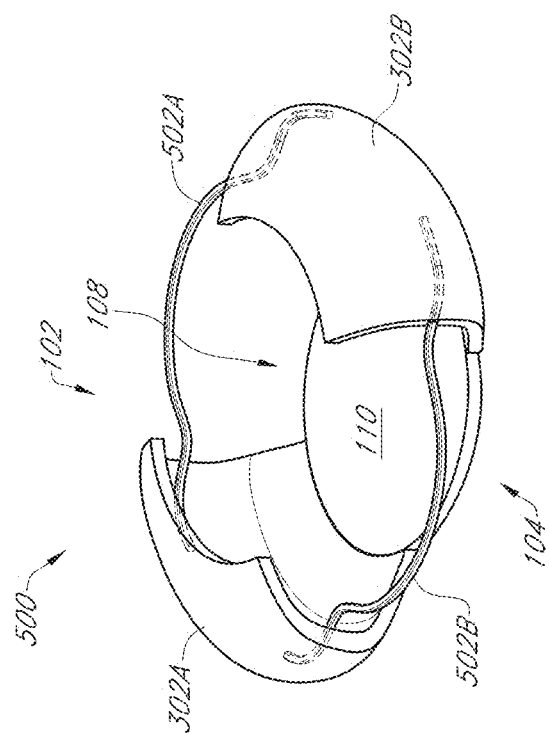
FIG. 5A is an anterior side perspective view of another example prosthetic capsular device.

FIG. 5A illustrates an anterior side perspective view of another example prosthetic capsular device. FIG. 5B illustrates a posterior side perspective view of the example prosthetic capsular device of FIG. 5A. The prosthetic capsular device of FIG. 5A includes some or all of the features of the prosthetic capsular devices of FIGS. 1A-4A, and like reference numerals include like features.

More specifically, in some embodiments, the device 500 can comprise one or more sidewalls 302 which can include some or all of the features of the sidewalls 302 of device 300. For example, in certain embodiments, one or more sidewalls 302 of the device 500 can extend from only about 90° of the circumference of the posterior side 104 and/or refractive surface 110. The sidewalls 302 can also include any and all other features of sidewalls 106 described above in relation to FIGS. 1A-4A.

Similarly, the device 500 can comprise one or more haptics 502 which can include some or all of the features of the haptics 202 of device 200. For example, one or more haptics 502 of the device 500 can connect two sidewalls 302A, 302B. Moreover, one or both ends of a haptic 502 can be anchored or over-molded on a sidewall 302A, 302B of the device 500.

Figure 5D:
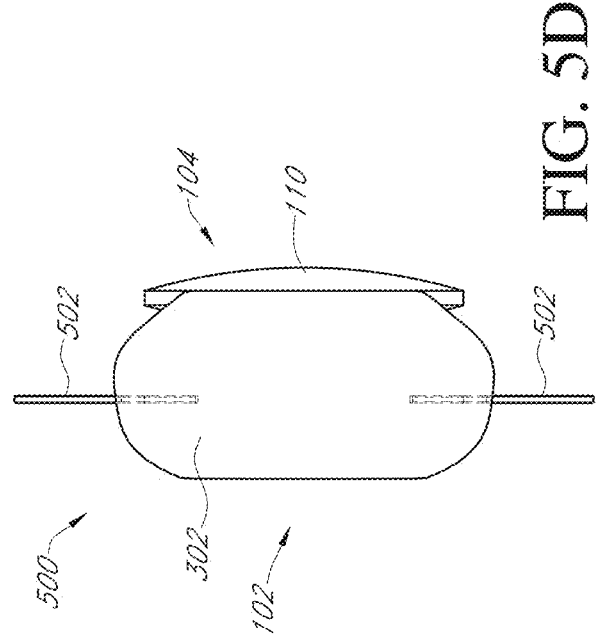
FIG. 5D is a side plan view of the example prosthetic capsular device of FIG. 5A.
Figure 5E:
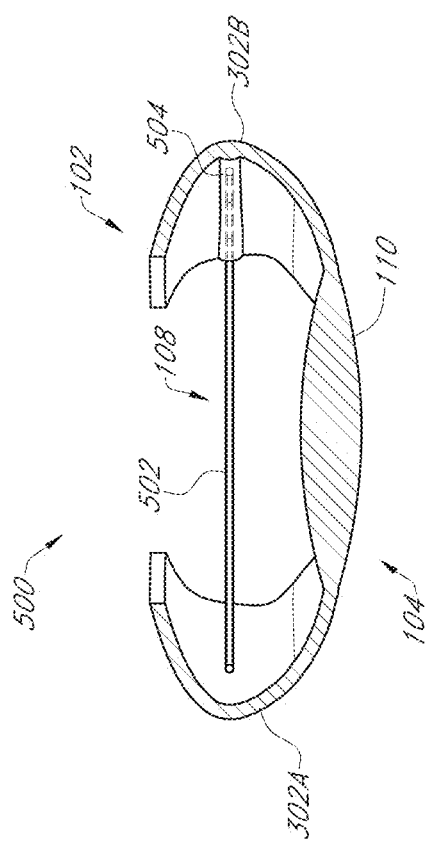
FIG. 5E is a cross-sectional view of the example prosthetic capsular device of FIG. 5A along the line 5E-5E of FIG. 5C.
Figure 5C:
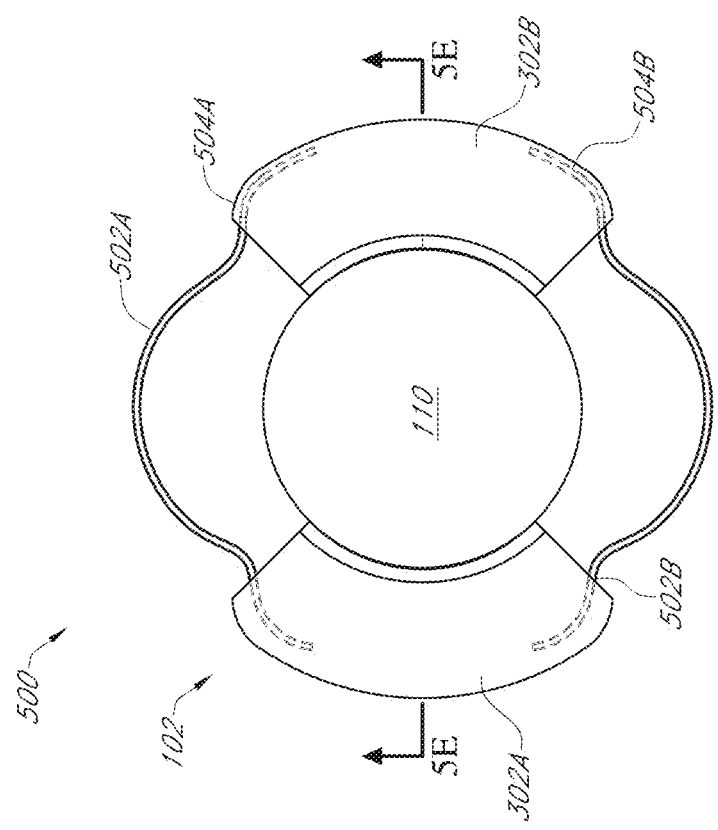
FIG. 5C is an anterior plan view of the example prosthetic capsular device of FIG. 5A.
Figure 5G:
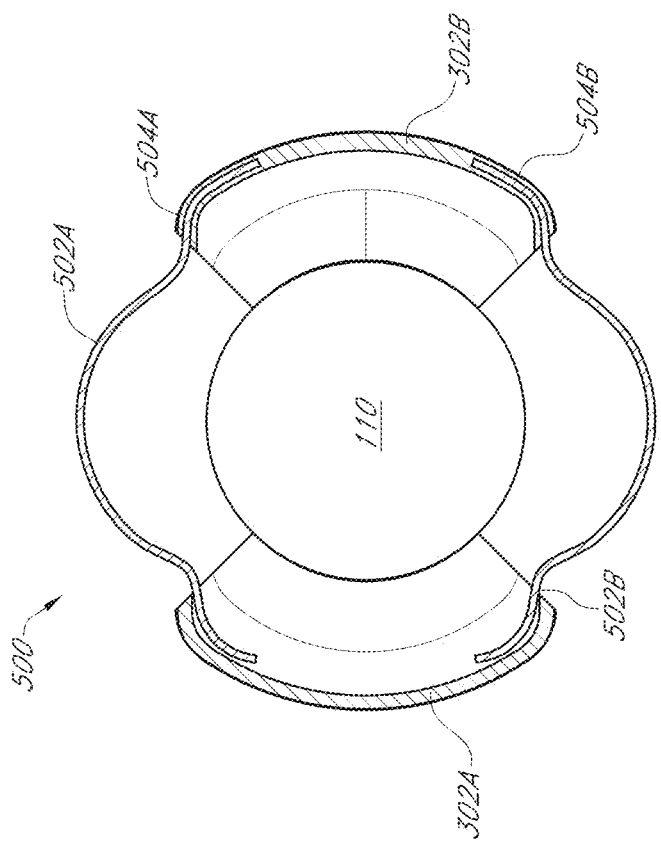
FIG. 5G is a cross-sectional view of the example prosthetic capsular device of FIG. 5A along the line 5G-5G of FIG. 5F.
Figure 5F:
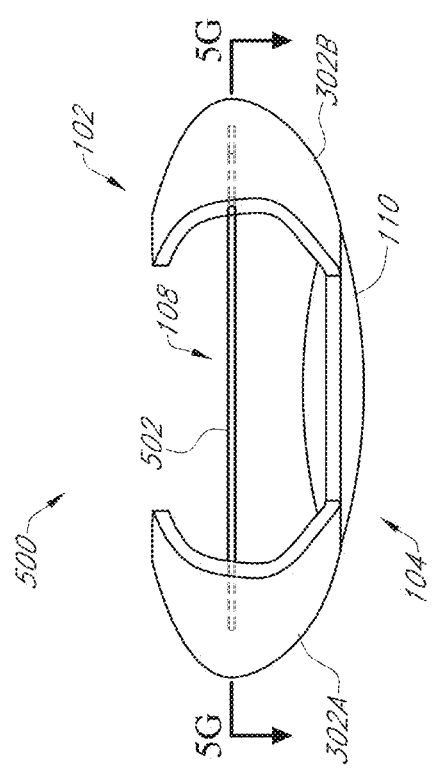
FIG. 5F is another side plan view of the example prosthetic capsular device of FIG. 5A.

FIG. 5C illustrates an anterior plan view of the example prosthetic capsular device of FIG. 5A. FIG. 5D illustrates a side plan view of the example prosthetic capsular device of FIG. 5A. FIG. 5E illustrates a cross-sectional view of the example prosthetic capsular device of FIG. 5A along the line 5E-5E of FIG. 5C. FIG. 5F illustrates another side plan view of the example prosthetic capsular device of FIG. 5A. FIG. 5G illustrates a cross-sectional view of the example prosthetic capsular device of FIG. 5A along the line 5G-5G of FIG. 5F.

In certain embodiments, only one end of a haptic 502 is anchored or over-molded on a sidewall 302A, 302B of the device 500. For example, in the embodiment illustrated in FIG. 5A, one of a haptic 502A can be over-molded onto a sidewall 302A, while the other end of the haptic 502A is not molded or rigidly anchored to the other sidewall 302B. Likewise, only one end of haptic 502B can be molded or rigidly anchored to the same sidewall 302A that haptic 502A is anchored to, while the other end of the haptic 502B is not rigidly anchored to the other sidewall 302B. The other end of the haptic 502B can be configured to be tucked into the interior of the other sidewall 302B similar to a safety-pin-like configuration.

In some embodiments, the device 500 comprises a ridge 504 on one or more sidewalls 302A, 302B for receiving and/or embedding the haptics 502 without rigidly anchoring the haptic 502. For example, in certain embodiments, only one of two sidewalls 302B comprises said ridge 504. The other sidewall 302A does not comprise a ridge 504 in some embodiments. Within the ridge 504, the haptics 502A, 502B can be free to move along the ridge 504. For example, the end of a haptic 502 can be allowed to move up and down along the length of the ridge 504 as the exposed portion of the haptic 502 is compressed or allowed to expand.

In certain embodiments, a device 500 that comprises a ridge 504 on only one of two sidewalls 302B can be configured to be injected into the eye in a general direction from the other sidewall 302A without a ridge towards the sidewall 302B with the ridge 504. Insertion into the eye in this general direction will allow the exposed portion of the haptics 502 to compress more closely towards the refractive surface 110 as the ends of the haptics 502 will be allowed to move more into the ridge 504.

Once implanted within the eye, the device 500 can be allowed to unfold naturally. The haptics 502 can be allowed to naturally decompress as well, moving the ends of the haptics 502 more towards the openings of the ridge 504. Accordingly, the device 500 can comprise radially extending haptics 502 to maintain the shape and/or size of the natural capsular bag without the ends thereof adding complications to the surgical procedure. In some embodiments, when in an expanded or relaxed state, the outermost perimeter or portion of the sidewalls 302A, 302B and the haptics 502A, 502B can form a perfect or substantially perfect circle with a constant radius or diameter. For example, in some embodiments, an outer or maximum diameter of the device 500, accounting for the haptics 502, may be about 10 mm. In certain embodiments, the outer or maximum diameter of the device 500 can be about 7 mm, about 8 mm, about 9 mm, about 10 mm, about 11 mm, about 12 mm, about 13 mm, and/or within a range defined by two of the aforementioned values.

In certain embodiments, because portions of the haptics 502 can be squeezed and/or hidden during the surgical implantation, the device 500 can be injected in a manner substantially similar to those used for devices without such radially extending haptics, such as the device 100 illustrated in FIG. 1A. At the same time, because the haptics 502 are allowed to radially expand once the device 500 is implanted, the haptics 502, made of polyimide for example, can provide sufficient points of attachment for epithelial cells to anchor the device 500.

Figure 6B:
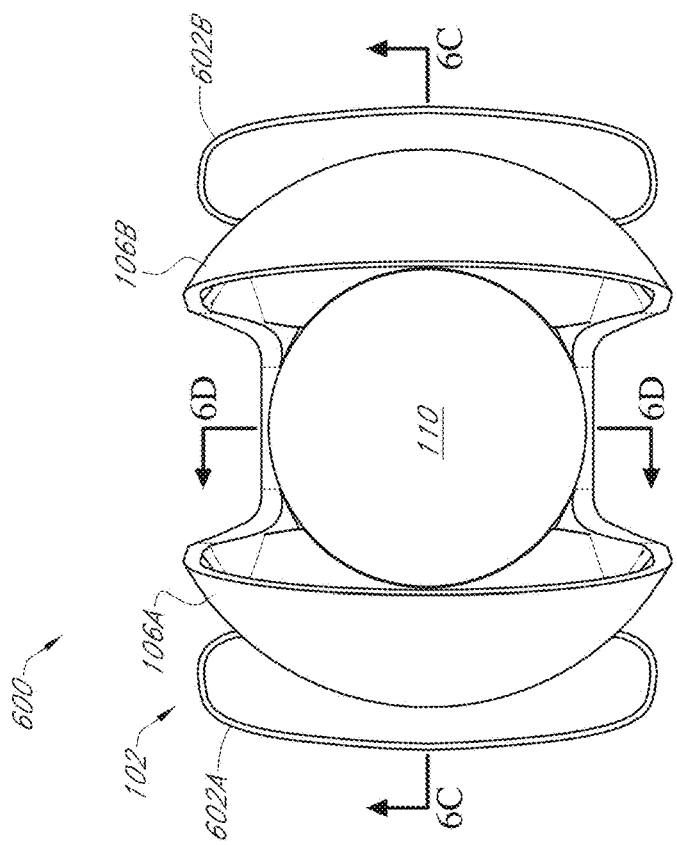
FIG. 6B is an anterior plan view of the example prosthetic capsular device of FIG. 6A.
Figure 6A:
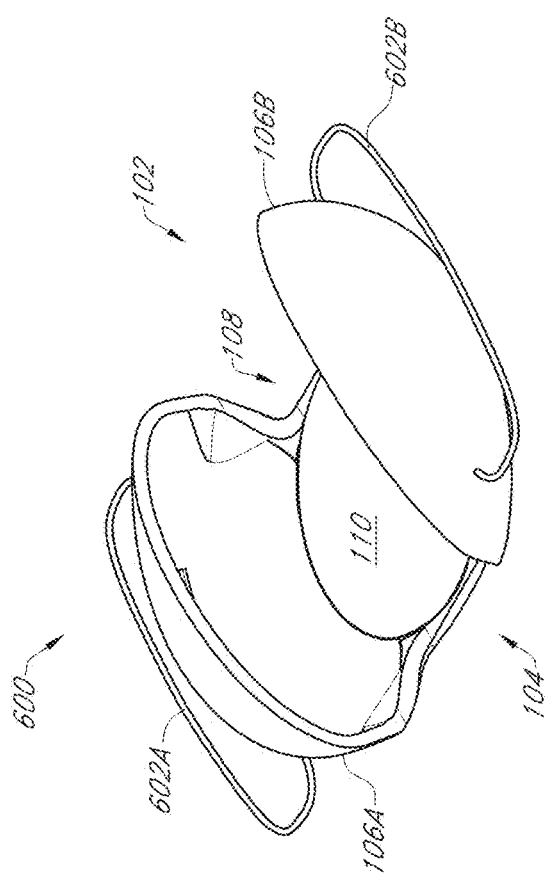
FIG. 6A is an anterior side perspective view of another example prosthetic capsular device.
Figure 6D:
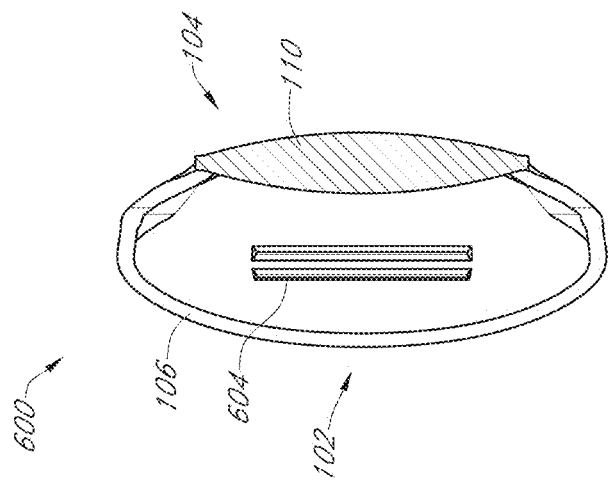
FIG. 6D is a cross-sectional view of the example prosthetic capsular device of FIG. 6A along the line 6D-6D of FIG. 6B.
Figure 6C:
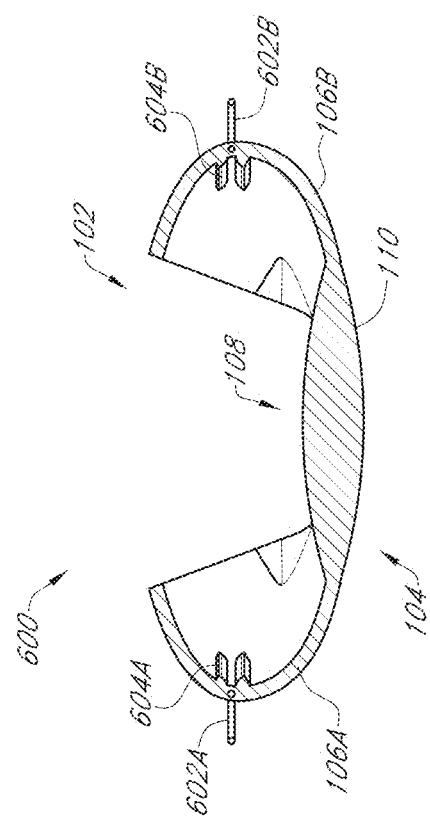
FIG. 6C is a cross-sectional view of the example prosthetic capsular device of FIG. 6A along the line 6C-6C of FIG. 6B.

FIG. 6A illustrates an anterior side perspective view of another example prosthetic capsular device. FIG. 6B illustrates an anterior plan view of the example prosthetic capsular device of FIG. 6A. FIG. 6C illustrates a cross-sectional view of the example prosthetic capsular device of FIG. 6A along the line 6C-6C of FIG. 6B. FIG. 6D illustrates a cross-sectional view of the example prosthetic capsular device of FIG. 6A along the line 6D-6D of FIG. 6B.

The prosthetic capsular device 600 of FIG. 6A includes some or all of the features of the prosthetic capsular devices of FIGS. 1A-5A, and like reference numerals include like features. In particular, the prosthetic capsular device 600 of FIG. 6A can be similar to the prosthetic capsular devices of FIGS. 1A and 2A, except for the haptics 112, 202 and/or other additional features.

More specifically, the device 600 can comprise one or more haptics 602 that extend radially outward from and to a single or same sidewall 106. For example, one end of a haptic 602 can be over-molded or otherwise be anchored to a portion of one sidewall 106, and the other end of the same haptic 602 can be over-molded or otherwise be anchored to another portion of the same sidewall 106, the portion of the haptic 602 in between the two ends forming a loop extending out of the sidewall 106. Each of the haptics 602 can form a closed loop. As a result, epithelial cells can be promoted to grow around the haptics 602 to substantially affix the device 600 within the eye.

In certain embodiments, one or more haptics 602 can be made of Gore-Tex or other soft material, and the rest of the device 600 can be made of silicone. The whole device 600 can be made exclusively of soft material in some embodiments, which can resolve concerns with implanting sharp or rigid materials. Also, cellular ingrowth can be facilitated, for example due to Gore-Tex's high biocompatibility in some embodiments. Accordingly, in some embodiments, a haptic comprises a single Gore-Tex string or tether, for example extending in a loop-like configuration out of a sidewall. Such Gore-Tex string or tether can provide a natural place for a fibrotic anchor to attach and also prevent the device 600 from slipping. As such, in certain embodiments, the natural capsular bag can be maintained in an open position due to the structural integrity of the device 600 and the Gore-Tex without need of a sharp or rigid material such as polyimide.

The device 600 can comprise a major axis, for example from a horizontal outermost portion of one haptic 602A to a horizontal outermost portion of another haptic 602B. The distance between horizontal outermost portions of the two haptics 602A, 602B can be about 11.15 mm in some embodiments. In other embodiments, the distance between horizontal outermost portions of the two haptics 602A, 602B can be about 5 mm, about 6 mm, about 7 mm, about 8 mm, about 9 mm, about 10 mm, about 11 mm, about 12 mm, about 13 mm, about 14 mm, about 15 mm, and/or within a range defined by two of the aforementioned values.

The device 600 can comprise a minor axis, for example from a vertical outermost portion of one haptic 602A, 602B to a vertical outermost portion of the same haptic 602A, 602B. The distance between vertical outermost portions of a single haptics 602A, 602B can be about 7.95 mm in some embodiments. In other embodiments, the distance between vertical outermost portions of a single haptic 602A, 602B can be about 5 mm, about 5.5 mm, about 6 mm, about 6.5 mm, about 7 mm, about 7.5 mm, about 8 mm, about 8.5 mm, about 9 mm, about 9.5 mm, about 10 mm, about 10.5 mm, about 11 mm, about 11.5 mm, about 12 mm, about 13 mm, about 14 mm, about 15 mm, and/or within a range defined by two of the aforementioned values.[0246] The device 600 can also comprise one or more notches 604. For example, in the illustrated embodiment, each capsular area comprises a notch 604A, 604B along the interior of each capsular area or sidewall 106A, 106B. The notch 604 can comprise one or more recessed areas or slots for insertion of one or more additional devices. For example, in some embodiments, the notch 604 can comprise one or more slots configured for insertion of a secondary IOL, an electronic device, and/or haptics of the secondary IOL electronic device or other secondary device. By providing a slot or recessed area, a secondary device can be inserted into the device 600 at a precise location within the device 600 and be stabilized at that location by preventing movement of the secondary device laterally, anteriorly and/or posteriorly within the device 600. For example, a secondary IOL can be inserted into the device 600 such that a distance between the secondary IOL and the refractive surface 110 is known and/or predetermined. Accordingly, one can determine an optimal or particular power of a secondary IOL based on the known refractive power of the refractive surface 110 and the known distance between the secondary IOL and the refractive surface 110. One or more functional aspects of an electronic device to be inserted into the device 600 may also depend on the particular location of the electronic device within the device 600 and/or particular distance from the refractive surface 110, which can be predetermined and/or controlled utilizing the one or more notches 604.

The device 600 can comprise a plurality of notches or slots 604 on the interior surface of each capsular area or sidewall 106A, 106B. Referring to the cross-section view along line 6D-6D as illustrated in FIG. 6D for example, a plurality of vertical notches or slots 604 can be formed generally parallel to one another. In other words, in addition to the vertical notch or slot 604 shown in FIG. 6D, one or more additional vertical notches or slots can be provided to the left and/or right of the illustrated notch or slot 604. This can allow for one or more secondary IOLs, electronic devices, or other devices to be inserted into the device 600 at varying locations or distances from the refractive surface 110. By doing so, one can control the particular location of insertion of a secondary device in the device 600 by selecting one of the plurality of notches or slots to hold the secondary device. In other words, the secondary device can be adjusted anteriorly and/or posteriorly within the device 600 when being inserted.

In some embodiments, a width of a notch or slot 604 can be about 0.142 mm wide. In certain embodiments, the width of a notch or slot 604 can be about 0.05 mm, about 0.1 mm, about 0.11 mm, about 0.12 mm, about 0.13 mm, about 0.14 mm, about 0.15 mm, about 0.16 mm, about 0.17 mm, about 0.18 mm, about 0.19 mm, about 0.2 mm, about 0.21 mm, about 0.22 mm, about 0.23 mm, about 0.24 mm, about 0.25 mm, and/or within a range defined by two of the aforementioned values.

In some embodiments, a length of a notch or slot 604 can be about 3.77 mm. In certain embodiments, the length of a notch or slot 604 can be about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, and/or within a range defined by two of the aforementioned values.

The sidewalls 106A, 106B when viewed in the direction illustrated in FIG. 6C can be separated by about 42° in some embodiments. In certain embodiments, the angle formed between the sidewalls 106A, 106B when viewed in the direction illustrated in FIG. 6C can be about 36°, about 37°, about 38°, about 39°, about 40°, about 41°, about 42°, about 43°, about 44°, about 45°, about 46°, about 47°, and/or within a range defined by two of the aforementioned values.

Figure 7D:
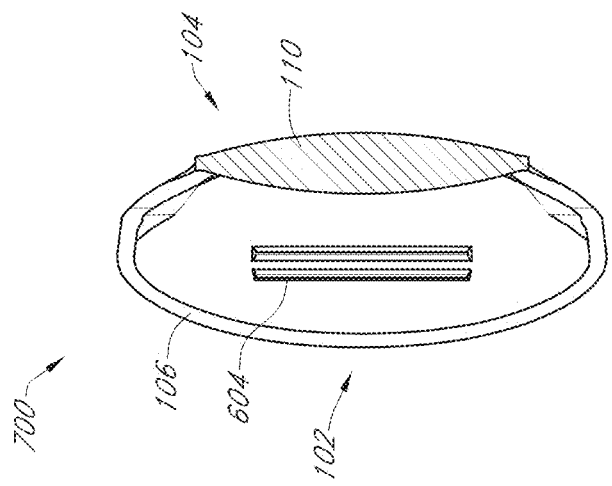
FIG. 7D is a cross-sectional view of the example prosthetic capsular device of FIG. 7A along the line 7D-7D of FIG. 7B.
Figure 7C:
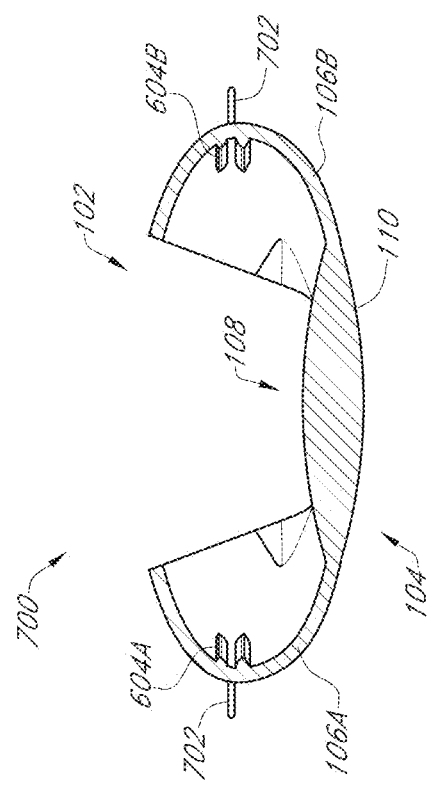
FIG. 7C is a cross-sectional view of the example prosthetic capsular device of FIG. 7A along the line 7C-7C of FIG. 7B.

FIG. 7A illustrates an anterior side perspective view of another example prosthetic capsular device. FIG. 7B illustrates an anterior plan view of the example prosthetic capsular device of FIG. 7A. FIG. 7C illustrates a cross-sectional view of the example prosthetic capsular device of FIG. 7A along the line 7C-7C of FIG. 7B. FIG. 7D illustrates a cross-sectional view of the example prosthetic capsular device of FIG. 7A along the line 7D-7D of FIG. 7B.

The prosthetic capsular device 700 of FIG. 7A includes some or all of the features of the prosthetic capsular devices of FIGS. 1A-6A, and like reference numerals include like features. In particular, the prosthetic capsular device 700 of FIG. 7A can be similar to the prosthetic capsular device of FIGS. 1A, 2A, and 6A, except for the haptics 112, 202, 602.

As with device 600 of FIG. 6A, the device 700 can comprise one or more haptics 702 that extend radially outward from and to a single or same sidewall 106. However, unlike the device 600 of FIG. 6A, each sidewall 106 of the device 700 can comprise more than one such haptics 702. For example, in the illustrated embodiment, each sidewall 106 or capsular area comprises two haptics 702 in a closed loop configuration. By having more than one haptics extending from each sidewall 106 or capsular area, epithelial cells can attach to the more than one haptics and prevent or substantially prevent the device 700 from sliding into a disadvantageous position, which may be a higher risk for the device 600 of FIG. 6A.

More specifically, a sidewall 106A can comprise a first haptic 702A that extends radially outward from one end of the sidewall 106A towards a center of the sidewall. The same sidewall 106A can also comprise a second haptic 702B that extends radially outward from another end of the sidewall 106A towards the center of the sidewall. Similarly, a second sidewall 106B can comprise a third haptic 702C that extends radially outward from one end of the sidewall 106B towards a center of the sidewall. The sidewall 106B can also comprise a fourth haptic 702D that extends radially outward from another end of the sidewall 106B towards the center of the sidewall. In other embodiments, a single sidewall 106 can comprise three, four, five, six, seven, eight, nine, or ten haptics 702. Any one or more feature of the haptics 702, such as material, flexibility, rigidity, attachment to the device 700, or the like, can be similar to the haptics 602 of the device 600 in FIG. 6A.

When viewed in the direction illustrated in FIG. 7B, a distance between a bottom end of one haptic 702A, 702D and a top end of another haptic 702B, 702C can be about 1 mm. In certain embodiments, the distance between a bottom end of one haptic 702A, 702D and a top end of another haptic 702B, 702C when viewed in the direction illustrated in FIG. 7B can about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, and/or within a range defined by two of the aforementioned values.

Figure 8B:
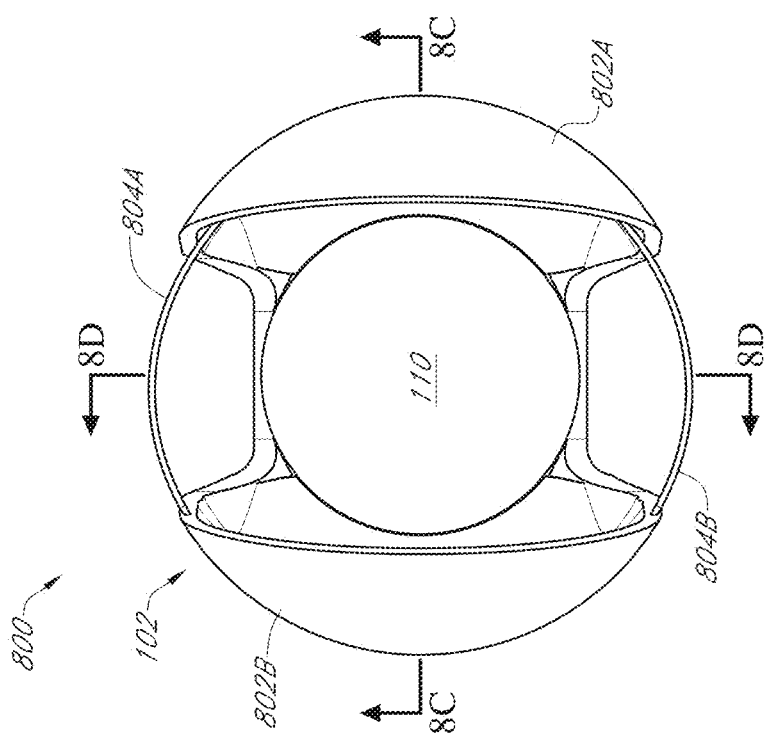
FIG. 8B is an anterior plan view of the example prosthetic capsular device of FIG. 8A.
Figure 8A:
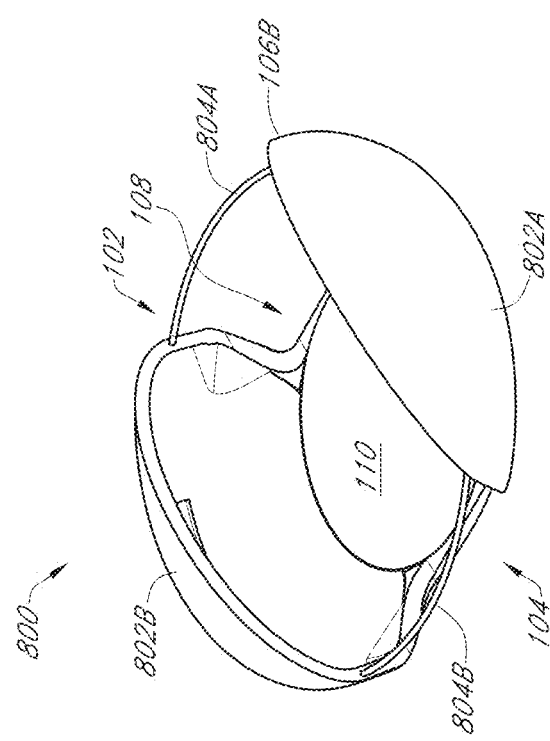
FIG. 8A is an anterior side perspective view of another example prosthetic capsular device.

FIG. 8A illustrates an anterior side perspective view of another example prosthetic capsular device. FIG. 8B illustrates an anterior plan view of the example prosthetic capsular device of FIG. 8A. FIG. 8C illustrates a cross-sectional view of the example prosthetic capsular device of FIG. 8A along the line 8C-8C of FIG. 8B. FIG. 8D illustrates a cross-sectional view of the example prosthetic capsular device of FIG. 8A along the line 8D-8D of FIG. 8B.

The prosthetic capsular device 800 of FIG. 8A includes some or all of the features of the prosthetic capsular devices of FIGS. 1A-7A, and like reference numerals include like features. In particular, the prosthetic capsular device 800 of FIG. 8A can be similar to the prosthetic capsular device of FIG. 2A, except for the haptics 202 and shape or configuration of the one or more sidewalls 106.

More specifically, the one or more sidewalls 802 of the device 800 can be larger than those of the device 200 of FIG. 2A. For example, the one or more sidewalls 802 can extend vertically upwards and/or downwards when viewed in an anterior side plan view as illustrated in FIG. 8B. As a result, the curvature of the outer periphery of the one or more sidewalls 802 can be larger than sidewalls 106 of the device 200 of FIG. 2A for example. The general shape of the outer periphery of the device 800 can be substantially circular when viewed from an anterior or posterior plan view, compared to the lenticular shape of some of the other devices described above in relation to FIG. 1A for example.

Similar to sidewalls 106A, 106B illustrated in other embodiments, the sidewalls 802A, 802B, when viewed in the direction illustrated in FIG. 8C can be separated by about 41° in some embodiments. In certain embodiments, the angle formed between the sidewalls 802A, 802B, when viewed in the direction illustrated in FIG. 8C, can be about 36°, about 37°, about 38°, about 39°, about 40°, about 41°, about 42°, about 43°, about 44°, about 45°, about 46°, about 47°, about 48°, about 49°, about 50°, and/or within a range defined by two of the aforementioned values.

In some embodiments, a substantially circular outermost periphery of the device 800 can comprise a diameter of about 9.68 mm. In certain embodiments, the outermost periphery of the device 800 can comprise a substantially circular shape with a diameter of about 6 mm, about 6.5 mm, about 7 mm, about 7.5 mm, about 8 mm, about 8.5 mm, about 9 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, about 15 mm, and/or within a range defined by two of the aforementioned values.

The device 800 can comprise a thickness between an anterior side 102 and a posterior side 104 of about 3.707 mm when viewed from the side as illustrated in FIG. 8D. In certain embodiments, the device 800 can comprise a thickness between an anterior side 102 and a posterior side 104 of about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, about 5 mm, and/or within a range defined by two of the aforementioned values.

In addition, due to the larger curvature of the one or more sidewalls 802, the one or more haptics 804 can comprise an arc of a substantially circular configuration from one end to the other end. In contrast, the one or more haptics 202 of the device 200 of FIG. 2A can comprise different curvatures along the haptic 202. More specifically, the curvature of the haptic 202 can be relatively flat on one or both ends of the haptic 202 located inside or behind a sidewall 106 or capsular area compared to the curvature of the central portion of the haptic 202.

Similar to the device 500 of FIG. 5A, the one or more haptics 804 can be over-molded or otherwise anchored to only one sidewall. For example, in the illustrated embodiment, a first end of the haptics 804A, 804B can be over-molded or otherwise anchored to one sidewall 802B. A second end of the haptics 804A, 804B can be configured to be tucked into the interior of the other sidewall 802A without being rigidly anchored to the sidewall 802A. As such, the second end of the haptics 804A, 804B can be inserted freely more or less into the other sidewall 802A as the exposed central portion of the haptics 804A, 804B is compressed or allowed to expand.

Also similar to the device 500 of FIG. 5A, the device 800 can be configured to be injected into the eye in a general direction from the sidewall 802B to which the haptics 804 is anchored towards the other sidewall 802B to which the haptics 804 is configured to be tucked into. Insertion into the eye in this general direction will allow the exposed portion of the haptics 804 to compress more closely towards the refractive surface 110 during insertion.

Once implanted within the eye, the device 800 can be allowed to unfold naturally, allowing the haptics 804 to naturally decompress. Because portions of the haptics 804 can be squeezed and/or hidden during the surgical implantation, the device 500 can be injected in a manner substantially similar to those used for devices without such radially extending haptics, such as the device 100 illustrated in FIG. 1A. At the same time, because the haptics 804 are allowed to radially expand once the device 800 is implanted, the haptics 804, made of polyimide for example, can provide sufficient points of attachment for epithelial cells to anchor the device 800. Any one or more other feature of the haptics 804, such as material, flexibility, rigidity or the like, can be similar to the haptics 602 of the device 600 in FIG. 6A.

Figure 9B:
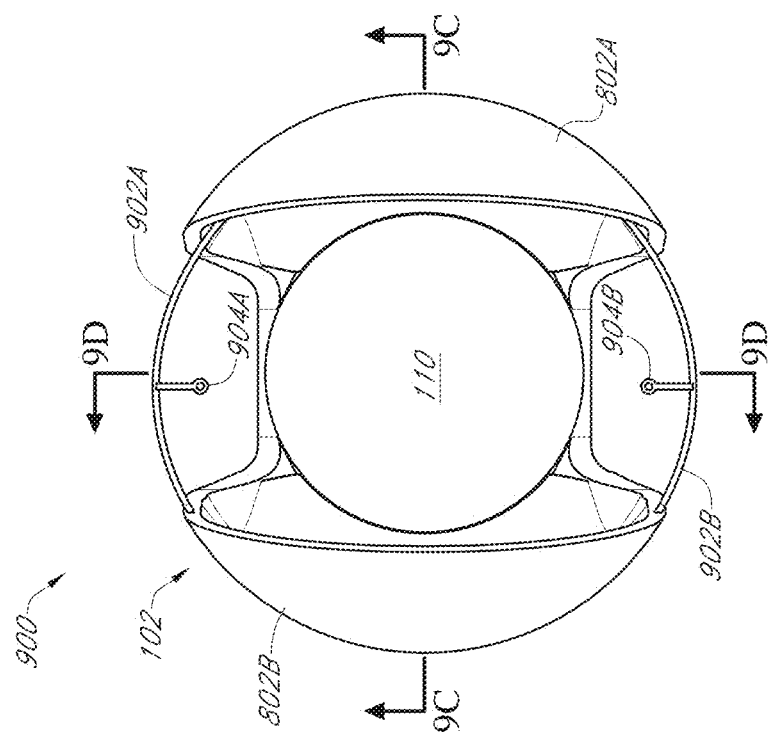
FIG. 9B is an anterior plan view of the example prosthetic capsular device of FIG. 9A.
Figure 9A:
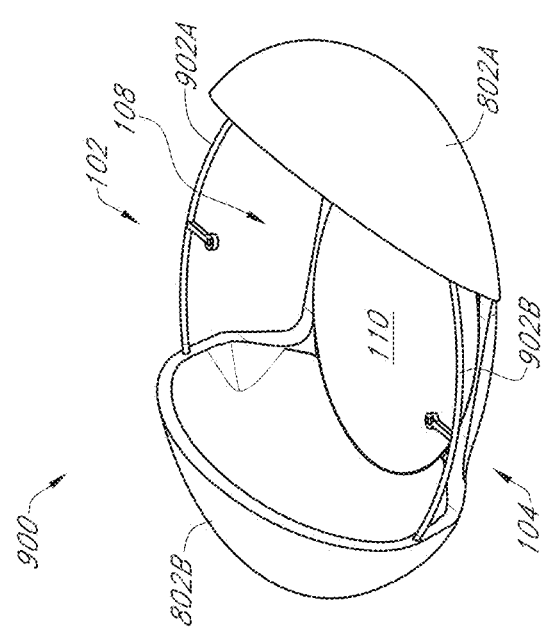
FIG. 9A is an anterior side perspective view of another example prosthetic capsular device.

FIG. 9A illustrates an anterior side perspective view of another example prosthetic capsular device. FIG. 9B illustrates an anterior plan view of the example prosthetic capsular device of FIG. 9A. FIG. 9C illustrates a cross-sectional view of the example prosthetic capsular device of FIG. 9A along the line 9C-9C of FIG. 9B. FIG. 9D illustrates a cross-sectional view of the example prosthetic capsular device of FIG. 9A along the line 9D-9D of FIG. 9B.

The prosthetic capsular device 900 of FIG. 9A includes some or all of the features of the prosthetic capsular devices of FIGS. 1A-8A, and like reference numerals include like features. In particular, the prosthetic capsular device 900 of FIG. 9A can be similar to the prosthetic capsular device of FIG. 8A, except for the haptics 804. More specifically, the haptics 902 of the device 900 can comprise a substantially vertical arm that extends radially inward towards the refractive surface 110 from a midpoint or a portion in between the two ends of the haptics 902 that is exposed. A first end of the vertical arm can be connected to the exposed portion of the haptics 902, while a second end of the vertical arm can be connected to one or more holes or openings 904.

The one or more holes or openings 904 can allow a surgical instrument, such as a Sinskey Hook, a Lester Hook or the like, to hook on and engage the device 900. For example, a surgical instrument can be coupled to one or more holes 904 to adjust the positioning of the device 900 in the eye. This can be advantageous during surgery because of the limited visual field, which can be for example about 5-6 mm. By coupling a surgical instrument to the one or more holes 904, the positioning of the device 900 can be adjusted so that it is viewable without risking damaging or tearing the capsule. Any other one or more features of the device 900 and/or haptics 902, such as size, material, flexibility, rigidity, attachment to the device 900 or the like, can be similar to the device 800 and/or haptics 804 of the device 800 in FIG. 8A.

Figure 10B:
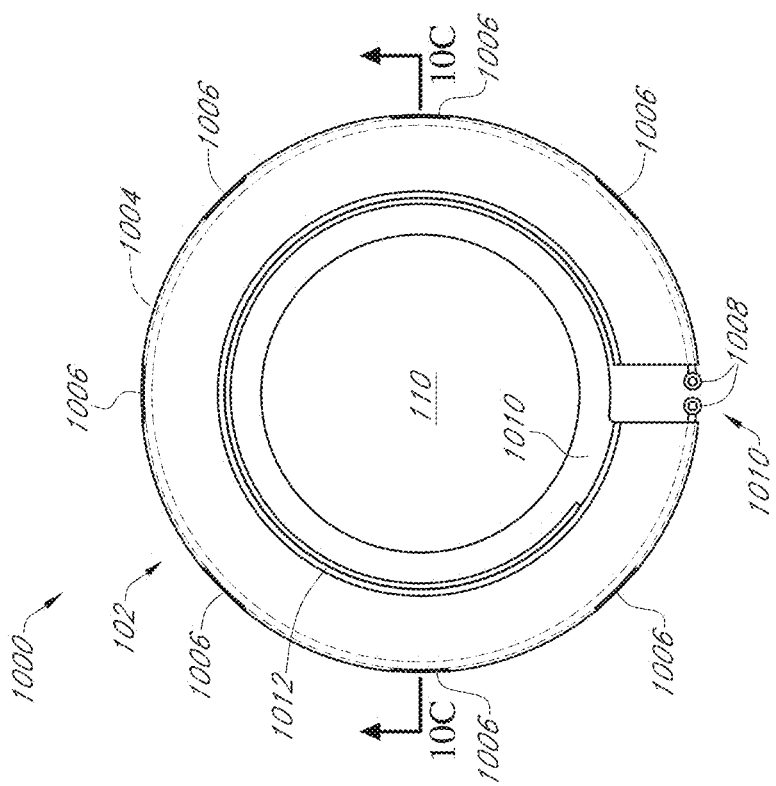
FIG. 10B is an anterior plan view of the example prosthetic capsular device of FIG. 10A.
Figure 10A:
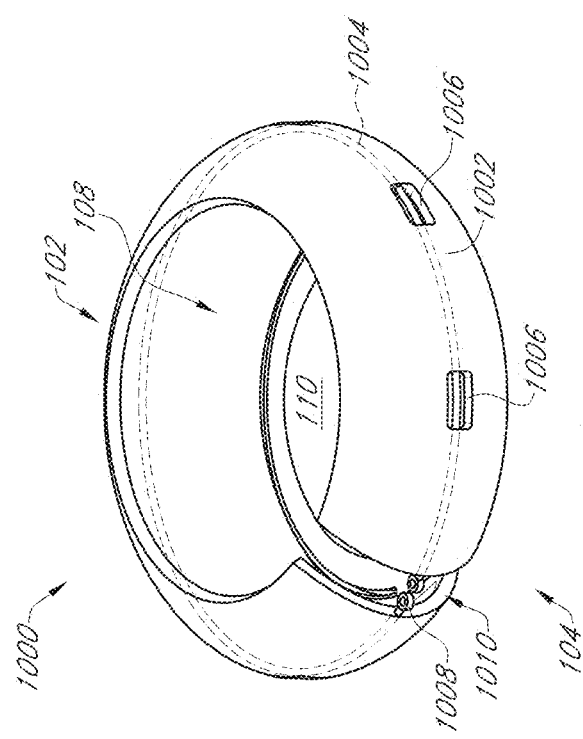
FIG. 10A is an anterior side perspective view of another example prosthetic capsular device.

FIG. 10A illustrates an anterior side perspective view of another example prosthetic capsular device. FIG. 10B illustrates an anterior plan view of the example prosthetic capsular device of FIG. 10A. FIG. 10C illustrates a cross-sectional view of the example prosthetic capsular device of FIG. 10A along the line 10C-10C of FIG. 10B. FIG. 10D illustrates a side plan view of the example prosthetic capsular device of FIG. 10A. The prosthetic capsular device 1000 of FIG. 10A includes some or all of the features of the prosthetic capsular devices of FIG. 1A-9A, and like reference numerals include like features.

Unlike some of the devices of FIGS. 1A-9A, the device 1000 can comprise a sidewall 1002 that covers substantially or almost the entire side circumference of the device 1000. The sidewall 1000 can continuously cover almost the entire side of the device 1000 except for a small opening or gap 1010. In the illustrated embodiment, the small opening or gap 1010 can comprise a width of about 1.00 mm. In other embodiments, this gap 1010 in the sidewall 1002 can be about 0.50 mm, about 1.50 mm, about 2.00 mm, about 2.50 mm, about 3.00 mm, about 3.50 mm, about 4.00 mm, about 4.50 mm, about 5.00 mm, and/or within a range defined by two of the aforementioned values. One or more other features of the sidewall, such as material, flexibility, rigidity, or the like can be similar to those of one or more devices of FIGS. 1A-9A. In other embodiments, the sidewall 1002 may not comprise a gap 1010. For example, additional portions of silicone may extend over the gap 1010 in the illustrated embodiment.

The device 1000 can comprise a capsular tension ring 1004 coupled to the sidewall. For example, the capsular tension ring 1004 can be over-molded into the sidewall 1002. The capsular tension ring 1004 can comprise a rigid or semi-rigid material, such as polyimide, PMMA, polypropylene, and/or nylon. The capsular tension ring 1004 can provide rigidity and maintain the structure and/or position of the device 1000 inside the eye after implantation. The capsular tension ring 1004 can generally follow the shape of the circumference of the sidewall 1002 as in the illustrated embodiment. Each end of the capsular tension ring 1004 can extend from each end of the sidewall 1002 where the gap 1010 in the sidewall 1002 is present. Each or one end of the capsular tension ring 1004 can comprise an opening or a hole 1008, similar to the holes 904 in the device 900 of FIG. 9A and be used in a similar manner to position the device 1000 after implantation in the eye.

The device 1000 can comprise one or more recessed areas 1006 along the exterior of the sidewall 1002. The one or more recessed areas can expose portions of the capsular tension ring 1004. The exposed portions of the capsular tension ring 1004 can provide areas for epithelial cells to attach to. Accordingly, with the attachment or growth of epithelial cells around the exposed capsular tension ring 1004, the device 1000 can be substantially fixed and stabilized in a particular position within the eye. The recessed areas 1006 can also be used to suture the device as necessary. In the illustrated embodiment, the device 1000 or exterior sidewall 1002 thereof comprises seven recessed areas 1006. In other embodiments, the device 1000 can comprise one, two, three, four, five, six, eight, nine, or ten recessed areas 1006. The number of recessed areas 1006 in the device 1000 can also be between a range defined two of the aforementioned values.

As illustrated in the view of FIG. 10B, the length of each recessed area 1006 along the circumference of the sidewall 1002 or the length of each exposed portion 1006 of the capsular tension ring 1004 can be about 1.00 mm. In certain embodiments, the length of each recessed area 1006 along the circumference of the sidewall 1002 or the length of each exposed portion 1006 of the capsular tension ring 1004 can be about 0.50 mm, about 1.50 mm, about 2.00 mm, about 2.50 mm, about 3.00 mm, about 3.50 mm, about 4.00 mm, about 4.50 mm, about 5.00 mm, and/or within a range defined by two of the aforementioned values.

As illustrated in the view of FIG. 10D, the width of each recessed area 1006, when viewed from a side plan view, can be about 0.49 mm. In certain embodiments, the width of each recessed area 1006, when viewed from a side plan view, can be about 0.35 mm, about 0.40 mm, about 0.45 mm, about 0.50 mm, about 0.55 mm, about 0.60 mm, about 0.65 mm, about 0.70 mm and/or within a range defined by two of the aforementioned values.

The refractive surface 110 can be connected to the sidewall 1002 at only a portion of the sidewall. For example, in the illustrated embodiment, the refractive surface 100 comprises a hinge portion 1010 which is connected to the sidewall 1002. A gap 1012 can exist between all other portions of the refractive surface 110 other than the hinge portion 1010 and the sidewall 1002. As such, the entire device 1000 can comprise a single piece, rather than a multi-piece assembly. Alternatively, in other embodiments, the device 1000 can be a multi-piece assembly comprising multiple pieces that are coupled together after the initial manufacturing.

The sidewall 1002 and the capsular tension ring 1004 can be configured to be twisted without breaking. Also, the sidewall 1002 can be foldable or capable of being rolled into a more compact configuration. The refractive surface 1010 and the hinge portion 1010 can also be foldable or capable of being rolled into a more compact configuration.

As discussed above, one advantage of removing portions of the sidewall, for example in the device 100 of FIG. 1A, can be to allow the device to be folded or rolled in a more compact configuration for insertion through a small incision during surgery. Even though the device 1000 of FIG. 10A comprises a near continuous sidewall, it can still be configured to be inserted through a small incision, for example no larger than required for insertion of the device 100 of FIG. 1A, without removing portions of the sidewall 1002, due to the structure and method of insertion as described herein.

More specifically, instead of squeezing the device 1000 for insertion, the device 1000 or the sidewall 1002 and/or capsular tension ring 1004 of the device 1000 can be inserted into the eye in a rotational fashion segment by segment through a standard injector. For example, the sidewall 1002 can be folded or rolled around the length of the capsular tension ring 1004 into a tube-like configuration. The sidewall 1002 and capsular tension ring 1004 can be optionally twisted or otherwise partially straightened. A portion of the sidewall 1002 and/or capsular tension ring 1004 can be fed into a small incision in the eye, advancing one portion at a time rotationally, for example as each portion is substantially straightened at the point of insertion, allowing the capsular tension ring 1004 to retain its memory and curl around upon insertion.

The end of the sidewall 1002 and capsular tension ring 1004 away from the hinge portion 1010 can be inserted first towards the other end where the hinge portion 1010 is attached to. Upon reaching the portion of the sidewall 1002 and capsular tension ring 1004 where the hinge portion 1010 is attached, the refractive surface 110 can be slid into the injector and into the eye in a linear fashion. In other words, the sidewall 1002 and capsular tension ring 1004 can be inserted through a small incision into the eye in a rotational manner first and the lens or refractive surface 110 can be subsequently inserted in a longitudinal manner.

Once completely inserted into the eye, the device 1000 can return to its substantially circular configuration. By doing so, the device 1000 can be inserted through a small incision, while maintaining the structural integrity necessary for the device 1000 to remain intact and centered in the eye for a substantial period of time.

The device 1000 can be configured to protect the entire capsule and preserve the entire capsular space. More specifically, all or substantially the entire the circular or substantially circular sidewall 1002 or outer circumference of the device 1000 can be configured to contact the natural capsular bag and maintain the general space of the natural capsular bag without collapsing in the vitreous. Also, the device 1000 eliminates any trail in the haptics, with the capsular tension ring 1004 embedded inside the device. The generally circular shape of the device 1000 can also follow the physiological shape of the capsule and preserve the volume of the capsule unlike certain devices that decrease the open volume inside after implantation. Also, the device and/or secondary lens to be placed inside the device 1000 may be freely rotated, which may not be possible with certain devices.

The refractive surface 110 can also comprise one or more tabs extending radially outward from the outer circumference of the refractive surface 110. The one or more tabs can be configured to be placed or tucked underneath the sidewall 1002 after insertion to prevent the refractive surface 110 from being tilted over. The one or more tabs can comprise the same material as the sidewall 1002, for example silicone.

Alternatively, the refractive surface 110 can be circumferentially surrounded by a flange of soft material, such as silicone. The width of the flange can be about 0.25 mm, about 0.50 mm, 0.75 mm, 1.00 mm, or between a range defined by two of the aforementioned values. The outer flange of the refractive surface 110 or some portion thereof can be configured to be tucked underneath the bottom of the sidewall 1002 upon insertion into the eye.

Both the refractive surface 110 and the flange can be made of the same material, such as silicone. In other embodiments, the refractive surface 110 can be acrylic while the flange can be made of silicone. Acrylic can provide a higher index of refraction while allowing the refractive surface 110 to be thinner than when made from silicone. Also, the optical properties and power of an acrylic lens or refractive surface 110 can be altered using one or more laser treatments, such as phase wrapping to alter the hydrophilicity or hydrophobicity of the acrylic and causing the lens to either swell and increase in power or shrink and decrease in power. The lens or refractive surface 110 can also be made from any other biocompatible and optically clear materials known in the art. The refractive surface 110 may have a refractive power between −35 D and +35D.

Figure 11D:
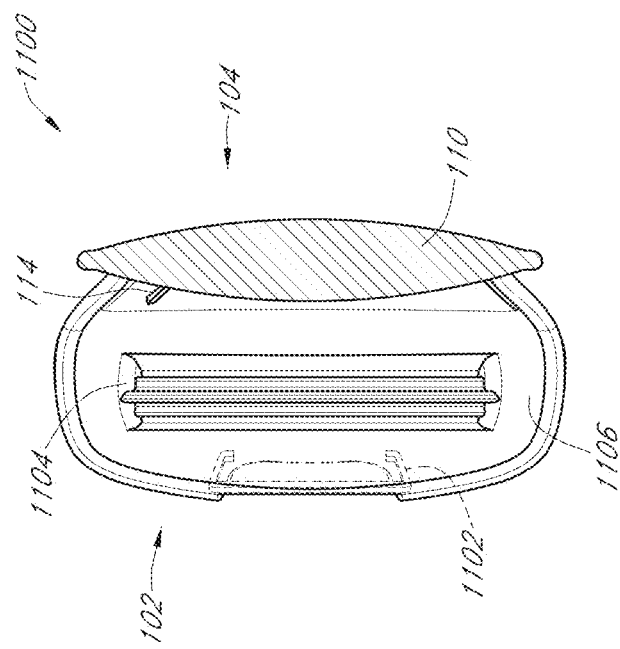
FIG. 11D is a cross-sectional view of the example prosthetic capsular device of FIG. 11A along the line 11D-11D of FIG. 11B.
Figure 11C:
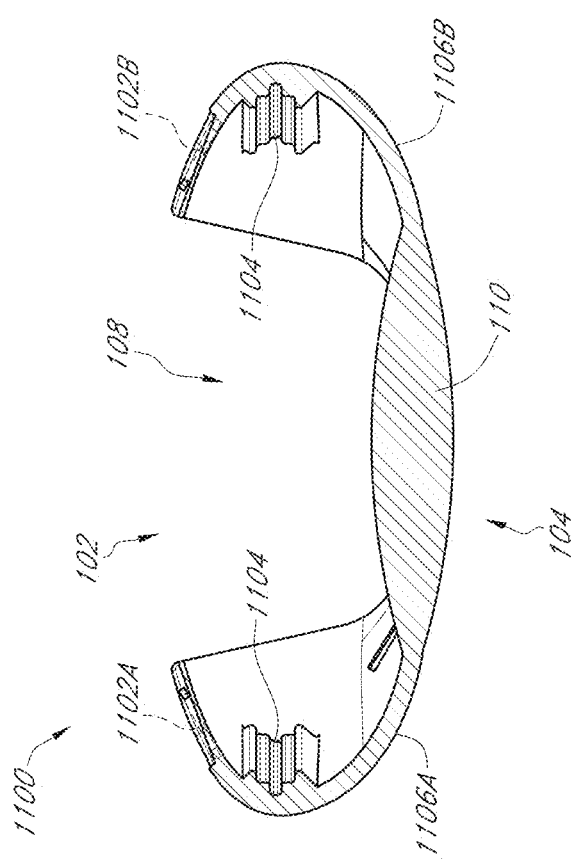
FIG. 11C is a cross-sectional view of the example prosthetic capsular device of FIG. 11A along the line 11C-11C of FIG. 11B.

FIG. 11A illustrates an anterior side perspective view of another example prosthetic capsular device. FIG. 11B illustrates an anterior plan view of the example prosthetic capsular device of FIG. 11A. FIG. 11C illustrates a cross-sectional view of the example prosthetic capsular device of FIG. 11A along the line 11C-11C of FIG. 11B. FIG. 11D illustrates a cross-sectional view of the example prosthetic capsular device of FIG. 11A along the line 11D-11D of FIG. 11B.

The prosthetic capsular device of FIG. 11A includes some or all of the features of the prosthetic capsular device of FIG. 1A-10A, and like reference numerals include like features. In particular, the prosthetic capsular device of FIG. 11A can be similar to the prosthetic capsular device of FIG. 1A and FIG. 6A, except for the configuration of notches 1104 and/or sidewalls 1106A, 1106B. All or some other features of the device 1100, notches 1104, and/or sidewalls 1106A, 1106B, such as material, flexibility, function, or the like, can be similar to such features described above in relation to FIGS. 1A-10A.

More specifically, the device 1100 can comprise one or more notches 1104 along the interior of each capsular area or sidewall 1106A, 1106B, similar to notches 604. A notch 1104 can comprise one or more recessed areas or slots to facilitate insertion of one or more additional devices, such as a secondary IOL, an electronic device, and/or a haptics thereof. Similar to the notch 604 and device 600 of FIG. 6A, a secondary device can be inserted into the device 1100 at a precise location within the device 1100 and be stabilized at that location by insertion of the secondary device or a portion thereof into the notch 1104. By doing so, a secondary device can be prevented from moving laterally, anteriorly and/or posteriorly within the device 1100. The notches 1104 can be molded together with the device 1100 at the same time as a single piece assembly. In other embodiments, the notches 1104 can be formed separately from the device 1100 and be subsequently attached to the device 1100.

When viewed in the cross section depicted in FIG. 11D, the one or more notches 1104 can comprise a generally elongated shape along the short axis, or the axis parallel to line 11F-11F of FIG. 11B. The one or more notches 1104 can be located at a predetermined and/or known distance from the anterior of the device 110. For example, in the embodiment illustrated in FIG. 11C, a distance between a center of the one or more notches 1104 and a top end of the interior anterior or refractive surface 110 can be about 1.23 mm, for example for a 20D lens. This distance can be different depending on the power and/or thickness of the lens or the refractive surface 110. For example, depending on the power of the lens or refractive surface 110, this distance can be about 0.50 mm, about 0.60 mm, about 0.70 mm, about 0.80 mm, about 0.90 mm, about 1.00 mm, about 1.10 mm, about 1.20 mm, about 1.30 mm, about 1.40 mm, about 1.50 mm, about 1.60 mm, about 1.70 mm, about 1.80 mm, about 1.90 mm, about 2.00 mm, and/or within a range defined by two of the aforementioned values.

The particular location of the one or more notches 1104 with respect to the overall device 1100 can also be measured in terms of a distance between the center of the one or more notches 1104 and the split point of the optic 110. For example, in certain embodiments, the two thirds of the power of the optic 110 can be configured to be placed inside the device 1100 while one third of the power of the optic 110 is located external to the device 1100. The split point, for example the ⅓, ⅔ split point, can be configured to be constant in the device 1100 regardless of the power of the lens 110. In other embodiments, the split point of the optic 110 may be ¼, ¾ or ½, ½. In other words, ¼, ½, or ¾ of the refractive power of the optic 110 can be configured to be located external to the device 1100 while ¾, ½, or ¼ of the refractive power of the optic 110 can be configured to be located internal to the device 1100.

The distance measured from the center of the notches 1104 to a split point of the optic 110, when viewed in the cross-sectional view illustrated in FIG. 11C, can be about 1.38 mm. This distance from the center of the notches 1104 to a split point of the optic 110 can be constant regardless of the power or thickness of the refractive surface 110. In certain embodiments, this distance can be about 0.50 mm, about 0.60 mm, about 0.70 mm, about 0.80 mm, about 0.90 mm, about 1.00 mm, about 1.10 mm, about 1.20 mm, about 1.30 mm, about 1.40 mm, about 1.50 mm, about 1.60 mm, about 1.70 mm, about 1.80 mm, about 1.90 mm, about 2.00 mm, and/or within a range defined by two of the aforementioned values.

In some embodiments, each of the notches 1104A, 1104B can comprise a vertical width of about 0.15 mm when viewed in the direction of FIG. 11C. In certain embodiments, each of the notches 1104A, 1106B, when viewed in the direction of FIG. 11C, can comprise a width of about 0.05 mm, about 0.1 mm, about 0.11 mm, about 0.12 mm, about 0.13 mm, about 0.14 mm, about 0.15 mm, about 0.16 mm, about 0.17 mm, about 0.18 mm, about 0.19 mm, about 0.2 mm, about 0.21 mm, about 0.22 mm, about 0.23 mm, about 0.24 mm, about 0.25 mm, and/or within a range defined by two of the aforementioned values.

In some embodiments, each of the notches 1104 can comprise an angular length of about 60° when measured from the center of the refractive 110 in an anterior plan view as illustrated in FIG. 11B. In certain embodiments, the angular length of each of the notches 1104, when measured from the center of the refractive 110 in an anterior plan view as illustrated in FIG. 11B, can be about 10°, about 20°, about 30°, about 40°, about 50°, about 60°, about 70°, about 80°, about 90°, about 100°, about 110°, about 120°, about 130°, about 140°, about 150°, about 160°, about 170°, and/or within a range defined by two of the aforementioned values.

The sidewalls 1106A, 1106B, when viewed in the direction illustrated in FIG. 11C, can be separated by about 25° in some embodiments. In certain embodiments, the angle formed between the sidewalls 1106A, 1106B, when viewed in the direction illustrated in FIG. 11C, can be about 10°, about 15°, about 20°, about 25°, about 30°, about 35°, about 40°, about 45°, about 50°, about 55°, about 60°, about 65°, about 70°, about 75°, about 80°, and/or within a range defined by two of the aforementioned values.

The device 1100 can be configured to be folded, rolled, or otherwise compressed and injected into the eye through a small incision and/or small injector as device 100 described above in relation to FIG. 1A. For example, in some embodiments, the device 1100 can be inserted through an incision of about 2.75 mm or less. In other embodiments, the device 1100 can be inserted into the eye through an incision of about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, about 3.5 mm, and/or within a range defined by two of the aforementioned values.

Figure 12A:
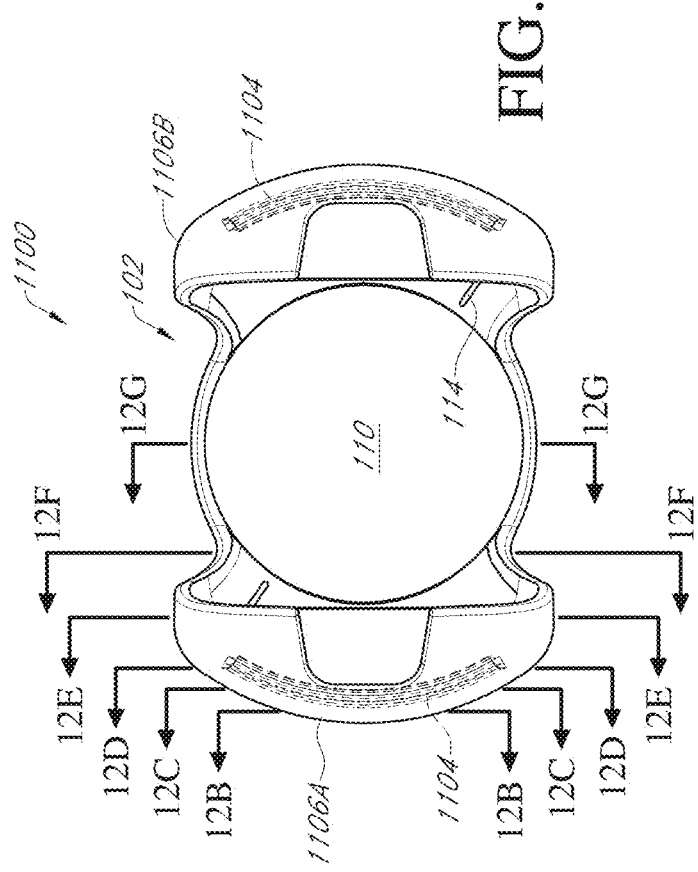
FIG. 12A is another anterior plan view of the example prosthetic capsular device of FIG. 11A.
Figure 12D:
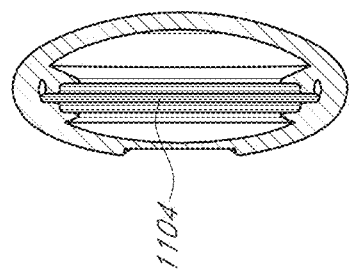
FIG. 12D is a cross-sectional view of the example prosthetic capsular device of FIG. 11A along the line 12D-12D of FIG. 12A.
Figure 12C:
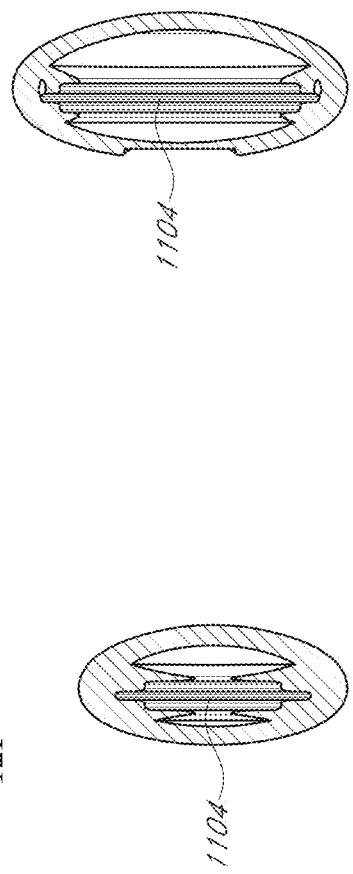
FIG. 12C is a cross-sectional view of the example prosthetic capsular device of FIG. 11A along the line 12C-12C of FIG. 12A.
Figure 12B:
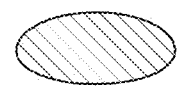
FIG. 12B is a cross-sectional view of the example prosthetic capsular device of FIG. 11A along the line 12B-12B of FIG. 12A.
Figure 12G:
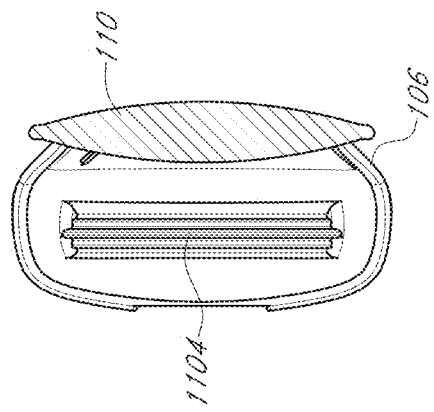
FIG. 12G is a cross-sectional view of the example prosthetic capsular device of FIG. 11A along the line 12G-12G of FIG. 12A.
Figure 12F:
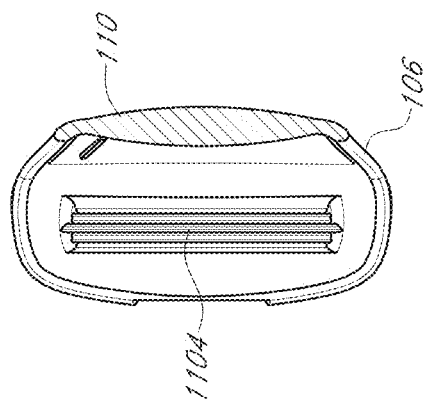
FIG. 12F is a cross-sectional view of the example prosthetic capsular device of FIG. 11A along the line 12F-12F of FIG. 12A.
Figure 12E:
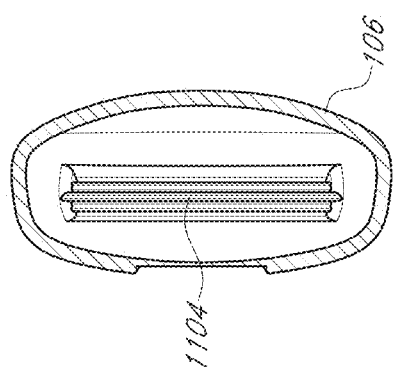
FIG. 12E is a cross-sectional view of the example prosthetic capsular device of FIG. 11A along the line 12E-12E of FIG. 12A.

FIG. 12A illustrates another anterior plan view of the example prosthetic capsular device of FIG. 11A. FIG. 12B illustrates a cross-sectional view of the example prosthetic capsular device of FIG. 11A along the line 12B-12B of FIG. 12A. FIG. 12C illustrates a cross-sectional view of the example prosthetic capsular device of FIG. 11A along the line 12C-12C of FIG. 12A. FIG. 12D illustrates a cross-sectional view of the example prosthetic capsular device of FIG. 11A along the line 12D-12D of FIG. 12A. FIG. 12E illustrates a cross-sectional view of the example prosthetic capsular device of FIG. 11A along the line 12E-12E of FIG. 12A. FIG. 12F illustrates a cross-sectional view of the example prosthetic capsular device of FIG. 11A along the line 12F-12F of FIG. 12A. FIG. 12G illustrates a cross-sectional view of the example prosthetic capsular device of FIG. 11A along the line 12G-12G of FIG. 12A.

In some embodiments, the cross-sectional area of the device 1100 along the line 12B-12B can be about 2.67 mm$^2$. Similarly, in some embodiments, the cross-sectional area of the device 1100 along the line 12C-12C can be about 4.83 mm$^2$. In some embodiments, the cross-sectional area of the device 1100 along the line 12D-12D can be about 4.24 mm$^2$. In some embodiments, the cross-sectional area of the device 1100 along the line 12E-12E can be about 3.65 mm$^2$. In some embodiments, the cross-sectional area of the device 1100 along the line 12F-12F can be about 2.42 mm$^2$. In some embodiments, the cross-sectional area of the device 1100 along the line 12G-12G can be about 4.34 mm$^2$. As such, the amount of material of the device 1100 may not necessarily depend on the size of the total outermost periphery of a cross section of the device 1100.

Figure 13D:
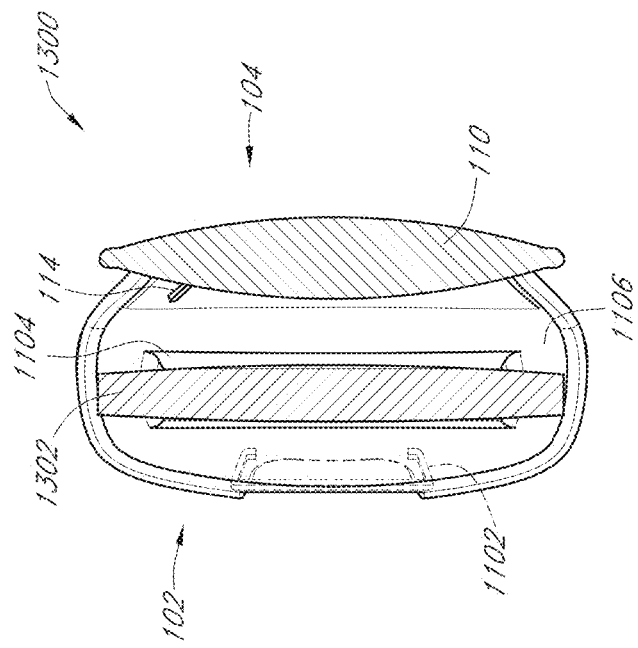
FIG. 13D is a cross-sectional view of the example prosthetic capsular device of FIG. 11A with a secondary device inserted therein along the line 13D-13D of FIG. 13B.
Figure 13C:
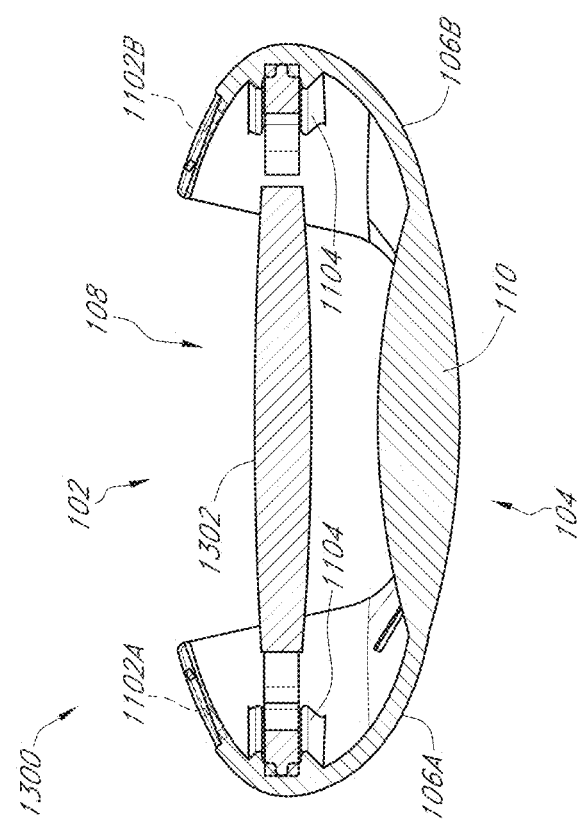
FIG. 13C is a cross-sectional view of the example prosthetic capsular device of FIG. 11A with a secondary device inserted therein along the line 13C-13C of FIG. 13B.

FIG. 13A illustrates an anterior side perspective view of the example prosthetic capsular device of FIG. 11A with a secondary device inserted therein. FIG. 13B illustrates an anterior plan view of the example prosthetic capsular device of FIG. 11A with a secondary device inserted therein. FIG. 13C illustrates a cross-sectional view of the example prosthetic capsular device of FIG. 11A with a secondary device inserted therein along the line 13C-13C of FIG. 13B. FIG. 13D illustrates a cross-sectional view of the example prosthetic capsular device of FIG. 11A with a secondary device inserted therein along the line 13D-13D of FIG. 13B. The secondary device can comprise acrylic or other haptics that are configured to be inserted into the one or more notches 1104.

In some embodiments, the device 1100 can be configured to be used in conjunction with a secondary device 1302, such as a secondary IOL, electronic device, and/or other device. The secondary device 1302 can be any device that is configured to take advantage of the notches 1104. For example, the secondary device 1302 can comprise one or more haptics and/or other features that are configured to be inserted into the notches 1104. The secondary device 1302 can be inserted into the device 1100 prior to implantation of the device 1100. Alternatively, the secondary device 1302 can be inserted into the device 1100 after the device 1100 has been implanted into the eye. As illustrated and as discussed above, the secondary device 1302 can be inserted and stabilized at a particular location within the device 1100 by attaching, inserting, or otherwise fixating the secondary device 1302 or a feature thereof into the one or more notches 1104.

Figure 14B:
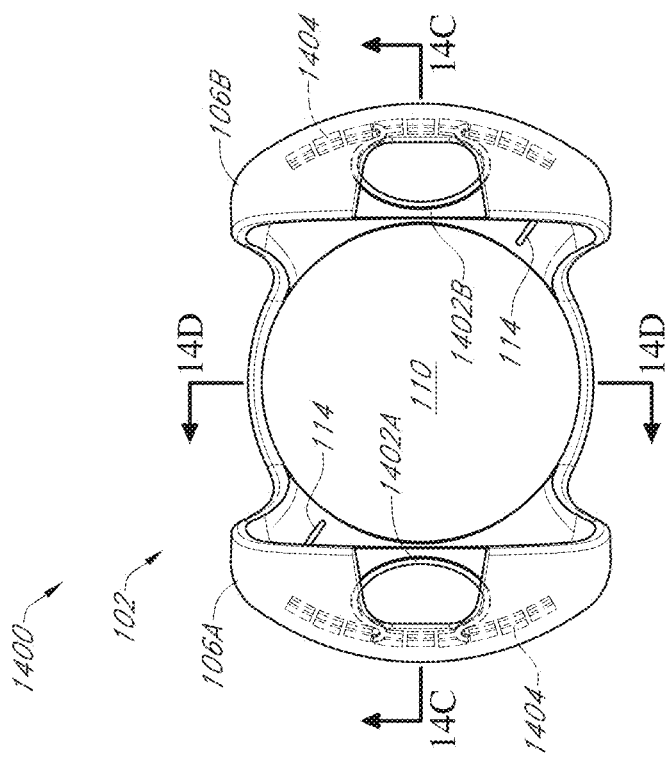
FIG. 14B is an anterior plan view of the example prosthetic capsular device of FIG. 14A.
Figure 14A:
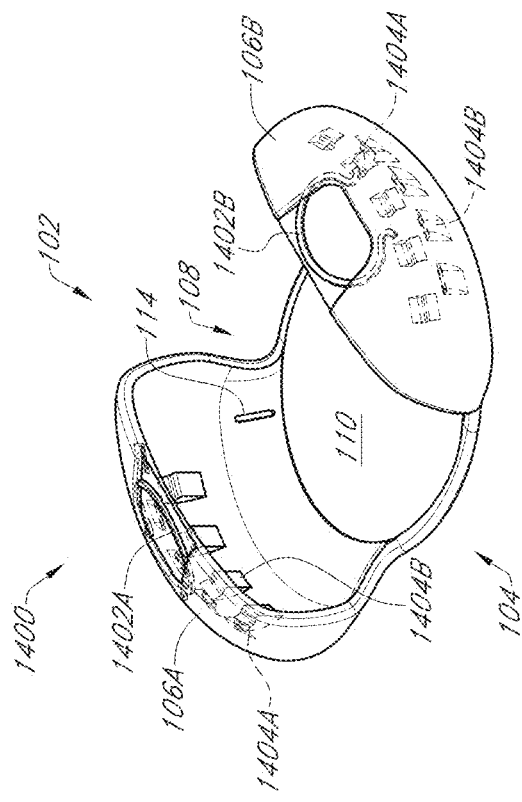
FIG. 14A is an anterior side perspective view of another example prosthetic capsular device.
Figure 14D:
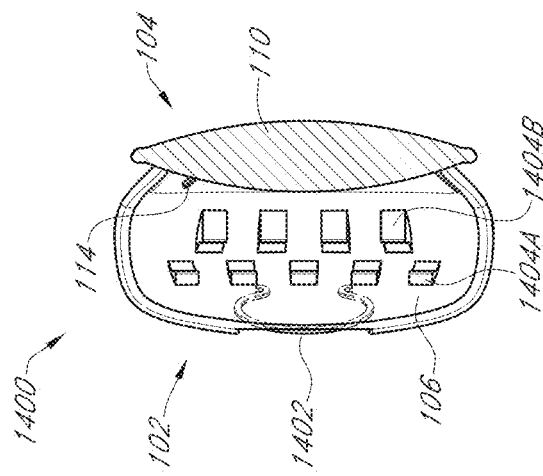
FIG. 14D is a cross-sectional view of the example prosthetic capsular device of FIG. 14A along the line 14D-14D of FIG. 14B.
Figure 14C:
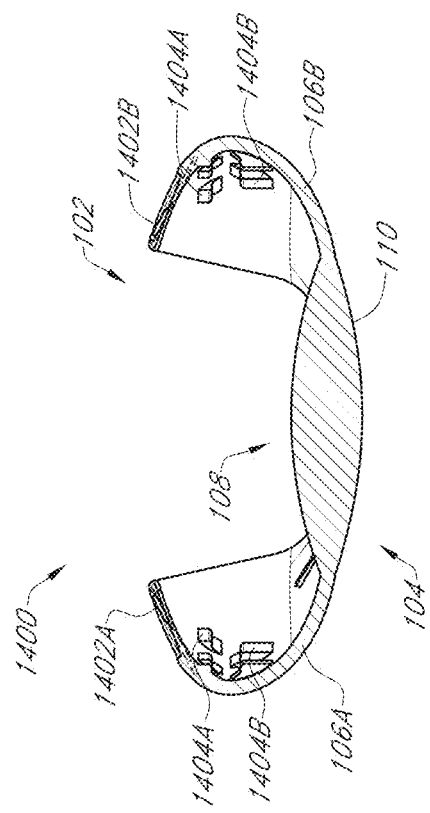
FIG. 14C is a cross-sectional view of the example prosthetic capsular device of FIG. 14A along the line 14C-14C of FIG. 14B.
Figure 15D:
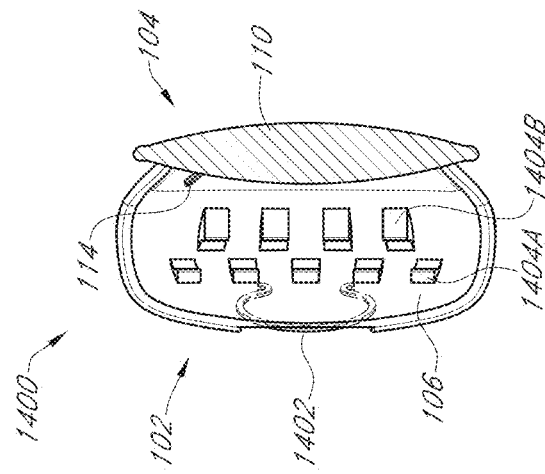
FIG. 15D is another cross-sectional view of the example prosthetic capsular device of FIG. 14A along the line 15D-15D of FIG. 15B.
Figure 15C:
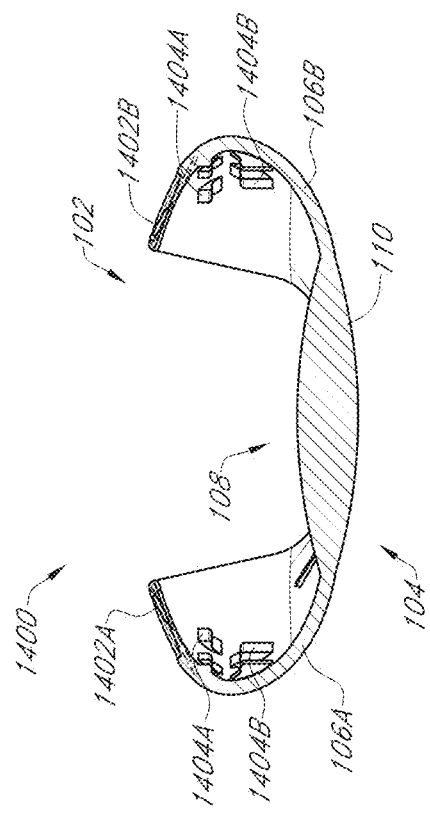
FIG. 15C is another cross-sectional view of the example prosthetic capsular device of FIG. 14A along the line 15C-15C of FIG. 15B.

FIG. 14A illustrates an anterior side perspective view of another example prosthetic capsular device. FIG. 14B illustrates an anterior plan view of the example prosthetic capsular device of FIG. 14A. FIG. 14C illustrates a cross-sectional view of the example prosthetic capsular device of FIG. 14A along the line 14C-14C of FIG. 14B. FIG. 14D illustrates a cross-sectional view of the example prosthetic capsular device of FIG. 14A along the line 14D-14D of FIG. 14B. FIG. 15A illustrates another anterior side perspective view of the example prosthetic capsular device of FIG. 14A. FIG. 15B illustrates another anterior plan view of the example prosthetic capsular device of FIG. 14A. FIG. 15C illustrates another cross-sectional view of the example prosthetic capsular device of FIG. 14A along the line 15C-15C of FIG. 15B. FIG. 15D illustrates another cross-sectional view of the example prosthetic capsular device of FIG. 14A along the line 15D-15D of FIG. 15B.

The prosthetic capsular device of FIG. 14A includes some or all of the features of the prosthetic capsular device of FIG. 1A-11A, and like reference numerals include like features. In particular, the prosthetic capsular device of FIG. 14A can be similar to the prosthetic capsular device of FIG. 1A and/or FIG. 11A, except for the configuration of notches 1404 and/or haptics 1402. All or some other features of the notches 1404, such as material, flexibility, function, or the like, can be similar to such features of the notches 604 described above in relation to FIGS. 6A-6D and/or the notches 1104 described above in relation to FIGS. 11A-11D. All or some other features of the haptics 1402, such as material, flexibility, function, or the like, can be similar to such features of the haptics 112 described above in relation to FIGS. 1A-1G and/or the haptics 1102 described above in relation to FIGS. 11A-11D.

In particular, the device 1400 can comprise notches 1404 with alternating tabs instead of continuous notches 1104 as described above in relation to FIGS. 11A-11D. For example, each of the notches 1404 located on the interior of each capsular area or sidewall 106A, 106B can comprise a set of large tabs 1404B and a set of small tabs 1404A to provide an anterior ridge and a posterior ridge. The set of small tabs 1404A can be located further away from the refractive surface 110 compared to the set of large tabs 1404B as illustrated in FIG. 14C. In other words, the set of small tabs 1404A can be positioned closer to the posterior 102 of the device 1400 than the set of larger tabs 1404B. The particular location of the set of small tabs 1404A and/or the set of large tabs 1404B in relation to the device 1400 can be similar to the location of notches 1104 of the device 1100 as described above in relation to FIGS. 11A-11D. The set of small tabs 1404A and/or the set of large tabs 1404B can prevent movement of a secondary device laterally, anteriorly and/or posteriorly within the device 1400. The set of small tabs 1404A and/or the set of large tabs 1404B can be molded together with the device 1400 at the same time as a single piece assembly. In other embodiments, the set of small tabs 1404A and/or the set of large tabs 1404B can be formed separately from the device 1400 and be subsequently attached to the device 1400.

The two sets of tabs 1404A, 1404B can provide two distinct shelves, such as a posterior ridge and an anterior ridge, for supporting the insertion and positioning of a secondary device or a portion thereof such as haptics of the secondary device. For example, in the embodiment illustrated in FIG. 14D, a first shelf or ridge can be formed between a lower end of the set of small tabs 1404A closer to the posterior 104 of the device and an upper end of the set of large tabs 1404B closer to the anterior 102 of the device. This first shelf or ridge can be about 0.16 mm in width along a posterior-anterior axis of the device 1400. This first shelf or ridge can be configured to fit a proline haptic, for example, from a three piece secondary IOL such as a Bausch and Lomb Li61A0. In certain embodiments, this first shelf or ridge can comprise a width of about 0.10 mm, about 0.11 mm, about 0.12 mm, about 0.13 mm, about 0.14 mm, about 0.15 mm, about 0.16 mm, about 0.17 mm, about 0.18 mm, about 0.19 mm, about 0.20 mm, about 0.21 mm, about 0.22 mm, about 0.23 mm, about 0.24 mm, about 0.25 mm, and/or within a range defined by two of the aforementioned values.

In addition, in the embodiment illustrated in FIG. 14D, a second shelf or ridge can be formed between an interior portion of the set of small tabs 1404A and an interior portion of the set of large tabs 1404B. This second shelf or ridge can be about 0.50 mm in width along a posterior-anterior axis of the device 1400. This second shelf or ridge can be configured to fit an acrylic or other haptic of a secondary device for example. In certain embodiments, this second shelf or ridge can comprise a width of about 0.10 mm, about 0.15 mm, about 0.20 mm, about 0.25 mm, about 0.30 mm, about 0.35 mm, about 0.40 mm, about 0.45 mm, about 0.50 mm, about 0.55 mm, about 0.60 mm, about 0.65 mm, about 0.70 mm, about 0.75 mm, about 0.80 mm, about 0.85 mm, about 0.90 mm, about 0.95 mm, about 1.00 mm, and/or within a range defined by two of the aforementioned values.

Notches 1404 with alternating tabs 1404A, 1404B can comprise less material compared to continuous notches 1104 as described above in relation to FIGS. 11A-11D. For example, notches 1404 with alternating tabs 1404A, 1404B can require only about 50 percent of the material required for continuous notches 1104. In certain embodiments, the amount of material necessary to provide notches 1404 with alternating tabs 1404A, 1404B, when compared to the amount of material necessary to provide continuous notches 1104, can be about 10 percent, about 15 percent, about 20 percent, about 25 percent, about 30 percent, about 35 percent, about 40 percent, about 45 percent, about 50 percent, about 55 percent, about 60 percent, about 65 percent, about 70 percent, about 75 percent, about 80 percent, about 85 percent, about 90 percent, about 95 percent, and/or between a range defined by two of the aforementioned values.

As such, the device 1400 comprising notches 1404 with alternating tabs 1404A, 1404B can comprise less mass and volume compared to the device 1100 comprising continuous notches 1104 while providing the same or similar functionality. When the device 1400 is compressed for insertion, the alternative tabs 1404A, 1404B can be configured to fold into a void space between two tabs, thereby decreasing the volume. Accordingly, the device 1400 comprising notches 1404 with alternating tabs 1404A, 1404B can be inserted through a smaller injector and incision in the eye compared to the device 1100 comprising continuous notches 1104. For example, in some embodiments, the device 1400 can be inserted through an incision of about 2.20 mm or less. In certain embodiments, the device 1400 can be inserted into the eye through an incision of about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, and/or within a range defined by two of the aforementioned values.

The device 1400 can also comprise one or more haptics 1402. The one or more haptics 1402 can comprise a general shape similar to the Greek alphabet omega or a All or some other features of the haptics 1402 can be similar to those of the haptics 112 described above in relation to FIGS. 1A-1G.

In the embodiment illustrated in FIGS. 14A-14D, the device 1400 comprises two haptics 1402A, 1402B each attached to the exterior surface of each capsular area or side wall 106A, 106B. Both ends of the omega-shaped haptic 1402A, 1402B can be over-molded or otherwise affixed to the exterior surface of each capsular area or side wall 106A, 106B. The central portion of each omega-shaped haptic 1402A, 1402B can be surrounded by void space, for example due to a recessed area of the device 1400 underneath the central portion, to facilitate cellular growth as discussed above.

In comparison to the haptics 112A, 112B of FIG. 1, the continuously curved configuration of the haptics 1402A, 1402B can reduce kinking and may also better accommodate stretching that may occur when the device 1400 is compressed through an injection cartridge for implantation into the eye. In contrast, haptics 112A, 112B with generally straight segments may be more likely to tear away from the body of the lens when stretched. Also, the curved configuration of the haptics 1402A, 1402B can allow for the length of the haptics to be longer than that of a generally rectangular haptic 112 while covering a similar or substantially similar amount of space. In other words, a curved haptics of a device, such as the omega-shaped haptics 1402, can provide redundancy in the material for the haptics. Accordingly, cellular growth may be better facilitated due to the additional length of the haptics 1402A, 1402B.

Figure 16H:
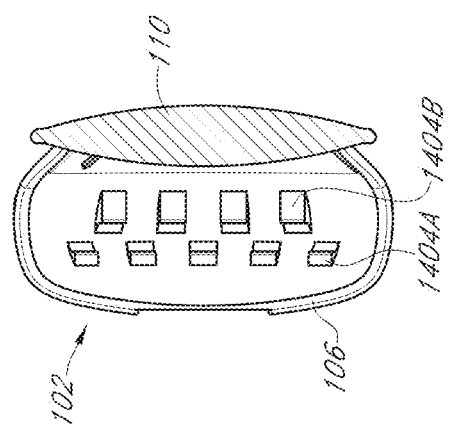
FIG. 16H is a cross-sectional view of the example prosthetic capsular device of FIG. 14A along the line 16G-16G of FIG. 16A.
Figure 16G:
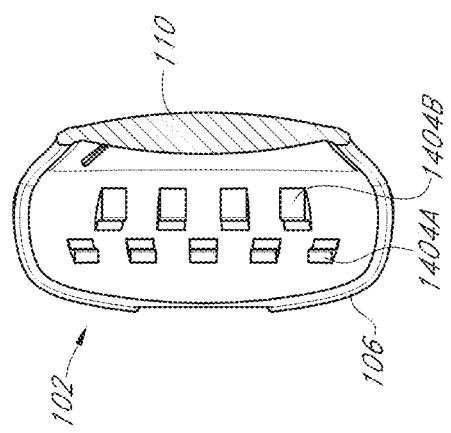
FIG. 16G is a cross-sectional view of the example prosthetic capsular device of FIG. 14A along the line 16G-16G of FIG. 16A.
Figure 16F:
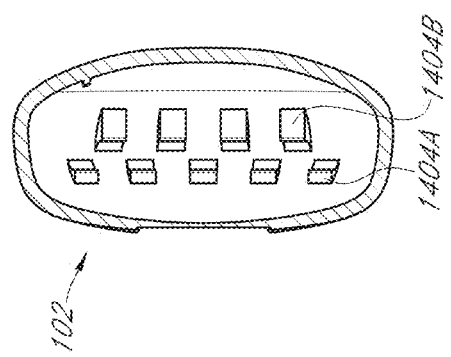
FIG. 16F is a cross-sectional view of the example prosthetic capsular device of FIG. 14A along the line 16F-16F of FIG. 16A.
Figure 16E:
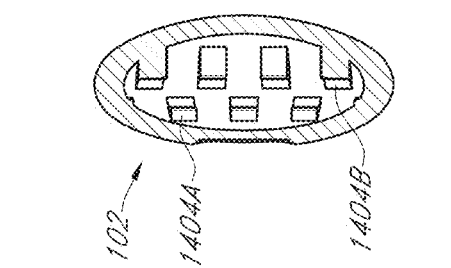
FIG. 16E is a cross-sectional view of the example prosthetic capsular device of FIG. 14A along the line 16E-16E of FIG. 16A.

FIG. 16A illustrates another anterior plan view of the example prosthetic capsular device of FIG. 14A. FIG. 16B illustrates a cross-sectional view of the example prosthetic capsular device of FIG. 14A along the line 16B-16B of FIG. 16A. FIG. 16C illustrates a cross-sectional view of the example prosthetic capsular device of FIG. 14A along the line 16C-16C of FIG. 16A. FIG. 16D illustrates a cross-sectional view of the example prosthetic capsular device of FIG. 14A along the line 16D-16D of FIG. 16A. FIG. 16E illustrates a cross-sectional view of the example prosthetic capsular device of FIG. 14A along the line 16E-16E of FIG. 16A. FIG. 16F illustrates a cross-sectional view of the example prosthetic capsular device of FIG. 14A along the line 16F-16F of FIG. 16A. FIG. 16G illustrates a cross-sectional view of the example prosthetic capsular device of FIG. 14A along the line 16G-16G of FIG. 16A. FIG. 16H illustrates a cross-sectional view of the example prosthetic capsular device of FIG. 14A along the line 16H-16H of FIG. 16A.

In some embodiments, the cross-sectional area of the device 1400 along the line 16B-16B can be about 3.39 mm$^2$. Similarly, in some embodiments, the cross-sectional area of the device 1400 along the line 16C-16C can be about 4.03 mm$^2$. In some embodiments, the cross-sectional area of the device 1400 along the line 16D-16D can be about 4.26 mm$^2$. In some embodiments, the cross-sectional area of the device 1400 along the line 16E-16E can be about 4.10 mm$^2$. In some embodiments, the cross-sectional area of the device 1400 along the line 16F-16F can be about 3.50 mm$^2$. In some embodiments, the cross-sectional area of the device 1400 along the line 16G-16G can be about 2.42 mm². In some embodiments, the cross-sectional area of the device 1400 along the line 16H-16H can be about 4.43 mm². As such, the amount of material of the device 1400 may not necessarily depend on the size of the total outermost periphery of a cross section of the device 1400.

Figure 17C:
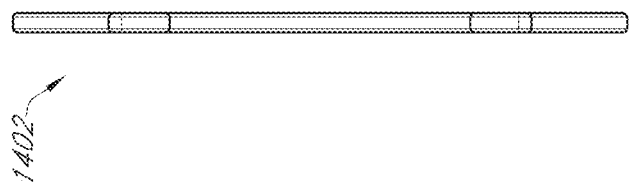
FIG. 17C is a side view of the example haptics of FIG. 17A.
Figure 17B:
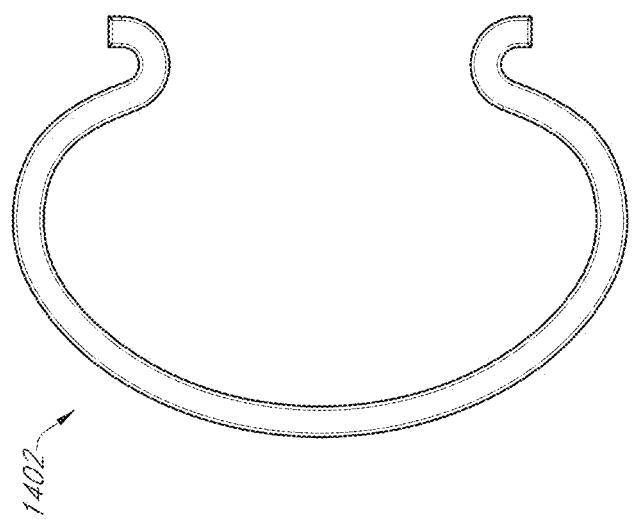
FIG. 17B is an anterior plan view of the example haptics of FIG. 17A.
Figure 17A:
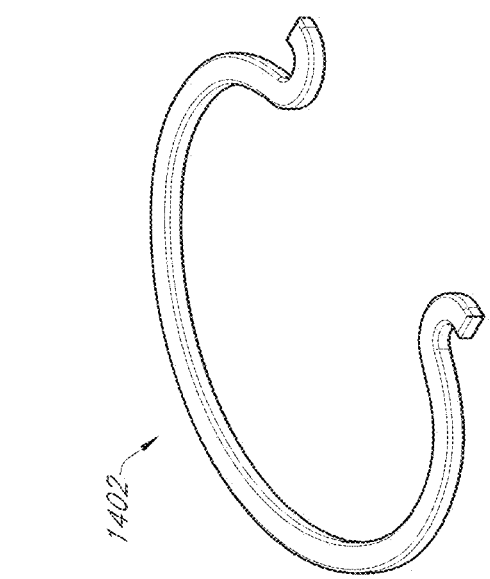
FIG. 17A is an anterior side perspective view of an example haptics configured to be used in conjunction with a prosthetic capsular device.

FIG. 17A illustrates an anterior side perspective view of an example haptics configured to be used in conjunction with a prosthetic capsular device, such as for example the example prosthetic capsular device 1400 of FIG. 14A. FIG. 17B illustrates an anterior plan view of the example haptics of FIG. 17A. FIG. 17C illustrates a side view of the example haptics of FIG. 17A.

As illustrated in FIGS. 17A-17C, the generally omega-shaped haptics 1402 can comprise a continuously curved configuration. A central portion and/or a substantially large portion of the haptics 1402 configured for cellular ingrowth can comprise a curvature in a first general direction. The central portion can extend generally at both ends along a curvature in a second general direction that is flipped or opposite to the first general direction terminating at two ends of the haptics 1402. The two ends of the haptics 1402 can be configured to be over-molded or otherwise attached to the device 1400 and sealed off.

In some embodiments, the haptics 1402 can comprise a thickness of about 0.08 mm when viewed from a side view as illustrated in FIG. 17C. In certain embodiments, when viewed from the side, the haptics 1402 can comprise a thickness of about 0.03 mm, about 0.04 mm, about 0.05 mm, about 0.06 mm, about 0.07 mm, about 0.08 mm, about 0.09 mm, about 0.10 mm, about 0.11 mm, about 0.12 mm, about 0.13 mm, about 0.14 mm, about 0.15 mm, and/or within a range defined by two of the aforementioned values.

In certain embodiments, when viewed in an anterior plan view as illustrated in FIG. 17B, the haptics 1402 can comprise a total height of about 2.41 mm when measured from the top of the haptics 1402 to the bottom. In some embodiments, the total height of the haptics 1402 when viewed in an anterior plan view can be about 1.50 mm, about 1.60 mm, about 1.70 mm, about 1.80 mm, about 1.90 mm, about 2.00 mm, about 2.10 mm, about 2.20 mm, about 2.30 mm, about 2.40 mm, about 2.50 mm, about 2.60 mm, about 2.70 mm, about 2.80 mm, about 2.90 mm, about 3.00 mm, about 3.10 mm, about 3.20 mm, about 3.30 mm, about 3.40 mm, about 3.50 mm, and/or within a range defined by two of the aforementioned values.

Further, when viewed in an anterior plan view, the haptics 1402 can comprise a total width of about 1.65 mm. In certain embodiments, when viewed in an anterior plan view, the total width of the haptics 1402 can be about 1.00 mm, about 1.10 mm, about 1.20 mm, about 1.30 mm, about 1.40 mm, about 1.50 mm, about 1.60 mm, about 1.70 mm, about 1.80 mm, about 1.90 mm, about 2.00 mm, about 2.10 mm, about 2.20 mm, about 2.30 mm, about 2.40 mm, about 2.50 mm, and/or within a range defined by two of the aforementioned values.

In addition, when viewed in an anterior plan view, a vertical distance between the two terminal ends of the haptics 1402 can be about 1.66 mm. In certain embodiments, when viewed in an anterior plan view, the vertical distance between the terminal ends of the haptics 1402 can be about 1.00 mm, about 1.10 mm, about 1.20 mm, about 1.30 mm, about 1.40 mm, about 1.50 mm, about 1.60 mm, about 1.70 mm, about 1.80 mm, about 1.90 mm, about 2.00 mm, about 2.10 mm, about 2.20 mm, about 2.30 mm, about 2.40 mm, about 2.50 mm, and/or within a range defined by two of the aforementioned values.

Moreover, when viewed in an anterior plan view, a thickness of the haptics 1402 can be about 0.12 mm. In certain embodiments, when viewed from the top or in an anterior plan view, the haptics 1402 can comprise a thickness of about 0.03 mm, about 0.04 mm, about 0.05 mm, about 0.06 mm, about 0.07 mm, about 0.08 mm, about 0.09 mm, about 0.10 mm, about 0.11 mm, about 0.12 mm, about 0.13 mm, about 0.14 mm, about 0.15 mm, and/or within a range defined by two of the aforementioned values.

Figure 18E:
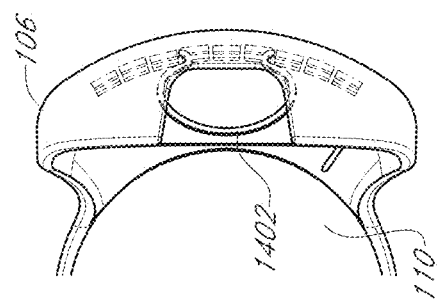
FIG. 18E is an anterior plan view of a portion of the example prosthetic capsular device of FIG. 14A.
Figure 18D:
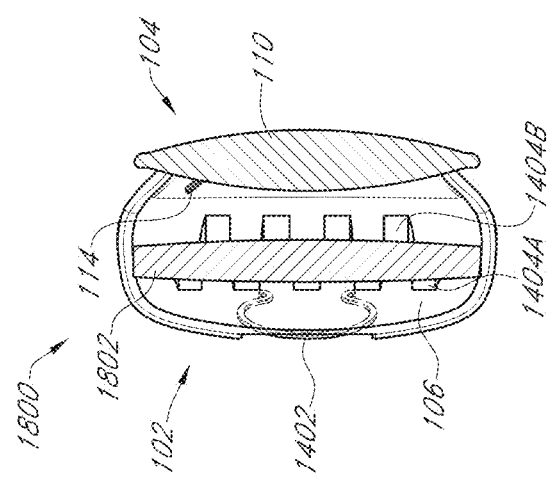
FIG. 18D is a cross-sectional view of the example prosthetic capsular device of FIG. 14A with a secondary device inserted therein along the line 18D-18D of FIG. 18B.
Figure 18C:
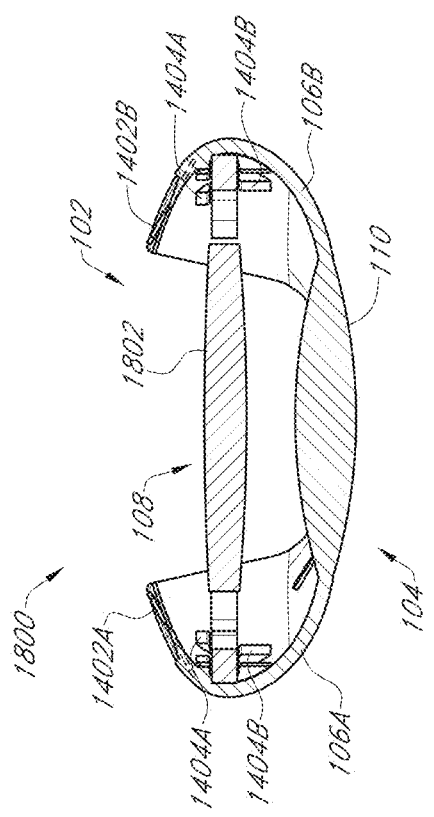
FIG. 18C is a cross-sectional view of the example prosthetic capsular device of FIG. 14A with a secondary device inserted therein along the line 18C-18C of FIG. 18B.

FIG. 18A illustrates an anterior side perspective view of the example prosthetic capsular device of FIG. 14A with a secondary device inserted therein. FIG. 18B illustrates an anterior plan view of the example prosthetic capsular device of FIG. 14A with a secondary device inserted therein. FIG. 18C illustrates a cross-sectional view of the example prosthetic capsular device of FIG. 14A with a secondary device inserted therein along the line 18C-18C of FIG. 18B. FIG. 18D illustrates a cross-sectional view of the example prosthetic capsular device of FIG. 14A with a secondary device inserted therein along the line 18D-18D of FIG. 18B. FIG. 18E illustrates an anterior plan view of a portion of the example prosthetic capsular device of FIG. 14A.

As previously discussed, the device 1400 can be configured to be used in conjunction with a secondary device 1802, such as a secondary IOL, electronic device, and/or other device. The secondary device 1802 can be any device that is configured to take advantage of the set of small tabs 1404A and/or the set of large tabs 1404B of the notches 1404. For example, the secondary device 1802 can comprise one or more haptics and/or other features that are configured to be inserted into one or more ridges or shelves formed by the set of small tabs 1404A and/or the set of large tabs 1404B of the notches 1404. The secondary device 1802 can be inserted into the device 1400 prior to and/or after implantation of the device 1400 in the eye.

Figure 19B:
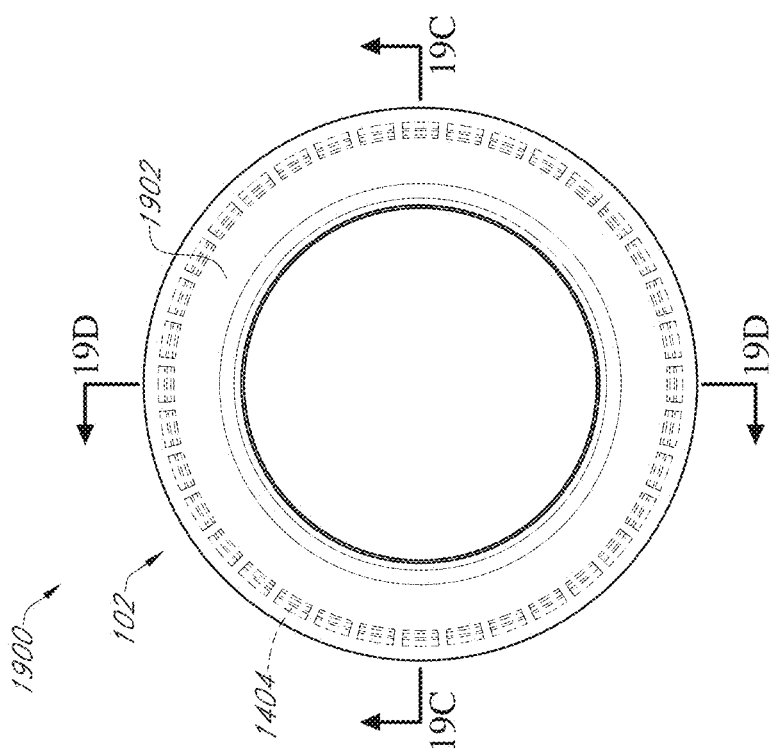
FIG. 19B is an anterior plan view of the example prosthetic capsular device of FIG. 19A.
Figure 19A:
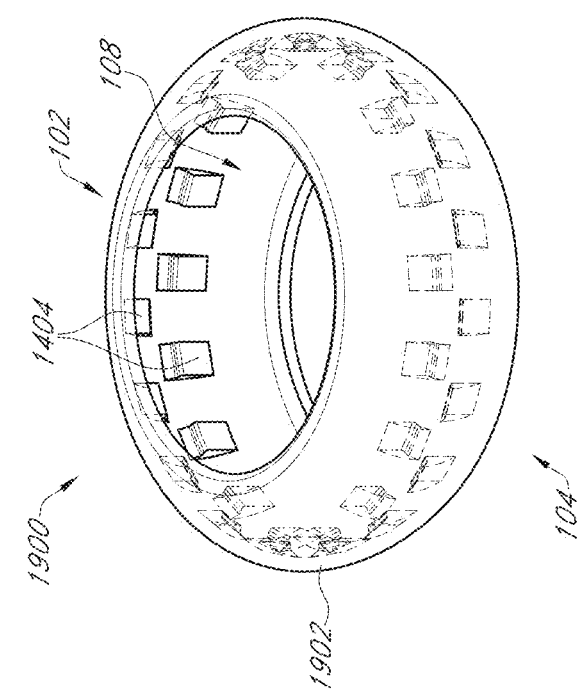
FIG. 19A is an anterior side perspective view of another example prosthetic capsular device.
Figure 19F:
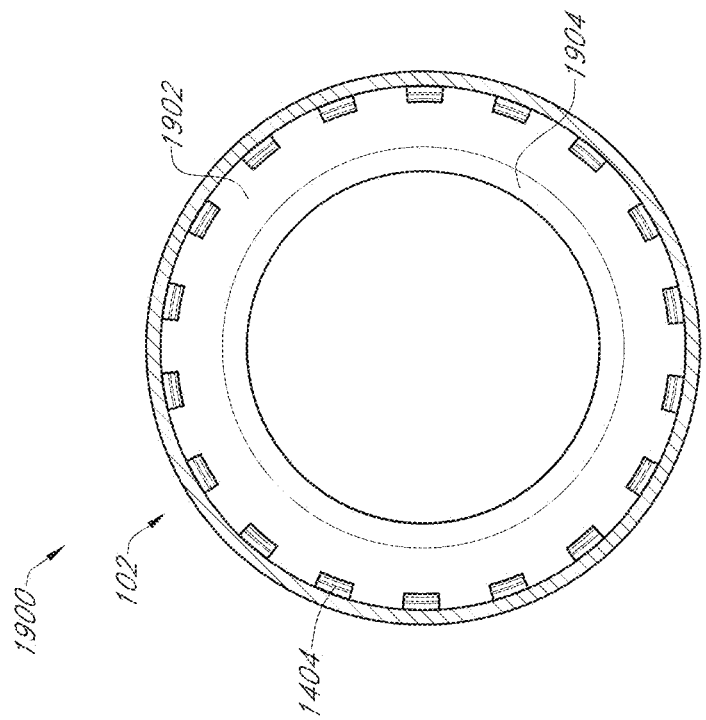
FIG. 19F is a cross-sectional view of the example prosthetic capsular device of FIG. 19A along the line 19F-19F of FIG. 19D.
Figure 19E:
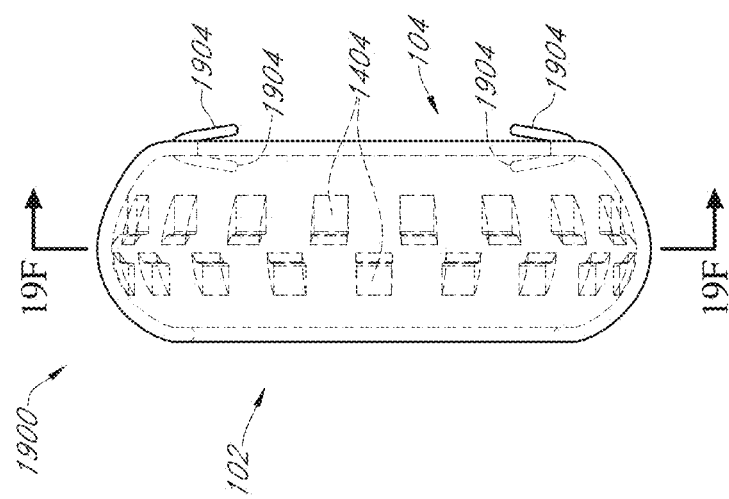
FIG. 19E is a side plan view of the example prosthetic capsular device of FIG. 19A.

FIG. 19A illustrates an anterior side perspective view of another example prosthetic capsular device. FIG. 19B illustrates an anterior plan view of the example prosthetic capsular device of FIG. 19A. FIG. 19C illustrates a cross-sectional view of the example prosthetic capsular device of FIG. 19A along the line 19C-19C of FIG. 19B. FIG. 19D illustrates a cross-sectional view of the example prosthetic capsular device of FIG. 19A along the line 19D-19D of FIG. 19B. FIG. 19E illustrates a side plan view of the example prosthetic capsular device of FIG. 19A. FIG. 19F illustrates a cross-sectional view of the example prosthetic capsular device of FIG. 19A along the line 19F-19F of FIG. 19D.

The prosthetic capsular device 1900 of FIG. 19A includes some or all of the features of the prosthetic capsular device of FIG. 10A and/or 14A, and like reference numerals include like features. Some or all features of the prosthetic capsular device 1900 can be similar to those of other prosthetic capsular devices disclosed herein. For example, the prosthetic capsular device 1900 can comprise one or more notches 1404 with alternating tabs. Some or all features of the one or more notches 1404, alternating tabs, and/or functions, characteristics and/or materials thereof can be similar to those discussed above in relation to FIG. 14A. In certain embodiments, the one or more alternating tabs 1404 can all comprise the same or similar size and/or shape.

The prosthetic capsular device 1900 can comprise a continuous sidewall portion 1902 that encompasses the whole perimeter of the device 1900. The overall general shape or configuration of the prosthetic capsular device 1900 can be similar to the overall general shape of the prosthetic capsular device 1000 of FIG. 10A. However, in contrast to the prosthetic capsular device of FIG. 10A, the sidewall 1902 of the prosthetic capsular device 1900 of FIG. 19A may not comprise a break or void space.

By providing a continuous sidewall 1902, the prosthetic capsular device 1900 can be more effective than certain other embodiments in keeping the natural capsular bag of the eye open upon insertion. That is, because there is no void space along the side wall, the tendency of the prosthetic capsular device 1900 to fold or collapse within the natural capsular bag can be lower than certain other embodiments. However, at the same time, the continuous configuration of the sidewall 1902 can present technical difficulties in inserting the device 1900 through a small incision.

Accordingly, to address this potential shortcoming, some embodiments of the example prosthetic capsular device 1900 do not comprise a pre-existing posterior surface. Rather, some embodiments of the example prosthetic capsular device 1900 can comprise an empty or void posterior and/or anterior side. As such, the device 1900 can be configured to be coupled with a posterior and/or anterior refractive surface or optic after insertion in the eye. In other words, rather than comprising a single piece assembly that includes both a framework and a posterior refractive surface, the prosthetic capsular device 1900 may comprise a two-piece assembly, in which the framework and posterior refractive surface are provided and/or inserted separately into the natural capsular bag or eye.

More specifically, upon implantation, the framework or prosthetic capsular device 1900 can be inserted into the eye first, which can keep the entire natural capsule stinted open. An optic or refractive surface can be subsequently inserted into the eye and be placed or coupled with the framework or prosthetic capsular device 1900, for example near or at the posterior and/or anterior side of the device. By separating the framework 1900 from the posterior refractive surface, the volume of a single insertion, for example the framework or device 1900, can be smaller.

In addition, because the posterior optic is inserted separately, the posterior optic can be rather easily replaced in the future. At the same time, by placing this optic near or at the posterior end of the prosthetic capsular device 1900, an additional lens, technology device, and/or other component can be placed in the interior and/or anterior side of the device 1900 as well.

An optic can be attached or coupled to the device 1900 in a number of ways. For example, an optic can be sutured to a posterior side or other portion of the device 1900 or can be attached or coupled via a friction fit, chemical adhesive, mechanical locking, and/or a combination of the above. In particular, in some embodiments, the void posterior and/or anterior end or opening of the device 1900 can comprise a lip 1904. In other words, the posterior or anterior opening or end of the device 1900 can comprise two layers of extended material 1904 that create a groove in between the two layers. This groove formed by the extended material 1904 can extend throughout the posterior and/or anterior opening of the device 1900, for example to create a circular annulus. Each of the extended material 1904 can comprise one or more triangular fixations configured to maintain a position of the optic. The optic or periphery or portion thereof, such as a tongue portion, can be configured to be inserted into the groove formed by the two layers of extended material 1904, for example made of silicone.

As illustrated in FIG. 19F, in some embodiments, the posterior and/or anterior opening of the device 1900 can comprise a diameter of about 6.150 mm or 6.250 mm in some embodiments. In certain embodiments, the posterior and/or anterior opening of the device 1900 can comprise a diameter of about 5 mm, about 5.1 mm, about 5.2 mm, about 5.3 mm, about 5.4 mm, about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, about 6.5 mm, about 6.6 mm, about 6.7 mm, about 6.8 mm, about 6.9 mm, about 7.0 mm, about 7.1 mm, about 7.2 mm, about 7.3 mm, about 7.4 mm, about 7.5 mm, about 8.0 mm, about 8.5 mm, about 9.0 mm, about 9.5 mm, about 10 mm, and/or within a range defined by two of the aforementioned values.

In certain embodiments, the lip portion 1904 surrounding the posterior and/or anterior opening can comprise a certain thickness when viewed from an anterior plan view as illustrated in FIG. 19F. As such, the diameter of a circular portion formed around the interior circumference of the anterior and/or posterior opening of the device 1900, excluding the lip portion 1904, can be about 7.00 mm and/or larger than the posterior and/or anterior opening. In certain embodiments, the diameter of a circular portion formed around the interior circumference of the anterior and/or posterior opening of the device 1900, excluding the lip portion 1904, can be about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, about 6.5 mm, about 6.6 mm, about 6.7 mm, about 6.8 mm, about 6.9 mm, about 7.0 mm, about 7.1 mm, about 7.2 mm, about 7.3 mm, about 7.4 mm, about 7.5 mm, about 8.0 mm, about 8.1 mm, about 8.2 mm, about 8.3 mm, about 8.4 mm, about 8.5 mm, about 9.0 mm, about 9.5 mm, about 10 mm, about 10.5 mm and/or within a range defined by two of the aforementioned values.

Figure 20D:
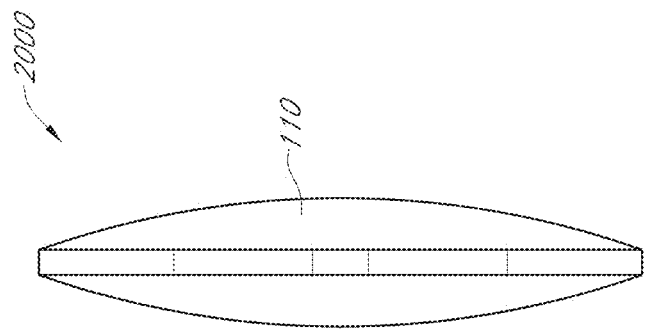
FIG. 20D is a side plan view of the example optic of FIG. 20A along a minor axis of the anterior plan view illustrated in FIG. 20B.
Figure 20C:
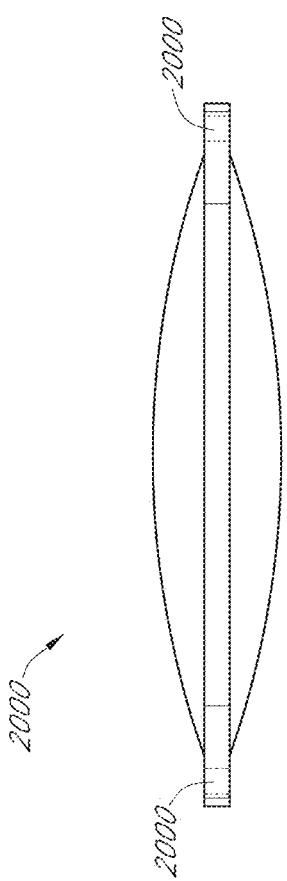
FIG. 20C is a side plan view of the example optic of FIG. 20A along a major axis of the anterior plan view illustrated in FIG. 20B.

In some embodiments, the device 1900 can comprise a plurality of notches 1404 placed circumferentially throughout the interior of the sidewall 1902. Each or some of the plurality of notches 1404 can comprise an angular width of about 8° when viewed in an anterior plan view as illustrated in FIG. 19B. In certain embodiments, when viewed in an anterior plan view, each or some of the plurality of notches 1404 can comprise an angular width of about 1°, about 2°, about 3°, about 4°, about 5°, about 6°, about 7°, about 8°, about 9°, about 10°, about 11°, about 12°, about 13°, about 14°, about 15°, about 20°, about 25°, about 30°, about 40°, about 45°, about 60°, about 75°, about 90°, and/or within a range defined by two of the aforementioned values. [0331] FIG. 20A illustrates an anterior side perspective view of an example optic configured to be used in conjunction with a prosthetic capsular device, such as the example prosthetic capsular device of FIG. 19A or any other example prosthetic capsular device described herein. FIG. 20B illustrates an anterior plan view of the example optic of FIG. 20A. FIG. 20C illustrates a side plan view of the example optic of FIG. 20A along a major axis of the anterior plan view illustrated in FIG. 20B. FIG. 20D illustrates a side plan view of the example optic of FIG. 20A along a minor axis of the anterior plan view illustrated in FIG. 20B.

In some embodiments, the optic or refractive surface 2000 can comprise a diameter of about 6.00 mm. In certain embodiments, the optic of refractive surface 2000 can comprise a diameter of about 5.00 mm, about 5.50 mm, about 6.00 mm, about 6.50 mm, about 7.00 mm, about 7.50 mm, about 8.00 mm, about 8.50 mm, about 9.00 mm, about 9.50 mm, about 10.00 mm, and/or within a range defined by two of the aforementioned values.

An optic or refractive surface 2000 can comprise one or more tongue portions 2002. The one or more tongue portions 2002 can extend outwardly from the refractive portion of the optic 2000. The one or more tongue portions 2002 can be configured to be inserted into a groove of a prosthetic capsular device. For example, the one or more tongue portions 2002 can be inserted into the groove formed by the two layers of extended material 1904 in device 1900.

An optic 2000 can comprise one, two, three, four, five, six, seven, eight, nine, or ten tongue portions 2002. Each of the one or more tongue portions 2002 of an optic 2000 can extend radially from about 20°, about 40°, about 60°, about 80°, about 100°, about 120°, about 140°, about 160°, about 180°, about 200°, about 220°, about 240°, about 260°, about 280°, about 300°, about 320°, about 340°, about 360° of the circumference of the refractive portion of the optic 2000 and/or within a range defined by two of the aforementioned values.

A tongue portion 2002 of an optic 2000 can comprise one or more eyelets 2004. The one or more eyelets 2004 can be used to fasten or fixate the optic 2000 in a particular location or configuration within a prosthetic capsular device, such as device 1900. In some embodiments, each of the eyelets 2004 can comprise a diameter and/or thickness of about 0.25 mm. In certain embodiments, each of the eyelets 2004 can comprise a diameter and/or thickness of about 0.05 mm, about 0.10 mm, about 0.15 mm, about 0.20 mm, about 0.25 mm, about 0.30 mm, about 0.35 mm, about 0.40 mm, about 0.45 mm, about 0.50 mm, and/or within a range defined by two of the aforementioned values.

Figure 21B:
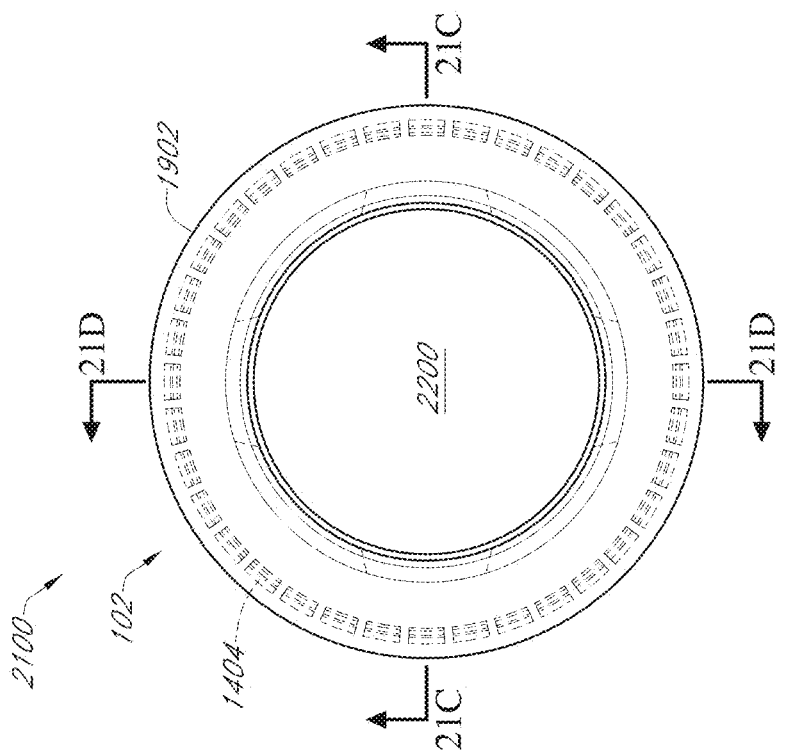
FIG. 21B is an anterior plan view of the example prosthetic capsular device of FIG. 21A.
Figure 21A:
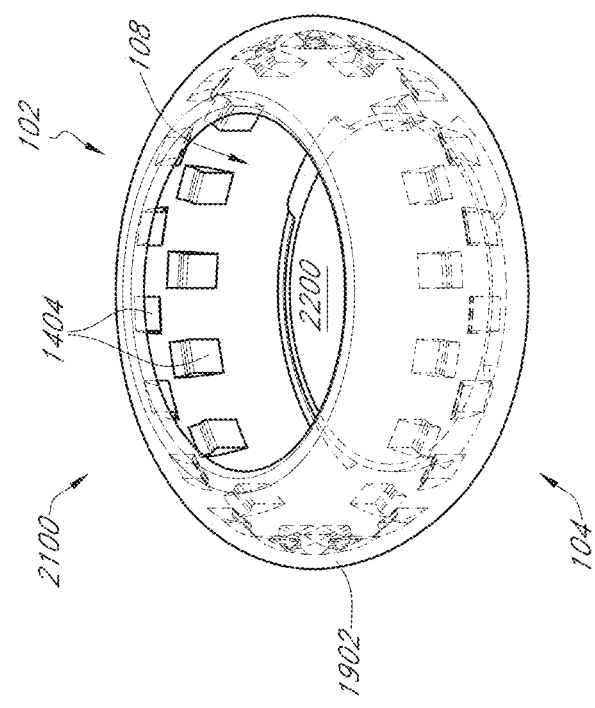
FIG. 21A is an anterior side perspective view of another example prosthetic capsular device.
Figure 21D:
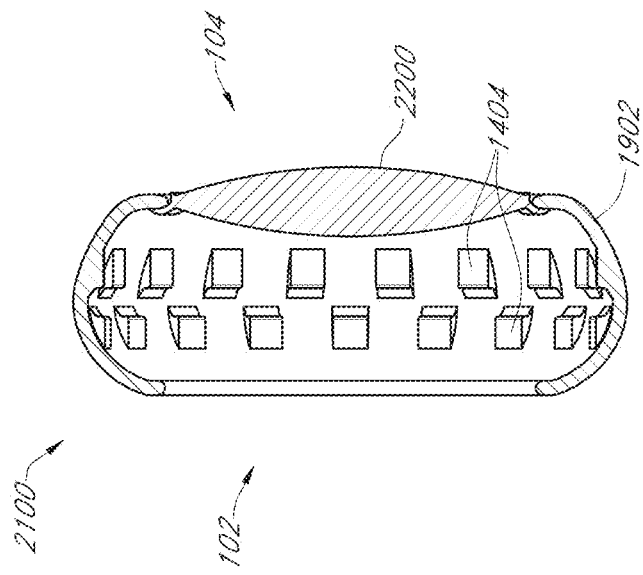
FIG. 21D is a cross-sectional view of the example prosthetic capsular device of FIG. 21A along the line 21D-21D of FIG. 21B.
Figure 21C:
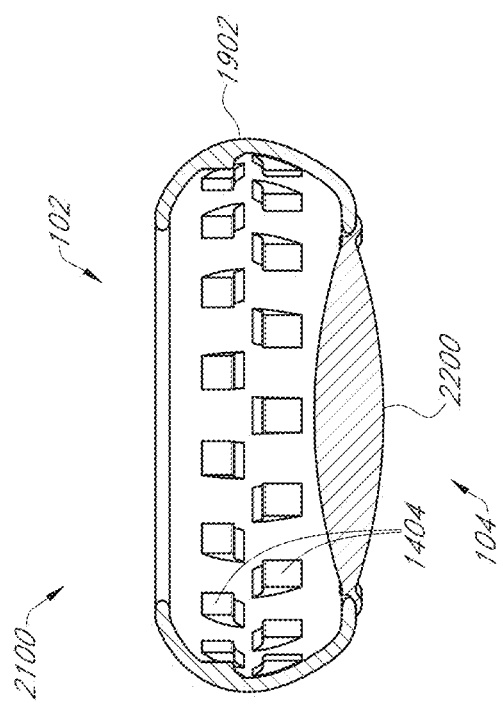
FIG. 21C is a cross-sectional view of the example prosthetic capsular device of FIG. 21A along the line 21C-21C of FIG. 21B.

FIG. 21A illustrates an anterior side perspective view of another example prosthetic capsular device. FIG. 21B illustrates an anterior plan view of the example prosthetic capsular device of FIG. 21A. FIG. 21C illustrates a cross-sectional view of the example prosthetic capsular device of FIG. 21A along the line 21C-21C of FIG. 21B. FIG. 21D illustrates a cross-sectional view of the example prosthetic capsular device of FIG. 21A along the line 21D-21D of FIG. 21B.

The example prosthetic device of FIG. 21A can comprise one or more similar features as the example prosthetic device of FIG. 19A. The example prosthetic device of FIG. 21A can be configured to be used in conjunction with a refractive surface or an IOL 2200 as depicted in FIG. 21A. For example, an example prosthetic device 2100 can comprise a posterior refractive surface 2200, similar to one or more other embodiments described herein. The posterior refractive surface 2200 can be configured to be attachable or selectively removable from a prosthetic device 2100.

In some embodiments, the device 2100 can comprise an overall diameter of about 9.650 mm when viewed in an anterior plan view as illustrated in FIG. 21B. In certain embodiments, when viewed in an anterior plan view, the device 2100 can comprise an overall diameter of about 7.0 mm, about 7.5 mm, about 8.0 mm, about 8.5 mm, about 9.0 mm, about 9.5 mm, about 10.0 mm, about 10.5 mm, about 11.0 mm, about 11.5 mm, about 12.0 mm, and/or within a range defined by two of the aforementioned values.

In some embodiments, the device 2100, from a cross-sectional view along the line 21D-21D as illustrated in FIG. 21D, can comprise a thickness of about 3.5 mm excluding the refractive surface 2200. Depending on the thickness of the refractive surface 2200, the total thickness of the device 2100 including the refractive surface 2200 can be about 3.980 mm. In certain embodiments, the thickness of the device 2100, from a cross-sectional view along the line 21D-21D and/or from a side view and including and/or excluding the refractive surface 2200, can be about 2.5 mm, about 3 mm, about 3.5 mm, about 4 mm, about 4.5 mm, about 5 mm, about 5.5 mm, about 6 mm, and/or within a range defined by two of the aforementioned values.

As illustrated in FIG. 21C, in some embodiments, the posterior and/or anterior opening of the device 2100 can comprise a diameter of about 6.250 mm, 6.250 mm, and/or 6.350 mm. In certain embodiments, the posterior and/or anterior opening of the device 2100 can comprise a diameter of about 5 mm, about 5.1 mm, about 5.2 mm, about 5.3 mm, about 5.4 mm, about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, about 6.5 mm, about 6.6 mm, about 6.7 mm, about 6.8 mm, about 6.9 mm, about 7.0 mm, about 7.1 mm, about 7.2 mm, about 7.3 mm, about 7.4 mm, about 7.5 mm, about 8.0 mm, about 8.5 mm, about 9.0 mm, about 9.5 mm, about 10 mm, and/or within a range defined by two of the aforementioned values.

In certain embodiments, a lip portion can surround the posterior and/or anterior opening with a certain thickness when viewed from an anterior plan view as illustrated in FIG. 21B. The diameter of a circular portion formed around the interior circumference of the anterior and/or posterior opening of the device 2100, excluding the lip portion, can be about 7.00 mm and/or larger than the posterior and/or anterior opening. In certain embodiments, the diameter of a circular portion formed around the interior circumference of the anterior and/or posterior opening of the device 2100, excluding the lip portion can be about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, about 6.5 mm, about 6.6 mm, about 6.7 mm, about 6.8 mm, about 6.9 mm, about 7.0 mm, about 7.1 mm, about 7.2 mm, about 7.3 mm, about 7.4 mm, about 7.5 mm, about 8.0 mm, about 8.1 mm, about 8.2 mm, about 8.3 mm, about 8.4 mm, about 8.5 mm, about 9.0 mm, about 9.5 mm, about 10 mm, about 10.5 mm, and/or within a range defined by two of the aforementioned values.

In some embodiments, the device 2100 can comprise a plurality of notches 1404 placed circumferentially throughout the interior of the sidewall 1902. Each or some of the plurality of notches 1404 can comprise an angular width of about 8° when viewed in an anterior plan view as illustrated in FIG. 21B. In certain embodiments, when viewed in an anterior plan view, each or some of the plurality of notches 1404 can comprise an angular width of about 1°, about 2°, about 3°, about 4°, about 5°, about 6°, about 7°, about 8°, about 9°, about 10°, about 11°, about 12°, about 13°, about 14°, about 15°, about 20°, about 25°, about 30°, about 40°, about 45°, about 60°, about 75°, about 90°, and/or within a range defined by two of the aforementioned values.

Figure 22B:
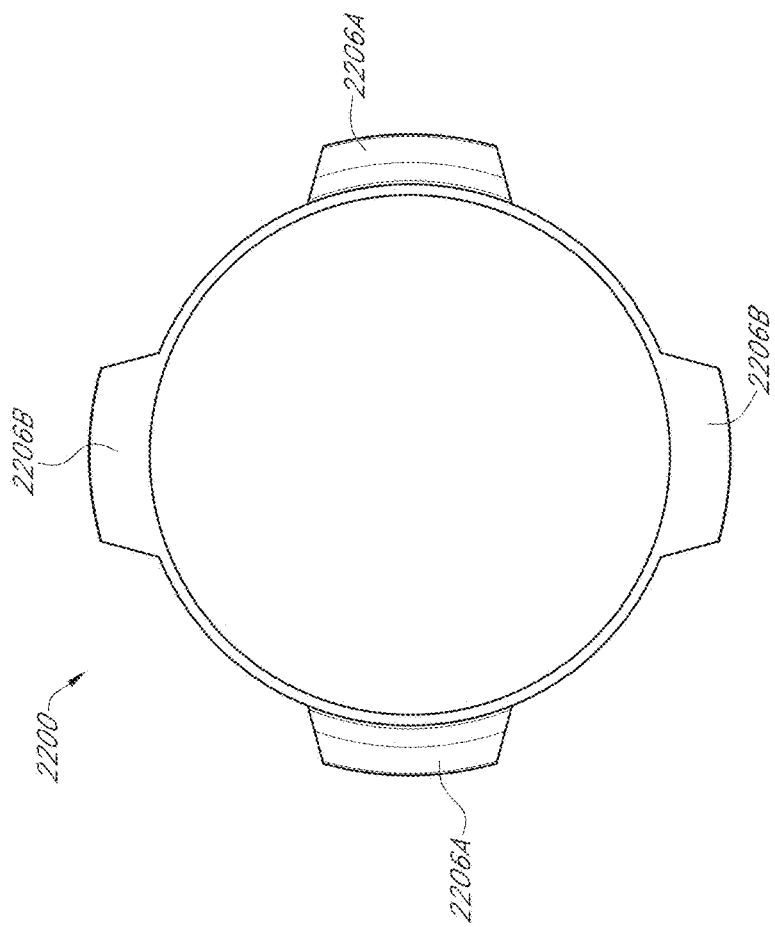
FIG. 22B is an anterior plan view of the example refractive surface or intraocular lens of FIG. 22A.
Figure 22A:
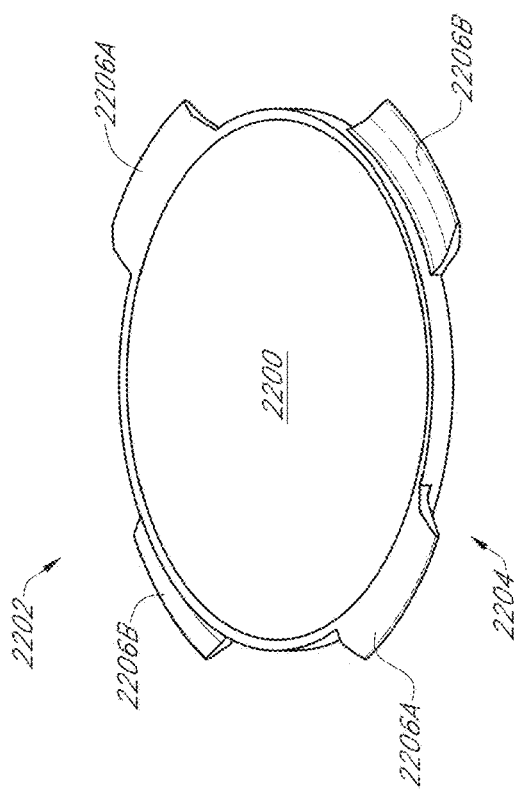
FIG. 22A is an anterior side perspective view of an example refractive surface or intraocular lens that can be configured to be used in conjunction with a prosthetic capsular device.
Figure 22D:
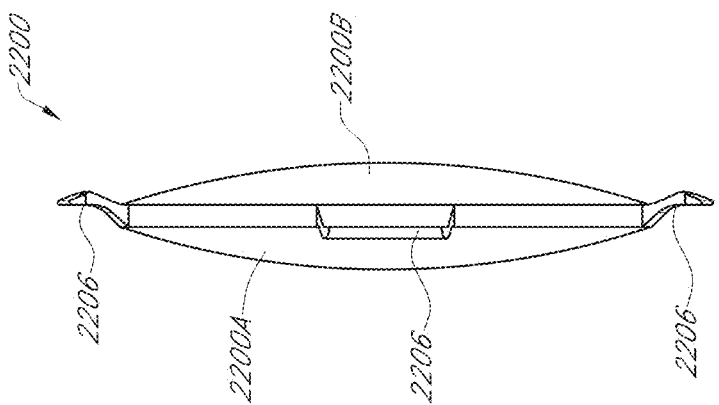
FIG. 22D is another side plan view of the example refractive surface or intraocular lens of FIG. 22A.
Figure 22C:
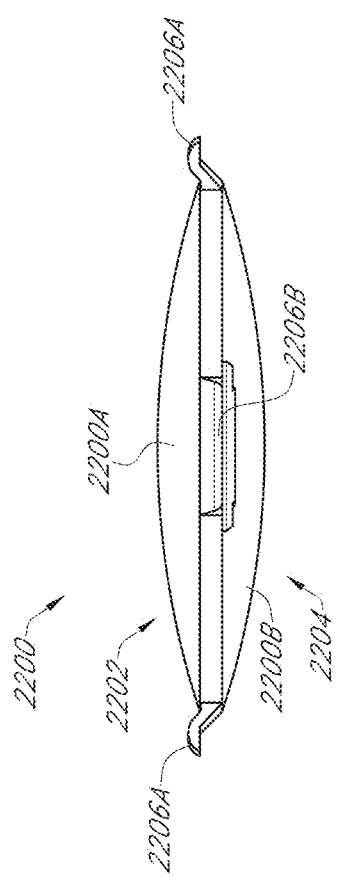
FIG. 22C is a side plan view of the example refractive surface or intraocular lens of FIG. 22A.

FIG. 22A illustrates an anterior side perspective view of an example refractive surface or intraocular lens that can be configured to be used in conjunction with a prosthetic capsular device, such as the prosthetic capsular device of FIG. 21A or any other example prosthetic capsular device described herein. FIG. 22B illustrates an anterior plan view of the example refractive surface or intraocular lens of FIG. 22A. FIG. 22C illustrates a side plan view of the example refractive surface or intraocular lens of FIG. 22A. FIG. 22D illustrates another side plan view of the example refractive surface or intraocular lens of FIG. 22A.

The example refractive surface or intraocular lens 2200 of FIG. 22A can be configured to be used in conjunction with one or more example prosthetic devices disclosed herein. For example, the example refractive surface or intraocular lens 2200 of FIG. 22A can be attached to and/or selectively removed from the prosthetic capsular device of FIG. 21A.

In some embodiments, the optic or refractive surface 2200 can comprise a diameter of about 6.250 mm. In certain embodiments, the optic of refractive surface 2200 can comprise a diameter of about 5.00 mm, about 5.50 mm, about 6.00 mm, about 6.50 mm, about 7.00 mm, about 7.50 mm, about 8.00 mm, about 8.50 mm, about 9.00 mm, about 9.50 mm, about 10.00 mm, and/or within a range defined by two of the aforementioned values.

An example refractive surface or intraocular lens 2200 can comprise one or more tabs 2206 to facilitate attachment of the refractive surface or intraocular lens 2200 to a prosthetic capsular device and/or to fixate the two. For example, in some embodiments, a refractive surface or intraocular lens 2200 can comprise four tabs 2206. Each of the tabs 2206 can comprise a curvature when viewed from a side plan view as illustrated in FIG. 22D. For example, in certain embodiments, a refractive surface or intraocular lens 2200 can comprise two upwardly curved tabs 2206A and two downwardly curved tabs 2206B. As such, two of the four tabs 2206 can be configured to be placed in the interior of a posterior or anterior end of a prosthetic capsular device and the other two tabs 2206 can be configured to be placed exterior to the posterior or anterior end of the prosthetic capsular device. This way, the refractive surface or intraocular lens 2200 can be held substantially in place with respect to the posterior end of a prosthetic capsular device.

Each of the plurality of tabs 2206 can extend from the refractive surface 2200 at an angle when viewed from a side plan view as illustrated in FIG. 22D. For example, in some embodiments, each or some of the plurality of tabs 2206 can initially extend from the refractive surface 2200 at an angle of about 45° in either direction. In certain embodiments, each or some of the plurality of tabs 2206 can initially extend from the refractive surface 2200 at an angle of about +/−10°, about +/−20°, about +/−25°, about +/−30°, about +/−35°, about +/−40°, about +/−45°, about +/−50°, about +/−55°, about +/−60°, about +/−70°, about +/−80°, about +/−90°, and/or within a range defined by two of the aforementioned values.

In some embodiments, each or some of the tabs 2206, when viewed from a side plan view as illustrated in FIG. 22D, can comprise a height of about 0.50 mm. In certain embodiments, each or some of the tabs 2206, when viewed from a side plan view as illustrated in FIG. 22D, can comprise a height of about 0.10 mm, about 0.20 mm, about 0.30 mm, about 0.40 mm, about 0.50 mm, about 0.60 mm, about 0.70 mm, about 0.80 mm, about 0.90 mm, about 1.0 mm, and/or within a range defined by two of the aforementioned values.

In some embodiments, the optic 2200 can comprise one, two, three, four, five, six, seven, eight, nine, or ten tabs 2206. In certain embodiments, each or some of the one or more tabs 2206 can extend radially from about 30° of the circumference of the refractive portion of the optic 2200. In some embodiments, each of the one or more tabs 2206 of an optic 2000 can extend radially from about 20°, about 40°, about 60°, about 80°, about 100°, about 120°, about 140°, about 160°, about 180°, about 200°, about 220°, about 240°, about 260°, about 280°, about 300°, about 320°, about 340°, about 360° of the circumference of the refractive portion of the optic 2000, and/or within a range defined by two of the aforementioned values.

In some embodiments, each or some of the tabs 2206, when viewed from an anterior plan view as illustrated in FIG. 22B, can comprise a width of about 2.0 mm. In certain embodiments, each or some of the tabs 2206, when viewed from an anterior plan view as illustrated in FIG. 22B, can comprise a width of about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, and/or within a range defined by two of the aforementioned values.

A refractive surface or intraocular lens 2200 can comprise two convex portions 2200A, 2200B. One of the two convex portions 2200A can be configured to be placed in the interior of a prosthetic capsular device and the other convex portion 2200B can be configured to be placed exterior to the prosthetic capsular device upon attachment thereto. In some embodiments, the two convex portions 2200A, 2200B can comprise substantially the same shape, area, and/or refractive power. This way, a refractive surface or intraocular lens 2200 can be configured such that the posterior-anterior configuration thereof does not matter when attaching to a prosthetic capsular device. In other words, the refractive surface or intraocular lens 2200 can be flipped when attaching to a prosthetic capsular device and still obtain substantially the same function.

Some embodiments described herein are directed to and/or can be used in conjunction with an accommodating optic system, device, and/or method for controlling the same. An accommodating optic or lens can generally refer to an optic or lens that helps a user view clearly at varying distances. In other words, an accommodating optic or lens can provide varying refractive or optical powers to correct the vision of the user to varying degrees as the visual needs of the user changes. Accommodating optics or lenses can comprise a number of different forms and/or designs. One example is an electronic or electro-accommodating lens, which is also known as an electroactive accommodating lens, electroactive lens, or electroactive intraocular lens. An electroactive accommodating lens, for example, can comprise liquid crystals that are configured to change in configuration according to an electrical signal or input to alter the optical or focal power of the lens. An electroactive accommodating lens can be configured to be implanted into the eye as an intraocular lens (IOL).

One common problem that arises in connection with electroactive accommodating IOLs relates to the size and overall configuration of the electroactive accommodating IOL. For example, electroactive accommodating lenses or LCD power-changing lenses generally comprises liquid crystals placed between two wafers of Plexiglas, which is not foldable. At the same time, an IOL generally requires an optic comprising a diameter or width of at least 5 mm in order to provide a lens that functions in most environments, for example to avoid the halo effect and/or mismatch when the pupil is larger than the optic when in darker or other environments. In addition, it is generally advantageous to insert an IOL through a small incision, for example smaller than 3 mm. As such, in order to address and balance such criteria, certain electroactive accommodating IOLs comprise a generally rectangular or elongated bar shape to allow a rigid or semi-rigid electroactive accommodating IOL with a length or width of about 5 mm or larger, or larger than at least 3 mm, to be inserted through a small incision in the eye. This is contrast to most IOLs, which generally comprise a round or circular shape.

Figure 23A:
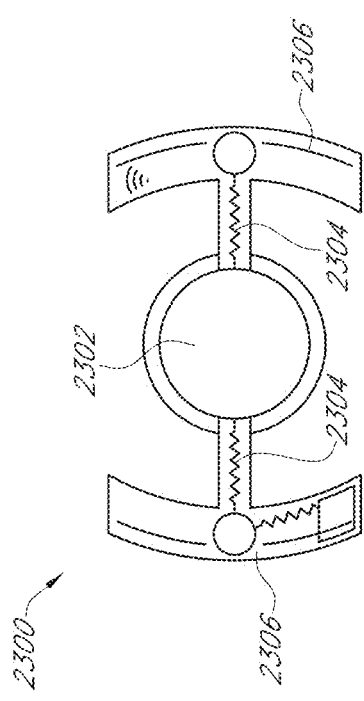
FIG. 23A is an anterior plan view of an example accommodating optic device configured to be used in conjunction with a prosthetic capsular device.
Figure 23C:
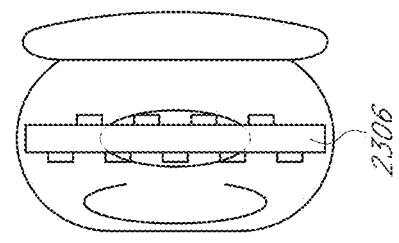
FIG. 23C is a cross-sectional view of the example accommodating optic system of FIG. 23B along a short axis of the prosthetic capsular device.
Figure 23B:
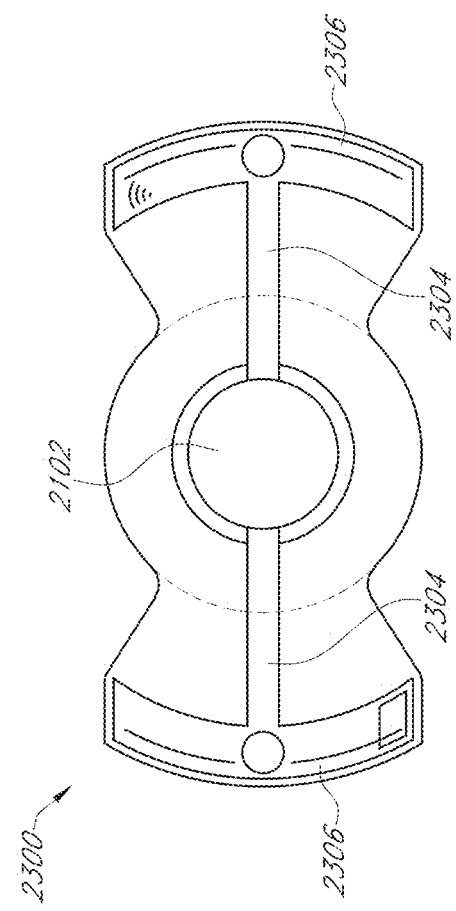
FIG. 23B is an anterior plan view of an example accommodating optic system comprising the example accommodating optic device of FIG. 23A used in conjunction with a prosthetic capsular device.

Certain accommodating optic systems, devices, and methods herein address these shortcomings. FIG. 23A illustrates an anterior plan view of an example accommodating optic device configured to be used in conjunction with a prosthetic capsular device. FIG. 23B illustrates an anterior plan view of an example accommodating optic system comprising the example accommodating optic device of FIG. 23A used in conjunction with a prosthetic capsular device. FIG. 23C illustrates a cross-sectional view of the example accommodating optic system of FIG. 23B along a short axis of the prosthetic capsular device.

In particular, the example accommodating optic 2300 is configured to be used in conjunction with any of the prosthetic capsular devices described herein. For example, the accommodating optic 2300 can be configured to be placed or inserted inside the prosthetic capsular device 1400. The accommodating optic 2300 can be configured to be placed anterior to the posterior refractive surface of a prosthetic capsular device, in which the posterior refractive surface can act as a base lens that can be supplemented by the accommodating optic 2300 to effectively change the focal point of a human optical system.

The accommodating optic 2300 can be configured to provide varying refractive or optical power in a similar manner as electroactive accommodating optics. A key difference is that the accommodating optic 2300 is configured to be used in conjunction with one or more of the prosthetic capsular devices described herein, which comprises a posterior refractive surface. In other words, because the accommodating optic 2300 is configured to be used in conjunction with a separate refractive surface or lens, the accommodating optic 2300 does not need to comprise an optic with a diameter or width of about 5 mm or larger as in certain electroactive accommodating optics.

The accommodating optic 2300 can comprise an optic 2302 that is only about 3 mm or smaller in diameter while being able to mitigate the halo effect or mismatch when the pupil is larger than the optic by use with a separate base lens or posterior refractive surface. As such, the accommodating optic 2300 can comprise a generally round or circular optic 2302 due to the smaller size. In certain embodiments, the optic or refractive portion 2302 of the accommodating optic 2300 can comprise a diameter of about 4.5 mm, about 4.0 mm, about 3.5 mm, about 3.0 mm, about 2.5 mm, about 2.0 mm, about 1.5 mm, about 1.0 mm, about 0.5 mm, and/or within a range defined by two of the aforementioned values.

Due to the smaller size, a substantially circular or round accommodating optic 2300 can be inserted through a small incision that is about the same or slightly larger than the diameter of the optics portion 2302. For example, an accommodating optic 2300 with an optics 2302 diameter of about 3 mm can be inserted through an incision of about 3 mm in the eye. As another example, an accommodating optic 2300 with an optics 2302 diameter of about 1 mm can be inserted through an incision of about 1 mm in the eye.

As discussed above, the accommodating optic 2300 can be configured to be placed anterior to the posterior refractive surface of a prosthetic capsular device. In other words, the posterior refractive surface of the prosthetic capsular device can act as a base lens that can be supplemented by the accommodating optic 2300. The accommodating optic 2300 can be capable of providing a variety of optical or refractive power. For example, the accommodating optic 2300 can be configured to provide an optical or refractive power of about 0 diopters, about 0.25 diopters, about 0.50 diopters, about 0.75 diopters, about 1.00 diopters, about 1.25 diopters, about 1.50 diopters, about 1.75 diopters, about 2.00 diopters, about 2.25 diopters, about 2.50 diopters, about 2.75 diopters, about 3.00 diopters, about 3.25 diopters, about 3.50 diopters, about 3.75 diopters, about 4.00 diopters, about 4.25 diopters, about 4.50 diopters, about 4.75 diopters, about 5.00 diopters, and/or within a range defined by any two of the aforementioned values. The accommodating optic 2300 can also be configured to correct wavefront higher order aberrations and/or correct or induce astigmatism.

As an illustrative example, the accommodating optic 2300 can be clear when in its non-powered or resting state so it would have an effective power of 0 diopters. However, based on input for example, the refractive power of the accommodating optic 2300 may be changed from 0 diopters through about 1, about 2, about 3, about 4, or about 5 diopters to provide an accommodated shift. As the accommodating optic 2300 is placed anterior to a posterior refractive surface of base optic, the vision of the user would effectively be corrected according to the power of the accommodating optic 2300.

The refractive or optical power of the accommodating optic 2300 can be changed based on user input in some embodiments. For example, the accommodating optic 2300 can be configured to change or alter its power based on user input received from a smartphone or other electronic device. The user input could be a particular value or range of optical power. The user input can be received through a dial or representation of a dial, in which the user can make a gradual selection from lower power and higher power and vice versa. If the user has two accommodating optics 2300 implanted, one in each eye, the user can control the power of just one or both of the accommodating optics 2300 at once. For instance, a user may control an accommodating optic 2300 of one eye to accommodate for far vision, while the accommodating optic 2300 in the other eye is controlled to accommodate for near vision, creating a monovision effect.

In addition, in certain embodiments, the accommodating optic 2300 may comprise or be configured to be used in conjunction with one or more other sensors, eye tracking software, and/or artificial intelligence. For example, one or more sensors or electrodes may detect muscle contracting, pupil retracting, head tilt or position tracking, or the like to control or contribute to automatic controlling the focal power of the accommodating optic 2300. However, there is a general risk that the one or more sensor may be imperfect and/or a user is not satisfied with the automatically determined power of the accommodating lens 2300. In such situations, a user may manually override the automated system by controlling the refractive or focal power of the accommodating optic 2300 using a user input device to fine tune the user's vision. The user input device can be a smartphone, smartwatch, electronic ring, electronic bracelet, or the like or other electronic device capable of communicating with the accommodating optic 2300, for example through wireless communication.

By using the accommodating lens in conjunction with a separate base lens, halo effects can also be mitigated despite the smaller size of the optics portion 2302 of the accommodating lens 2300. Generally speaking, the size of a human pupil in ambient lighting conditions can be said to be around 3 mm or less. In most functional states, the human pupil will likely be smaller than 3 mm. In dark environments, however, the pupil can become larger than 3 mm. In embodiments in which the optics portion 2302 of an accommodating optic 2300 has a diameter of 3 mm, some unfocused light may come in around the periphery of the optics 2302 of the accommodating optic 2300. This light will still be focused by the base lens or posterior refractive surface of the prosthetic capsular device. As such, similar to a multi-focal lens, light coming into the central portion through the accommodating lens 2300 will be focused at a different point than light coming in around the accommodating lens 2300 and going through just the posterior refractive surface or base lens. In darker environments, and in situations where the user does not require a near focus, for example while driving at nighttime or watching a concert, the user can tune the refractive power of the accommodating lens to adapt their needs. In other words, a user can easily eliminate halos by turning the accommodating lens 2300 into its resting state, thereby obtaining essentially a single focus distance lens.

To attach or otherwise couple the accommodating lens 2300 to a prosthetic capsular device, the accommodating lens 2300 can comprise one or more arm portions 2304 and/or haptics 2306 configured to be attached to the prosthetic capsular device. For example, one or more arm portions 2304 can extend radially outward from an optics portion 2302 of the accommodating lens 2300. Each of the arm portions 2304 can also comprise one or more haptics 2306 at the end, which can be configured to be inserted or attached to a groove or other locking mechanism or feature of the prosthetic capsular device.

In the embodiment illustrated in FIGS. 23A-23C, the accommodating lens 2300 can comprise two arm portions 2304 extending from the optics portion 2302, wherein each of the two arm portions 2304 comprises a curved anchor-shaped haptics 2306 that is configured to be inserted into a slot or groove located along the interior of the sidewall of a prosthetic capsular device. The optics portion 2302 can be configured to be centrally placed anterior to the posterior refractive surface of the prosthetic capsular device upon fixation of the haptics 2306. For example, a 3 mm optics portion 2302 can be placed substantially in the center anterior to a posterior 5.5 mm refractive surface. An accommodating lens 2300 can comprise one, two, three, four, five, six, seven, eight, nine, or ten arm portions 2304. Each of the arm portions 2304 can extend radially outward from the optics portion 2302, for example separated from each other by a similar angle. Each of the arm portions 2304 can comprise one, two, three, four, five, six, seven, eight, nine, or ten haptics 2306.

The length of accommodating lens 2300 along a longitudinal axis can be about 9.5 mm, including a 3 mm diameter of the optics portion 2302 for example. In certain embodiments, the length of the accommodating lens 2300 along a longitudinal axis can be about 8.0 mm, about 8.5 mm, about 9.0 mm, about 10.0 mm, about 10.5 mm, about 11.0 mm, about 11.5 mm, about 12.0 mm, and/or within a range defined by two of the aforementioned values.

One or more other components, such as electronic components can be placed within the haptics. For example, in addition to the optics portion 2302, the accommodating lens 2300 can also comprise one or more batteries or other power sources, one or more induction coils, one or more capacitors, one or more wireless antennas, wireless receivers, and/or one or more microprocessors. The one or more wireless antennas and/or receivers can be one or more of a radiofrequency antenna, Bluetooth antenna, Wi-Fi antenna, or the like that is configured to wirelessly communicate with a user input device or other electronic device.

Once user input or other electronic signal is received by the wireless antenna and/or receiver, a microprocessor or microchip can be configured to receive the input and determine an input/output decision for controlling a state of the LCD optics portion to control the focal power. The determined output can be transmitted to a capacitor that is configured to output an electric charge to appropriately change the refractive index of the optics portion as desired.

Figure 23D:
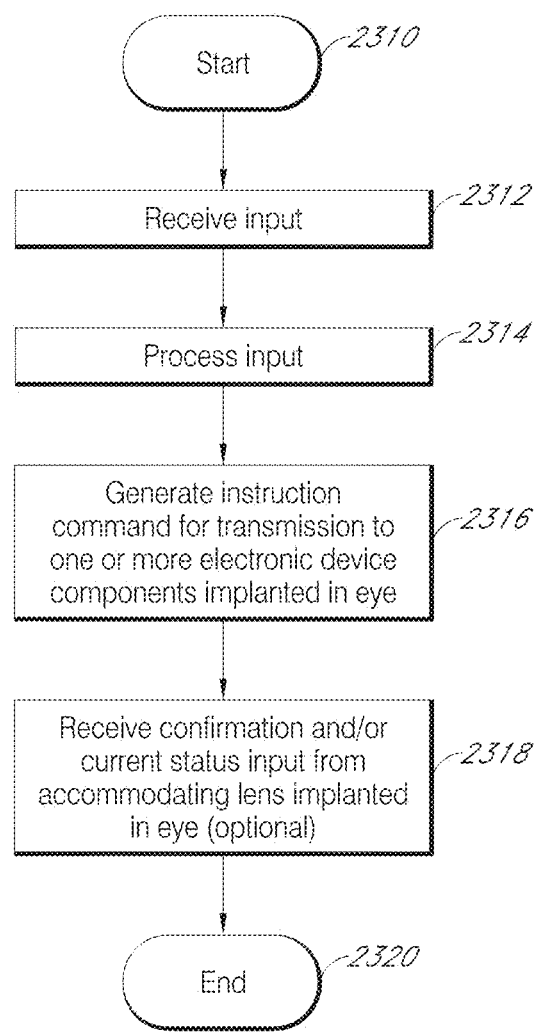
FIG. 23D is a block diagram depicting an example control process for an accommodating optic system.

FIG. 23D is a block diagram depicting an example control process for an accommodating optic system. As illustrated in FIG. 23D, in some embodiments, the system can be configured to receive one or more inputs at block 2312. The input can be a user input or an automated input. For example, the input received by the system may be from a user-initiated input through a user access point system. In addition or alternatively, the input received by the system can be from one or more sensors, such as an intraocular sensor and/or external light sensor that automatically determine a desired refractive power for the accommodating lens at a particular time and/or situation.

Once the input is received, the system can be configured to further process the input at block 2314. In certain embodiments, the system can be configured to combine or otherwise process a plurality of inputs, for example an automated input and a user input. In some embodiments, the system can be configured to process a single input, whether a user input or an automated input.

Processing one or more inputs by the system can involve one or more processes. In some embodiments, the system can be configured to process one or more inputs to determine whether to initiate one or more additional processes configured to increase and/or decrease the refractive power or other characteristic of an accommodating optic system or device. For example, if an input received by the system comprises data that corresponds to instructions and/or a determined need to increase the refractive power, the system can be configured to initiate one or more processes that are expected to increase the refractive power. Conversely, if an input received by the system comprises data that corresponds to instructions and/or a determined need to decrease the refractive power, the system can be configured to initiate one or more processes that are expected to decrease the refractive power.

If an input received by the system comprises data showing that the current refractive power and/or other characteristic of the accommodating optic system or device is optimal or operable, the system can be configured not to initiate any processes to change the refractive power and/or other characteristic of the accommodating optic device or system.

Based on such determination, the system can be further configured to generate one or more instruction commands for transmission to one or more electronic device components of the system implanted in the eye at block 2316. Each electronic device component that received an instruction command can be further configured to perform one or more processes according to the received instruction command. Optionally, in some embodiments, the system can be further configured to determine whether the one or more electronic device components that received an instruction command in fact performed the corresponding one or more processes at block 2318. If confirmation and/or a current status input are received by the system that the one or more corresponding processes were performed, the process can end at block 2320 in some embodiments. However, if such confirmation and/or a current status input is not received, the system can be configured to repeat one or more processes from blocks 2312 to 2318.

Further, in some embodiments, the system can be configured to repeat one or more processes described in relation to FIG. 8 periodically, in real-time, or in near real-time. For example, the system can be configured to repeat processes 2312 through 2316 and/or processes 2312 through 2318 periodically, in real-time, or in near real-time. The one or more processes can be repeated every about 1 second, about 2 seconds, about 3 seconds, about 4 seconds, about 5 seconds, about 6 seconds, about 7 seconds, about 8 seconds, about 9 seconds, about 10 seconds, about 20 seconds, about 30 seconds, about 40 seconds, about 50 seconds, about 1 minute, about 2 minutes, about 3 minutes, about 4 minutes, about 5 minutes, and/or within a range defined by two of the aforementioned values.

Figure 23E:
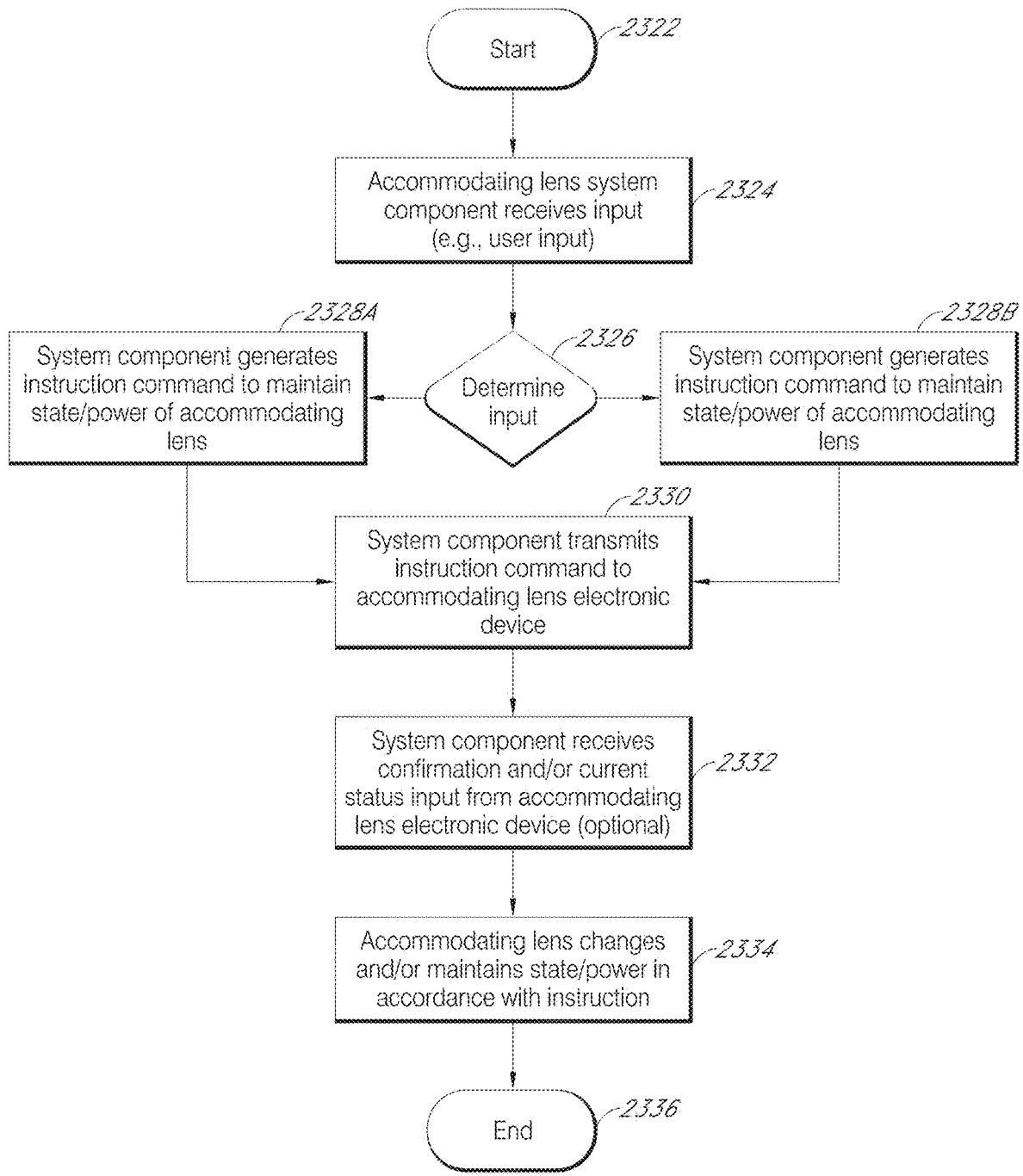
FIG. 23E is a block diagram depicting another example control process for an accommodating optic system.

FIG. 23E is a block diagram depicting another example control process for an accommodating optic system. In some embodiments, an electronic system component of the accommodating lens system, for example a control unit, can receive one or more inputs at block 2324. The one or more inputs can comprise a user input or data relating to the strain on the eye, external lighting conditions, muscular contractions, or any other data that can be indicative of a need or desire to increase or decrease the refractive power of the accommodating optic system or device. The user input can be achieved by a user through a user access point system, such as a smartphone or other handheld electronic device. Other data can be collected and/or received from one or more intraocular and/or external sensors for use in conjunction with the accommodating optic system.

The system component can be configured to further process the received input at block 2326. The system may determine that the received input corresponds to increasing, decreasing, and/or maintaining the refractive power and/or other characteristic of the accommodating optic system or device. If the system determines that the received input requires or corresponds to changing the state and/or power of the accommodating optic system or device, the system can be configured to generate an instruction command to appropriately change the state and/or power of the accommodating optic system or device at block 2328A. If the system determines that the received input requires or corresponds to maintain a current state and/or power of the accommodating optic system or device, the system can be configured to generate an instruction command to maintain state and/or power of the accommodating optic system or device at block 2328B.

The system component can be further configured to electronically transmit the generated instruction command to the same or another electronic device component of the accommodating lens or optic system at block 2330. In some embodiments, the generated instruction command can be transmitted through a wired connection. In certain embodiments, the generated instruction command can be transmitted through a wireless connection.

In some embodiments, the system component can be further configured to receive confirmation and/or a current status input from the accommodating optic system at block 2332. At block 2334, the accommodating lens or optic system or device can increase, decrease, and/or maintain a refractive power and/or other characteristic of the system based on the system instructions.

Figure 24B:
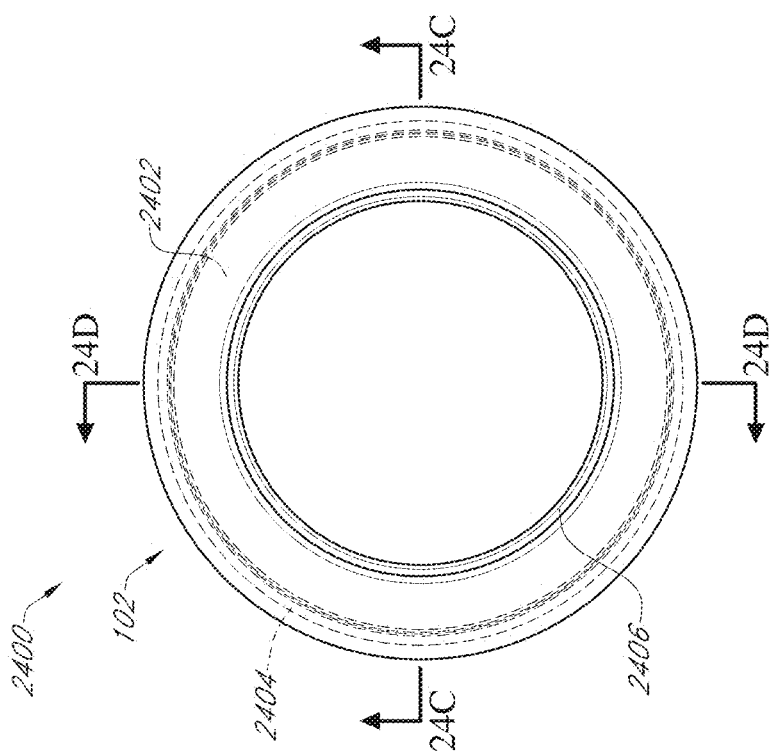
FIG. 24B is an anterior plan view of the example prosthetic capsular device of FIG. 24A.
Figure 24A:
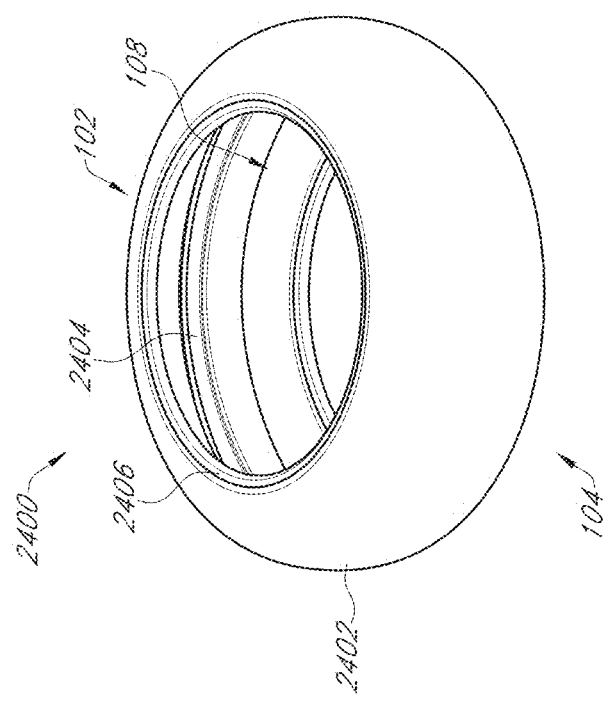
FIG. 24A is an anterior side perspective view of another example prosthetic capsular device.
Figure 24D:
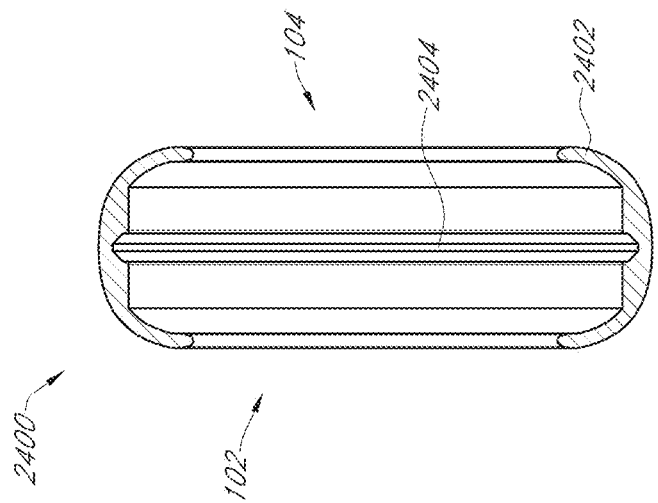
FIG. 24D is a cross-sectional view of the example prosthetic capsular device of FIG. 24A along the line 24D-24D of FIG. 24B.
Figure 24C:
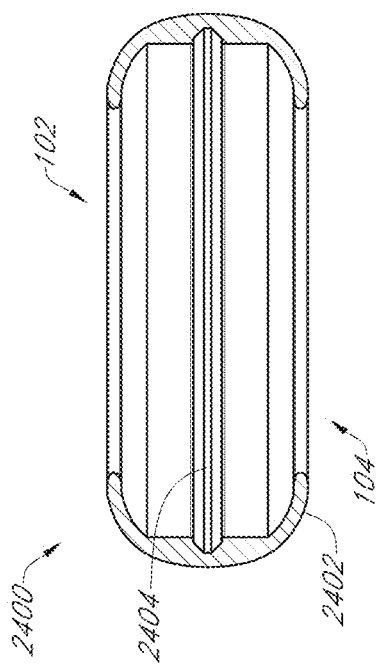
FIG. 24C is a cross-sectional view of the example prosthetic capsular device of FIG. 24A along the line 24C-24C of FIG. 24B.
Figure 24F:
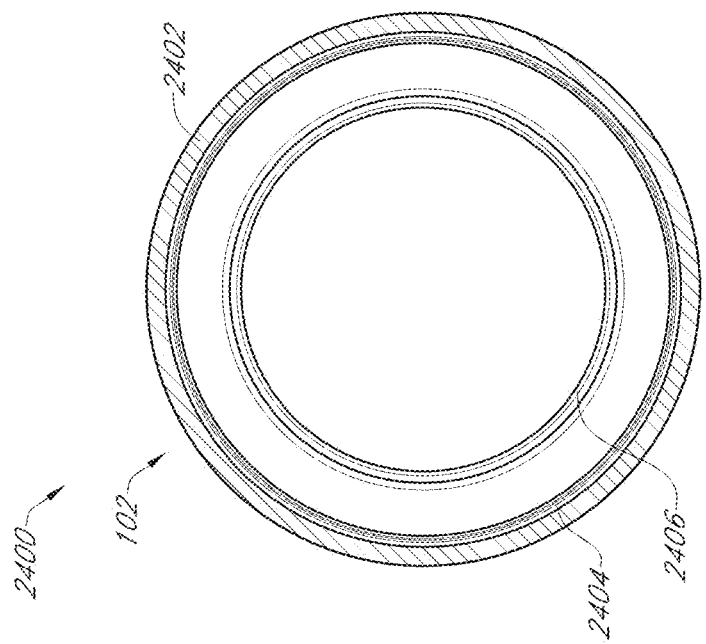
FIG. 24F is a cross-sectional view of the example prosthetic capsular device of FIG. 24A along the line 24F-24F of FIG. 24D.
Figure 24E:
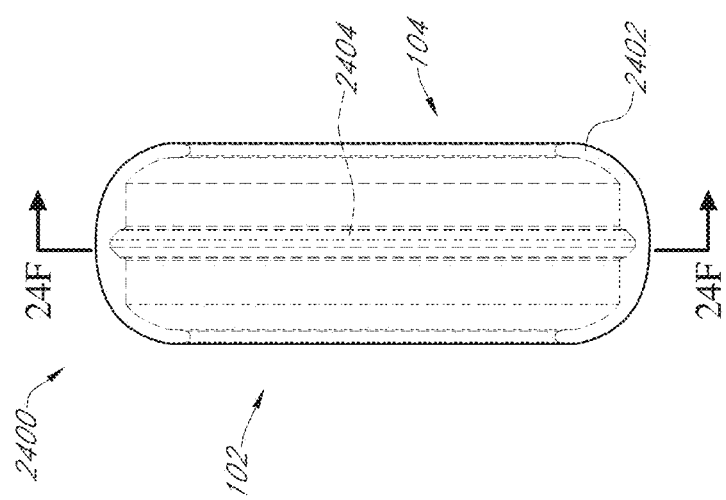
FIG. 24E is a side plan view of the example prosthetic capsular device of FIG. 24A.

FIG. 24A illustrates an anterior side perspective view of another example prosthetic capsular device. FIG. 24B illustrates an anterior plan view of the example prosthetic capsular device of FIG. 24A. FIG. 24C illustrates a cross-sectional view of the example prosthetic capsular device of FIG. 24A along the line 24C-24C of FIG. 24B. FIG. 24D illustrates a cross-sectional view of the example prosthetic capsular device of FIG. 24A along the line 24D-24D of FIG. 24B. FIG. 24E illustrates a side plan view of the example prosthetic capsular device of FIG. 24A. FIG. 24F illustrates a cross-sectional view of the example prosthetic capsular device of FIG. 24A along the line 24F-24F of FIG. 24D.

The example prosthetic capsular device 2400 illustrated in FIG. 24A includes some or all of the features of the example prosthetic capsular devices illustrated in FIGS. 1A-21A, and like reference numerals include like features. For example, similar to the example prosthetic capsular device 600 of FIG. 6A, the example prosthetic capsular device 2400 of FIG. 24A can include one or more ridges 2404. Also, similar to the example prosthetic capsular device 1000 of FIG. 10A, the example prosthetic capsular device 2400 of FIG. 24A can include a single, continuous sidewall 2402.

In particular, the example prosthetic capsular device 2400 can comprise a single continuous sidewall 2402 without any breaks or void spaces. The sidewall 2402 can be made of silicone. The device 2400 can comprise an anterior opening and a posterior opening. A void space or cavity 108 can be formed through the device 2400 connecting the anterior opening and the posterior opening. Accordingly, the device 2400 can comprise a substantially tire or doughnut-like shape or configuration.

The device 2400 can be configured such that the anterior side 102 and the posterior side 104 are substantially the same. As such, it may not matter whether the anterior side 102 and the posterior side 104 are flipped. In other words, an anterior half of the device 2400 can substantially be a mirror image of the posterior half of the device 2400. The device 2400 can be configured to be used in conjunction with one or more refractive surfaces or IOLs. For example, a refractive surface or IOL can be configured to be placed to cover the anterior opening 102 and/or posterior opening 104. A refractive surface or IOL configured to be affixed to the anterior opening 102 and/or posterior opening 104 can also be symmetrical along the posterior-anterior axis. In other words, in some embodiments, a refractive surface or IOL configured to be affixed to the anterior opening 102 and/or posterior opening 104 can comprise the same power on both sides of the lens or refractive surface. As such, both the refractive surface or IOL and the device 2400 can be fully reversible over a plane that divides the anterior and posterior portions of the device and lens, for example for ease of use during surgery and to decrease risk related to the configuration of the device and/or lens. A refractive surface, IOL, electronic device, and/or other intraocular device can also be placed inside the cavity 108 of the device in between the anterior opening 102 and the posterior opening 104.

Further, the device 2400 can comprise one or more ridges 2404. The one or more ridges 2404 can be configured to provide mechanical support or otherwise affix an additional IOL, electronic device, or the like to be placed inside the device 2400. For example, haptics or other anchoring mechanisms of an IOL, electronic device, or the like can be configured to be slid into the one or more ridges 2404. The one or more ridges 2404 can be located in between the anterior opening 102 and the posterior opening 104. For example, the one or more ridges 2404 can be located at a substantially midpoint location between the anterior opening 1202 and the posterior opening 104.

As such, the device 2400 can comprise three or more planes or positions within the device 2400 for affixing or placing an intraocular device, such as an IOL, electronic device, or the like. For example, a first intraocular device can be placed or affixed at the anterior end or opening 102, a second intraocular device can be placed or affixed at the posterior end or opening 104, and a third intraocular device can be placed or affixed at the one or more ridges 2404 and/or in the cavity 108 of the device. In certain embodiments, the device 2400 can be configured to hold more than one intraocular device inside the cavity 108 of the device, for example by providing more than one ridges 2404. As such, in some embodiments, the device 2400 can be configured to hold three or more IOLs, refractive surfaces, other intraocular devices, and/or combination thereof within a single device 2400.

In some embodiments, the anterior end 102 and/or posterior end 104 can be configured to affix a refractive surface 110, intraocular lens, or other intraocular device specifically designed for use with the device 2400. In contrast, the cavity 108 of the device 2400 can be configured to hold any generic and/or third-party designed or manufactured intraocular device and/or IOL.

In some embodiments, the device 2400, when viewed from an anterior plan view as illustrated in FIG. 24B, can comprise a generally circular shape with an outer diameter of about 9.650 mm. In certain embodiments, the device 2400, when viewed from an anterior plan view, can comprise a substantially circular shape with an outer diameter of about 6.0 mm, about 6.5 mm, about 7.0 mm, about 7.5 mm, about 8.0 mm, about 8.5 mm, about 9.0 mm, about 9.5 mm, about 10.0 mm, about 10.5 mm, about 11.0 mm, about 11.5 mm, about 12.0 mm, and/or within a range defined by two of the aforementioned values.

In certain embodiments, the device 2400, when viewed from a side view, can comprise a thickness, excluding any refractive surface or IOL attached, of about 3.50 mm. In some embodiments, the device 2400, when viewed from a side view and excluding any refractive surface or IOL, can comprise a thickness of about 0.50 mm, about 1.00 mm, about 1.50 mm, about 2.00 mm, about 2.50 mm, about 3.00 mm, about 3.50 mm, about 4.00 mm, about 4.50 mm, about 5.00 mm, about 5.50 mm, about 6.00 mm, about 6.50 mm, about 7.00 mm, and/or within a range defined by two of the aforementioned values.

In some embodiments, the device 2400 can comprise an anterior opening 102 and/or posterior opening, for example to receive a refractive surface or IOL, comprising a diameter of about 6.350 mm. In certain embodiments, the device 2400 can comprise an anterior opening 102 and/or posterior opening, for example to receive a refractive surface or IOL, comprising a diameter of about 3.00 mm, about 3.50 mm, about 4.00 mm, about 4.50 mm, about 5.00 mm, about 5.50 mm, about 6.00 mm, about 6.50 mm, about 7.00 mm, about 7.50 mm, about 8.00 mm, about 8.50 mm, about 9.00 mm, and/or within a range defined by two of the aforementioned values.

In some embodiments, the one or more ridges 2404, when viewed from an anterior plan view as illustrated in FIG. 24B, can comprise an outer diameter of about 9.150 mm and an inner diameter of about 8.60 mm. In certain embodiments, the one or more ridges 2404, when viewed from an anterior plan view, can comprise an outer diameter and/or inner diameter of about 6.0 mm, about 6.5 mm, about 7.0 mm, about 7.5 mm, about 8.0 mm, about 8.5 mm, about 9.0 mm, about 9.5 mm, about 10.0 mm, about 10.5 mm, about 11.0 mm, about 11.5 mm, about 12.0 mm, and/or within a range defined by two of the aforementioned values. In certain embodiments, the one or more ridges 2404, when viewed from a side view, can comprise a thickness of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 2.0 mm, about 2.5 mm, about 3.0 mm, about 3.5 mm, about 4.0 mm, about 4.5 mm, about 5.0 mm, and/or within a range defined by two of the aforementioned values.

Similar to the device illustrated in FIG. 19A, the device 2400 can also comprise a lip portion 2406 surrounding the posterior and/or anterior opening 102, 104 to receive one or more tongue portions, one or more tabs, and/or one or more haptics of a refractive surface or IOL. The lip portion 2406 can comprise a certain thickness when viewed from an anterior plan view as illustrated in FIG. 24F. As such, the diameter of a circular portion formed around the interior circumference of the anterior and/or posterior opening 102, 104 of the device 2400, excluding the lip portion 2406, can be about 7.00 mm and/or larger than the posterior and/or anterior opening. In certain embodiments, the diameter of a circular portion formed around the interior circumference of the anterior and/or posterior opening 102, 104 of the device 2400, excluding the lip portion 2406 can be about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, about 6.5 mm, about 6.6 mm, about 6.7 mm, about 6.8 mm, about 6.9 mm, about 7.0 mm, about 7.1 mm, about 7.2 mm, about 7.3 mm, about 7.4 mm, about 7.5 mm, about 8.0 mm, about 8.1 mm, about 8.2 mm, about 8.3 mm, about 8.4 mm, about 8.5 mm, about 9.0 mm, about 9.5 mm, about 10 mm, about 10.5 mm and/or within a range defined by two of the aforementioned values.

Figure 25B:
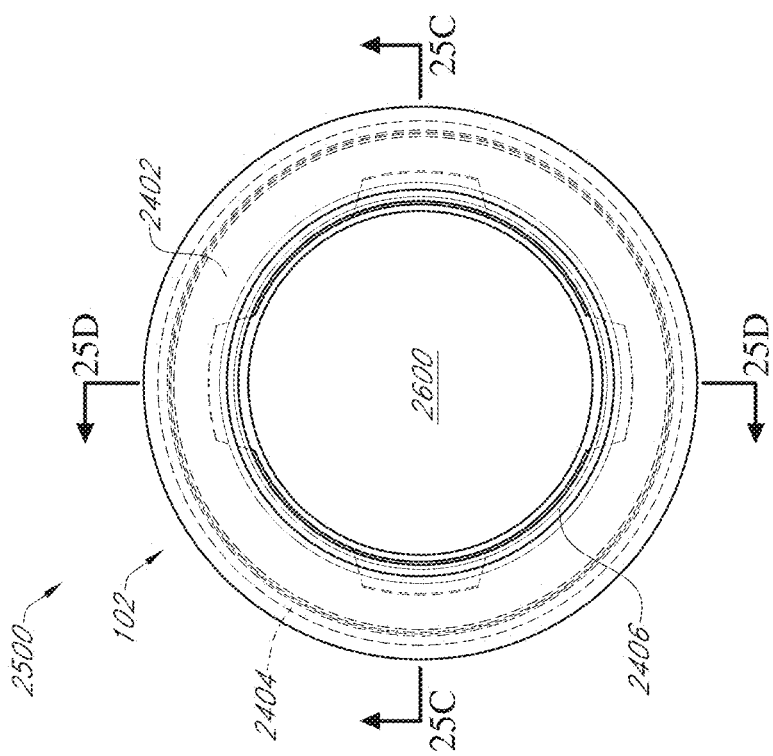
Figure 25A:
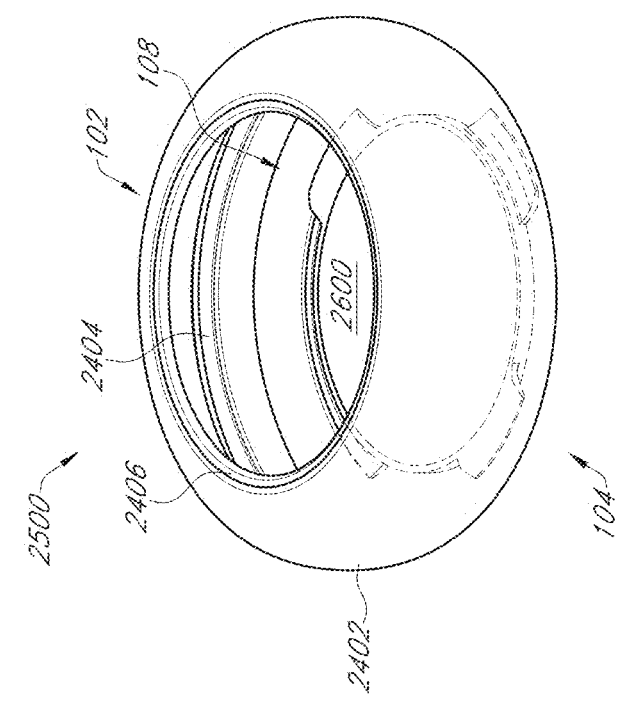
Figure 25D:
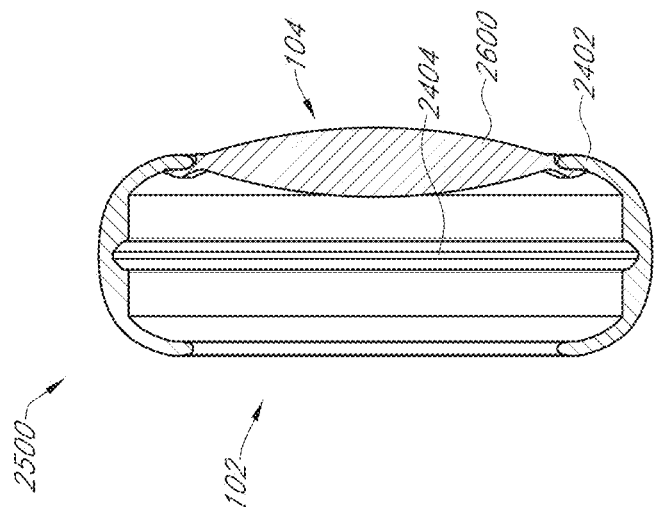
Figure 25C:
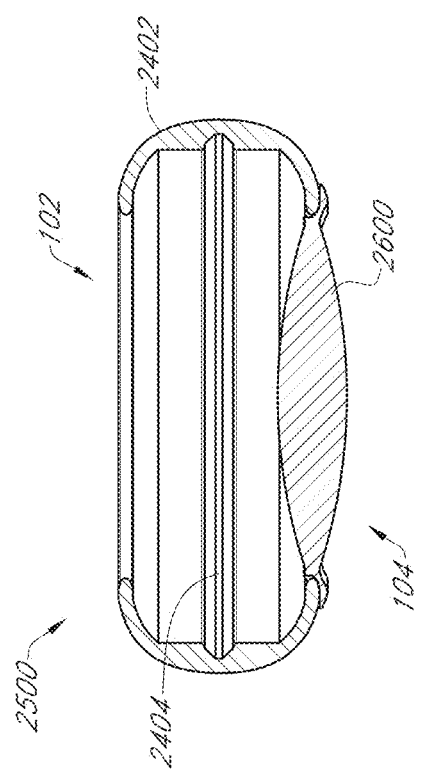

FIG. 25A illustrates an anterior side perspective view of another example prosthetic capsular device. FIG. 25B illustrates an anterior plan view of the example prosthetic capsular device of FIG. 25A. FIG. 25C illustrates a cross-sectional view of the example prosthetic capsular device of FIG. 25A along the line 25C-25C of FIG. 25B. FIG. 25D illustrates a cross-sectional view of the example prosthetic capsular device of FIG. 25A along the line 25D-25D of FIG. 25B.

The example prosthetic capsular device 2500 of FIG. 25A includes some or all of the features of the example prosthetic capsular device 2400 illustrated in FIG. 24A, and like reference numerals include like features. For example, similar to the example prosthetic capsular device 2400 of FIG. 24A, the example prosthetic capsular device 2500 of FIG. 25A can include one or more ridges 2404, a single continuous sidewall 2402, a posterior opening or end 104, and an anterior opening or end 102.

The example prosthetic capsular device 2500 shown in FIG. 25A further comprises a refractive surface or IOL 2600 attached thereto. The refractive surface or IOL 2600 can be attached to the posterior end 104 and/or substantially cover the posterior opening 104. Similarly, the refractive surface or IOL 2600 can be attached to the anterior end 102 and/or substantially cover the anterior opening 102. Due to the fact that the device 2600, when separated from the refractive surface or IOL 2600, comprises an anterior half that is substantially equal to the posterior half, it may not matter functionally whether the refractive surface or IOL 2600 is attached to the posterior end 104 or the anterior end 102. In other words, the device 2500 can be said to comprise a posterior refractive surface or an anterior refractive surface. As discussed above in relation to FIG. 24A, one or more additional refractive surfaces or IOLs, electronic devices, or other intraocular devices can further be attached to the device, for example at the posterior or anterior end and/or along one or more ridges.

Figure 26D:
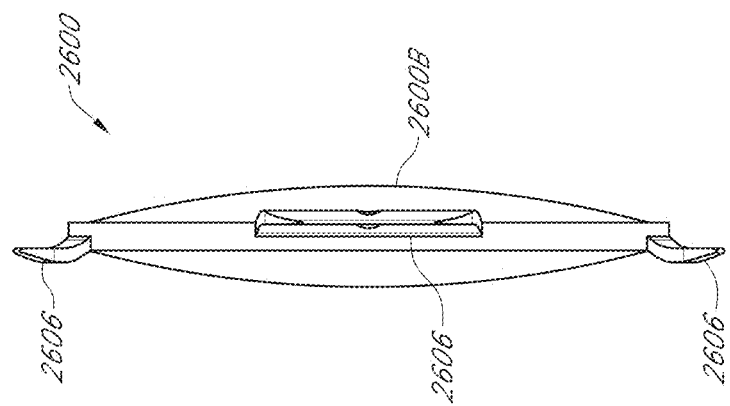
Figure 26C:
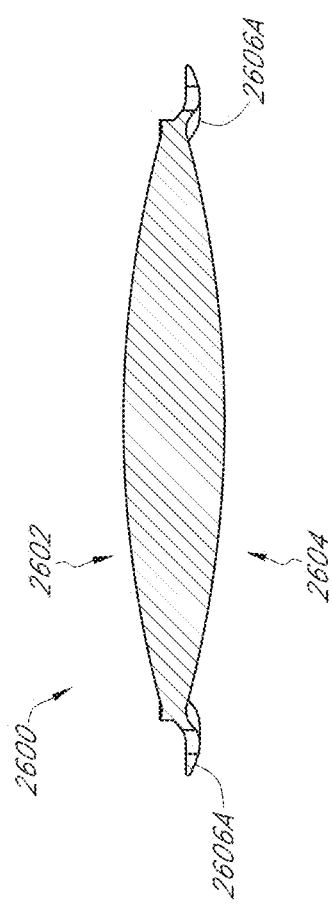

FIG. 26A illustrates an anterior side perspective view of an example refractive surface or intraocular lens that can be configured to be used in conjunction with a prosthetic capsular device, such as the prosthetic capsular device of FIG. 25A and/or any other prosthetic capsular device described herein. FIG. 26B illustrates an anterior plan view of the example refractive surface or intraocular lens of FIG. 26A. FIG. 26C illustrates a cross-sectional view of the example refractive surface or intraocular lens of FIG. 26A along the line 26C-26C of FIG. 26B. FIG. 26D is a side plan view of the example refractive surface or intraocular lens of FIG. 26A.

The refractive surface or IOL 2600 can comprise one or more similar features as those described in relation to the refractive surface 2200 in relation to FIG. 22A. The refractive surface or IOL 2600 can be configured to be attached to any one of the example prosthetic capsular devices disclosed herein. In particular, the refractive surface or IOL 2600 can be configured to be attached to the anterior and/or posterior end of the prosthetic capsular devices 2400, 2500.

In some embodiments, the optic or refractive surface 2600 can comprise a diameter of about 6.250 mm. In certain embodiments, the optic of refractive surface 2600 can comprise a diameter of about 5.00 mm, about 5.50 mm, about 6.00 mm, about 6.50 mm, about 7.00 mm, about 7.50 mm, about 8.00 mm, about 8.50 mm, about 9.00 mm, about 9.50 mm, about 10.00 mm, and/or within a range defined by two of the aforementioned values.

The refractive surface or IOL 2600 can comprise an anterior side or end 2602 and a posterior side or end 2604. In some embodiments, the anterior side 2602 can be substantially equal to the posterior side 2604, such that the anterior-posterior configuration of the refractive surface of IOL 2600 does not affect the operability or functionalities when affixing to a prosthetic capsular device. In other embodiments, the anterior side 2602 and the posterior side 2604 can have one or more different features, such as thickness, curvature, refractive power, or the like.

The refractive surface or intraocular lens 2600 can comprise two convex portions 2600A, 2600B. One of the two convex portions 2600A can be configured to be placed in the interior of a prosthetic capsular device and the other convex portion 2600B can be configured to be placed exterior to the prosthetic capsular device upon attachment thereto. In some embodiments, the two convex portions 2600A, 2600B can comprise substantially the same shape, area, and/or refractive power. This way, a refractive surface or intraocular lens 2600 can be configured such that the posterior-anterior configuration does not matter when attaching to a prosthetic capsular device. In other words, the refractive surface or intraocular lens 2600 can be flipped when attaching to a prosthetic capsular device and still obtain substantially the same function.

In some embodiments, the refractive surface or IOL 2600 comprises one or more tabs 2600 to facilitate attachment of the refractive surface or IOL 2600 to a prosthetic capsular device. For example, in the embodiment illustrated in the FIG. 26A, the refractive surface or IOL 2600 comprises four tabs 2606. In other embodiments, a refractive surface or IOL 2600 can comprise one, two, three, five, six, seven, eight, nine, or ten tabs 2606.

Each of the tabs 2606 can comprise a flap that is curved. Each of the tabs 2606 can comprise a flap that is curved in the same direction. Alternatively, some of the tabs 2606 can be curved in one direction and certain other tabs 2606 can be curved in another direction. For example, in the illustrated embodiment, two tabs 2606A can extend towards the anterior end 2602 curving towards the posterior end 2604, and the other two tabs 2606B can extend towards the posterior end 2604 curving towards the anterior end 2602. In other embodiments, the tabs 2606 can be substantially flat or planar.

In attaching a refractive surface or IOL 2600 to a prosthetic capsular device, one or more of the tabs can be configured to be placed through to the anterior end 102 or posterior end 104 of the device. Accordingly, as shown in FIG. 25A, two of four tabs 2606 can be placed in the interior of the device 2500, while the other two tabs 2606 are placed exterior to a posterior end 104 of the device. Similarly, one tab 2606 can be placed in the interior of the device 2500, while other tabs 2606 are placed exterior to the device.

Each of the plurality of tabs 2606 can extend from the refractive surface 2600 at an angle when viewed from a side plan view as illustrated in FIG. 26D. For example, in some embodiments, each or some of the plurality of tabs 2606 can initially extend from the refractive surface 2600 at an angle of about 45° in either direction. In certain embodiments, each or some of the plurality of tabs 2606 can initially extend from the refractive surface 2600 at an angle of about +/−10°, about +/−20°, about +/−25°, about +/−30°, about +/−35°, about +/−40°, about +/−45°, about +/−50°, about +/−55°, about +/−60°, about +/−70°, about +/−80°, about +/−90°, and/or within a range defined by two of the aforementioned values.

In some embodiments, each or some of the tabs 2606, when viewed from a side plan view as illustrated in FIG. 26D, can comprise a height of about 0.50 mm. In certain embodiments, each or some of the tabs 2606, when viewed from a side plan view as illustrated in FIG. 22D, can comprise a height of about 0.10 mm, about 0.20 mm, about 0.30 mm, about 0.40 mm, about 0.50 mm, about 0.60 mm, about 0.70 mm, about 0.80 mm, about 0.90 mm, about 1.0 mm, and/or within a range defined by two of the aforementioned values.

In certain embodiments, each or some of the one or more tabs 2606 can extend radially from about 30° of the circumference of the refractive portion of the optic 2600. In some embodiments, each of the one or more tabs 2606 of an optic 2600 can extend radially from about 20°, about 40°, about 60°, about 80°, about 100°, about 120°, about 140°, about 160°, about 180°, about 200°, about 220°, about 240°, about 260°, about 280°, about 300°, about 320°, about 340°, about 360° of the circumference of the refractive portion of the optic 2600, and/or within a range defined by two of the aforementioned values.

In some embodiments, each or some of the tabs 2606, when viewed from an anterior plan view as illustrated in FIG. 26B, can comprise a width of about 2.0 mm. In certain embodiments, each or some of the tabs 2606, when viewed from an anterior plan view as illustrated in FIG. 26B, can comprise a width of about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, and/or within a range defined by two of the aforementioned values.

The refractive surface or IOL 2600 can comprise equal refractive power on each of the anterior and posterior halves. In other words, the refractive surface or IOL 2600 can be an equi-convex lens. As such, the orientation or direction in which the lens 2600 is inserted into the device can be disregarded as the lens can be reversible and symmetric along the anterior-posterior axis.

Figure 27B:
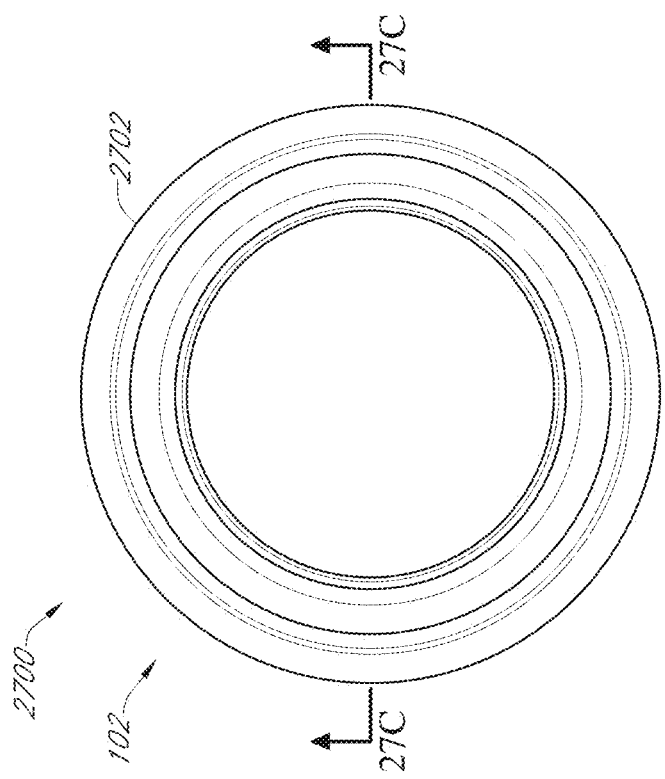
Figure 27A:
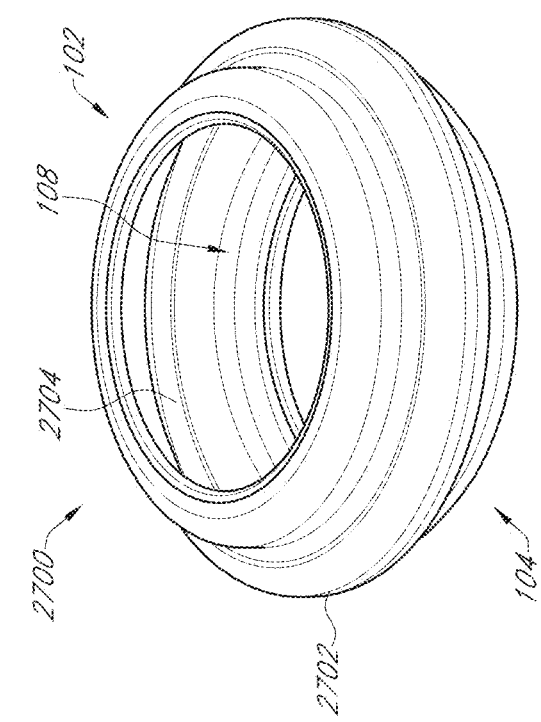

FIG. 27A illustrates an anterior side perspective view of another example prosthetic capsular device. FIG. 27B illustrates an anterior plan view of the example prosthetic capsular device of FIG. 25A. FIG. 27C illustrates a cross-sectional view of the example prosthetic capsular device of FIG. 27A along the line 27C-27C of FIG. 27B. FIG. 27D illustrates a side plan view of the example prosthetic capsular device of FIG. 27A.

FIG. 28A illustrates an anterior side perspective view of another example prosthetic capsular device. FIG. 28B illustrates an anterior plan view of the example prosthetic capsular device of FIG. 28A. FIG. 28C is a cross-sectional view of the example prosthetic capsular device of FIG. 28A along the line 28C-28C of FIG. 28B. FIG. 28D illustrates a side plan view of the example prosthetic capsular device of FIG. 28A.

The devices 2700, 2800 can include some or all of the features of the example prosthetic capsular device 2400 illustrated in FIG. 24A, and like reference numerals include like features. The devices 2700, 2800 can be self-expandable to keep the capsule fully open. The devices 2700, 2800 can comprise three different planes. For example, a first plane can correspond with the posterior end 104 of the device, where a refractive surface or IOL can be attached. A second plane can correspond with the anterior end 102 of the device, where another refractive surface or IOL can be attached. A third plane can be positioned in between the posterior end and the anterior end, for example along ridges 2704, 2804.

The ridges 2704, 2804 can be formed by the shape or curvature of the device 2700, 2800. In other words, instead of adding material to form the ridges, material can be removed from the device 2700, 2800 to form ridges 2704, 2804. For example, a central portion of the device 2700, 2800 when viewed from the view in FIG. 27D, can comprise a vertical portion that extends substantially perpendicular to anterior and posterior portions. The thickness of this vertical portion can be controlled to provide a slot or ridge of varying thickness.

In some embodiments, a prosthetic capsular device configured to be inserted in a natural capsular bag of an eye after removal of a lens can comprise a housing structure 2700, 2800 capable of containing an intraocular device and/or an equiconvex refractive surface. In particular, the housing structure can comprise an anterior portion, wherein the anterior portion comprises a circular anterior opening, wherein the circular anterior opening is capable of allowing at least one of insertion, removal, or replacement of the intraocular device, and wherein the anterior opening is further configured to be coupled to a refractive surface to cover the circular anterior opening; a posterior portion, wherein the posterior portion comprises a circular posterior opening wherein the circular posterior opening is capable of allowing at least one of insertion, removal, or replacement of the intraocular device, and wherein the posterior opening is further configured to be coupled to a refractive surface to cover the circular posterior opening; and a continuous lateral portion interposed between the anterior portion and the posterior portion, wherein the continuous lateral portion protrudes radially beyond the anterior portion and the posterior portion, wherein the continuous lateral portion fully encloses a lateral side of the housing structure, wherein an internal cavity of the continuous lateral portion forms a groove for containing the intraocular device. The continuous lateral portion may not have any openings, for example along the lateral portion of the device in some embodiments. The housing structure 2700, 2800 can be symmetrical over a plane at a midpoint of the continuous lateral portion between the anterior portion and the posterior portion. In certain embodiments, the equiconvex refractive surface can comprise a plurality of tabs for affixing the refractive surface to at least one of the circular anterior opening or the circular posterior opening, wherein the plurality of tabs protrudes from the refractive surface in alternating posterior and anterior directions.

As discussed above, one or more refractive surfaces, IOLs, lenses, optics, and/or other intraocular devices can be placed in the device 2700, 2800 at the posterior opening 104 and/or anterior opening 102. For example, a surgeon may initially insert a device with a posterior refractive surface into an eye of a patient. Depending on the outcome, the surgeon may insert a secondary IOL on the anterior opening of the device 2700, 2800 to obtain better results. In other words, a secondary IOL can be placed on the anterior opening for fine tuning. Moreover, a diametric sensor and/or another IOL can be placed in the interior of the device 2700, 2800 as well, for example along the ridges on the third plane.

The devices 2700, 2800 can be symmetric and/or reversible so that they are the same right side up as upside down along the anterior-posterior axis. This can be advantageous in that the devices 2700, 2800 can have a tendency to want to flip around as they are being inserted and a surgeon would not need to worry about the device flipping way or the other. In other words, the anterior half and the posterior half of the device 2700, 2800 can be mirror images of each other. The device 2700, 2800 can be made of silicone, while a refractive surface or IOL can be made of acrylic, and cut with a lathe such as CNC Lathing for example. It can be advantageous for the device 2700, 2800 to be made of a material that can accommodate for stretching without tearing, but also has a sufficiently high durometer rating so that it maintains sufficient rigidity and stiffness inside the eye. For example, Med 6210 silicone can be used in some embodiments. In some embodiments, the device 2700, 2800 can be substantially clear. In other embodiments, the device 2700, 2800 can be made of opaque silicone and/or may comprise different colors, for example to accommodate for dysphotopsias from angles and/or ridges of the device 2700, 2800. A mold for the device 2700, 2800 can be sandblasted so that the silicone forming the device 2700, 2800 can comprise some texture in certain embodiments. It can be advantageous for the device to comprise a texturized surface to reduce glare and to diffuse light. In other embodiments, the device 2700, 2800 can comprise a smooth surface.

The refractive surface or IOL of FIG. 26A, for example, can be attached to the devices 2700, 2800. For example, a refractive surface or IOL can have four tabs, two of which can be placed in the interior of the device and two of which can be placed exterior to the device to lock the refractive surface or IOL in place. To secure the refractive surface or IOL with respect to the device 2700, 2800, two tabs can be pushed down to the exterior of the device 2700, 2800 using an irrigation-aspiration (IA) device tip for example while the other two tabs remain inside the device 2700, 2800. In some embodiments, the tabs of the refractive surface or IOL, as shown in FIG. 26A, can be curved. The curvature of the refractive surface or IOL and/or the rigidity of the device 2700, 2800 and tabs can substantially keep the lens in place with respect to the device 2700, 2800.

The tabs can comprise one or more eyelet openings in some embodiments. The one or more eyelet openings of each tab can be used for dialing or rotating the lens to a specific meridian. In addition, or alternatively, a surgeon may use the one or more eyelet openings to suture the optic to the device as necessary.

As discussed above, the device 2700, 2800 and a lens for insertion into the device can both be symmetric and reversible along the posterior-anterior axis. Because the lens or refractive surface, for example shown in FIG. 26A, can comprise the equal refractive power on the anterior and posterior portions, there is no refractive surprise. Accordingly, the orientation or direction in which the device 2700, 2800 and/or lens 2600 is inserted will not matter in some embodiments. A surgeon would not need to flip the device 2700, 2800 or lens 2600 over too obtain the correct orientation, as either orientation, whether anterior-posterior or posterior-anterior, will be the same.

In some embodiments, the device 2700, 2800 can be made in a number of different sizes or scales to accommodate for different patient biometry. For example, there can be a large, medium, and small sized device 2700, 2800 (or any other combination of sizes) to accommodate for patients with different sized cataracts. By providing a number of devices 2700, 2800 of varying sizes, surgeons can be able to select a particular device and/or optic for insertion in a particular patient.

In some embodiments, the devices 2700, 2800 can comprise an anterior portion 2750, a central portion 2760, and a posterior portion 2770. The anterior portion 2750 and the central portion 2760 can be mirror images of each other. The central portion 2760 can comprise a midline along which one-half of the central portion 2760 can be a mirror image of the other half of the central portion 2760. The central portion 2760 can extend radially outward from the anterior portion 2750 and/or posterior portion 2770. The central portion 2760 can extend from the anterior portion 2750 and/or posterior portion 2770 at an angle of substantially 90°, for example to prevent or substantially prevent post-operative capsular opacification (PCO). In certain embodiments, the central portion 2760 can extend from the anterior portion 2750 and/or posterior portion 2770 at an angle of about 10°, about 20°, about 30°, about 40°, about 50°, about 60°, about 70°, about 80°, about 90°, and/or within a range defined by two of the aforementioned values.

The anterior portion 2750 and the posterior portion 2770 can be configured to hold a refractive surface, IOL, or another intraocular device. For example, a refractive surface and/or IOL can be configured to be placed in and/or over the anterior portion 2750 and/or posterior portion 2770. The central portion 2760 can be configured to hold one or more intraocular devices, such as an IOL, refractive surface, intraocular pressure sensor, electronic device, and/or any other intraocular device, for example by use of one or more grooves. As such, the device 2700, 2800 can comprise one or more shelves, for example three or more shelves, to hold intraocular devices. The anterior portion 2750 and/or posterior portion 2770 can be configured to hold an intraocular device(s) specifically designed for use with the device 2700, 2800, for example comprising one or more features that allow fixation of the intraocular device(s) at the posterior portion 2770 and/or anterior portion 2750. The central portion 2760 can be configured to hold any generic intraocular device, refractive surface, IOL, or the like.

As such, as a non-limiting example, the device 2700, 2800 can allow implantation of three or more lenses to obtain an optimal refractive power and/or a refractive power that is desired. Also, due to the symmetrical nature and/or configuration of the device 2700, 2800 across a horizontal line, a surgeon can easily implant the device 2700, 2800 without risk of inserting the device 2700, 2800 in the wrong anterior-posterior orientation. Further, the optics or lens to be used in conjunction with the device 2700, 2800 can also comprise a symmetrical configuration to allow for ease of implantation as discussed herein. Further, tabs on the lens or IOL can also be fully reversible.

As discussed herein, by providing one or more grooves and/or a central portion 2760, it can be possible to exactly the pinpoint the location of an IOL or other intraocular device to be placed in the central portion 2760 and/or elsewhere in the device 2700, 2800. Further, the device 2700, 2800 can also be used in conjunction with drug release devices, which can be placed inside the device 2700, 2800 for example, to release drugs within the eye. As previously discussed, the device 2700, 2800 can also provide a stable device for housing lenses and easy removal and/or insertion of lenses and/or other intraocular devices. Moreover, by use of lenses with positive and/or negative refractive powers, for example greater than +35D and/or less than −35D, a Galilean and/or reverse Galilean telescope can be provided within the eye by utilizing the space between the lenses within the device 2700, 2800. In other words, by using high powered plus and/or minus lenses, Galilean telescopes and/or microscopes can be created, for example for the purpose of object magnification and/or minimization. As non-limiting examples, such embodiments can have applications for certain conditions, such as macular degeneration and/or other conditions that cause loss of central vision. In certain embodiments, complex optical systems as such can be obtained by utilizing the ability of the device to separate lens optics within the capsule of the device. Such complex optical system can also be further fine-tuned over time by adjusting one or more optics placed inside the device through exchange.

In some embodiments, the anterior portion 2750 and/or posterior portion 2770 can comprise an outer diameter of about 8 mm and an inner diameter within the device 2700, 2800 of about 7.50 mm. The opening(s) of the anterior portion 2750 and/or posterior portion 2770 can comprise a diameter of about 6.35 mm. In some embodiments, the central portion 2760 can comprise an outer diameter of about 10.0 mm and an inner diameter within the interior of the device 2700, 2800 of about 9.50 mm. In certain embodiments, the outer diameter of the anterior portion 2750 and/or posterior portion 2770, the inner diameter of the anterior portion 2750 and/or posterior portion 2770 within the device 2700, 2800, the opening(s) of the anterior portion 2750 and/or posterior portion 2770, the outer diameter of the central portion 2760, and/or the inner diameter of the central portion 2760 within the interior of the device 2700, 2800 can be about 3.00 mm, about 4.00 mm, about 5.00 mm, about 5.50 mm, about 6.00 mm, about 6.50 mm, about 7.00 mm, about 7.50 mm, about 8.00 mm, about 8.50 mm, about 9.00 mm, about 9.50 mm, about 10.00 mm, about 10.50 mm, about 11.00 mm, about 11.50 mm, about 12.00 mm, about 12.50 mm, about 13.00 mm, about 14.00 mm, about 15.00 mm, and/or within a range defined by two of the aforementioned values.

In some embodiments, a thickness of the device 2700, 2800 when viewed from a side view and measured from an outer end of the anterior portion 2750 to an outer end of the posterior portion 2770 can be about 3.50 mm. In other embodiments, a thickness of the device 2700, 2800, when viewed from a side view and measured from an outer end of the anterior portion 2750 to an outer end of the posterior portion 2770, can be about 3.00 mm. In certain embodiments, a thickness of the device 2700, 2800, when viewed from a side view and measured from an outer end of the anterior portion 2750 to an outer end of the posterior portion 2770, can be about 0.50 mm, about 1.00 mm, about 1.50 mm, about 2.00 mm, about 2.50 mm, about 3.00 mm, about 3.50 mm, about 4.00 mm, about 4.50 mm, about 5.00 mm, about 5.50 mm, about 6.00 mm, about 6.50 mm, about 7.00 mm, about 8.00 mm, about 9.00 mm, about 10.00 mm, and/or within a range defined by two of the aforementioned values.

In some embodiments, when viewed from a side view, the anterior portion 1750, central portion 2760, and/or posterior portion 1770 can comprise an inner thickness, as measured between two internal surfaces of the device 2700, 2800, of about 1.25 mm. In certain embodiments, the anterior portion 1750, central portion 2760, and/or posterior portion 1770, when viewed from a side view, can comprise an inner thickness, as measured between two internal surfaces of the device 2700, 2800, of about 0.25 mm, about 0.50 mm, about 0.75 mm, about 1.00 mm, about 1.25 mm, about 1.50 mm, about 1.75 mm, about 2.00 mm, about 2.25 mm, about 2.50 mm, about 2.75 mm, about 3.00 mm, and/or within a range defined by two of the aforementioned values.

FIG. 29A illustrates an anterior side perspective view of another example prosthetic capsular device. FIG. 29B illustrates an anterior plan view of the example prosthetic capsular device of FIG. 29A. FIG. 29C illustrates a cross-sectional view of the example prosthetic capsular device of FIG. 29A along the line 29C-29C of FIG. 29B. FIG. 29D illustrates a side plan view of the example prosthetic capsular device of FIG. 29A.

The device 2900 can include some or all of the features of the example prosthetic capsular devices 2700, 2800 illustrated in FIGS. 27A and 28A, and like reference numerals include like features. The device 2900 is shown with an IOL 2901 placed in the interior of the device 2900 and/or a central portion thereof, for example along the ridges therein. As illustrated, one or more haptics of the IOL 2901 can be configured to be placed within the ridge of the device 2900.

FIG. 30A illustrates an anterior plan view of another example prosthetic capsular device. FIG. 30B illustrates a cross-sectional view of the example prosthetic capsular device of FIG. 30A along the line 30B-30B of FIG. 30A.

FIG. 31A illustrates an anterior side perspective view of another example prosthetic capsular device. FIG. 31B illustrates an anterior plan view of the example prosthetic capsular device of FIG. 31A. FIG. 31C illustrates a cross-sectional view of the example prosthetic capsular device of FIG. 31A along the line 31C-31C of FIG. 31B. FIG. 31D illustrates a side plan view of the example prosthetic capsular device of FIG. 31A.

The device 3100 can include some or all of the features of the example prosthetic capsular devices 2700, 2800 illustrated in FIGS. 27A and 28A, and like reference numerals include like features. In contrast to the devices 2700, 2800, a central portion of the device 3100 that extends upwards and downwards, when viewed in the orientation of FIG. 31D, may not be perpendicular to the posterior portion and/or the anterior portion. Rather, this central portion or the outer surface thereof can be angled, for example at 70 degrees. This can be advantageous for providing additional rigidity and structure to the device; however, this configuration may add to the amount of material to the device. All other features of the device 3100 can be similar to those described in conjunction with devices 2700, 2800.

FIG. 32A illustrates an anterior side perspective view of another example refractive surface or intraocular lens that can be configured to be used in conjunction with a prosthetic capsular device. FIG. 32B illustrates an anterior plan view of the example refractive surface or intraocular lens of FIG. 32A. FIG. 32C illustrates a cross-sectional view of the example refractive surface or intraocular lens of FIG. 32A along the line 32C-32C of FIG. 32B. FIG. 32D illustrates a side plan view of the example refractive surface or intraocular lens of FIG. 32A.

FIG. 32 illustrates an anterior plan view of another example refractive surface or intraocular lens. The refractive surface, IOL, lens, or optic 3200 shown in FIG. 32 can be configured to be attached to any prosthetic capsular device disclosed herein, such as the devices 2400, 2500, 2700, 2800, 3100 illustrated in FIGS. 24, 25, 27, 28, and 31 among others. In particular, the refractive surface or IOL 3200 can be configured to be attached to the anterior and/or posterior end of a prosthetic capsular device 2400, 2500, 2700, 2800, 3100.

The optic 3200 can include one or more features as the optic 2600 of FIG. 26A. For example, in some embodiments, the refractive portion of the optic 3200 can comprise a diameter of about 6.250 mm. In certain embodiments, the refractive portion of the optic 3200 can comprise a diameter of about 5.00 mm, about 5.50 mm, about 6.00 mm, about 6.50 mm, about 7.00 mm, about 7.50 mm, about 8.00 mm, about 8.50 mm, about 9.00 mm, about 9.50 mm, about 10.00 mm, and/or within a range defined by two of the aforementioned values.

Similar to the optic 2600, the refractive surface or IOL 3200 can comprise an anterior side or end 3202 and a posterior side or end 3204. In some embodiments, the anterior side 3202 can be substantially equal to the posterior side 3204, such that the anterior-posterior configuration of the refractive surface of IOL 3200 does not affect the operability or functionality when affixing to a prosthetic capsular device. In other embodiments, the anterior side 3202 and the posterior side 3204 can have one or more different features, such as thickness, curvature, refractive power, or the like.

The refractive surface or intraocular lens 3200 can comprise two convex portions 3200A, 3200B. One of the two convex portions 3200A can be configured to be placed in the interior of a prosthetic capsular device and the other convex portion 3200B can be configured to be placed exterior to the prosthetic capsular device upon attachment thereto. In some embodiments, the two convex portions 3200A, 3200B can comprise substantially the same shape, area, and/or refractive power. In other words, the optic 3200 can be an equiconvex lens and/or be symmetrical along the anterior-posterior axis. This way, a refractive surface or intraocular lens 3200 can be configured such that the posterior-anterior configuration thereof does not matter when attaching to a prosthetic capsular device. In other words, the refractive surface or intraocular lens 3200 can be flipped when attaching to a prosthetic capsular device and still obtain substantially the same function.

In contrast to the optic 2600 of FIG. 26A, the optic 3200 can include six tabs 3206 in some embodiments. For example, three of the six tabs 3206A can be curved towards the posterior end of the lens, and the other three tabs 3206B can be curved towards the anterior end of the lens. One or more tabs 3206 can facilitate attachment of the refractive surface or IOL 3200 to a prosthetic capsular device. In certain embodiments, a refractive surface or IOL 3200 can comprise one, two, three, four, five, six, seven, eight, nine, or ten tabs 2606.

Each of the tabs 3206 can comprise a flap that is curved in the same or alternating direction. For example, in the illustrated embodiment, three tabs 3206B can extend from the anterior side 3202, and the other three tabs 3606A can extend from the posterior end 3204. In other embodiments, the tabs 2606 can be substantially flat or planar.

In attaching a refractive surface or IOL 3200 to a prosthetic capsular device, one or more of the tabs can be configured to be placed through the anterior end 102 or posterior end 104 of the device. For example, three of the six tabs 3206 can be placed in the interior of the device, while the other tabs can be placed exterior to the device.

In certain embodiments, each or some of the one or more tabs 3206 can extend radially from about 30° of the circumference of the refractive portion of the optic 3200. In some embodiments, each or some of the one or more tabs 3206 of an optic 3200 can extend radially from about 20°, about 40°, about 60°, about 80°, about 100°, about 120°, about 140°, about 160°, about 180°, about 200°, about 220°, about 240°, about 260°, about 280°, about 300°, about 320°, about 340°, about 360° of the circumference of the refractive portion of the optic 3200, and/or within a range defined by two of the aforementioned values.

In some embodiments, each or some of the tabs 3206, when viewed from an anterior plan view can comprise a width of about 2.0 mm. In certain embodiments, each or some of the tabs 3206, when viewed from an anterior plan view, can comprise a width of about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, and/or within a range defined by two of the aforementioned values.

Each of the tabs can further comprise one or more eyelet openings 3204. The one or more eyelets 3204 can be used to fasten or fixate the optic 3200 in a particular location or configuration relative to a prosthetic capsular device. In some embodiments, an angle between the center points of two eyelet openings 3204 can be about 60°. In certain embodiments, an angle between the center points of two eyelet openings 3204 can be about 10°, about 20°, about 30°, about 40°, about 50°, about 60°, about 70°, about 80°, about 90°, about 100°, about 110°, about 120°, about 130°, about 140°, about 150°, about 160°, about 170°, about 180°, and/or within a range defined by two of the aforementioned values.

Tubular Devices, Systems, and Methods

FIG. 33A illustrates an anterior side perspective view of an example prosthetic capsular device. FIG. 33B illustrates an anterior plan view of the example prosthetic capsular device of FIG. 33A. FIG. 33C illustrates a cross-sectional view of the example prosthetic capsular device of FIG. 33A along the line 33C-33C of FIG. 33B.

In some embodiments, the device 3300 includes features described with respect to the devices described in U.S. Pat. No. 9,358,103, which is hereby incorporated by reference in its entirety, or modifications thereof. For example, the device 3300 can comprise an anterior side 3302, a posterior side 3304, and sidewalls 3306 extending between the anterior side 3302 and the posterior side 3304; the anterior side 3302 comprises an opening 3308; the posterior side 3304 optionally comprises a refractive surface 3310; the prosthetic device 3300 comprises a ring structure 3320 (e.g., comprising ring structure portions 3320A, 3320B, 3320C, 3320D) coupled to a housing structure 3312 comprising the anterior side 3302, posterior side 3304, and sidewalls 3306; and the ring portions 3320A, 3320B, 3320C, 3320D comprising aperture sections 3327 comprising openings 3328, which may also or alternatively be slits.

The device 3300 comprises openings 3326A, 3326B in the posterior side 3304 of the housing structure 3312. Each of the openings 3326A, 3326B may be the same as the others of the openings 3326A, 3326B. At least one of the openings 3326A, 3326B may be different than at least one of the other openings 3326A, 3326B. The openings 3326A, 3326B may inhibit or prevent entrapment of fluid or potentially residual viscoelastic material after implantation of the device 3300, for example by allowing anterior-posterior fluid flow along with the anterior opening 3308.

The openings 3326A, 3326B may be formed during formation of the housing structure 3312 (e.g., as part of a molding process) and/or formed after formation of the housing structure 3312 (e.g., by a laser, chemical, or mechanical removal process). In some implementations, the housing structure 3312 may comprise a different material around the openings 3326A, 3326B (e.g., the housing structure 3312 comprising silicone and the opening surrounding material comprising polyimide). In some implementations, the housing structure 3312 may comprise thicker material around the openings 3326A, 3326B (e.g., to buttress the openings 3326A, 3326B, for example if another device is to be anchored to the openings 3326A, 3326B). In some implementations, the housing structure 3312 may comprise thinner material around the openings 3326A, 3326B (e.g., for easier removal of material and/or opening formation).

The openings 3326A, 3326B can allow evacuation of prosthetic capsular device 3300 viscoelastic material from behind the refractive surface 3310 and/or the posterior wall of the housing structure 3312. The openings 3326A, 3326B can provide access to the posterior capsule. For example, if a primary posterior capsulotomy was created (e.g., using a femtosecond laser after implantation of the device 3300), the openings 3326A, 3326B could allow use of forceps to grab a cut posterior capsulorhexis and remove it from the eye. Openings 3326A, 3326B on each side of the refractive surface 3310 may allow the refractive surface 3310 to tilt (e.g., along the major axis if the openings 3326A, 3326B are on opposite sides of the major axis), which may allow greater access to an area posterior to the refractive surface 3310.

The openings 3326A, 3326B can hold or otherwise interact with a drug eluting device. The openings 3326A, 3326B can allow a medicament access to the posterior capsule (e.g., for treatment of retinal and/or uveal diseases). The openings 3326A, 3326B may allow a drug contained in the device 3300 to reach a posterior segment of the eye (e.g., vitreous, retina, choroid). The openings 3326A, 3326B may allow a slow release anti-VEGF injectable (e.g., ranibizuman (e.g., Lucentis® from Genentech), aflibercept (e.g., Eylea® from Regerneron Pharmacueticals) or anti-VEGF produced from cells (e.g., from Neurotech) contained in the device 3300 to reach a posterior segment of the eye (e.g., vitreous, retina, choroid) for treatment of macular degeneration.

The refractive surface 3310 may have a diameter between about 4 mm and about 9 mm (e.g., about 4 mm, about 5 mm, about 6 mm, about 7 mm, about 8 mm, about 9 mm, ranges between such values, etc.). In some embodiments, the openings 3326A, 3326B are spaced from the outer circumference of the refractive surface 3310 by between about 0.2 mm and about 1 mm (e.g., about 0.2 mm, about 0.3 mm, about 0.4 mm, about 0.5 mm, about 0.6 mm, about 0.7 mm, about 0.8 mm, about 0.9 mm, about 1 mm, ranges between such values, etc.). In some embodiments, the openings 3326A, 3326B comprise arcs of a circle having a diameter 3330 between about 4.5 mm and about 9.5 mm (e.g., about 4.5 mm, about 5.5 mm, about 4.5 mm, about 4.5 mm, about 4.5 mm, about 9.5 mm, ranges between such values, etc.). For example, if the refractive surface 3310 has a diameter of 5 mm and the openings 3326A, 3326B are spaced from the outer circumference of the refractive surface 3310 by 0.5 mm, the openings 3326A, 3326B would have a diameter 3330 of 5.5 mm.

The outer or under certain circumstances maximum diameter 3332 of the device 3300, for example accounting for extension of the ring structure 3320, may be between about 9 mm and about 12 mm (e.g., about 9 mm, about 9.5 mm, about 10 mm, about 10.3 mm, about 10.5 mm, about 11 mm, about 12 mm, ranges between such values, etc.).

The openings 3326A, 3326B may have a thickness or width 3334 between about 0 mm (e.g., being slits as described with to FIG. 33F) and about 0.5 mm (e.g., about 0 mm, about 0.1 mm, about 0.2 mm, about 0.3 mm, about 0.4 mm, about 0.5 mm, ranges between such values, etc.). In some embodiments, the openings 3326A, 3326B are sized such that there is little or no pressure gradient from posterior to anterior, for example during anterior decompression. The openings 3326A, 3326B may be small enough in size that there is a low likelihood of vitreous prolapse through the openings 3326A, 3326B.

In some embodiments, the openings 3326A, 3326B comprise arcs of a circle. The openings 3326A, 3326B may comprise a circumferential angle between about 30° and about 120° (e.g., about 30°, about 45°, about 60°, about 75°, about 90°, about 105°, about 120°, ranges between such values, etc.). The openings 3326A, 3326B are illustrated as being mirror-image circular arc openings, but other shapes are also possible (e.g., polygonal (e.g., rectangular), arcuate (e.g., circular, ellipsoid, oval), slits, combinations thereof, and the like). The openings 3326A, 3326B are illustrated as being on opposite sides of the major axis, but openings can also or alternatively be on opposite sides of the minor axis, on one side of an axis, crossing one or more axes, etc.

In some embodiments, the device 3300 comprises a bulge 3316. In some embodiments, the bulge 3316 extends radially outward of the sidewalls 3306 (e.g., as shown in FIGS. 33A and 33B). In some embodiments, the bulge 3316 extends radially inward of the sidewalls 3306. In some embodiments, the bulge 3316 extends radially inward and radially outward of the sidewalls 3306. The device 3300 includes a bulge 3316 on each end portion. In some embodiments, the bulge 3316 can be limited to portions around ring structure portion anchors. The housing structure 3312 may comprise the bulge 3316 (e.g., the bulge 3316 being integral with the housing structure 3312). In some implementations, the ring structure 3320 is placed in a mold and the housing structure 3312 is over-molded around the ring structure 3320. The bulge 3316 may be coupled to the housing structure 3312. The bulge 3316 may comprise the same material as the housing structure 3312 or a different material than the housing structure 3312. The bulge 3316 may allow the anchors to be substantially radially aligned with, radially outward of, or radially inward of the sidewalls 3306. The bulge 3316 may provide extra material in which the ring structure 3320 may anchor, for example maintaining a wall thickness (e.g., about 0.2 mm) on one or both sides of the ring structure 3320 with or without the use of a primer. The bulge 3316 may allow the material of the housing structure 3312 to surround (e.g., completely surround) the anchoring portions of the ring structure portion 3320, which can avoid an area of weakness and/or discontinuity of the housing structure 3312. The device 3300 includes bulges 3316 that extend along the entire edge portions of the housing structure 3312, even beyond the termination of the anchor portions. In some implementations, the device includes bulges 3316 that extend slightly beyond the termination of the anchor portions.

The device 3300 optionally comprises a posterior fin 3324. The device 3300 shown includes two posterior fins 3324. The posterior fins 3324 are aligned along a diameter of the refractive surface 3310 and in line with the major axis of the prosthetic device 3300. In some implementations, a plurality of posterior fins 3324 (e.g., 2, 3, 4, 5, 6, or more fins 3324) may be circumferentially offset (e.g., by about 180°, by about 120°, by about 90°, by about 72°, by about 60°, and the like). In some implementations, at least some or all of a plurality of posterior fins 3324 (e.g., 2, 3, 4, 5, 6, or more fins 3324) may be unaligned. The posterior fins 3324 are aligned along a major axis of the device 3300. In some implementations, the posterior fins 3324 may be aligned along a minor axis of the device 3300. In some implementations, the posterior fins 3324 may be unaligned along an axis of the device 3300 (e.g., at an angle with respect to the major axis and/or the minor axis). The housing structure 3312 may comprise the posterior fin 3324 (e.g., the posterior fin 3324 being integral with the housing structure 3312). The posterior fin 3324 may be coupled to the housing structure 3312. The posterior fin 3324 may comprise the same material as the housing structure 3312 or a different material than the housing structure 3312. The posterior fin 3324 may help to space a posterior surface of a natural capsular bag from the posterior end 3304 of the housing structure 3312 radially outward of the refractive surface 3310. Spacing the posterior surface of the natural capsular bag from the posterior end 3304 of the housing structure 3312 radially outward of the refractive surface 3310 may allow fluid flow radially outward of the refractive surface 3310, which may help to reduce opacification. Spacing the posterior surface of the natural capsular bag from the posterior end 3304 of the housing structure 3312 radially outward of the refractive surface 3310 may reduce the chance of retaining viscoelastic that has some residual trapped fibrin or inflammatory precipitate contained within it. In some embodiments, the posterior fin 3324 may extend anterior from the posterior of the housing structure 3312 into the cavity of the housing structure 3312. In some embodiments, the posterior fin comprises a roughened or opacified interior and/or exterior surface of the housing structure 3312 (e.g., having the same thickness and material as the posterior wall radially outward of the refractive surface 3310 but treated to provide an alignment mark).

In embodiments in which the fins 3324 are aligned with the major axis of the device 3300, the device 3300 can be strategically aligned in an eye. For example, if an eye has astigmatism, a device 3300 in which the refractive surface 3310 comprises a toric lens can be used to at least partially correct the astigmatism if the device 3300 is properly oriented (e.g., with the steep axis of a cornea). In some implementations, at least one of the fins 3324 can be different (e.g., different shape, dimensions, etc.) to indicate a top or bottom of the device 3300. In devices allowing any rotational orientation of an IOL inserted therein, a toric IOL can be rotated. The device 3300 includes truncated sides, reducing volume and in some cases advantageously limiting rotation of an IOL inserted therein. Aligning the device 3300 for alignment of a toric refractive surface 3310 and/or a toric IOL contained in the device 3300 can advantageously provide the advantages of limited IOL rotation, reduced volume, and astigmatism correction.

FIG. 34 illustrates an anterior side perspective view of another example prosthetic capsular device 3400. The device 3400 includes some or all of the features of the device 3300, and like reference numerals include like features. The device 3400 additionally comprises a first side aperture 3330A and a second side aperture 3330B. The side apertures 3330A, 3330B are configured to couple a tubular device to the housing structure 3312 of the capsular device 3400.

In some embodiments, the device 3400 may comprise a single side aperture 3330. In some embodiments, the device 3400 may comprise more than two side apertures 3330. The side apertures 3330A, 3330B are shown on flat sides of the housing structure 3312, although other locations (e.g., including towards ends of flat sides, on arcuate sidewalls, on the anterior side 3302, on the posterior side 3304, and combinations thereof) are also possible. The side apertures 3330A, 3330B are show as through-holes. In some embodiments, the side apertures 3330A, 3330B may also or alternatively comprise slits.

Any of the devices and systems described herein, such as the devices and systems shown in FIGS. 1A, 2A, 3A, 4A, 5A, 6A, 7A, 8A, 9A, 10A, 11A, 12A, 13A, 14A, 15A, 16A, 18A, 19A, 21A, 23B, 24A, 25A, 27A, 28A, 29A, 31A, 33A, and modifications and combinations thereof can comprise a side aperture configured to be coupled to a tubular device like side apertures 3330A, 3330B. In addition, any of the devices and systems described in U.S. Pat. No. 9,358,103, which is hereby incorporated by reference in its entirety, may be modified in accordance with the present disclosure. For example, the devices and systems shown in FIGS. 2, 4H, 6, 8, 9A, 10A, 11A, 11D, 12A, 13, 14, 16, 17, 18, 19, 20, 21, 22A, 22B, 23, 24, 25, 26, 27, 28, 29, 30, 31, 32, 33, 34, 35, 36, 37A, 38A, 39, 40, 41, 42, 43A, 43E, 57A, 58A, 58E, 58F, 58G, 58H, 58I, 58J, 58K, 58L, 59A, 61A, 61D, 62A, 63A, 64A, 65A, 66A, 67A, 68A, 69A, 70A, 72A, 73A, 74B, 74C, 74D, 74E, 75A, 75E, 76A, 76B, 76C, 76D, 76E, 76F, 77C, 77D, 77I, and modifications and combinations thereof could comprise a side aperture configured to be coupled to a tubular device like the side apertures 230A, 230B. Modifications to other prosthetic capsular devices or systems in accordance are also possible.

FIG. 35A is a side perspective view of an example tubular device 3500. The tubular device 3500 is configured to be coupled to a side aperture 3330 of the device 3400. The tubular device 3500 provides a fluid flow pathway from inside the cavity 3306 of the device 3400 to a second location. In some embodiments, the second location is through the pars plana and on top of the sclera, which can be beneath the Tenon's capsule and conjunctiva.

The tubular device 3500 comprises a tubular portion 3532. The tubular portion 3532 has a generally cylindrical shape that is flexible enough to bend and rigid enough to resist collapsing and kinking. The tubular portion 3532 can be made of a biologically compatible material including but not limited to silicone, silicone polymers, SIBS (poly(styrene-block-isobutylene-block-styrene)), acrylic, acrylic polymers, polypropylene, polycarbonate, and Gore-Tex.

The tubular portion 3532 at least partially defines a lumen 3536 configured to allow fluid flow. The lumen 3536 and/or tubular portion 3532 may have an internal diameter between about 30 and about 100 microns. In certain embodiments, the lumen 3536 and/or tubular portion 3532 may have an internal diameter between about 1 micron and about 200 microns. The lumen 3536 and/or tubular portion 3532 may also have a length between 3 mm and 10 mm. In certain embodiments, the lumen 3536 and/or tubular portion 3532 may have a length between about 1 mm and about 20 mm. The lumen 3536 and/or tubular portion 3532 may also be longer with the ability for the implanting surgeon to trim the length to the appropriate size for a given patient.

In some embodiments, the tubular device 3500 is a "dumb" or passive tubular device in that the lumen 3536 is not restricted and can allow fluid flow therethrough at all times. The tubular portion 3532 can comprise an inflow end and an outflow end. The inflow end can be located at or near the device 3400 to allow inflow of fluid from inside the device 3400 or the eye. The outflow end can be located at or near the second location to allow outflow of fluid to the second location.

The tubular device 3500 is also illustrated as comprising an optional flange 3534. The optional flange 3534 can have a generally cylindrical shape with a diameter larger than the diameter of the tubular portion 3532. The flange 3534 can be configured to be inserted into a side aperture 3330 to couple the tubular device 3500 to a housing structure 3312 of a capsular device 3400. The circumference of the flange 3534 can be substantially the same or slightly smaller than the circumference of a side aperture 3330 of a housing structure 3312.

In some embodiments, the flange 3534 is made of the same material as the tubular portion 3532. In certain embodiments, however the flange 3534 may also or alternatively be made of a combination of biocompatible materials including but not limited to silicone, silicone polymers, SIBS (poly(styrene-block-isobutylene-block-styrene)), acrylic, acrylic polymers, polypropylene, polycarbonate, and Gore-Tex. A diameter of the flange 3534 can be between approximately 1 mm and 3 mm. In certain embodiments, the diameter of the flange 3534 can be between about 0.1 mm and about 10 mm.

The flange 3534 can be configured to be substantially anchored in place in a side aperture 3330 by friction or chemical glue to substantially fixate the tubular device 3500. In some embodiments, the flange 3534 can comprise a deformable material that can be compressed to fit the flange 3534 in a side aperture 3330. Once fit inside a side aperture 3330, the flange can expand to substantially anchor the flange 3534 in place inside the side aperture 3330.

In certain embodiments, the circumference of the flange 3534 can be larger than the circumference of a side aperture 3330 of a housing structure 312. As such, only the tubular portion 3532 can be configured to be inserted into a side aperture 3330, while the flange 3534 remains inside the cavity of the housing structure 3312. A flange 3534 with a circumference that is larger than a circumference of a side aperture 3330 can substantially prevent the tubular device 3500 from being pushed out of the side aperture 3330 in a general direction away from the cavity of the housing structure 3312. The larger circumference of the flange 3534 can provide a stopping mechanism to prevent the tubular device 3500 from falling out of the side aperture 3330 with a smaller circumference.

FIG. 35B is a side perspective view of another example tubular device 3502. Similar to the tubular device 3500 illustrated in FIG. 35A, the tubular device 3502 is configured to be coupled to a side aperture 3330 of the device 3400. The tubular device 3502 includes some or all of the features of the tubular device 3500, and like reference numerals include like features. The tubular device 3502 can be similar to the tubular device 3500 except for the flange 3538 and fluid control 3540.

In some embodiments, the shape of the flange 3538 can comprise a trapezoidal cylinder shape. For example, the flange 3538 can comprise a top surface and a bottom surface, in which the top surface, and/or a diameter or circumference thereof, is larger than the bottom surface, and/or a diameter or circumference thereof. In other embodiments, the top surface, and/or a diameter or circumference thereof, can be smaller than the bottom surface and/or a diameter or circumference thereof. Both the top and bottom surfaces, and/or diameters or circumferences thereof, can be larger than the tubular portion 3532 and/or a diameter or circumference thereof.

The flange 3538 can be configured to be inserted into a side aperture 3330 to couple the tubular device 3500 to a housing structure 3312 of a capsular device 3400. The side aperture 3330, and/or a diameter or circumference thereof, can be larger than a bottom surface of the flange 3538, and/or a diameter or circumference thereof, and smaller than a top surface of the flange 3538 and/or a diameter or circumference thereof. Similarly, in other embodiments, a side aperture 3330 can be smaller than a bottom surface of the flange 3538, and/or a diameter or circumference thereof, and larger than a top surface of the flange 3538 and/or a diameter or circumference thereof. In some embodiments, the size of a side aperture 3330, and/or a diameter or circumference thereof, can be substantially equal to an average of a top surface and a bottom surface of the flange 3538, and/or diameters or circumferences thereof.

In embodiments in which the top surface of the flange 3538 is larger than the bottom surface of the flange 3538, the tubular device 3502 can be configured to be inserted into a side aperture 3330 starting with the bottom surface of the flange 3538 towards the top surface. As the tubular device 3502 is being inserted into a side aperture 3330, the flange 3538 may become stuck in the side aperture 3330 at a point between the bottom surface and the top surface of the flange 3538, for example where the diameter or circumference of the side aperture 3330 is substantially equal to that of the flange 3538. Accordingly, the tubular device 3502 can be substantially anchored or fixated in place in a side aperture 3330 by friction and/or mechanical fitting.

In some embodiments, the tubular device 3502 is a "smart" tubular device comprising a fluid control 3540. The fluid control 3540 can be configured to alter the lumen 3536 between an open configuration and a restricted configuration to allow or disallow fluid flow therethrough. In addition or alternatively, the fluid control 3540 can be configured to alter between a configuration that actively facilitates fluid flow through the lumen 3536 and a configuration that does not.

More specifically, the fluid control 3540 can be a valve that is configured to open or close to allow or disallow fluid flow through the lumen 3536. The valve can be located anywhere along the lumen 3536. For example, the valve can be located at or near an inflow end of the lumen 3536, at or near an outflow end of the lumen 3536, in between the inflow end and outflow end of the lumen 3536, or a substantially midpoint of the lumen 3536 between the inflow end and outflow end thereof.

The valve can be configured to be open and close based on an intraocular pressure setting. For example, if the intraocular pressure is too high or is above a predetermined level, the valve can be configured to open to allow fluid flow from the inside of the eye to the outside of the eye to decrease the intraocular pressure. Conversely, if the intraocular pressure is too low or is below a predetermined level, the valve can be configured to close to prevent fluid flow. In some embodiments, one or more intraocular pressure sensors of the device 3400 and/or tubular device 3500 can be configured to detect the intraocular pressure and electronically transmit the detected pressure to a processor configured to open and/or close the valve.

In some embodiments, the valve can be configured to open when the intraocular physiologic pressure is at or above about 20 mmHg. In certain embodiments, the valve can be configured to open when the intraocular physiologic pressure is at or above about 10 mmHg, 11 mmHg, 12 mmHg, 13 mmHg, 14 mmHg, 15 mmHg, about 16 mmHg, about 17 mmHg, about 18 mmHg, about 19 mmHg, about 20 mmHg, about 21 mmHg, about 22 mmHg, about 23 mmHg, about 24 mmHg, about 25 mmHg, about 26 mmHg, about 27 mmHg, about 28 mmHg, about 29 mmHg, about 30 mmHg, and/or within a range defined by two of the above-identified values.

In some embodiments, the valve can be configured to close when the intraocular physiologic pressure is at or below about 6 mmHg. In certain embodiments, the valve can be configured to open when the intraocular physiologic pressure is at or below about 1 mmHg, about 2 mmHg, about 3 mmHg, about 4 mmHg, about 5 mmHg, about 6 mmHg, about 7 mmHg, about 8 mmHg, about 9 mmHg, about 10 mmHg, about 11 mmHg, about 12 mmHg, about 13 mmHg, about 14 mmHg, about 15 mmHg, about 16 mmHg, about 17 mmHg, about 18 mmHg, about 19 mmHg, about 20 mmHg, and/or within a range defined by two of the above-identified values.[0473] The fluid control 3540 can also or alternatively be a pump or micro pump. The pump or micro pump can be located at or near an inflow end of the lumen 3536, at or near an outflow end of the lumen 3536, in between the inflow end and outflow end of the lumen 3536, or a substantially midpoint of the lumen 3536 between the inflow end and outflow end thereof. The pump or micro pump can be configured to actively force fluid from inside of the eye to the outside of the eye. For example, if the intraocular pressure is too high or is above a predetermined level, the pump or micro pump can be configured to actively force fluid to flow from the inside of the eye to the outside of the eye to decrease the intraocular pressure. Conversely, if the intraocular pressure is too low or is below a predetermined level, the pump or micro pump can be configured to stop. In some embodiments, one or more intraocular pressure sensors of the device 3400 and/or tubular device 3500 can be configured to detect the intraocular pressure and electronically transmit the detected pressure to a processor configured to turn the pump or micro pump on or off.

In some embodiments, the pump or micro pump can be configured to actively facilitate fluid removal when the intraocular physiologic pressure is at or above about 20 mmHg. In certain embodiments, the pump or micro pump can be configured to actively facilitate fluid removal when the intraocular physiologic pressure is at or above about 10 mmHg, 11 mmHg, 12 mmHg, 13 mmHg, 14 mmHg, 15 mmHg, about 16 mmHg, about 17 mmHg, about 18 mmHg, about 19 mmHg, about 20 mmHg, about 21 mmHg, about 22 mmHg, about 23 mmHg, about 24 mmHg, about 25 mmHg, about 26 mmHg, about 27 mmHg, about 28 mmHg, about 29 mmHg, about 30 mmHg, and/or within a range defined by two of the above-identified values.

In some embodiments, the pump or micro pump can be configured to stop facilitating fluid removal when the intraocular physiologic pressure is at or below about 6 mmHg. In certain embodiments, the pump or micro pump can be configured to stop facilitating fluid removal when the intraocular physiologic pressure is at or below about 1 mmHg, about 2 mmHg, about 3 mmHg, about 4 mmHg, about 5 mmHg, about 6 mmHg, about 7 mmHg, about 8 mmHg, about 9 mmHg, about 10 mmHg, about 11 mmHg, about 12 mmHg, about 13 mmHg, about 14 mmHg, about 15 mmHg, about 16 mmHg, about 17 mmHg, about 18 mmHg, about 19 mmHg, about 20 mmHg, and/or within a range defined by two of the above-identified values.

FIG. 35C is a side perspective view of another example tubular device 3504. Similar to the tubular devices 3500, 3502 illustrated in FIGS. 35A and 35B, the tubular device 3504 is configured to be coupled to a side aperture 3330 of the device 3400. The tubular device 3504 includes some or all of the features of the tubular devices 3500, 3502, and like reference numerals include like features. The tubular device 3504 can be similar to the tubular devices 3500, 3502 except for the tubular portion 3540, through holes 3544, and tab or plate 3546.

In some embodiments, the tubular portion 3540 and/or lumen 3536 is tapered towards the outflow end, for example to prevent conjunctival erosion. The tubular device 3504 can also comprise one or more tabs or plates 3544. The one or more tabs 3544 can be coupled to an outflow end of the tubular portion 3532. The one or more tabs 3544 can be configured to prevent encapsulation of the outflow end of the tubular portion 3532, for example in the pars plana. In some embodiments, the tubular device 3504 can comprise only one tab 3544. In certain embodiments, the tubular device 3504 can comprise two tabs 3544 in a substantially flat or planar configuration, in which an angle between the two tabs 3544 is about 180°. In other embodiments, the tubular device 3504 can comprise three tabs 3544, in which an angle between any two of the three tabs can be about 120°. In certain embodiments, the tubular device 3504 can comprise four, five, six, seven, eight, nine, or ten tabs, in which the angle between any two tabs can be substantially equal or different.

The one or more tabs 3544 may comprise one or more eyelets 3548. For example, one tab 3544 can comprise one, two, three, four, or five eyelets 3548. In some embodiments, each tab 3544 can comprise one eyelet 3548. The eyelet 3548 can be configured to fixate the outflow end of the tubular portion 3532. For example, the eyelet 3548 can be configured to fixate the outflow end of a sub-conjunctival tube to the sclera. The one or more eyelets 3548 can allow for sutures for fixating the outflow end of the tubular portion 3532.

The flange 3542 can comprise one or more through holes 3544. For example, the flange 3542 can comprise one, two, three, four, or five through holes 3544. The one or more through holes 3544 can be configured to fixate the inflow end of the tubular device 3504. For example, one or more screws, nuts, sutures, or the like can be inserted through the one or more through holes 3544 to fixate the tubular device 3504 to the housing structure 3312.

FIG. 35D is a side perspective view of another example tubular device 3506. Similar to the tubular devices 3500, 3502, 3504 illustrated in FIGS. 35A, 35B, and 35C, the tubular device 3506 is configured to be coupled to a side aperture 3330 of the device 3400. The tubular device 3506 includes some or all of the features of the tubular devices 3500, 3502, 3504, and like reference numerals include like features. The tubular device 3506 can be similar to the tubular devices 3500, 3502, 3504 except for comprising a plurality of flanges 3534, 3538.

In some embodiments, the tubular device 3506 comprises a plurality of flanges 3534, 3538. For example, the tubular device 3506 can comprise two, three, four, or five flanges. In some embodiments, the plurality of flanges can have the same or substantially same shape. In other embodiments, one or more of the plurality of flanges can have a different shape.

In the depicted embodiment, the tubular device 3506 comprises a first flange 3534 and a second flange 3538. The first flange 3534 can be similar to the flange described above in connection with FIG. 35A. The second flange 3538 can be similar to the flange described above in connection with FIG. 35B.

The tubular device 3506 can be inserted through a side aperture 3330 of the device 3400 in a general direction starting with the second flange 3538 towards the first flange 3534. The first flange 3534, the second flange 3538, and/or both can be made of a deformable or compressible material. For example, as the tubular device 3506 is being inserted through a side aperture 3330, the second flange 3538 can be configured to be compressed. The tapered configuration or trapezoidal cylinder shape of the second flange 3538 can allow the second flange 3538 to be inserted completely through the side aperture 3330. The first flange 3354, however, can be configured not to be inserted through the side aperture 3330 due its cylindrical shape and/or non-compressible material. Accordingly, the periphery of the side aperture 3330 can be configured to be located between the first flange 3534 and the second flange 3538 when the tubular device 3536 is coupled to the housing structure 3312, thereby preventing the tubular device 3506 from moving in either direction.

FIG. 35E is a side perspective view of another example tubular device 3508. Similar to the tubular devices 3500, 3502, 3504, 3506 illustrated in FIGS. 35A, 35B, 35C, and 35D, the tubular device 3508 is configured to be coupled to a side aperture 3330 of the device 3400. The tubular device 3508 includes some or all of the features of the tubular devices 3500, 3502, 3504, and 3506, and like reference numerals include like features. The tubular device 3508 can be similar to the tubular devices 3500, 3502, 3504, 3506 except that the tubular device 3508 does not comprise a flange and that the tubular device 3508 comprises one or more tabs 3546a, 3546b at each end of the tubular device 3508.

In some embodiments, the tubular device 3508 does not comprise a flange. Instead, the tubular device 3508 can comprise one or more other structures for fixating the tubular device 3508 with respect to the housing structure 3312 and/or eye. For example, the tubular device 3508 can comprise one or more tabs or plates 3546a, 3546b.

In the depicted embodiment, the tubular device 3508 comprises one tab or plate 3546a, 3546b at each end of the tubular portion 3536. In other words, the inflow end of the tubular portion can comprise a tab or plate 3546a, and the outflow end of the tubular portion can comprise a tab or plate 3546b. In certain embodiments, the inflow end and/or outflow end of the tubular portion can each comprise one, two, three, four, or five tabs or plates.

Each tab or plate 3546a, 3546b can comprise one or more eyelets 3548. For example, one tab can comprise one, two, three, four, or five eyelets 3548. In the depicted embodiment, each tab 3546a, 3546b comprises one eyelet 3548. The eyelet 3548 can be configured to fixate the inflow end and/or outflow end of the tubular portion 3532. For example, one or more screws, nuts, sutures, or the like can be inserted through an eyelet 3548 of a tab 3546a located at or near the inflow end to fixate the inflow end to the housing structure 3312, side aperture 3330, and/or natural capsular bag. Similarly, one or more screws, nuts, sutures, or the like can be inserted through an eyelet 3548 of a tab 3546b located at or near the outflow end to fixate the outflow end to the second location, such as the sub-Tenon's space.

FIG. 36 is an anterior side perspective view of an example prosthetic capsular device system 3600 including the device 3400 of FIG. 34A and the tubular device 3500 of FIG. 35A. As illustrated, the tubular device 3500 is coupled to the device 3400 through a side aperture 3330B of the device 3400. More specifically, a flange 3534 of the tubular device 3500 can be fixated in the side aperture 3330B, providing a first opening of the tubular portion 3532 to be in fluid connection with inside of the device 3400 and providing a second opening of the tubular portion 3532 in a second location.

FIG. 37 is an anterior side perspective view of the example prosthetic capsular device system of FIG. 36 in an eye. As illustrated, a flange 3534 of the tubular device 3500 can be fixated in the side aperture 3330B, providing a first opening of the tubular portion 3532 to be in fluid connection with inside of the device 3400. The tubular portion 3532 can be configured to extend away from the device 3400 implanted in the natural capsular bag of the eye. The tubular portion 3532 can extend through a puncture in a sidewall of the natural capsular bag 3700 and inserted through the pars plana. As such, a second opening or end of the tubular portion 3532 can be located in the sub-Tenon's space, for example 2-4 mm posterior to the limbus, but without reaching the conjunctiva 3702. Through the first and second openings, fluid can be configured to flow from inside of the device 3400 to the sub-Tenon's space through the lumen 3536.

After cataract surgery and implantation of the prosthetic device into the natural capsular bag, a fornix based limbal conjunctival peritomy can be performed in the quadrant that was planned to receive the tubular device 3500. The Tenon's capsule can be dissected from the sclera, and limited cautery can be performed for hemostasis. Mitomycin at variable concentrations can be placed on the sclera, for example using soaked sponges for a variable amount of time (ranging from 10 seconds to a five minutes), and can then copiously be washed away using balanced salt solution (BSS). A pars plana sclerostomy can be created with a sharp device such as a myringovitreoretinal (MVR) blade. In some cases, a trochar can be inserted through the sclera.

Other sclerostomies can be made through the conjunctiva in other quadrants for light and/or BSS infusion. Typically, a limited pars plana vitrectomy can be performed to clear vitreous away from the sclerostomy site, preventing retinal traction during the surgical intervention. In some cases, a vitrectomy would not need to be performed. A sharp instrument, possibly an MVR type blade, with the tubular device 3500 loaded overtop and downshaft can be inserted through the sclerostomy, and can sharply incise the natural capsule, docking with the prosthetic device. Using grasping forceps, the end of the tubular device 3500 can be held in place inside the prosthetic device, while the sharp instrument can be removed using a modified Seldinger technique. The internal end of the tubular portion can be seated within the prosthetic device 3400, and the external end of the tubular portion can be trimmed and/or fixated to the sclera using a suture (such as an 8-0 vicryl) or glue (such as Tisseel). The Tennon's capsule and conjunctive can be sutured back to the limbus using suture (such as 8-0 vicryl) or glue (such as Tisseel).

FIG. 38A is an anterior side perspective partially-exploded view of an example prosthetic capsular device system 3800 including the device 3400 of FIG. 34A, the tubular device 3500 of FIG. 35A, and a containment structure 3802. FIG. 38B is an anterior side perspective view of the example prosthetic capsular device system 3800 of FIG. 38A.

The containment structure 3802 can be configured to be coupled or attached to the device 3400. In some embodiments, the containment structure 3802 can comprise a foldable or otherwise deformable structure that can be inserted through an opening and into the interior of the device 3400. For example, the containment structure 3802 or a portion thereof can comprise a foldable or collapsible wire structure that allows for easy insertion of the containment structure 3802 through an opening of the device 3400. Once inserted, the containment structure 3802 can expand into an expanded state. The expanded state of the containment structure 3802 can be configured to fixate or anchor the containment structure 3802 within the interior of the device 3400. For example, a wire frame of the containment structure 3802 can be expanded in some embodiments to a configuration that substantially matches the shape of the interior of the device 3400. In certain embodiments, the containment structure 3802 in its expanded state can comprise two substantially straight portions and two arcuate portions to match the shape of the interior of the device 3400. The containment structure 3802 can be made of a semi-rigid material, such as PMMA, polyimide, polypropylene, and nylon. The containment structure can also or alternatively be made of a biocompatible material, such as silicone, silicone polymers, SIBS (poly(styrene-block-isobutylene-block-styrene)), acrylic, acrylic polymers, polypropylene, polycarbonate, and Gore-Tex.

The containment structure 3802 can comprise one or more fluid controls 3804. The one or more fluid controls 3804 can be located on one or more sides of the containment structure 3802. The one or more fluid controls 3804 can be configured to be coupled to the tubular device 3500 once the containment structure 3802 is coupled to the device 3400. For example, a fluid control 3804 of the containment structure 3804 can be located on the containment structure 3804 such that it covers a side aperture 3330A, 3330B of the device 3400, which can be coupled to a tubular device 3500, when the containment structure 3804 is installed. The number of fluid controls 3804 located on a containment structure 3804 can be equal to the number of side apertures 3330A, 3330B and/or number of tubular devices 3500 coupled to the device 3400. For example, if one tubular device 3500 is coupled to the device 3400, the containment structure 3802 can comprise one fluid control 3802. If device 3400 is coupled to two tubular devices 3500, for example to each of two side apertures 3330A, 3330B, a containment structure 3802 with two fluid controls 3804 can be implanted.

By providing a fluid control 3804 for the system 3800 through implantation of the containment structure 3802, fluid flow through the tubular device 3500 can be controlled even if the tubular device 3500 itself is a "dumb" or passive tubular device in that the lumen 3536 is not restricted and can allow fluid flow therethrough at all times.

The fluid control 3804 can be a valve that is configured to open or close to allow or disallow fluid flow through the tubular device 3500. The valve can be configured to be open and close based on an intraocular pressure setting. For example, if the intraocular pressure is too high or is above a predetermined level, the valve can be configured to open to allow fluid flow from the inside of the eye to the outside of the eye to decrease the intraocular pressure. Conversely, if the intraocular pressure is too low or is below a predetermined level, the valve can be configured to close to prevent fluid flow. The fluid control 3804 can also comprise an intraocular pressure sensor configured to detect the intraocular pressure and electronically transmit the detected pressure to a processor configured to open or close the valve.

In some embodiments, the valve can be configured to open when the intraocular physiologic pressure is at or above about 20 mmHg. In certain embodiments, the valve can be configured to open when the intraocular physiologic pressure is at or above about 10 mmHg, 11 mmHg, 12 mmHg, 13 mmHg, 14 mmHg, 15 mmHg, about 16 mmHg, about 17 mmHg, about 18 mmHg, about 19 mmHg, about 20 mmHg, about 21 mmHg, about 22 mmHg, about 23 mmHg, about 24 mmHg, about 25 mmHg, about 26 mmHg, about 27 mmHg, about 28 mmHg, about 29 mmHg, about 30 mmHg, and/or within a range defined by two of the above-identified values.

In some embodiments, the valve can be configured to close when the intraocular physiologic pressure is at or below about 6 mmHg. In certain embodiments, the valve can be configured to open when the intraocular physiologic pressure is at or below about 1 mmHg, about 2 mmHg, about 3 mmHg, about 4 mmHg, about 5 mmHg, about 6 mmHg, about 7 mmHg, about 8 mmHg, about 9 mmHg, about 10 mmHg, about 11 mmHg, about 12 mmHg, about 13 mmHg, about 14 mmHg, about 15 mmHg, about 16 mmHg, about 17 mmHg, about 18 mmHg, about 19 mmHg, about 20 mmHg, and/or within a range defined by two of the above-identified values.

The fluid control 3804 can also or alternatively be a pump or micro pump. The pump or micro pump can be configured to actively force fluid from inside of the eye to the outside of the eye. For example, if the intraocular pressure is too high or is above a predetermined level, the pump or micro pump can be configured to actively force fluid to flow from the inside of the eye to the outside of the eye to decrease the intraocular pressure. Conversely, if the intraocular pressure is too low or is below a predetermined level, the pump or micro pump can be configured to stop. The fluid control 3804 can also comprise an intraocular pressure sensor configured to detect the intraocular pressure and electronically transmit the detected pressure to a processor configured to turn the pump or micro pump on or off.

In some embodiments, the pump or micro pump can be configured to actively facilitate fluid removal when the intraocular physiologic pressure is at or above about 20 mmHg. In certain embodiments, the pump or micro pump can be configured to actively facilitate fluid removal when the intraocular physiologic pressure is at or above about 10 mmHg, 11 mmHg, 12 mmHg, 13 mmHg, 14 mmHg, 15 mmHg, about 16 mmHg, about 17 mmHg, about 18 mmHg, about 19 mmHg, about 20 mmHg, about 21 mmHg, about 22 mmHg, about 23 mmHg, about 24 mmHg, about 25 mmHg, about 26 mmHg, about 27 mmHg, about 28 mmHg, about 29 mmHg, about 30 mmHg, and/or within a range defined by two of the above-identified values.

In some embodiments, the pump or micro pump can be configured to stop facilitating fluid removal when the intraocular physiologic pressure is at or below about 6 mmHg. In certain embodiments, the pump or micro pump can be configured to stop facilitating fluid removal when the intraocular physiologic pressure is at or below about 1 mmHg, about 2 mmHg, about 3 mmHg, about 4 mmHg, about 5 mmHg, about 6 mmHg, about 7 mmHg, about 8 mmHg, about 9 mmHg, about 10 mmHg, about 11 mmHg, about 12 mmHg, about 13 mmHg, about 14 mmHg, about 15 mmHg, about 16 mmHg, about 17 mmHg, about 18 mmHg, about 19 mmHg, about 20 mmHg, and/or within a range defined by two of the above-identified values.

FIG. 39 is an anterior side perspective view of another example prosthetic capsular device system in an eye. The prosthetic capsular device system illustrated in FIG. 39 includes some or all of the features of the prosthetic capsular device system illustrated in FIG. 37, and like reference numerals include like features. The prosthetic capsular device system of FIG. 39 can be similar to that of FIG. 37 except for including a control unit 3902, an intraocular pressure sensor 3904, and a fluid control 3540.

In some embodiments, the prosthetic capsular device system can comprise a control unit 3902. The control unit 3902 can be configured to receive one or more inputs and control a fluid control 3540. The system can also comprise one or more intraocular pressure sensors 3904 configured to detect the intraocular pressure. The one or more intraocular pressure sensors 3904 can be built into the housing structure 3312 and/or a containment structure 3802 coupled to the housing structure 3312.

The one or more intraocular pressure sensors 3904 can be configured to detect and electronically transmit the detected intraocular pressure to the control unit 3902 repeatedly, periodically, and/or in real-time or near real-time. For example, the one or more intraocular pressure sensors 3904 can be configured to detect and/or transmit the detected intraocular pressure to the control unit 3902 every about 1 second, about 2 seconds, about 3 seconds, about 4 seconds, about 5 seconds, about 6 seconds, about 7 seconds, about 8 seconds, about 9 seconds, about 10 seconds, about 20 seconds, about 30 seconds, about 40 seconds, about 50 seconds, about 1 minute, about 2 minutes, about 3 minutes, about 4 minutes, about 5 minutes, and/or within a range defined by two of the aforementioned values.

The intraocular pressure detected by the one or more sensors 3904 can be electronically transmitted to the control 3902 through a wired connection 3906 and/or a wireless connection. For example, in some embodiments, the one or more pressure sensors 3904 can comprise a wireless transceiver configured to wirelessly transmit detected pressure data to the control unit 3902. Similarly, the control unit 3902 can comprise a wireless receiver configured to receive detected pressure data from the pressure sensor 3904.

The control unit 3902 can also or alternatively be configured to receive a user input, for example through wireless communication. In some embodiments, the user can input instructions to remove fluid from the eye, for example through a user input device such as a smartphone or other user access point system. Not to be limited to theory, glaucoma, a condition that causes loss of vision over time, can be treated by lowering eye pressure. As such, in some embodiments, patients suffering from glaucoma may control and/or lower intraocular pressure to prevent vision loss from glaucoma by inputting instructions to a user access point system to facilitate removal of fluid from the eye. The control unit 3902 can also or alternatively be configured to receive input from one or more other physiological sensors, for example through wireless communication.

Based on the received user input and/or detected intraocular pressure data, the control unit 3902 can be configured to instruct a fluid control 3540 to allow, disallow, actively facilitate, and/or not actively facilitate removal of fluid through the tubular device 3500. For example, if the intraocular pressure is above or at a predetermined level and/or the control unit 3902 receives corresponding user input, the control unit can be configured to instruct the fluid control 3540 to allow and/or actively facilitate fluid removal. Conversely, if the intraocular pressure is below or at a predetermined level and/or the control unit 3902 does not receive corresponding user input, the control unit can be configured to instruct the fluid control 3540 to disallow and/or not to actively facilitate fluid removal.

The control unit 3902 can be configured to electronically transmit instructions to allow and/or disallow fluid removal to the fluid control 3540 through a wired connection 3908 and/or a wireless connection. For example, in some embodiments, the control unit 3902 can comprise a wireless transceiver configured to transmit instructions to the fluid control 3540. Similarly, the fluid control 3540 can comprise a wireless receiver configured to receive instructions from the control unit 3902. The fluid control 3540 can be a valve and/or pump or micro-pump as described above.

FIG. 40 is a block diagram depicting an example control process for a prosthetic capsular device system. As illustrated in FIG. 40, in some embodiments, the system can be configured to receive one or more inputs at block 4004. The input can be a user input or an automated input. For example, the input received by the system may be from a user-initiated input through a user access point system. In addition or alternatively, the input received by the system can be from one or more sensors, such as an intraocular pressure sensor configured to detect the intraocular pressure and/or other physiological sensors.

Once the input is received, the system can be configured to further process the input at block 4004. In certain embodiments, the system can be configured to combine or otherwise process a plurality of inputs, for example an automated input and a user input. In some embodiments, the system can be configured to process a single input, whether a user input or an automated input.

Processing one or more inputs by the system can involve one or more processes at block 4006. In some embodiments, the system can be configured to process one or more inputs to determine whether to initiate one or more additional processes configured to lower intraocular pressure. For example, if an input received by the system comprises data that corresponds to intraocular pressure at or above a predetermined level, the system can be configured to initiate one or more additional processes configured to remove fluid from the eye, thereby lowering the intraocular pressure. Similarly, in an input received by the system comprises a user input corresponding to removal of fluid from the eye and/or lowering intraocular pressure, the system can be configured to initiate one or more additional processes configured to remove fluid from the eye, thereby lowering the intraocular pressure.

Conversely, if an input received by the system comprises data that corresponds to intraocular pressure at or below a predetermined level, the system can be configured not to initiate any additional processes and/or stop one or more currently operating processes that are configured to remove fluid from the eye and/or lower intraocular pressure. Similarly, in an input received by the system comprises a user input corresponding to stopping removal of fluid from the eye and/or lowering intraocular pressure, the system can be configured to stop one or more currently operating processes that are configured to remove fluid from the eye and/or lower intraocular pressure.

The system can be further configured to generate one or more instruction commands for transmission to one or more electronic device components of the system implanted in the eye at block 4008. If the system determined that one or more processes to lower intraocular pressure should be initiated based on the processed input(s), the system can be further configured to generate one or more specific instruction commands and transmit the same to one or more electronic device components implanted in the eye. In such circumstances, the system can be configured to generate and transmit instructions to an electronically controlled pump or micro pump to initiate and/or increase the rate of fluid removal from the eye through the tubular device. In addition or alternatively, in such circumstances, the system can be configured to generate and transmit instructions to an electronically controlled valve to open and/or widen an opening of the valve to increase the rate of fluid removal from the eye through the tubular device.

Conversely, if the system determined that one or more processes to lower intraocular pressure should not be initiated or that one or more currently operating processes to lower intraocular pressure should be stopped based on the processed input(s), the system can also be further configured to generate one or more specific instruction commands and transmit the same to one or more electronic device components implanted in the eye. In such circumstances, the system can be configured to generate and transmit instructions to an electronically controlled pump or micro pump to stop and/or decrease the rate of fluid removal from the eye through the tubular device. In addition or alternatively, in such circumstances, the system can be configured to generate and transmit instructions to an electronically controlled valve to close and/or narrow an opening of the valve to decrease the rate of fluid removal from the eye through the tubular device.

Each electronic device component that received an instruction command can be further configured to perform one or more processes according to the received instruction command. Optionally, in some embodiments, the system can be further configured to determine whether the one or more electronic device components that received an instruction command in fact performed the corresponding one or more processes at block 4010. If confirmation and/or a current status input is received by the system that the one or more corresponding processes were performed, the process can end at block 4012 in some embodiments. However, if such confirmation and/or a current status input is not received, the system can be configured to repeat one or more processes from blocks 4004 to block 4010.

Further, in some embodiments, the system can be configured to repeat one or more processes described in relation to FIG. 40 periodically, in real-time, or in near real-time. For example, the system can be configured to repeat processes 4004 through 4008 and/or processes 4004 through 4010 periodically, in real-time, or in near real-time. The one or more processes can be repeated every about 1 second, about 2 seconds, about 3 seconds, about 4 seconds, about 5 seconds, about 6 seconds, about 7 seconds, about 8 seconds, about 9 seconds, about 10 seconds, about 20 seconds, about 30 seconds, about 40 seconds, about 50 seconds, about 1 minute, about 2 minutes, about 3 minutes, about 4 minutes, about 5 minutes, and/or within a range defined by two of the aforementioned values.

FIG. 41 is a block diagram depicting another example control process for a prosthetic capsular device system. In some embodiments, an electronic device in the capsular device, for example a control unit, can receive one or more inputs at block 4104. The one or more inputs can comprise a user input or data relating to intraocular pressure (TOP). The user input can be achieved by a user through a user access point system, such as a smartphone or other handheld electronic device. The IOP-related data can be detected and/or received from one or more pressure sensors implanted in the eye.

The electronic device in the capsular device can be configured to further determine the received input at block 4106. The electronic device may determine that the received input corresponds to lowering the IOP and/or removal of fluid from the eye. For example, the received input may be a user input indicating discomfort in the eye or other input corresponding to lowering the IOP and/or removal of fluid from the eye. The received input may also be IOP data that is at or above a certain level.

Conversely, the electronic device in the capsular device may determine that the received input corresponds to maintaining the IOP and/or preventing or stopping removal of fluid from the eye. For example, the received input may be a user input indicating alleviation of discomfort in the eye or other input corresponding to maintaining current IOP and/or preventing or stopping removal of fluid from the eye. The received input may also be TOP data that is at or below a certain level.

If the electronic device in the capsular device determines that the received input corresponds to lowering the TOP and/or removal of fluid from the eye, the electronic device can be further configured to generate an instruction command to cause fluid flow through a tubular device at block 4108*a*. Conversely, if the electronic device in the capsular device determines that the received input corresponds to maintaining the IOP and/or preventing or stopping removal of fluid from the eye, the electronic device can be further configured to generate an instruction command to prevent and/or stop fluid flow through a tubular device at block 4108*b*.

The electronic device in the capsular device can be further configured to electronically transmit the generated instruction command to an electronic device component of the tubular device at block 4110. In some embodiments, the generated instruction command can be transmitted through a wire connection between the electronic device in the capsular device and the electronic device in the tubular device. In certain embodiments, the generated instruction command can be transmitted through a wireless connection between a wireless transceiver of the electronic device in the capsular device and a wireless transceiver and/or receiver of the electronic device in the tubular device.

In some embodiments, the electronic device in the capsular device can be further configured to receive confirmation and/or a current status input from an electronic device of the tubular device at block 4112. At block 4114, the electronic device of the tubular device can further be configured to initiate a change in the state of the tubular device in accordance with the instruction. For example, the electronic device of the tubular device can cause a valve to open or close and/or cause a pump to cause or prevent fluid flow from inside of the eye to a second location.

FIG. 42 is an anterior side perspective view of another example prosthetic capsular device system in an eye. As illustrated in FIG. 42, a prosthetic capsular device 4200 can be implanted in the eye. The prosthetic capsular device 4200 can comprise a housing structure 4202 and one or more rings or haptics 4204. The one or more rings or haptics 4204 can be configured to be in contact with the natural capsular bag 3710 of the eye.

The prosthetic capsular device 4200 can further comprise an aperture 4206 that is configured to allow fluid connection between the interior and exterior of the housing structure 4202. A tubular device can be coupled to the aperture 4206. More specifically, a tubular portion 3532 of the tubular device can be configured to provide fluid connection between the interior of the housing structure 4202 and a second location. For example, a first opening of the tubular portion 3532 can be connected to the interior of the housing structure 4202 to provide the fluid connection. A second opening of the tubular portion 3532 can be located at the second location. The tubular portion 3532 can be configured to extend away from the device 4200 implanted in the natural capsular bag of the eye 3710.

In some embodiments, a first puncture or incision 3712 can be made in a sidewall of the natural capsular bag 3712 of the eye and the tubular portion 3532 can be inserted through the first puncture 3712. A second puncture or incision 3704 can also be made in the sclera 3700 of the eye. The tubular portion 3532 can further be inserted through the second puncture or incision 3704. By inserting the tubular portion through the first puncture or incision 3712 and the second puncture or incision 3704, the second opening of the tubular portion 3532 can be located in the sub-Tenon's space, thereby allowing fluid connection between inside of the housing structure 4202 of the device 4200 implanted in the eye and the sub-Tenon's space. For example, the second opening of the tubular portion 3532 can be located 2-4 mm posterior to the limbus, but without reaching the conjunctiva. As such, fluid from inside of the eye can enter through the first opening of the tubular portion 3532 inside the housing structure 4202, flow through the tubular portion 3532, and exit through the second opening of the tubular portion 3532 and into the Sub-Tenon's space.

AR/VR Systems, Methods, and Devices

With the development of technology, augmented reality (AR) and virtual reality (VR) devices are able to provide users with AR and VR. For example, AR devices can provide a user with a multitude of information, such as for example directions, locations of particular areas of interest, data, instructions, messages, entertainment, images, videos, content, and the like, based on the current location of the user and the visual range of the user. Some AR devices are in the form of glasses that allow a user to view directions, locations of convenience stores, restaurants, gas stations, or the like, as imposed on the user's normal visual field. Some other uses of AR devices may include providing a head-up display (HUD) of any information, such as directions, GPS, email, notes, presentations, video, graphics, text messages, or the like.

However, one shortcoming of existing technologies is that the AR must be viewed through or from a device or display means located between the eyes of the user and the location of interest. In certain existing AR devices, information or other graphics are projected onto or otherwise displayed on an intermediary display which must be positioned between the user's eyes and the location or object that the user is viewing. For example, some AR devices display the AR images on glasses or goggles to be worn by the user. Similarly, for certain AR devices, a user may be required to hold and view a smartphone or other device in order to view the information or other graphics. Otherwise, the AR information and/or graphics must be projected directly onto the macula of the user, but this would generally require a projector to be positioned generally within the central visual field of the user in order for the device to directly project the image onto the retina of the user to provide a clear image. Existing VR devices share similar shortcomings. In either case, the user's visual field is occluded or blocked, either partially or entirely, in one way or another by such AR or VR devices.

Such technical limitations lie in the fact that some device must be located directly within a central portion of the visual field of a user in order for that device to display or project an image that is clearly viewable by the user. A projector or other source of display must generally be located within the central visual field of the user, which will necessarily occlude the user's visual field. As a result, many technical or design limitations exist for AR and VR devices and certain safety concerns may arise as well from obstructing the user's visual field. As such, it can be advantageous for a user to be able to view AR and/or VR without the use of a device that occludes or obstructs the user's direct visual field. Accordingly, some embodiments of the devices, systems, and methods described herein are configured to provide AR and/or VR to a user without occluding or obstructing the direct or central visual field of the user.

In some embodiments, the information or other graphics to be projected or displayed must be viewable by the user without occluding or obstructing the user's direct visual field. In other words, in some embodiments, the projector that projects the information or other graphics, whether in AR or VR, is not located generally along the direct line of vision of the user. Rather, the projector can be located elsewhere, for example near the peripheral visual field of the user. However, if the projector is not located along the user's direct line of vision and is located near the user's peripheral view, the projected information will likely reach the peripheral retina and not the macula of the user. As a result, the user may not be able to view a clear image.

To remedy such technical problem, some embodiments of the devices, methods, and systems disclosed herein comprise one or more prisms or prism bars that are configured to be implanted within the user's eye(s). The implanted one or more prisms or prism bars can be strategically located within the user's eye(s) to bend or redirect information or other graphics projected from a peripherally located projector or projector or other display means that is not located at a substantially central position within the user's visual field. The bended or redirected information or other graphics can then reach the macula of the user after traveling through the one or prisms or prism bars. By doing so, a clear image of augmented or virtual information, text, graphics, or other display can be viewable by a user without the need of a device being placed along the direct line of sight of the user or at a central location within the user's visual field.

Any of the devices and systems described herein, such as the devices and systems shown in FIGS. 1A, 2A, 3A, 4A, 5A, 6A, 7A, 8A, 9A, 10A, 11A, 12A, 13A, 14A, 15A, 16A, 18A, 19A, 21A, 23B, 24A, 25A, 27A, 28A, 29A, 31A, 33A, and modifications and combinations thereof can be configured to hold one or more prisms for use in conjunction with an AR/VR system, device, or method as described herein. In addition, any of the devices and systems described in U.S. Pat. No. 9,358,103, which is hereby incorporated by reference in its entirety, may be modified in accordance with the present disclosure. For example, the devices and systems shown in FIGS. 2, 4H, 6, 8, 9A, 10A, 11A, 11D, 12A, 13, 14, 16, 17, 18, 19, 20, 21, 22A, 22B, 23, 24, 25, 26, 27, 28, 29, 30, 31, 32, 33, 34, 35, 36, 37A, 38A, 39, 40, 41, 42, 43A, 43E, 57A, 58A, 58E, 58F, 58G, 58H, 58I, 58J, 58K, 58L, 59A, 61A, 61D, 62A, 63A, 64A, 65A, 66A, 67A, 68A, 69A, 70A, 72A, 73A, 74B, 74C, 74D, 74E, 75A, 75E, 76A, 76B, 76C, 76D, 76E, 76F, 77C, 77D, 77I, and modifications and combinations thereof can be configured to hold one or more prisms for use in conjunction with an AR/VR system, device, or method as described herein. Modifications to other prosthetic capsular devices or systems in accordance are also possible.

In some embodiments, the system comprises one projection device located or placed near the peripheral vision field of the user and one prism device or prism bar implanted inside the user's eye. The implanted prism device or prism bar can effectively bend or redirect light or image projected by the projection device onto the macula of the user to provide a clear display without occluding the central visual field of the user. In certain embodiments, the system comprises one or more projection devices and/or one or more prism devices or prism bars. For example, the system can comprise one or more prism devices or prism bars implanted within both eyes of the user and one or more projection devices configured to project light or images through the one or more prism devices or prism bars onto the macula of both eyes of the user. In such embodiments, the system can be configured impose certain light and/or images bilaterally in both eyes to create three-dimensional effects viewable by the user.

System/Device Components

In some embodiments, the system or devices disclosed herein can comprise one or more projection devices and one or more prisms or prism bars. The one or more prisms or prism bars can be configured to be implanted into the user's eye(s). The one or more projection devices can be configured to be placed not along the direct line of sight of the user or a central portion of the user's visual field. Rather, the one or more projection devices can be configured to be placed at a location near or along the peripheral visual field of the user.

The one or more projection devices can comprise a device housing. The device housing can be configured to comprise one or more electronic and/or computer components for processing the information or other graphics to be displayed to the user and for projecting such information or other graphics into the user's eye and through the one or more prisms or prism bars to cause the information or other graphics to reach the macula or substantially near the macula of the user.

In some embodiments, the device housing can comprise one or more different materials. For example, the device housing or a portion thereof can be made of wire, plastic, deformable rubber, deformable foam, silicone, silicone elastomers, polymers, polypropylene, Styrofoam, acrylics, heat deformable laminates, thermoplastics, one or more corrugated forms of plastic, polyimide, propylene, shape memory alloys (SMA), or the like. It can be advantageous for the device housing to comprise moldable and/or flexible material in some embodiments. For example, moldable and/or flexible materials can allow the device housing to be adapted and placed along curved or movable surfaces, such as over the user's nose bridge, cheekbones, eyebrows, forehead, or the like. Moldable and/or flexible materials can also be advantageous for placing the device housing on or at locations that can differ in shape or configuration among different users. In certain embodiments, the device housing or a portion thereof can comprise a material that provides thermal and/or electrical insulation. In some embodiments, the device housing can comprise one or more flexible circuits.

In certain embodiments, the device housing or a portion thereof can comprise a rigid material. For example, the device housing can comprise a rigid plastic, metal, alloy, wood, polymers, acrylics, resins, polysiloxane, polymethyl methacrylate (PMMA), or the like. In some embodiments, the device housing or a portion thereof can comprise one or more materials that are oxygen-permeable, rigid gas permeable, and/or chemically inert. Such rigid material can be advantageous for embodiments in which the device housing is configured to be placed on or at locations that allow for the device housing to generally retain its configuration. For example, in embodiments where the device housing is to be placed on peripheral areas of glasses, such as on the stems of a pair of glasses, the device housing can comprise a rigid material.

In certain embodiments, the device housing can comprise one or more components of the system. For example, the system can comprise one or more projectors, cameras, power sources or battery sources, CPUs, communication modules, sensors, gyroscopes, GPS modules, accelerometers, or the like. The one or more projectors can be a DLP type projector, LED type projector, LCD type projector, laser projector and/or any other type of projector. The one or more projectors can comprise a light source, wherein the light source can be an LED or standard lamp. The power source or battery source can comprise a stretchable battery for flexible circuits. The system can also comprise one or more computer components as described herein. The system can also be configured to communicate with one or more computer components of other computer systems to implement one or more embodiments. In some embodiments, the device housing comprises a subset of the components of the system. In certain embodiments, a subset of the components of the system can be located elsewhere, for example as part of another device or as a standalone device, such as a smartphone, computer, laptop computer, personal electronic device, or the like.

FIG. 43 illustrates an embodiment in which the projection device 4300 comprises one or more battery power sources 4308, CPUs 4304, communication modules 4306 such as Wi-Fi or Bluetooth receivers, cameras 4302, and/or AR projectors 4310.

In some embodiments, the system or projection device 4300 can comprise one or more cameras 4302. The one or more cameras 4302 can be configured to scan and/or view the surroundings of a user. For example, one or more cameras 4302 can be configured to view objects and/or points of reference generally viewable by the user and within the visual field of the user. In certain embodiments, the one or more cameras 4302 can be moved to point in different directions as desired by the user. For example, in some embodiments, the one or more cameras 4302 can comprise and/or be configured to be moved by one or more motors or actuators to be pointed in different directions in response to an input by a user via a user device. In other embodiments, the one or more cameras 4302 can be moved by mechanical input by a user, such as by physically altering the direction in which the one or more cameras 4302 is pointing.

The objects, locations, and/or points of reference captured by the one or more cameras 4302 can be identified by the one or more CPUs 4304. The one or more CPUs 4304 can be configured to process the objects, locations, and/or points of reference or portion(s) thereof captured by the one or more cameras 4302. In some embodiments, the one or more CPUs 4304 can be configured to process additional information provided by one or more other electronic and/or computer components described herein.

In certain embodiments, the system or projection device 4300 can comprise one or more GPS modules. The one or more GPS modules can be configured to detect the current location of the user in substantially real-time, near real-time and/or periodically. In some embodiments, the system or projection device 4300 can comprise one or more gyroscopes and/or accelerometers. The one or more gyroscopes and/or accelerometers can be configured to detect the current positioning of a user in substantially real-time, near real-time, and/or periodically.

In some embodiments, information or data collected by the one or more cameras 4302, GPS modules, gyroscopes, and/or accelerometers can be combined by the system 4300 to enhance accuracy. For example, in certain embodiments, one or more CPUs 4304 of the system or projection device 4300 can be configured to receive and/or combine the information or data collected by the one or more cameras 4302, GPS modules, gyroscopes, and/or accelerometers to determine and/or provide more accurate data to be displayed and/or imposed onto the user's visual field.

In certain embodiments, the system or projection device 4300 can comprise one or more communication modules 4306. For example, the one or more communication modules 4306 can comprise Bluetooth, Wi-Fi, LTE, NFC, or other receivers and/or transceivers for electronic communication. In some embodiments, the information or data collected by the one or more cameras 4302, GPS modules, gyroscopes, and/or accelerometers can be electronically communicated to the one or more CPUs 4304 by the one or more communication means 4306. For example, in embodiments where the GPS module is not within the projection device 4300 but is located as part of a separate device, such a smartphone, the location detected by the GPS module can be electronically received by a communication module 4306 of the projection device 4300. In turn, the location information can be transmitted to a CPU module 4304 within the projection device 4300.

Based on the information or data collected by the one or more cameras 4302, GPS modules, gyroscopes, and/or accelerometers, the system, projection device, 4300 and/or CPU module 4304 can be configured to determine the particular information or graphics to be displayed to the user. Once determined, data relating to the determined information or graphics can be transmitted to the one or more projectors 4310, which can then project such into the user's eye(s).

In some embodiments, the system and/or device 4300 can comprise one or more infrared light sources, radar/sonar transceivers, and/or one or more cameras for night vision. By use of one or more infrared light sources and/or radar/sonar transceivers, the system 4300 can be configured to process a more robust environmental mapping system, for example in combination with the information gathered from the one or more cameras 4302. For instance, the system 4300 can be configured to map areas and generate a three-dimensional AR of the physical surroundings, even in total darkness, by use of one or more infrared light sources, radar/sonar transceivers, and/or one or more cameras for night vision.

More specifically, in some embodiments, the radar and/or sonar transceivers can be configured to transmit signals of various frequencies and/or receive signals in response. The response signals can then be transmitted to a CPU, which could then process the data to generate a map. The generated map can be overlaid with GPS, gyroscope, and/or accelerometer data, in certain embodiments, to produce a more robust map. In some embodiments, the generated map can be overlaid without GPS data when used in an unknown indoor or outdoor environment.

One or more systems and/or devices described herein can also be used to measure and/or estimate distances, identify moving and/or non-moving objects, such as other people, animals, cars, or the like, map obstacles, and/or assist with covert operations in total or near darkness. In certain embodiments, one or more systems and/or devices described herein can be configured to be used to assist with aiming a weapon at a target. For example, some embodiments are configured to determine an estimated and/or exact trajectory, type and position of the weapon, type of weapon ammunition, and/or distance to and speed of an object of target and relay one or more such information to be viewable by a user.

Positioning

In some embodiments, the system can comprise one or more non-occluding projection devices and one or more prisms or prism bars. The particular location or positioning of the one or more projection devices and one or more prisms or prism bars, as well as their locations relative to one another, can be important to provide a clear image or projection viewable by a user while ensuring that the one or more projection devices themselves do not occlude the direct or central visual field of the user. As such, the user can be allowed to maintain his or her entire visual field, even while utilizing one or more AR or VR devices, methods, or systems disclosed herein.

In certain embodiments, one or more projection devices can be located near or along the peripheral field of vision of the user and not along the user's general direct line of vision or near the central portion of the user's visual field. For example, in certain embodiments, the one or more projection devices can be configured to be located or placed near or on the user's nose, nose bridge, cheekbone, forehead, eyebrows, lips or the like.

In certain embodiments, the system can comprise one or more projection devices located near or along the nasal periphery of the user's visual field. For example, one or more projection devices can be configured to be placed or located on the nose and/or one or both sides of a user's nose. Similarly, one or more projection devices can be configured to be placed over a user's nose or nose bridge. In such embodiments, one or more prisms or prism bars can be placed vertically within a user's eye. For example, in embodiments in which one or more projection devices are configured to be placed on the user's nose or generally along the nasal periphery of the user's visual field, one or more prisms or prism bars can be configured to be placed temporally in a vertical manner within one or both eyes of the user. More specifically, in certain embodiments, the one or more prisms or prism bars can be placed vertically at the right end within the user's right eye and/or vertically at the left end within the user's left eye.

FIG. 43 illustrates an embodiment in which a projection device 4300 is configured to be placed over the nose bridge of a user. As depicted in FIG. 43, in some embodiments, the projection device 4300 comprises two projectors 4310 or AR projectors that are configured to project light or image(s) to the eye(s) of a user from a nasal location.

In other embodiments, the system can comprise one or more projection devices located near or generally within the temporal periphery of the user's visual field. For example, one or more projection devices can be configured to placed or located temporally. One or more projection devices can be configured to be placed near or generally near the user's temporal field of vision, such as on one or more legs of a pair of standard or specially produced glasses. In such embodiments, one or more prisms or prism bars can be placed nasally in a vertical manner within a user's eye(s). In certain embodiments, the system can comprise one or more prisms or prism bars located vertically at the left end within the user's right eye and/or one or more prisms or prism bars located vertically at the right end within the user's left eye.

In some embodiments, the system can comprise one or more projection devices located near or generally along the lower periphery of the user's field of vision. For example, one or more projection devices can be configured to be placed near or generally near the user's lower field of vision, such as on or generally near the user's cheekbone and/or along the bottom of the frame of glasses. In such embodiments, one or more prisms or prism bars can be placed horizontally within a user's eye(s). In certain embodiments, the system can comprise one or more prisms or prism bars located horizontally at or near the top end within the user's eye(s).

In certain embodiments, the system can comprise one or more projection devices located near or generally along the upper periphery of the user's field of vision. In other words, one or more projection devices can be configured to placed or located generally above a user's eye(s). For example, one or more projection devices can be configured to be placed near or generally near the user's upper peripheral field of vision, such as on or generally near the user's eyebrow(s) or forehead or along the top of the frame of glasses. In such embodiments, one or more prisms or prism bars can be placed horizontally within a user's eye(s) at or near the bottom end within the user's eye(s).

However, in some embodiments, an issue of double vision may arise. The probabilities and/or risks related to double vision may be higher in certain embodiments than others, such as due to the relative location or placement of the one or more projection devices and one or more prisms or prism bars. For example, in embodiments in which the one or more projection devices are to be placed on or near the temporal periphery of a user's field of vision, the one or more prisms or prism bars can generally be placed inside the user's eye(s) in a vertical configuration near the nasal end. In such case, when the one or more projection devices are not projecting any light and/or the one or more projection devices are not installed, for example onto the stem(s) of a pair of glasses, the prism or prism bar may still bend natural light entering from the temporal periphery of the user's visual field. Such light can then reach the macula after exiting through the one or more prisms or prism bars and produce a double vision effect to the user. Similar effects or risks relating to double vision can also be present or more attenuated in embodiments in which the one or more projection devices are to be placed near or at the top or bottom of the periphery of the user's visual field.

In contrast, embodiments in which the one or more projection devices are to be placed nasally or near or at the nasal periphery of the user's field of vision, such risks relating to double vision may be mitigated. More specifically, in such embodiments, the one or more prisms or prism bars can generally be located or placed in a vertical configuration near or at the temporal end(s) within the user's eye(s). The one or more prisms located in such manner may substantially only bend light that is entered from the nasal periphery of the user's field of vision. In such case, however, the user's nose can effectively block most or a substantial amount of the user's nasal periphery view. Accordingly, the probability or risk arising from double vision may be mitigated.

Movement of Projection Device(s) and/or Prism(s)

As described herein, in some embodiments, the projection device(s) and prism(s) or prism bar(s) can be strategically placed in locations relative to one another in order to effectively redirect light and/or an image projected by the projector(s) onto the macula or near the macula of the user. By doing so, the system can be configured to provide an overlay of information to a user's vision without requiring a projection device to occlude the user's visual field. However, in certain situations, it may not be desirable for the light and/or image projected by the one or more projection devices to end up at or substantially at the center of the user's macula. Also, in some situations, the angle of the projected light and/or image may be altered unexpectedly, for example due to movement of the user and/or movement of the projection device or a portion thereof relative to the location of the one or more prisms or prism bars. In such circumstances, the projected image and/or light may not be redirected or bent in an ideal angle through the one or prisms or prism bars and may not be clearly viewable by the user. As such, it can be advantageous for the one or more projection devices and/or one or more prisms or prism bars and/or angles thereof to be movable or altered as desired by the user.

As such, in some embodiments, the particular location(s) and/or angle(s) the one or more prisms or prism bars and/or one or more projection devices can be manipulated by the user. In certain embodiments, the one or more prisms or prism bars and/or one or more projection devices comprise a motor and/or actuator. The motor and/or actuator can be configured to alter the location(s) and/or angle(s) of the one or more prisms or prism bars and/or the one or more projection devices as desired by the user. As such, the motor and/or actuator can allow the user to change the location of the imposed image or light within the user's visual field and/or allow the user to alter the definition of the projected image or light viewable by the user.

In certain embodiments, the motor and/or actuator for moving the one or more prisms or prism bars and/or one or more projection devices can be configured to be manipulated electronically by a user, for example by inputting certain instructions into a user device. In some embodiments, the angle and/or location of the one or more prisms or prism bars and/or one or more projection devices can be altered mechanically by the user, for example via a manual slider.

In certain embodiments, the one or more projection devices and/or one or more prisms or prism bars can be configured to alter its location and/or angle automatically relative to one another. In other words, the one or more projection devices and/or one or more prisms or prism bars can be configured to automatically track the location, angle, or other configuration of the other and/or location, angle, or other configuration of itself relative to the other and alter its location, angle, or other configuration accordingly.

Prism/Prism Bar(s)

In some embodiments, one or more prisms or prism bars can be configured to be implanted into a user's eye(s). For example, in certain embodiments, one or more prisms or prism bars can be configured to be implanted directly into the natural capsular bag of a user's eye(s). In some embodiments, one or more prisms or prism bars can be configured to be implanted into the capsular bag of a user's eye indirectly, for example by being placed inside an implant housing structure or device. The implant housing structure or device can be configured to be implanted into a user's capsular bag and substantially hold the one or more prisms or prism bars in place. The implant housing structure can provide stability to the placement of the one or more prisms. In some embodiments, the one or more prisms or prism bars can be configured to be implanted into a user's eyes after the implant housing structure or device is first implanted.

FIG. 44 depicts an embodiment of an implantable housing 4402 configured to be implanted into the eye of a user with a prism or prism bar 4400 placed inside the implantable housing 4402. As illustrated, a prism bar 4400 can be configured to be placed vertically within an implantable device housing 4402, which itself is configured to be implanted into the capsular bag of a user. Light or images projected by one or more projectors can be bent or redirected by the prism or prism bar 4400 inside the implantable housing 4402 to reach the retina or macula of the user.

In some embodiments, the prism and/or prism bar 4400 itself is foldable for implanting the prism and/or prism bar 4400 into the eye(s) of a user. In certain embodiments, the prism and/or prism bar 4400 is rigid. The prism and/or prism bar 4400 can comprise one or more haptics or closed loops. For example, the one or more haptics or closed loops can be self-expanding or otherwise configured to expand once the prism and/or prism bar 4400 is implanted into the natural capsular bag to anchor and/or hold the prism and/or prism bar 4400 in place within the capsular bag. The one or more haptics or closed loops can be foldable.

In certain embodiments, the prism and/or prism bar 4400 is configured to be injected into the eye(s) of a user through an injector. The injector can comprise one or more similar aspects of a standard intraocular lens injector. In some embodiments, the prosthetic device or implantable housing 4402 comprises one or more openings. For example, the prosthetic device or implantable housing 4402 can comprise an opening on a sidewall of the prosthetic device or implantable housing 4402. In some embodiments, the prism and/or prism bar 4400 can be configured to be injected into the opening of the prosthetic device or implantable housing 4402. The size and/or configuration of an opening of the prosthetic device or implantable housing 4402 and the size and/or configuration of the prism or prism bar 4400 can be substantially the same as to hold or anchor the prism or prism bar 4400 in place without the need for a haptic. In other words, in certain embodiments, a prism or prism bar 4400 can be configured to be inserted or slid into an opening on a sidewall of the prosthetic device 4402, extending into the recess of the natural capsular bag.

In some embodiments, a prism and/or prism bar 4400 do not comprise any haptics or closed loops. For example, the prism or prism bar 4400 can be configured to be inserted into an opening of a prosthetic device 4402, which is configured to anchor or hold the prism or prism bar 4400 in place. In certain embodiments, the prism or prism bar 4400 can be self-expanding and/or self-retaining, either by use of a haptic system or by fitting into an opening.

The one or more prisms or prism bars 4400 can be a Fresnel prism or a regular prism. It can be advantageous for the one or more prisms or prism bars 4400 to comprise a Fresnel prism to save space within the user's eye or implant device. In some embodiments, one or more Fresnel prisms can be used in conjunction with one or more regular prisms. In some embodiments, one or more prisms 4400 can be stacked before and/or after implanting into the eye(s) of a user. For example, one or more prisms 4400 can be stacked to form a prism bar or other configuration. In certain embodiments, one or more prisms 4400 can be configured to be binocular, monocular, or both.

In some embodiments, the one or more prisms or prism bars 4400 can be configured to bend or redirect the projected image by about 10°, about 20°, about 30°, about 40°, about 50°, about 60°, about 70°, about 80°, about 90°, about 100°, about 110°, about 120°, about 130°, about 140°, about 150°, about 160°, and/or about 170°. In certain embodiments, the one or more prisms 4400 can be configured to bend or redirect the projected image by an angle within a range defined by two of the angles identified above.

In certain embodiments, the one or more prisms 4400 can comprise a general configuration of a bar, cube, rectangle, square, or the like. In some embodiments, the one or more prisms or prism bars 4400 can comprise a width of about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, and/or about 10 mm. In some embodiments, the width of the one or more prisms 4400 can be within a range defined by two of the aforementioned values.

In some embodiments, the one or more prisms or prism bars 4400 can comprise a length of about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, and/or about 30 mm. In certain embodiments, the length of the one or more prisms or prism bars 4400 can be within a range defined by two of the aforementioned values.

In certain embodiments, the particular size and/or shape of one or more prisms or prism bars 4400 to be implanted into the eye(s) of a user can vary. For example, the particular size and/or shape of one or more prisms or prism bars 4400 to be implanted into the eye of a user can depend on the particulars of the user's eyes, such as the size of the user's natural capsular bag, size of an implantable housing 4402, and the like.

In some embodiments, the projected image from the one or more projectors can be configured to enter one of the hypotenuse sides of the one or more prisms or prism bars 4400 and exit through the other hypotenuse side of the prism or prism bar 4400. FIG. 45 depicts an embodiment of a prism or prism bar 4400 configured to be implanted into the eye of a user. As illustrated in FIG. 45, in certain embodiments, a self-retained prism lens or bar implant 4400 is configured to receive an image(s) or light projected from a projector and bends or redirects the image or light onto the retina of a user.

Prism Performance Characteristics

As discussed above, with one or more prisms 4400 being implanted inside a user's capsular bag, the user may in some situations encounter double vision when the one or more projectors is not projected an image into the prism 4400. For example, even if the one or more projectors is not currently generating and projecting an image, the one or more prisms or prism bars 4400 may still function to bend or redirect light entering into the prism or prism bar 4400. As a result, the user may encounter double vision to various degrees depending on the location or placement of the one or more prisms 4400. As such, it can be advantageous to provide a way for the one or prisms or prism bars 4400 not to bend or redirect light when one or more projectors is not in operation.

Accordingly, in some embodiments, the one or more prisms or prism bars 4400 can comprise a particular color and/or coating configured to allow only particular light to enter through the prism or prism bars 4400 and be bended or redirected onto the macula of the user. In other words, in certain embodiments, the one or more prisms or prism bars 4400 can be configured to allow only light generated by the one or more projection devices to enter into the prism 4400 and/or be redirected onto the macula of the user. For example, the angle, color, opacity, polarity, certain photo gray characteristics of the one or more prisms 4400 can be utilized to prevent the one or more prisms from bending or redirecting light when the one or more projection devices are not projecting an image or light.

Safety Features

Some safety concerns may be present if the projection device continuously projects light onto the macula of the user at damaging levels. Accordingly, in some embodiments, the one or more projection devices does not continuously project light, but projects light at a flicker rate to protect against continuously damaging the retina. For example, the flicker rate can be about 10 Hz, about 20 Hz, about 30 Hz, about 40 Hz, about 50 Hz, about 60 Hz, about 70 Hz, about 80 Hz, about 90 Hz, about 100 Hz, about 110 Hz, about 120 Hz, and/or within a range defined by two or more aforementioned rates. Although the projected light or image is at a particular flicker rate, this may not be perceptible by the user.

In certain embodiments, the flicker rate can be selectable by a user. In some embodiments, the brightness of the projected light or image can be selected by the user. For example, in certain embodiments, the projection device and/or other user device can comprise a flicker rate, dimmer switch, timer, and/or on/off switch that allows the user the control the manner and/or amount of time in which the light and/or image is projected by the projection device(s).

Projected Image

In some embodiments, the projected light or image can be imposed onto the visual field of the user to generate AR or VR effects. In certain embodiments, the projected image or light can be a single color or light. In some embodiments, the type of image and/or color to be projected into the prism or prism bar can be user-selectable. For example, the user can in some embodiments select the mode or particular light or image to be projected via a user input device. The CPU can be configured process and electronically transmit the user selection to the one or more projectors. In certain embodiments, the user input device can be a separate device, handheld or otherwise. The selection made by a user can be communicated via Wi-Fi, Bluetooth or other means of communication via a communications means that is receivable by the projection device(s).

In certain embodiments, the projection device can be configured to project a single color, light, or other image to be portrayed and visible on the user retina via the one or more prisms. For example, in some embodiments, the projection device can be configured to project a single color of light within the visible spectrum or any other color. In certain embodiments, the projector can be configured to project a striped pattern, checkered pattern, concentric circles, and/or any other shape. In other configurations, the projector may be configured to project images such as pictures, text, diagrams, or any other graphical display of data.

The projected image or color can be portrayed onto the user's iris and be viewable by a third person. For example, if a particular color is projected onto the user's iris directly, the projected color may be viewable by others and have a cosmetic effect. As such, in certain embodiments, the user can be able to change the color of his or her irises to be viewable by others, for example for cosmetic purposes.

Medical Signals

In some embodiments, the system can be configured to detect the medical or health status of a user and display such on the user's eyes. For example, in certain embodiments, the system can comprise one or more sensors and/or be configured to communicate with one or more sensors that detect the medical, health, and/or distress status of a user. Some sensors can include intraocular pressure sensors, drug delivery sensors, SpO2 sensors, heart rate monitors, blood pressure monitors, glucose sensors, blood alcohol concentration sensors, temperature sensors (thermometers), or the like. In some embodiments, one or more sensors can be embedded into a contact lens(es) to be worn by the user and configured to detect glucose levels or the like.

In certain embodiments, the medical or health status of a user can be detected by one or more sensors and be transmitted electronically to the CPU of the projection device. For example, the communications module of the projection device can receive detected medical or health status signals and transmit such to the CPU.

In certain embodiments, the CPU can be configured to process the detected health or medical status of the user and assign one or more colors or other visual signals. For example, a mapping table or process can assign a color red if the medical or health status of a user is within a particular predetermined range that corresponds to a serious health risk of the user. Similarly, a yellow or orange color can be assigned if the medical or health status of a user is within a particular predetermined range that corresponds to an intermediate status. If the health or medical status of the user is within a predetermined range that corresponds to a normal state, no color can be assigned.

The assigned color or other visual signal can be projected by one or more projectors onto the retina or macula of a user via one or more implanted prisms. As a result, the assigned color or other visual signal can be recognizable by a third party immediately by viewing the eye(s) of the user. From the particular color or other visual signal that is projected onto and viewable from the eye(s) of the user, a medical personnel or other person may be able to easily and immediately assess the health or medical status of the user. For example, the system can be configured to make the user's eye(s) appear red when the temperature of the user is above a predetermined level or when the user is overheated. Similarly, the system can be configured to make the user's eye(s) appear blue when the user is showing low blood oxygen concentration. The system can also be configured to make the user's eye(s) appear yellow when the user's blood sugar levels are above a predetermined level.

Computer System

In some embodiments, the systems, processes, and methods described herein are implemented using a computing system, such as the ones illustrated in FIGS. 46, 47, and 48. The computing systems illustrated in FIGS. 46, 47, and 48 include certain similar features, and like reference numerals include like features.

Each of the example computer systems 4602, 4702, 4802 are in communication with one or more computing systems 4620 and/or one or more data sources 4622 via one or more networks 4618. While FIGS. 46-48 illustrate embodiments of computing systems 4602, 4702, 4802, it is recognized that the functionality provided for in the components and modules of a computer system may be combined into fewer components and modules, or further separated into additional components and modules.

The computer system 4602 includes a tubular device control module 4614 that carries out one or more functions, methods, acts, and/or processes described herein relating to tubular devices, systems, and methods, for example described in connection with FIGS. 33A-42. The computer system 4702 includes an accommodating lens control module 4714 that carries out one or more functions, methods, acts, and/or processes described herein relating to accommodating lens devices, systems, and methods, for example described in connection with FIGS. 23A-23E. The computer system 4802 includes an AR/VR control module 4814 that carries out one or more functions, methods, acts, and/or processes described herein relating to AR/VR devices, systems, and methods, for example described in connection with FIGS. 43-45. Each of the tubular device control module 4614, accommodating lens control module 4714, and AR/VR control module 4814 is executed on a computer system 4602, 4702, 4802 by a central processing unit 4610 discussed further below.

In general the word "module," as used herein, refers to logic embodied in hardware or firmware or to a collection of software instructions, having entry and exit points. Modules are written in a program language, such as JAVA, C or C++, or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems, and may be stored on or within any suitable computer readable medium, or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

Each of the computer systems 4602, 4702, 4802 include one or more processing units (CPU) 4606, which may include a microprocessor. Each of the computer systems 4602, 4702, 4802 further include a physical memory 4610, such as random access memory (RAM) for temporary storage of information, a read only memory (ROM) for permanent storage of information, and a mass storage device 4604, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of a computer system 4602, 4702, 4802 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

A computer system 4602, 4702, 4802 can include one or more input/output (I/O) devices and interfaces 4612, such as a keyboard, mouse, touch pad, and printer. The I/O devices and interfaces 4612 can include one or more display devices, such as a monitor, that allows the visual presentation of data to a user. More particularly, a display device provides for the presentation of GUIs as application software data, and multi-media presentations, for example. The I/O devices and interfaces 4612 can also provide a communications interface to various external devices. A computer system 4602, 4702, 4802 may include one or more multi-media devices 4608, such as speakers, video cards, graphics accelerators, and microphones, for example.

A computer system 4602, 4702, 4802 may run on a variety of computing devices, such as a server, a Windows server, a Structure Query Language server, a Unix Server, a personal computer, a laptop computer, and so forth. A computing system 4602, 4702, 4802 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

Each of the computer systems 4602, 4702, 4802 is coupled to a network 4618, such as a LAN, WAN, or the Internet via a communication link 4616 (wired, wireless, or a combination thereof). Network 4618 communicates with various computing devices and/or other electronic devices. Network 4618 is communicating with one or more computing systems 4620 and one or more data sources 4622. Each of the tubular device control module 4614, accommodating lens control module 4714, and AR/VR control module 4814 may access or may be accessed by computing systems 4620 and/or data sources 4622 through a web-enabled user access point. Connections may be a direct physical connection, a virtual connection, and other connection type. The web-enabled user access point may include a browser module that uses text, graphics, audio, video, and other media to present data and to allow interaction with data via the network 4618.

The output module may be implemented as a combination of an all-points addressable display such as a cathode ray tube (CRT), a liquid crystal display (LCD), a plasma display, or other types and/or combinations of displays. The output module may be implemented to communicate with input devices 4612 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

A computing system 4602, 4702, 4802 may include one or more internal and/or external data sources (for example, data sources 4622). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

A computer system 4602, 4702, 4802 may also access one or more databases 4622. The databases 4622 may be stored in a database or data repository. A computer system 4602, 4702, 4802 may access the one or more databases 4622 through a network 4618 or may directly access the database or data repository through 110 devices and interfaces 4612. The data repository storing the one or more databases 4622 may reside within a computer system 4602, 4702, 4802.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. For example, actions such as "inserting an intraocular lens into a prosthetic capsular device" include "instructing the insertion of an intraocular lens into a prosthetic capsular device." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

What is claimed is:

1. A prosthetic capsular device configured to be inserted in a natural capsular bag of an eye after removal of a lens, the device comprising:
    a housing structure capable of containing an intraocular device, the housing structure comprising:
        an anterior portion, wherein the anterior portion comprises an anterior opening, wherein the anterior opening is capable of allowing at least one of insertion, removal, or replacement of the intraocular device, wherein the anterior opening is surrounded by a continuous anterior wall defining a first capsular-engaging surface, and wherein the anterior opening is further configured to be coupled to a refractive surface to substantially enclose the anterior opening upon securement therein;
        a posterior portion, wherein the posterior portion comprises a posterior opening, wherein the posterior opening is capable of allowing at least one of insertion, removal, or replacement of the intraocular device, and wherein the posterior opening is surrounded by a continuous posterior wall defining a second capsular-engaging surface;

a continuous lateral portion interposed between the anterior portion and the posterior portion, wherein the continuous lateral portion protrudes radially beyond the anterior portion and the posterior portion, wherein the continuous lateral portion fully encloses a lateral side of the housing structure, wherein an internal cavity of the continuous lateral portion forms a groove for containing the intraocular device, wherein the continuous lateral portion comprises an exterior surface comprising a rounded bulge, the rounded bulge extending radially beyond the anterior portion and the posterior portion, wherein the continuous lateral portion comprises an interior surface comprising the groove, wherein at least a portion of the interior surface is formed at an acute angle or an obtuse angle relative to the anterior portion and the posterior portion, and wherein the housing structure is adapted to contain the intraocular device.

2. The prosthetic capsular device of claim 1, wherein the continuous lateral portion comprises a first curved portion adjacent to an anterior straight-walled portion and a second curved portion adjacent to a posterior straight-walled portion.

3. The prosthetic capsular device of claim 2, wherein the first curved portion extends from the anterior portion, and wherein the second curved portion extends from the posterior portion.

4. The prosthetic capsular device of claim 1, wherein the housing structure further comprises a continuous central cavity, the continuous central cavity at least partially defined by the continuous anterior wall, the continuous posterior wall, and the continuous lateral portion.

5. The prosthetic capsular device of claim 1, wherein the refractive surface is capable of being inserted separately from the housing structure into the natural capsular bag without being attached to the housing structure.

6. The prosthetic capsular device of claim 1, wherein the refractive surface comprises a refractive power between −35D and +35D.

7. The prosthetic capsular device of claim 1, wherein the refractive surface is affixed to the anterior opening using a friction fit.

8. The prosthetic capsular device of claim 1, wherein the refractive surface is affixed to the anterior opening using sutures.

9. The prosthetic capsular device of claim 1, wherein the groove is configured to contain haptics or a capsular tension ring of the intraocular device.

10. The prosthetic capsular device of claim 1, wherein the intraocular device is at least one of an intraocular lens, intraocular pressure sensor, electronic intraocular pressure sensor, photovoltaic cells, solar cells, battery, computer, antennae, sensor, fixation device, capsular tension ring, electronic device, electronic accommodating intraocular lens, liquid crystal display optic, input/output device, or one or more components thereof.

11. The prosthetic capsular device of claim 1, wherein the prosthetic capsular device comprises at least one of silicone, hydrogel, collamer, acrylic, or an acrylic derivative.

12. The prosthetic capsular device of claim 1, wherein the prosthetic capsular device is self-expandable upon insertion in the natural capsular bag.

13. The prosthetic capsular device of claim 1, wherein the prosthetic capsular device is deformable for insertion in the natural capsular bag.

14. The prosthetic capsular device of claim 1, wherein the intraocular device comprises at least one of a Galilean telescope or microscope.

15. The prosthetic capsular device of claim 1, wherein the intraocular device comprises an electronic accommodating intraocular lens.

16. The prosthetic capsular device of claim 1, wherein the refractive surface comprises a refractive power of less than −35D.

17. The prosthetic capsular device of claim 1, wherein the intraocular device and/or refractive surface form an accommodating optic system.

18. The prosthetic capsular device of claim 1, wherein the housing structure is symmetrical over a plane at a midpoint of the continuous lateral portion between the anterior portion and the posterior portion.

19. The prosthetic capsular device of claim 1, wherein the prosthetic capsular device is sized and scaled to accommodate a size of the eye.

* * * * *

UNITED STATES PATENT AND TRADEMARK OFFICE
CERTIFICATE OF CORRECTION

Page 1 of 2

PATENT NO. : 10,898,315 B2
APPLICATION NO. : 16/128233
DATED : January 26, 2021
INVENTOR(S) : Gary N. Wortz It is certified that error appears in the above-identified patent and that said Letters Patent is hereby corrected as shown below:

On the Title Page

On Page 4, Column 2, Item (56), under Other Publications, Line 13, delete "Opinoin" and insert --Opinion--.

On Page 5, Column 1, Item (56), Line 19, under Other Publications, delete "Postive" and insert --Positive--.

On Page 5, Column 1, Item (56), Line 26, under Other Publications, delete "posiiton" and insert --position--.

In the Specification

In Column 10, Line 63, delete "including+35" and insert --including +35--.

In Column 12, Line 24, delete "1-F-1F" and insert --1F-1F--.

In Column 27, Line 25, delete "defined" and insert --defined by--.

In Column 34, Line 9, delete "a" and insert --$\Omega$--.

In Column 52, Line 51, delete "equi-convex" and insert --equiconvex--.

In Column 60, Line 33, delete "(e.g.," and insert --e.g.,--.

In Column 60, Line 33, delete "ranibizuman" and insert --ranibizumab--.

In Column 60, Line 35, delete "Regerneron Pharmacueticals)" and insert --Regeneron Pharmaceuticals)--.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,898,315 B2

In Column 74, Line 41, delete "(TOP)." and insert --(IOP).--.

In Column 74, Line 63, delete "TOP" and insert --IOP--.

In Column 74, Line 66, delete "TOP" and insert --IOP--.

In Column 75, Line 5, delete "TOP" and insert --IOP--.